US012648815B2

(12) United States Patent
Spitler et al.

(10) Patent No.: US 12,648,815 B2
(45) Date of Patent: Jun. 9, 2026

(54) APPARATUS, SYSTEM, AND METHOD FOR GENERATING PATIENT-SPECIFIC IMPLANTS AND/OR INSTRUMENTATION FOR OSTEOTOMIES

(71) Applicant: Treace Medical Concepts, Inc., Ponte Vedra, FL (US)

(72) Inventors: James Q. Spitler, Winter Garden, FL (US); Adam D. Perler, St. Petersburg, FL (US); Adam Schiff, Highland Park, IL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 174 days.

(21) Appl. No.: 18/212,027

(22) Filed: Jun. 20, 2023

(65) Prior Publication Data

US 2023/0404673 A1     Dec. 21, 2023

Related U.S. Application Data

(60) Provisional application No. 63/353,317, filed on Jun. 17, 2022.

(51) Int. Cl.
A61B 17/17        (2006.01)
A61B 34/10        (2016.01)
              (Continued)

(52) U.S. Cl.
CPC .......... A61B 34/10 (2016.02); A61B 17/1775 (2016.11); A61B 17/0642 (2013.01);
              (Continued)

(58) Field of Classification Search
CPC ............ A61B 17/1739; A61B 17/1757; A61B 17/1775; A61B 17/151; A61B 17/152; A61B 17/8095
See application file for complete search history.

(56) References Cited

U.S. PATENT DOCUMENTS 3,664,022 A     5/1972  Small
4,069,824 A     1/1978  Weinstock
              (Continued)

FOREIGN PATENT DOCUMENTS

AU     2009227957 B2     7/2014
AU     2009222469 B2     2/2015
              (Continued)

OTHER PUBLICATIONS

D'Amico et al., "Motion of the First Ray: Clarification Through Investigation," Journal of the American Podiatry Association, vol. 69, No. 1, Jan. 1979, pp. 17-23.
              (Continued)

*Primary Examiner* — Anu Ramana
(74) *Attorney, Agent, or Firm* — Fredrikson & Byron, P.A.

(57)              ABSTRACT

An apparatus, system, and method is disclosed for correcting a condition present in a patient. In some aspects, the apparatus may include a resection guide having: a body, resection features that define trajectories that are at least partially determined based on a bone model of at least a portion of the patient's foot. The bone model can be based on medical imaging of the patient's foot. The apparatus includes a first bone attachment feature and second bone attachment feature configured to secure the resection guide to the bone. Also, the apparatus may include at least one complementary component selected from the group having of: an alignment guide; a rotation guide; a compression guide; a correction guide; a positioning guide; a pin guide; and a fixation guide.

10 Claims, 62 Drawing Sheets

(51) Int. Cl.
      *A61B 17/064*        (2006.01)
      *A61B 17/56*         (2006.01)
(52) U.S. Cl.
      CPC ...  *A61B 2017/565* (2013.01); *A61B 2017/568*
            (2013.01); *A61B 2034/105* (2016.02); *A61B*
                              *2034/108* (2016.02)

(56)                References Cited

U.S. PATENT DOCUMENTS

| | | | |
|---|---|---|---|
| 4,159,716 A | 7/1979 | Borchers |
| 4,187,840 A | 2/1980 | Watanabe |
| 4,335,715 A | 6/1982 | Kirkley |
| 4,338,927 A | 7/1982 | Volkov et al. |
| 4,349,018 A | 9/1982 | Chambers |
| 4,409,973 A | 10/1983 | Neufeld |
| 4,436,684 A | 3/1984 | White |
| 4,440,168 A | 4/1984 | Warren |
| 4,509,511 A | 4/1985 | Neufeld |
| 4,565,191 A | 1/1986 | Slocum |
| 4,570,624 A | 2/1986 | Wu |
| 4,628,919 A | 12/1986 | Clyburn |
| 4,736,737 A | 4/1988 | Fargie et al. |
| 4,750,481 A | 6/1988 | Reese |
| 4,754,746 A | 7/1988 | Cox |
| 4,757,810 A | 7/1988 | Reese |
| 4,839,822 A | 6/1989 | Dormond et al. |
| 4,895,141 A | 1/1990 | Koeneman et al. |
| 4,959,066 A | 9/1990 | Dunn et al. |
| 4,978,347 A | 12/1990 | Ilizarov |
| 4,988,349 A | 1/1991 | Pennig |
| 4,995,875 A | 2/1991 | Coes |
| 5,049,149 A | 9/1991 | Schmidt |
| 5,053,039 A | 10/1991 | Hofmann et al. |
| 5,112,334 A | 5/1992 | Alchermes et al. |
| 5,147,364 A | 9/1992 | Comparetto |
| 5,171,244 A | 12/1992 | Caspari et al. |
| 5,176,685 A | 1/1993 | Rayhack |
| 5,207,676 A | 5/1993 | Canadell et al. |
| 5,254,119 A | 10/1993 | Schreiber |
| 5,312,412 A | 5/1994 | Whipple |
| 5,358,504 A | 10/1994 | Paley et al. |
| 5,364,402 A | 11/1994 | Mumme et al. |
| 5,374,271 A | 12/1994 | Hwang |
| 5,417,694 A | 5/1995 | Marik et al. |
| 5,449,360 A | 9/1995 | Schreiber |
| 5,470,335 A | 11/1995 | Du Toit |
| 5,490,854 A | 2/1996 | Fisher et al. |
| 5,529,075 A | 6/1996 | Clark |
| 5,540,695 A | 7/1996 | Levy |
| 5,578,038 A | 11/1996 | Slocum |
| 5,586,564 A | 12/1996 | Barrett et al. |
| 5,601,565 A | 2/1997 | Huebner |
| 5,613,969 A | 3/1997 | Jenkins, Jr. |
| 5,620,442 A | 4/1997 | Bailey et al. |
| 5,643,270 A | 7/1997 | Combs |
| 5,662,656 A | 9/1997 | White |
| 5,667,510 A | 9/1997 | Combs |
| H1706 H | 1/1998 | Mason |
| 5,722,978 A | 3/1998 | Jenkins, Jr. |
| 5,749,875 A | 5/1998 | Puddu |
| 5,779,709 A | 7/1998 | Harris, Jr. et al. |
| 5,788,695 A | 8/1998 | Richardson |
| 5,803,924 A | 9/1998 | Oni et al. |
| 5,810,822 A | 9/1998 | Mortier |
| 5,836,950 A | 11/1998 | Hansson |
| 5,839,438 A | 11/1998 | Graettinger et al. |
| 5,843,085 A | 12/1998 | Graser |
| 5,893,553 A | 4/1999 | Pinkous |
| 5,911,724 A | 6/1999 | Wehrli |
| 5,935,128 A | 8/1999 | Carter et al. |
| 5,941,877 A | 8/1999 | Viegas et al. |
| 5,951,556 A | 9/1999 | Faccioli et al. |
| 5,957,927 A | 9/1999 | Magee et al. |
| 5,980,526 A | 11/1999 | Johnson et al. |
| 5,984,931 A | 11/1999 | Greenfield |
| 6,007,535 A | 12/1999 | Rayhack et al. |
| 6,030,391 A | 2/2000 | Brainard et al. |
| 6,162,223 A | 12/2000 | Orsak et al. |
| 6,171,309 B1 | 1/2001 | Huebner |
| 6,203,545 B1 | 3/2001 | Stoffella |
| 6,248,109 B1 | 6/2001 | Stoffella |
| 6,391,031 B1 | 5/2002 | Toomey |
| 6,416,465 B2 | 7/2002 | Brau |
| 6,478,799 B1 | 11/2002 | Williamson |
| 6,511,481 B2 | 1/2003 | Von Hoffmann et al. |
| 6,676,662 B1 | 1/2004 | Bagga et al. |
| 6,712,824 B2 | 3/2004 | Millard et al. |
| 6,719,773 B1 | 4/2004 | Boucher et al. |
| 6,743,233 B1 | 6/2004 | Baldwin et al. |
| 6,755,838 B2 | 6/2004 | Trnka |
| 6,780,190 B2 | 8/2004 | Maroney |
| 6,796,986 B2 | 9/2004 | Duffner |
| 6,859,661 B2 | 2/2005 | Tuke |
| 6,944,518 B2 | 9/2005 | Roose |
| 6,964,645 B1 | 11/2005 | Smits |
| 7,033,361 B2 | 4/2006 | Collazo |
| 7,097,647 B2 | 8/2006 | Segler |
| 7,153,310 B2 | 12/2006 | Ralph et al. |
| 7,182,766 B1 | 2/2007 | Mogul |
| 7,241,298 B2 | 7/2007 | Nemec et al. |
| 7,282,054 B2 | 10/2007 | Steffensmeier et al. |
| 7,351,203 B2 | 4/2008 | Jelliffe et al. |
| 7,377,924 B2 | 5/2008 | Raistrick et al. |
| 7,465,303 B2 | 12/2008 | Riccione et al. |
| 7,473,255 B2 | 1/2009 | Mcgarity et al. |
| 7,540,874 B2 | 6/2009 | Trumble et al. |
| 7,572,258 B2 | 8/2009 | Stiernborg |
| 7,641,660 B2 | 1/2010 | Lakin et al. |
| D610,257 S | 2/2010 | Horton |
| 7,670,345 B2 | 3/2010 | Plassky et al. |
| 7,686,811 B2 | 3/2010 | Byrd et al. |
| 7,691,108 B2 | 4/2010 | Lavallee |
| 7,763,026 B2 | 7/2010 | Egger et al. |
| 7,789,885 B2 | 9/2010 | Metzger |
| D629,900 S | 12/2010 | Fisher |
| 7,875,058 B2 | 1/2011 | Holmes, Jr. |
| 7,972,338 B2 | 7/2011 | O'Brien |
| 7,983,777 B2 | 7/2011 | Melton et al. |
| D646,389 S | 10/2011 | Claypool et al. |
| 8,057,473 B2 | 11/2011 | Orsak et al. |
| 8,057,478 B2 | 11/2011 | Kuczynski et al. |
| D651,315 S | 12/2011 | Bertoni et al. |
| D651,316 S | 12/2011 | May et al. |
| 8,080,010 B2 | 12/2011 | Schulz et al. |
| 8,080,045 B2 | 12/2011 | Wotton, III |
| 8,114,087 B2 | 2/2012 | Long et al. |
| 8,123,753 B2 | 2/2012 | Poncet |
| 8,147,530 B2 | 4/2012 | Strnad et al. |
| 8,167,918 B2 | 5/2012 | Strnad et al. |
| 8,172,848 B2 | 5/2012 | Tomko et al. |
| 8,187,280 B2 | 5/2012 | May et al. |
| 8,192,441 B2 | 6/2012 | Collazo |
| 8,197,487 B2 | 6/2012 | Poncet et al. |
| 8,206,153 B2 | 6/2012 | Suttin et al. |
| 8,231,623 B1 | 7/2012 | Jordan |
| 8,231,663 B2 | 7/2012 | Kay et al. |
| 8,246,561 B1 | 8/2012 | Agee et al. |
| 8,246,680 B2 | 8/2012 | Betz et al. |
| D666,721 S | 9/2012 | Wright et al. |
| 8,262,664 B2 | 9/2012 | Justin et al. |
| 8,262,665 B2 | 9/2012 | Massoud |
| 8,277,455 B2 | 10/2012 | Couture et al. |
| 8,282,644 B2 | 10/2012 | Edwards |
| 8,282,645 B2 | 10/2012 | Lawrence et al. |
| 8,287,541 B2 | 10/2012 | Nelson et al. |
| 8,292,966 B2 | 10/2012 | Morton |
| 8,303,596 B2 | 11/2012 | Plaky et al. |
| 8,323,281 B2 | 12/2012 | Hotchkiss et al. |
| 8,323,289 B2 | 12/2012 | Re |
| 8,357,111 B2 | 1/2013 | Caillouette et al. |
| 8,377,105 B2 | 2/2013 | Bscher |
| 8,388,690 B2 | 3/2013 | Singhatat et al. |
| D679,395 S | 4/2013 | Wright et al. |
| 8,435,246 B2 | 5/2013 | Fisher et al. |

(56)          References Cited

U.S. PATENT DOCUMENTS

| | | | |
|---|---|---|---|
| 8,475,462 | B2 | 7/2013 | Thomas et al. |
| 8,484,001 | B2 | 7/2013 | Glozman et al. |
| 8,518,045 | B2 | 8/2013 | Szanto |
| 8,523,870 | B2 | 9/2013 | Green, II et al. |
| 8,529,568 | B2 | 9/2013 | Bouadi |
| 8,532,807 | B2 | 9/2013 | Metzger |
| 8,551,106 | B2 | 10/2013 | Harrold |
| D694,884 | S | 12/2013 | Mooradian et al. |
| D695,402 | S | 12/2013 | Dacosta et al. |
| 8,641,721 | B2 | 2/2014 | Aram et al. |
| 8,652,142 | B2 | 2/2014 | Geissler |
| 8,657,820 | B2 | 2/2014 | Kubiak et al. |
| D701,303 | S | 3/2014 | Cook |
| 8,663,234 | B2 | 3/2014 | Grimm et al. |
| 8,668,700 | B2 | 3/2014 | Catanzarite et al. |
| 8,685,030 | B2 | 4/2014 | Gtte et al. |
| 8,696,719 | B2 | 4/2014 | Lofthouse et al. |
| 8,702,686 | B2 | 4/2014 | Geebelen et al. |
| 8,702,712 | B2 | 4/2014 | Jordan et al. |
| 8,715,289 | B2 | 5/2014 | Smith |
| 8,715,363 | B2 | 5/2014 | Ratron et al. |
| 8,728,084 | B2 | 5/2014 | Berelsman et al. |
| 8,758,354 | B2 | 6/2014 | Habegger et al. |
| 8,764,763 | B2 * | 7/2014 | Wong .................... A61B 17/66 |
| | | | 606/104 |
| 8,777,948 | B2 | 7/2014 | Bernsteiner |
| 8,784,457 | B2 | 7/2014 | Graham |
| 8,795,286 | B2 * | 8/2014 | Sand ................... A61B 17/1682 |
| | | | 606/96 |
| 8,808,298 | B2 | 8/2014 | Raub et al. |
| 8,808,301 | B1 | 8/2014 | Nofsinger |
| 8,808,302 | B2 | 8/2014 | Roose et al. |
| 8,828,012 | B2 | 9/2014 | May et al. |
| 8,838,263 | B2 | 9/2014 | Sivak et al. |
| 8,858,602 | B2 | 10/2014 | Weiner et al. |
| 8,864,773 | B2 | 10/2014 | Paul et al. |
| 8,882,778 | B2 | 11/2014 | Ranft |
| 8,882,816 | B2 | 11/2014 | Kartalian et al. |
| 8,892,235 | B2 | 11/2014 | Choi et al. |
| 8,898,043 | B2 | 11/2014 | Ashby et al. |
| D720,456 | S | 12/2014 | Dacosta et al. |
| 8,900,247 | B2 | 12/2014 | Tseng et al. |
| 8,911,444 | B2 | 12/2014 | Bailey |
| 8,920,428 | B2 | 12/2014 | Zakaria et al. |
| 8,926,612 | B2 | 1/2015 | Graham |
| 8,932,299 | B2 | 1/2015 | Bono et al. |
| 8,939,982 | B2 | 1/2015 | Chellaoui |
| 8,939,984 | B2 | 1/2015 | Budoff |
| 8,945,132 | B2 | 2/2015 | Play et al. |
| 8,965,075 | B2 | 2/2015 | Arnaud et al. |
| 8,974,460 | B2 | 3/2015 | Fuente et al. |
| 8,979,856 | B2 | 3/2015 | Catanzarite et al. |
| 8,992,531 | B2 | 3/2015 | Chow et al. |
| 8,992,532 | B2 | 3/2015 | Wong |
| 8,998,903 | B2 | 4/2015 | Price et al. |
| 8,998,904 | B2 | 4/2015 | Zeetser et al. |
| 8,998,907 | B2 | 4/2015 | Myers |
| 8,998,909 | B2 | 4/2015 | Gillman et al. |
| 9,005,207 | B2 | 4/2015 | Dodds et al. |
| 9,011,451 | B2 | 4/2015 | Long et al. |
| 9,011,452 | B2 | 4/2015 | Iannotti et al. |
| 9,011,456 | B2 | 4/2015 | Ranawat et al. |
| 9,014,835 | B2 | 4/2015 | Azernikov et al. |
| 9,017,329 | B2 | 4/2015 | Tyber et al. |
| 9,017,336 | B2 | 4/2015 | Park et al. |
| 9,023,052 | B2 | 5/2015 | Lietz et al. |
| 9,044,250 | B2 | 6/2015 | Olsen et al. |
| 9,060,788 | B2 | 6/2015 | Bollinger |
| 9,060,822 | B2 | 6/2015 | Wright et al. |
| 9,089,376 | B2 | 7/2015 | Medoff et al. |
| 9,101,421 | B2 | 8/2015 | Blacklidge |
| 9,107,715 | B2 | 8/2015 | Blitz et al. |
| 9,113,915 | B2 | 8/2015 | Thomas et al. |
| 9,113,957 | B2 | 8/2015 | Axelson, Jr. et al. |
| 9,138,237 | B2 | 9/2015 | Meade et al. |
| 9,138,332 | B2 | 9/2015 | Harris et al. |
| D740,424 | S | 10/2015 | Dacosta et al. |
| 9,173,665 | B2 | 11/2015 | Couture |
| 9,173,691 | B2 | 11/2015 | Orbay et al. |
| 9,186,154 | B2 | 11/2015 | Li |
| 9,186,160 | B1 | 11/2015 | Song |
| 9,198,678 | B2 | 12/2015 | Frey et al. |
| 9,204,897 | B2 | 12/2015 | Jones et al. |
| 9,211,128 | B2 | 12/2015 | Gillman et al. |
| 9,220,509 | B2 | 12/2015 | Boyer et al. |
| 9,220,518 | B2 | 12/2015 | Neal et al. |
| 9,220,519 | B2 | 12/2015 | Kaneyama et al. |
| 9,220,551 | B2 | 12/2015 | Waizenegger |
| 9,232,951 | B2 | 1/2016 | Johannaber |
| 9,232,955 | B2 | 1/2016 | Bonin, Jr. et al. |
| 9,254,155 | B2 | 2/2016 | Iannotti et al. |
| 9,295,497 | B2 | 3/2016 | Schoenefeld et al. |
| 9,301,768 | B2 | 4/2016 | Buza et al. |
| 9,301,783 | B2 | 4/2016 | Gerold et al. |
| 9,308,006 | B2 | 4/2016 | Martin et al. |
| 9,308,037 | B2 | 4/2016 | Richter et al. |
| 9,320,609 | B2 | 4/2016 | Schon et al. |
| 9,345,497 | B2 | 5/2016 | Gonzalvez et al. |
| 9,351,738 | B2 | 5/2016 | Aram et al. |
| 9,351,743 | B2 | 5/2016 | Kehres et al. |
| 9,370,380 | B2 | 6/2016 | Riccione |
| 9,375,220 | B2 | 6/2016 | Horan et al. |
| 9,402,636 | B2 | 8/2016 | Collazo |
| 9,402,640 | B2 | 8/2016 | Reynolds et al. |
| 9,408,641 | B2 | 8/2016 | Zhang et al. |
| 9,414,846 | B2 | 8/2016 | Gillman et al. |
| 9,414,847 | B2 | 8/2016 | Kurtz |
| 9,414,877 | B2 | 8/2016 | Helenbolt et al. |
| 9,421,021 | B2 | 8/2016 | Keppler |
| 9,427,240 | B2 | 8/2016 | Von Zabern et al. |
| D765,844 | S | 9/2016 | Dacosta |
| D766,434 | S | 9/2016 | Dacosta |
| D766,437 | S | 9/2016 | Dacosta |
| D766,438 | S | 9/2016 | Dacosta |
| D766,439 | S | 9/2016 | Dacosta |
| 9,433,452 | B2 | 9/2016 | Weiner et al. |
| 9,445,823 | B2 | 9/2016 | Harris et al. |
| 9,452,050 | B2 | 9/2016 | Miles et al. |
| 9,456,902 | B2 | 10/2016 | Hacking et al. |
| 9,463,034 | B2 | 10/2016 | Wong et al. |
| 9,492,182 | B2 * | 11/2016 | Keefer ............... A61B 17/1666 |
| 9,517,145 | B2 | 12/2016 | Meridew et al. |
| 9,522,023 | B2 | 12/2016 | Haddad et al. |
| 9,526,514 | B2 | 12/2016 | Kelley et al. |
| 9,545,276 | B2 | 1/2017 | Buchanan et al. |
| 9,561,041 | B2 | 2/2017 | Snider et al. |
| 9,566,103 | B2 | 2/2017 | Mayer |
| 9,579,106 | B2 | 2/2017 | Lo et al. |
| 9,579,107 | B2 | 2/2017 | Schoenefeld |
| 9,579,112 | B2 | 2/2017 | Catanzarite et al. |
| 9,592,084 | B2 | 3/2017 | Grant |
| 9,603,605 | B2 | 3/2017 | Collazo |
| 9,603,640 | B2 | 3/2017 | Palmer et al. |
| 9,622,820 | B2 | 4/2017 | Baloch et al. |
| 9,629,726 | B2 | 4/2017 | Reiley et al. |
| 9,652,889 | B2 | 5/2017 | Young et al. |
| 9,662,220 | B2 | 5/2017 | Warburton |
| 9,668,746 | B2 | 6/2017 | Lee et al. |
| 9,675,471 | B2 | 6/2017 | Bojarski et al. |
| 9,687,261 | B2 | 6/2017 | Serbousek et al. |
| 9,693,787 | B2 | 7/2017 | Ammann et al. |
| 9,693,878 | B2 | 7/2017 | Kunz et al. |
| 9,700,433 | B2 | 7/2017 | Myers |
| 9,713,484 | B2 | 7/2017 | Sammarco |
| 9,737,311 | B2 | 8/2017 | Lavallee et al. |
| 9,737,367 | B2 | 8/2017 | Steines et al. |
| 9,750,538 | B2 | 9/2017 | Soffiatti et al. |
| 9,785,747 | B2 | 10/2017 | Geebelen |
| 9,788,958 | B2 | 10/2017 | Melamed et al. |
| 9,788,975 | B2 | 10/2017 | Li |
| 9,795,392 | B2 | 10/2017 | Zajac |
| 9,795,394 | B2 | 10/2017 | Bonutti |
| 9,814,474 | B2 | 11/2017 | Montoya et al. |
| 9,820,868 | B2 | 11/2017 | Witt et al. |

(56) References Cited

U.S. PATENT DOCUMENTS

| 9,826,981 B2 | 11/2017 | Schoenefeld et al. |
|---|---|---|
| 9,839,438 B2 | 12/2017 | Eash |
| 9,848,929 B2 | 12/2017 | Dacosta et al. |
| 9,849,019 B2 | 12/2017 | Miller et al. |
| 9,877,754 B2 | 1/2018 | Patel et al. |
| 9,883,954 B1 | 2/2018 | Murphy |
| 9,888,931 B2 | 2/2018 | Bake |
| 9,888,950 B2 | 2/2018 | Perez et al. |
| 9,918,658 B2 | 3/2018 | Mccaulley et al. |
| 9,918,769 B2 | 3/2018 | Provencher et al. |
| 9,925,049 B2 | 3/2018 | Goldstein et al. |
| 9,925,068 B2 | 3/2018 | Bays et al. |
| 9,956,089 B2 | 5/2018 | Kelman et al. |
| 9,968,456 B2 | 5/2018 | Song |
| 9,980,760 B2 | 5/2018 | Dacosta et al. |
| 9,987,092 B2 | 6/2018 | Hladio et al. |
| 9,990,765 B2 | 6/2018 | Ju et al. |
| 9,993,256 B2 | 6/2018 | Lipman et al. |
| 10,002,227 B2 | 6/2018 | Netravali et al. |
| 10,004,516 B2 | 6/2018 | Johannaber |
| 10,010,431 B2 | 7/2018 | Eraly et al. |
| 10,016,177 B2 | 7/2018 | Aram et al. |
| 10,022,170 B2 | 7/2018 | Leemrijse et al. |
| 10,028,756 B2 | 7/2018 | Liu |
| 10,034,753 B2 | 7/2018 | Dressler et al. |
| 10,052,114 B2 | 8/2018 | Keppler et al. |
| 10,055,536 B2 | 8/2018 | Maes et al. |
| 10,058,335 B2 | 8/2018 | Lee et al. |
| 10,089,413 B2 | 10/2018 | Wirx-Speetjens et al. |
| 10,098,761 B2 | 10/2018 | Sherman et al. |
| 10,105,145 B2 | 10/2018 | Lavallee |
| 10,123,807 B2 | 11/2018 | Geebelen |
| 10,130,378 B2 | 11/2018 | Bryan |
| 10,149,722 B2 | 12/2018 | Aram et al. |
| 10,159,480 B2 | 12/2018 | Tuten |
| 10,159,499 B2 | 12/2018 | Dacosta et al. |
| 10,159,512 B2 | 12/2018 | Robinson |
| 10,201,357 B2 | 2/2019 | Aram et al. |
| 10,206,692 B2 | 2/2019 | Sanders |
| 10,217,530 B2 | 2/2019 | Couture et al. |
| 10,219,812 B2 | 3/2019 | Torrie et al. |
| 10,226,292 B2 | 3/2019 | Lundquist et al. |
| 10,231,745 B2 | 3/2019 | Geebelen et al. |
| 10,238,382 B2 | 3/2019 | Terrill et al. |
| 10,251,654 B2 | 4/2019 | Fritzinger |
| 10,251,690 B2 | 4/2019 | Katrana et al. |
| 10,262,084 B2 | 4/2019 | Lavallee et al. |
| 10,265,080 B2 | 4/2019 | Hughes et al. |
| 10,271,886 B2 | 4/2019 | Abiven |
| 10,278,713 B2 | 5/2019 | Richter et al. |
| 10,282,488 B2 | 5/2019 | Eash |
| 10,286,197 B2 | 5/2019 | Pouliot et al. |
| 10,325,065 B2 | 6/2019 | Li et al. |
| 10,327,829 B2 | 6/2019 | Dacosta et al. |
| 10,342,529 B2 | 7/2019 | Fallin et al. |
| 10,350,022 B2 | 7/2019 | Jansen et al. |
| 10,357,261 B2 | 7/2019 | Kugler et al. |
| 10,357,299 B2 | 7/2019 | Weiner et al. |
| 10,363,052 B2 | 7/2019 | Park et al. |
| 10,398,510 B2 | 9/2019 | Goto |
| 10,420,613 B2 | 9/2019 | Azevedo Da Silva et al. |
| 10,456,205 B2 | 10/2019 | Meridew et al. |
| 10,512,470 B1 | 12/2019 | Bays et al. |
| 10,524,808 B1 | 1/2020 | Hissong et al. |
| 10,524,845 B2 | 1/2020 | Orsak et al. |
| 10,537,392 B2 | 1/2020 | Millahn et al. |
| 10,543,100 B2 | 1/2020 | Couture et al. |
| 10,548,667 B2 | 2/2020 | Flett et al. |
| 10,548,668 B2 | 2/2020 | Furrer et al. |
| 10,582,969 B2 | 3/2020 | Couture et al. |
| 10,610,241 B2 | 4/2020 | Wagner et al. |
| 10,631,878 B2 | 4/2020 | Fritzinger |
| 10,631,902 B2 | 4/2020 | Weiner et al. |
| 10,653,432 B2 | 5/2020 | Luttrell et al. |
| 10,653,464 B2 | 5/2020 | Hill et al. |
| 10,653,467 B2 | 5/2020 | Brumfield et al. |
| 10,675,096 B2 | 6/2020 | Utz et al. |
| 10,682,147 B2 | 6/2020 | Grant et al. |
| 10,709,567 B2 | 7/2020 | Welker et al. |
| 10,716,581 B2 | 7/2020 | Fritzinger et al. |
| 10,722,309 B2 | 7/2020 | Gillman |
| 10,722,310 B2 | 7/2020 | Luby |
| 10,779,867 B2 | 9/2020 | Penzimer et al. |
| 10,779,890 B2 | 9/2020 | Weir |
| 10,786,291 B2 | 9/2020 | Weiner et al. |
| 10,792,081 B2 | 10/2020 | Weiner et al. |
| 10,806,469 B2 | 10/2020 | Fiechter et al. |
| 10,849,665 B2 | 12/2020 | Singh et al. |
| 10,849,670 B2 | 12/2020 | Santrock et al. |
| 10,856,891 B2 | 12/2020 | Rhodes et al. |
| 10,856,925 B1 | 12/2020 | Pontell |
| 10,869,722 B2 | 12/2020 | Caldwell et al. |
| 10,874,408 B2 | 12/2020 | Couture |
| 10,881,416 B2 | 1/2021 | Couture et al. |
| 10,881,417 B2 | 1/2021 | Mahfouz |
| 10,888,340 B2 | 1/2021 | Awtrey et al. |
| 10,898,211 B2 | 1/2021 | Fallin et al. |
| 10,905,444 B2 | 2/2021 | Siccardi et al. |
| 10,912,574 B2 | 2/2021 | Kim et al. |
| 10,925,622 B2 | 2/2021 | Kehres et al. |
| 10,939,926 B2 | 3/2021 | Kam et al. |
| 10,939,939 B1 | 3/2021 | Gil et al. |
| 10,973,529 B2 | 4/2021 | Lavallee et al. |
| 11,000,327 B2 | 5/2021 | Schlotterback et al. |
| 11,020,128 B2 | 6/2021 | Guilloux et al. |
| 11,033,333 B2 | 6/2021 | Singh et al. |
| 11,033,336 B2 | 6/2021 | Bohl |
| 11,065,011 B2 | 7/2021 | Bake et al. |
| 11,074,688 B2 | 7/2021 | Chabin et al. |
| 11,090,069 B2 | 8/2021 | Park |
| 11,090,161 B2 | 8/2021 | Hodorek |
| 11,112,770 B2 | 9/2021 | Roh et al. |
| 11,116,518 B2 | 9/2021 | Hafez |
| 11,129,625 B2 | 9/2021 | Song et al. |
| 11,129,678 B2 | 9/2021 | Park |
| 11,154,362 B2 | 10/2021 | Kim et al. |
| 11,158,047 B2 | 10/2021 | Shah |
| 11,160,567 B2 | 11/2021 | Fallin et al. |
| 11,160,568 B1 | 11/2021 | Park |
| 11,166,732 B2 | 11/2021 | Maxson et al. |
| 11,172,945 B1 | 11/2021 | Lian |
| 11,179,165 B2 | 11/2021 | Schoenefeld |
| 11,179,168 B2 | 11/2021 | Dacosta et al. |
| 11,207,134 B2 | 12/2021 | Hafez |
| 11,213,305 B2 | 1/2022 | Iannotti et al. |
| 11,213,406 B2 | 1/2022 | Rodriguez et al. |
| 11,219,526 B2 | 1/2022 | Mahfouz |
| 11,224,448 B2 | 1/2022 | Bailey |
| 11,259,817 B2 | 3/2022 | Fallin et al. |
| 11,284,909 B2 | 3/2022 | Castricini et al. |
| 11,304,705 B2 | 4/2022 | Fallin et al. |
| 11,304,735 B2 | 4/2022 | Sayger et al. |
| 11,324,522 B2 | 5/2022 | Metzger et al. |
| 11,324,607 B2 | 5/2022 | Mauldin et al. |
| 11,331,148 B2 | 5/2022 | Fritzinger |
| 11,331,205 B2 | 5/2022 | Parr |
| 11,344,347 B2 | 5/2022 | Treace et al. |
| 11,389,221 B2 | 7/2022 | Tyber et al. |
| 11,399,849 B2 | 8/2022 | Larche et al. |
| 11,419,726 B2 | 8/2022 | Miller et al. |
| 11,426,184 B2 | 8/2022 | Rivet-Sabourin et al. |
| 11,432,931 B2 | 9/2022 | Lang |
| 11,436,801 B2 | 9/2022 | Haslam et al. |
| 11,439,412 B2 | 9/2022 | Woodard et al. |
| 11,457,980 B2 | 10/2022 | Bonny et al. |
| 11,484,354 B2 | 11/2022 | Singh et al. |
| 11,497,557 B2 | 11/2022 | Haslam et al. |
| 11,508,102 B2 | 11/2022 | Su et al. |
| 11,510,738 B2 | 11/2022 | Stifter et al. |
| 11,532,402 B2 | 12/2022 | Farley et al. |
| 11,557,036 B2 | 1/2023 | Mansi et al. |
| 11,583,298 B2 | 2/2023 | Robichaud et al. |
| 11,596,421 B2 | 3/2023 | Saltzman et al. |
| 11,596,443 B2 | 3/2023 | Treace et al. |

(56) References Cited

U.S. PATENT DOCUMENTS

| | | | |
|---|---|---|---|
| 11,602,386 B2 | 3/2023 | Smith et al. |
| 11,607,250 B2 | 3/2023 | Treace et al. |
| 11,627,954 B2 | 4/2023 | May et al. |
| 11,628,003 B2 | 4/2023 | Nachtrab et al. |
| 11,633,195 B2 | 4/2023 | Dhillon |
| 11,648,019 B2 | 5/2023 | Bays et al. |
| 11,653,938 B2 | 5/2023 | Siegler |
| 11,684,423 B2 | 6/2023 | Jaramaz et al. |
| 11,690,725 B2 | 7/2023 | Gemon et al. |
| 11,717,359 B2 | 8/2023 | Chi |
| 11,741,277 B2 | 8/2023 | Dayal et al. |
| 11,751,892 B2 | 9/2023 | Woodard et al. |
| 11,756,051 B2 | 9/2023 | Indani et al. |
| 11,766,268 B2 | 9/2023 | Iannotti et al. |
| 11,779,467 B2 | 10/2023 | Mimnaugh et al. |
| 11,786,257 B2 | 10/2023 | Dayton et al. |
| 11,793,549 B2 | 10/2023 | Rhodes et al. |
| 11,812,978 B2 | 11/2023 | Trabish et al. |
| 11,819,223 B2 | 11/2023 | Lee |
| 11,819,224 B2 | 11/2023 | Allard et al. |
| 11,849,933 B2 | 12/2023 | Denham et al. |
| 11,849,957 B2 | 12/2023 | Couture et al. |
| 11,849,961 B2 | 12/2023 | Khatibi et al. |
| 11,849,962 B2 | 12/2023 | Singh et al. |
| 11,854,683 B2 | 12/2023 | Casey et al. |
| D1,011,524 S | 1/2024 | Santrock et al. |
| 11,857,206 B2 | 1/2024 | Robichaud et al. |
| 11,864,778 B2 | 1/2024 | Mcginley et al. |
| 11,864,959 B2 | 1/2024 | Basta |
| 11,911,046 B2 | 2/2024 | Carroll et al. |
| 11,925,417 B2 | 3/2024 | Mosnier et al. |
| 11,931,106 B2 | 3/2024 | Perler et al. |
| 11,944,546 B2 | 4/2024 | Puncreobutr et al. |
| 11,950,786 B2 | 4/2024 | Courtis et al. |
| 11,963,687 B2 | 4/2024 | Langhorn et al. |
| 11,963,703 B2 | 4/2024 | Dayton et al. |
| 11,963,729 B2 | 4/2024 | Aljuri et al. |
| 11,980,377 B2 | 5/2024 | Mauldin et al. |
| 12,004,789 B2 * | 6/2024 | McAleer ............ A61B 17/8061 |
| 12,004,814 B2 | 6/2024 | Ryan et al. |
| D1,034,985 S | 7/2024 | Hartson et al. |
| 12,035,929 B2 | 7/2024 | Athwal et al. |
| 12,045,943 B2 | 7/2024 | Chaoui et al. |
| 12,048,600 B2 | 7/2024 | Azernikov et al. |
| 12,050,999 B2 | 7/2024 | Poltaretskyi et al. |
| 12,053,242 B2 | 8/2024 | Landon et al. |
| 12,062,183 B2 | 8/2024 | Chaoui et al. |
| 12,097,129 B2 | 9/2024 | Deransart et al. |
| 12,115,083 B2 | 10/2024 | Mullen et al. |
| 12,121,272 B2 | 10/2024 | Marien et al. |
| 12,396,770 B2 * | 8/2025 | McAleer ............ A61B 17/8866 |
| 2002/0107519 A1 | 8/2002 | Dixon et al. |
| 2003/0236522 A1 | 12/2003 | Long et al. |
| 2004/0010259 A1 | 1/2004 | Keller et al. |
| 2004/0039394 A1 | 2/2004 | Conti et al. |
| 2004/0039396 A1 | 2/2004 | Couture et al. |
| 2004/0097946 A1 | 5/2004 | Dietzel et al. |
| 2004/0138669 A1 | 7/2004 | Horn |
| 2005/0059978 A1 | 3/2005 | Sherry et al. |
| 2005/0080424 A1 | 4/2005 | Cuckler et al. |
| 2005/0267482 A1 | 12/2005 | Hyde |
| 2005/0273112 A1 | 12/2005 | Mcnamara |
| 2006/0129163 A1 | 6/2006 | Mcguire |
| 2006/0206044 A1 | 9/2006 | Simon |
| 2006/0229621 A1 | 10/2006 | Cadmus |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2007/0010818 A1 | 1/2007 | Stone et al. |
| 2007/0123857 A1 | 5/2007 | Deffenbaugh et al. |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0009863 A1 | 1/2008 | Bond et al. |
| 2008/0039850 A1 | 2/2008 | Rowley et al. |
| 2008/0091197 A1 | 4/2008 | Coughlin |
| 2008/0140081 A1 | 6/2008 | Heavener et al. |
| 2008/0161815 A1 | 7/2008 | Schoenefeld et al. |
| 2008/0172054 A1 | 7/2008 | Claypool et al. |
| 2008/0288004 A1 | 11/2008 | Schendel |
| 2009/0036931 A1 | 2/2009 | Pech et al. |
| 2009/0089081 A1 | 4/2009 | Haddad |
| 2009/0093849 A1 | 4/2009 | Grabowski |
| 2009/0105767 A1 | 4/2009 | Reiley |
| 2009/0198244 A1 | 8/2009 | Leibel |
| 2009/0216089 A1 | 8/2009 | Davidson |
| 2009/0222047 A1 | 9/2009 | Graham |
| 2009/0254092 A1 | 10/2009 | Albiol Llorach |
| 2009/0254126 A1 | 10/2009 | Orbay et al. |
| 2009/0265012 A1 | 10/2009 | Engh et al. |
| 2009/0287309 A1 | 11/2009 | Walch et al. |
| 2010/0069910 A1 | 3/2010 | Hasselman |
| 2010/0130981 A1 | 5/2010 | Richards |
| 2010/0168799 A1 | 7/2010 | Schumer |
| 2010/0185202 A1 | 7/2010 | Lester et al. |
| 2010/0217270 A1 | 8/2010 | Polinski et al. |
| 2010/0256687 A1 | 10/2010 | Neufeld et al. |
| 2010/0274253 A1 | 10/2010 | Ure |
| 2010/0318088 A1 | 12/2010 | Warne et al. |
| 2011/0009865 A1 | 1/2011 | Orfaly |
| 2012/0065689 A1 | 3/2012 | Prasad et al. |
| 2012/0116203 A1 | 5/2012 | Vancraen et al. |
| 2012/0123420 A1 | 5/2012 | Honiball |
| 2012/0130434 A1 | 5/2012 | Stemniski |
| 2012/0150242 A1 | 6/2012 | Mannion |
| 2012/0191199 A1 | 7/2012 | Raemisch |
| 2012/0234329 A1 | 9/2012 | Vancraen et al. |
| 2012/0253350 A1 | 10/2012 | Anthony et al. |
| 2012/0265301 A1 | 10/2012 | Demers et al. |
| 2012/0277745 A1 | 11/2012 | Lizee |
| 2013/0211410 A1 | 8/2013 | Landes et al. |
| 2013/0236874 A1 | 9/2013 | Iannotti et al. |
| 2013/0237989 A1 | 9/2013 | Bonutti |
| 2013/0274778 A1 | 10/2013 | Mercier et al. |
| 2013/0289570 A1 | 10/2013 | Chao |
| 2013/0292870 A1 | 11/2013 | Roger |
| 2014/0005672 A1 | 1/2014 | Edwards et al. |
| 2014/0039501 A1 | 2/2014 | Schickendantz et al. |
| 2014/0074099 A1 | 3/2014 | Vigneron et al. |
| 2014/0094861 A1 | 4/2014 | Fallin |
| 2014/0163568 A1 | 6/2014 | Wong et al. |
| 2014/0257402 A1 | 9/2014 | Barsoum |
| 2014/0259629 A1 | 9/2014 | Dion et al. |
| 2014/0263674 A1 | 9/2014 | Cerveny |
| 2014/0343555 A1 | 11/2014 | Russi et al. |
| 2014/0371866 A1 | 12/2014 | Chao et al. |
| 2014/0371897 A1 | 12/2014 | Lin et al. |
| 2015/0032215 A1 | 1/2015 | Slamin et al. |
| 2015/0045903 A1 | 2/2015 | Neal |
| 2015/0066094 A1 | 3/2015 | Anderson et al. |
| 2015/0081029 A1 | 3/2015 | Bojarski et al. |
| 2015/0088142 A1 | 3/2015 | Gibson |
| 2015/0093283 A1 | 4/2015 | Miller et al. |
| 2015/0112348 A1 | 4/2015 | Schoenefeld et al. |
| 2015/0142000 A1 | 5/2015 | Seedhom et al. |
| 2015/0182342 A1 | 7/2015 | Hafez |
| 2015/0227679 A1 | 8/2015 | Kamer et al. |
| 2015/0230843 A1 | 8/2015 | Palmer et al. |
| 2015/0305752 A1 | 10/2015 | Eash |
| 2015/0342616 A1 | 12/2015 | Fryman |
| 2015/0351780 A1 | 12/2015 | Anderson et al. |
| 2015/0351916 A1 | 12/2015 | Kosarek et al. |
| 2016/0015426 A1 | 1/2016 | Dayton |
| 2016/0038161 A1 | 2/2016 | Gibson |
| 2016/0100773 A1 | 4/2016 | Ching et al. |
| 2016/0100847 A1 | 4/2016 | Maxson |
| 2016/0151165 A1 | 6/2016 | Fallin et al. |
| 2016/0175089 A1 | 6/2016 | Fallin et al. |
| 2016/0192951 A1 | 7/2016 | Gelaude et al. |
| 2016/0199198 A1 | 7/2016 | Dietz et al. |
| 2016/0256176 A9 | 9/2016 | Lowery et al. |
| 2016/0270829 A1 | 9/2016 | Duggal et al. |
| 2016/0270855 A1 | 9/2016 | Kunz et al. |
| 2016/0287395 A1 | 10/2016 | Khalili et al. |

(56) References Cited

U.S. PATENT DOCUMENTS

| | | | |
|---|---|---|---|
| 2016/0338715 A1 | 11/2016 | Bojarski et al. | |
| 2016/0354128 A1* | 12/2016 | Jeng | A61B 17/1728 |
| 2016/0367270 A1 | 12/2016 | Garlock et al. | |
| 2017/0014169 A1 | 1/2017 | Dean et al. | |
| 2017/0020537 A1 | 1/2017 | Tuten | |
| 2017/0027593 A1 | 2/2017 | Bojarski et al. | |
| 2017/0079803 A1 | 3/2017 | Lang | |
| 2017/0143511 A1 | 5/2017 | Cachia | |
| 2017/0209189 A9 | 7/2017 | Hatch et al. | |
| 2017/0231645 A1 | 8/2017 | Metzger et al. | |
| 2017/0245906 A1 | 8/2017 | Kugler et al. | |
| 2017/0245935 A1 | 8/2017 | Kugler et al. | |
| 2017/0249440 A1 | 8/2017 | Lang et al. | |
| 2017/0281353 A1 | 10/2017 | Al Hares et al. | |
| 2017/0360578 A1 | 12/2017 | Shin et al. | |
| 2018/0021145 A1 | 1/2018 | Seavey et al. | |
| 2018/0028325 A1 | 2/2018 | Bojarski et al. | |
| 2018/0049758 A1 | 2/2018 | Amis et al. | |
| 2018/0116804 A1 | 5/2018 | Hafez et al. | |
| 2018/0221071 A1 | 8/2018 | Isch | |
| 2018/0235706 A1 | 8/2018 | Asseln et al. | |
| 2018/0242987 A1 | 8/2018 | Lintula et al. | |
| 2018/0289423 A1 | 10/2018 | Singh et al. | |
| 2018/0317986 A1 | 11/2018 | Jackman et al. | |
| 2018/0344326 A1 | 12/2018 | Chan et al. | |
| 2019/0000629 A1 | 1/2019 | Winslow | |
| 2019/0008532 A1 | 1/2019 | Fitz et al. | |
| 2019/0117239 A1 | 4/2019 | Verma | |
| 2019/0175277 A1 | 6/2019 | Chav et al. | |
| 2019/0175351 A1 | 6/2019 | Bojarski et al. | |
| 2019/0307495 A1 | 10/2019 | Geldwert | |
| 2019/0365543 A1 | 12/2019 | Slamin et al. | |
| 2020/0008813 A1 | 1/2020 | Bonny et al. | |
| 2020/0046425 A1 | 2/2020 | Lopes et al. | |
| 2020/0100909 A1 | 4/2020 | Lang et al. | |
| 2020/0155323 A1 | 5/2020 | Lang et al. | |
| 2020/0163721 A1 | 5/2020 | Aghazadeh | |
| 2020/0214719 A1 | 7/2020 | Fraone et al. | |
| 2020/0337714 A1 | 10/2020 | Hafez et al. | |
| 2020/0356073 A1 | 11/2020 | Tokushima | |
| 2020/0405322 A1 | 12/2020 | Brailovski et al. | |
| 2021/0007760 A1 | 1/2021 | Reisin | |
| 2021/0022781 A1 | 1/2021 | Dacosta et al. | |
| 2021/0030429 A1 | 2/2021 | Rose et al. | |
| 2021/0045756 A1 | 2/2021 | Zakhary et al. | |
| 2021/0059691 A1 | 3/2021 | Zille | |
| 2021/0059837 A1 | 3/2021 | Rhodes | |
| 2021/0077120 A1 | 3/2021 | Hatch et al. | |
| 2021/0077192 A1 | 3/2021 | Perler et al. | |
| 2021/0085338 A1 | 3/2021 | Dacosta et al. | |
| 2021/0090248 A1 | 3/2021 | Choi et al. | |
| 2021/0106427 A1 | 4/2021 | Mahfouz | |
| 2021/0113223 A1 | 4/2021 | Schaumann et al. | |
| 2021/0121297 A1 | 4/2021 | Cavanagh et al. | |
| 2021/0137537 A1 | 5/2021 | Zille | |
| 2021/0161543 A1 | 6/2021 | Mcauliffe et al. | |
| 2021/0186704 A1 | 6/2021 | Fitz et al. | |
| 2021/0192759 A1 | 6/2021 | Lang | |
| 2021/0196290 A1 | 7/2021 | Iannotti et al. | |
| 2021/0212705 A1 | 7/2021 | Reynolds et al. | |
| 2021/0219989 A1 | 7/2021 | Chao | |
| 2021/0244477 A1 | 8/2021 | Singh et al. | |
| 2021/0256171 A1 | 8/2021 | Hosseini | |
| 2021/0275196 A1 | 9/2021 | Wodajo | |
| 2021/0282790 A1 | 9/2021 | Sellman et al. | |
| 2021/0282823 A1 | 9/2021 | Day et al. | |
| 2021/0290250 A1 | 9/2021 | Denham et al. | |
| 2021/0298766 A1 | 9/2021 | Loring et al. | |
| 2021/0307833 A1 | 10/2021 | Farley et al. | |
| 2021/0307834 A1 | 10/2021 | Gillman et al. | |
| 2021/0346038 A1 | 11/2021 | Fiechter et al. | |
| 2021/0378752 A1 | 12/2021 | Paul et al. | |
| 2021/0386437 A1 | 12/2021 | Dacosta et al. | |
| 2021/0391058 A1 | 12/2021 | Kostrzewski et al. | |
| 2021/0393304 A1 | 12/2021 | Geldwert | |
| 2022/0039965 A1 | 2/2022 | Casey et al. | |
| 2022/0087822 A1 | 3/2022 | Radermacher et al. | |
| 2022/0096157 A1 | 3/2022 | Pollock et al. | |
| 2022/0133484 A1 | 5/2022 | Lang | |
| 2022/0160405 A1 | 5/2022 | Casey et al. | |
| 2022/0167998 A1 | 6/2022 | Siccardi et al. | |
| 2022/0192685 A1 | 6/2022 | Gazonnet et al. | |
| 2022/0202495 A1 | 6/2022 | Pack | |
| 2022/0211387 A1 | 7/2022 | Perler et al. | |
| 2022/0233203 A1 | 7/2022 | Rhodes et al. | |
| 2022/0249106 A1 | 8/2022 | Akallal et al. | |
| 2022/0249143 A1 | 8/2022 | Hollis et al. | |
| 2022/0270762 A1 | 8/2022 | Crawford et al. | |
| 2022/0273450 A1 | 9/2022 | Steines et al. | |
| 2022/0296285 A1 | 9/2022 | Besque et al. | |
| 2022/0313284 A1 | 10/2022 | Korman | |
| 2022/0323086 A1 | 10/2022 | Stemniski et al. | |
| 2022/0338934 A1 | 10/2022 | Perler et al. | |
| 2022/0346806 A1 | 11/2022 | Leemrijse et al. | |
| 2023/0013727 A1 | 1/2023 | Korman et al. | |
| 2023/0014384 A1 | 1/2023 | Cordonnier et al. | |
| 2023/0077222 A1 | 3/2023 | Awtrey | |
| 2023/0157705 A1 | 5/2023 | Reynolds | |
| 2023/0190306 A1 | 6/2023 | Kowalczyk et al. | |
| 2023/0281842 A1 | 9/2023 | Ribeiro et al. | |
| 2023/0310013 A1 | 10/2023 | Perler et al. | |
| 2023/0310051 A1 | 10/2023 | Hafez et al. | |
| 2023/0363773 A1 | 11/2023 | Perler et al. | |
| 2023/0371966 A1 | 11/2023 | Spitler | |
| 2023/0389937 A1 | 12/2023 | Penner et al. | |
| 2023/0404673 A1 | 12/2023 | Spitler et al. | |
| 2024/0005504 A1 | 1/2024 | Ribeiro et al. | |

FOREIGN PATENT DOCUMENTS

| | | | |
|---|---|---|---|
| AU | 2015203808 | B2 | 9/2017 |
| AU | 2020220169 | A1 | 9/2020 |
| AU | 2021286392 | A1 | 1/2022 |
| CA | 2491824 | A1 | 9/2005 |
| CA | 2608464 | C | 7/2012 |
| CA | 2854997 | A1 | 5/2013 |
| CA | 2713309 | C | 7/2013 |
| CH | 695846 | A5 | 9/2006 |
| CN | 2930668 | Y | 8/2007 |
| CN | 201558162 | U | 8/2010 |
| CN | 201572172 | U | 9/2010 |
| CN | 201586060 | U | 9/2010 |
| CN | 201912210 | U | 8/2011 |
| CN | 101237835 | B | 11/2012 |
| CN | 202801773 | U | 3/2013 |
| CN | 103462675 | A | 12/2013 |
| CN | 103505276 | A | 1/2014 |
| CN | 203458450 | U | 3/2014 |
| CN | 102860860 | B | 5/2014 |
| CN | 203576647 | U | 5/2014 |
| CN | 104490460 | A | 4/2015 |
| CN | 104510523 | A | 4/2015 |
| CN | 104523327 | A | 4/2015 |
| CN | 104546102 | A | 4/2015 |
| CN | 204379413 | U | 6/2015 |
| CN | 204410951 | U | 6/2015 |
| CN | 204428143 | U | 7/2015 |
| CN | 204428144 | U | 7/2015 |
| CN | 204428145 | U | 7/2015 |
| CN | 204446081 | U | 7/2015 |
| CN | 106236185 | A | 12/2016 |
| CN | 205924106 | U | 2/2017 |
| CN | 206151532 | U | 5/2017 |
| CN | 105105853 | B | 7/2017 |
| CN | 108030532 | A | 5/2018 |
| CN | 207721902 | U | 8/2018 |
| CN | 112914724 | B | 2/2022 |
| CN | 117297772 | B | 2/2024 |
| CN | 117322951 | B | 2/2024 |
| CN | 109223098 | B | 5/2024 |
| DE | 2910627 | A1 | 9/1980 |
| DE | 202006010241 | U1 | 3/2007 |
| DE | 102007053058 | B3 | 4/2009 |
| EP | 685206 | B1 | 9/2000 |

(56) References Cited

FOREIGN PATENT DOCUMENTS

| | | | |
|---|---|---|---|
| EP | 1508316 | B1 | 5/2007 |
| EP | 1897509 | B1 | 7/2009 |
| EP | 2124832 | B1 | 8/2012 |
| EP | 2750617 | A1 | 7/2014 |
| EP | 2856951 | A1 | 4/2015 |
| EP | 2624764 | B1 | 12/2015 |
| EP | 3000443 | A3 | 7/2016 |
| EP | 2083758 | B1 | 11/2017 |
| EP | 2632349 | B1 | 3/2018 |
| EP | 3013256 | B1 | 11/2018 |
| EP | 3171795 | B1 | 11/2018 |
| EP | 3672535 | A1 | 7/2020 |
| EP | 2558010 | B1 | 5/2021 |
| EP | 3948895 | A1 | 2/2022 |
| EP | 3740141 | B1 | 4/2022 |
| EP | 2844162 | B1 | 7/2022 |
| FR | 2362616 | A1 | 3/1978 |
| FR | 2764183 | A1 | 12/1998 |
| FR | 2953120 | B1 | 1/2012 |
| FR | 3030221 | A1 | 6/2016 |
| FR | 3117328 | B1 | 3/2023 |
| GB | 2154143 | A | 9/1985 |
| GB | 2154144 | A | 9/1985 |
| GB | 2334214 | B | 1/2003 |
| GB | 2589960 | A | 6/2021 |
| JP | S635739 | A | 1/1988 |
| JP | 2004174265 | A | 6/2004 |
| JP | 2006158972 | A | 6/2006 |
| JP | 4134243 | B2 | 8/2008 |
| JP | 2011092405 | A | 5/2011 |
| JP | 4796943 | B2 | 10/2011 |
| JP | 2014511207 | A | 5/2014 |
| JP | 2014521384 | A | 8/2014 |
| KR | 100904142 | B1 | 6/2009 |
| KR | 1020160090006 | A | 7/2016 |
| KR | 1020180118476 | A | 10/2018 |
| KR | 101952368 | B1 | 2/2019 |
| MD | 756 | B1 | 7/1997 |
| RU | 2098036 | C1 | 12/1997 |
| RU | 2195892 | C2 | 1/2003 |
| RU | 2320287 | C1 | 3/2008 |
| RU | 2321366 | C2 | 4/2008 |
| RU | 2321369 | C1 | 4/2008 |
| RU | 2346663 | C2 | 2/2009 |
| RU | 2412662 | C1 | 2/2011 |
| RU | 182499 | U1 | 8/2018 |
| RU | 2789960 | C2 | 2/2023 |
| SU | 1333328 | A2 | 8/1987 |
| WO | 0166022 | A1 | 9/2001 |
| WO | 03075775 | A1 | 9/2003 |
| WO | 2004089227 | A2 | 10/2004 |
| WO | 2008051064 | A1 | 5/2008 |
| WO | 2009001083 | A1 | 12/2008 |
| WO | 2009029798 | A1 | 3/2009 |
| WO | 2009032101 | A2 | 3/2009 |
| WO | 2010099231 | A3 | 11/2010 |
| WO | 2011005327 | A1 | 1/2011 |
| WO | 2011037885 | A1 | 3/2011 |
| WO | 2012024317 | A2 | 2/2012 |
| WO | 2012029008 | A1 | 3/2012 |
| WO | 2012176077 | A1 | 12/2012 |
| WO | 2013026786 | A1 | 2/2013 |
| WO | 2013041618 | A1 | 3/2013 |
| WO | 2013134387 | A1 | 9/2013 |
| WO | 2013156816 | A2 | 10/2013 |
| WO | 2014020561 | A1 | 2/2014 |
| WO | 2014020562 | A1 | 2/2014 |
| WO | 2014022055 | A1 | 2/2014 |
| WO | 2014085882 | A1 | 6/2014 |
| WO | 2014147099 | A1 | 9/2014 |
| WO | 2014152219 | A2 | 9/2014 |
| WO | 2014200017 | A1 | 12/2014 |
| WO | 2015003284 | A2 | 1/2015 |
| WO | 2015094409 | A1 | 6/2015 |
| WO | 2015127515 | A2 | 9/2015 |
| WO | 2016012731 | A1 | 1/2016 |
| WO | 2016102025 | A1 | 6/2016 |
| WO | 2017031000 | A1 | 2/2017 |
| WO | 2017122076 | A2 | 7/2017 |
| WO | 2017151833 | A1 | 9/2017 |
| WO | 2018167369 | A1 | 9/2018 |
| WO | 2019060780 | A2 | 3/2019 |
| WO | 2019052622 | A4 | 5/2019 |
| WO | 2019180747 | A1 | 9/2019 |
| WO | 2020060349 | A1 | 3/2020 |
| WO | 2021054518 | A1 | 3/2021 |
| WO | 2021091071 | A1 | 5/2021 |
| WO | 2021118733 | A1 | 6/2021 |
| WO | 2021127625 | A1 | 6/2021 |
| WO | 2021240290 | A1 | 12/2021 |
| WO | 2022155208 | A1 | 7/2022 |
| WO | 2022182312 | A1 | 9/2022 |
| WO | 2023096516 | A1 | 6/2023 |
| WO | 2024025840 | A1 | 2/2024 |

OTHER PUBLICATIONS

Dayton et al., "Biwinged Excision for Round Pedal Lesions," The Journal of Foot and Ankle Surgery, vol. 35, No. 3, 1996, pp. 244-249.

Coughlin "Proximal Metatarsal Osteotomy and Distal Soft Tissue Reconstruction for Hallux Valgus in Juveniles" Orthopaedics and Traumatology, vol. 7, Published: Jun. 1999, pp. 133-143.

Dayton et al., "Medial Incision Approach to the First Metatarsophalangeal Joint," The Journal of Foot and Ankle Surgery, vol. 40, No. 6, Nov./Dec. 2001, pp. 414-417.

Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.

Dayton et al., "Use of the Z Osteotomy for Tailor Bunionectomy," The Journal of Foot and Ankle Surgery, vol. 42, No. 3, May/Jun. 2003, pp. 167-169.

Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.

Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.

Dayton et al., "The Extended Knee Hemilithotomy Position for Gastrocnemius Recession," The Journal of Foot and Ankle Surgery, vol. 49, 2010, pp. 214-216.

Dayton et al., "A User-Friendly Method of Pin Site Management for External Fixators," Foot and Ankle Specialist, Sep. 16, 2011, 4 pages.

Dayton et al., "Hallux Varus as Complication of Foot Compartment Syndrome," The Journal of Foot and Ankle Surgery, vol. 50, 2011, pp. 504-506.

Dayton et al., "Measurement of Mid-Calcaneal Length on Plain Radiographs: Reliability of a New Method," Foot and Ankle Specialist, vol. 4, No. 5, Oct. 2011, pp. 280-283.

Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.

Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.

Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.

Dayton et al., "Principles of Management of Growth Plate Fractures in the Foot and Ankle," Clinics in Podiatric Medicine and Surgery, Pediatric Foot Deformities, Oct. 2013, 17 pages.

(56)         References Cited

OTHER PUBLICATIONS

Crawford et al. "Metatarsus Adductus: Radiographic and Pathomechanical Analysis" Chapter 5, https://www.podiatryinstitute.com/pdfs/Update_2014/2014_05.pdf, Published 2014, pp. 25-30.
Dayton et al., "Clarification of the Anatomic Definition of the Bunion Deformity," The Journal of Foot and Ankle Surgery, vol. 53, 2014, pp. 160-163.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton, "Tarsal-Metatarsal Joint: Primary & Revision Arthrodesis" Disclosure: Speaker for Orthofix and Biomet, Apr. 2014, pp. 38.
Dalat et al. "Does arthrodesis of the first metatarsophalangeal joint correct the intermetatarsal M1M2 angle? Analysis of a continuous series of 208 arthrodeses fixed with plates" Orthopaedics & Traumatology: Surgery & Research 101, 2015, pp. 709-714.
Dayton et al., "A new triplanar paradigm for bunion management," Lower Extremity Review, Apr. 2015, 9 pages.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "Complications of Metatarsal Suture Techniques for Bunion Correction: A Systematic Review of the Literature," The Journal of Foot and Ankle Surgery, Article in Press, 2015, 3 pages.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
Dayton et al. "Comparison of Tibial Sesamoid Position on Anteroposterior and Axial Radiographs Before and After Triplane Tarsal Metatarsal Joint Arthrodesis" The Journal of Foot & Ankle Surgery 56, 2017, pp. 1041-1046.
Dayton "Evidence-Based Bunion Surgery: A Critical Examination of Current and Emerging Concepts and Techniques" Springer International Publishing, 2017, pp. 254.
Dayton et al. "Biomechanical Characteristics of Biplane Multiplanar Tension-Side Fixation for Lapidus Fusion" The Journal of Foot & Ankle Surgery, 2018, pp. 1-5.
Dayton et al. "Progression of Healing on Serial Radiographs Following First Ray Arthrodesis in the Foot Using a Biplanar Plating Technique Without Compression" The Journal of Foot & Ankle Surgery, 2018, pp. 1-7.

Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.
Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.
Conti et al., "Effect of the Modified Lapidus Procedure for Hallux Valgus on Foot Width," Foot & Ankle International, Feb. 1, 2020, published online: Oct. 30, 2019, 6 pages.
Conti et al., "Effect of the Modified Lapidus Procedure on Pronation of the First Ray in Hallux Valgus," Foot & Ankle International, Feb. 1, 2020, published online: Oct. 16, 2019, 8 pages.
Dayton et al. "Comparison of Radiographic Measurements Before and After Triplane Tarsometatarsal Arthrodesis for Hallux Valgus" The Journal of Foot & Ankle Surgery 59, 2020, pp. 291-297.
Curran et al. "Functional Capabilities After First Metatarsal Phalangeal Joint Arthrodesis Using a Locking Plate and Compression Screw Construct" The Journal of Foot & Ankle Surgery, 2021, pp. 1-5.
De Carvalho, et al. "Automated Three-dimensional distance and coverage mapping of hallux valgus: a case-control study" Journal of Foot and Ankle, 2022; 16(1), pp. 5.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot and Ankle Surgery, vol. 52, No. 3, May/Jun. 2013, pp. 348-354.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
De Heer et al., "Procedure-Specific Hardware Removal After Evans Osteotomy" Journal of the American Podiatric Medical Association, vol. 110, No. 2, Mar./Apr. 2020, pp. 1-7.
DeCarbo et al., "Locking Plates: Do They Prevent Complications?," Podiatry Today, Apr. 2014, 7 pages.
DeCarbo et al., "Resurfacing Interpositional Arthroplasty for Degenerative Joint Disease of the First Metatarsalphalangeal Joint," Podiatry Management, Jan. 2013, pp. 137-142.
DeCarbo et al., "The Weil Osteotomy: A Refresher," Techniques in Foot and Ankle Surgery, vol. 13, No. 4, Dec. 2014, pp. 191-198.
Defendant Fusion Orthopedics LLC's Invalidity Contentions, No. CV-22-00490-PHX-SRB, US District Court for the District of Arizona, Aug. 27, 2022, 41 pages.
Didomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
Didomenico et al., "Lapidus Bunionectomy: First Metatarsal-Cuneiform Arthrodesis," McGlamrys Comprehensive Textbook of Foot and Ankle Surgery, Fourth Edition, vol. 1, Chapter 31, 2013, 24 pages.
Dinapoli et al., "Metatarsal Osteotomy for the Correction of Metatarsus Adductus," Reconstructive Surgery of the Foot and Leg, 1989, pp. 242-250.
Disior, "Bonelogic Foot & Ankle Module", https://www.disior.com/foot--ankle.html, Downloaded Jun. 1, 2022, pp. 6.
Dobbe et al. "Patient-Tailored Plate for Bone Fixation and Accurate 3D Positioning in Corrective Osteotomy," Medical and Biological Engineering and Computing, vol. 51, No. 1-2, Feb. 2013, pp. 19-27, (Abstract Only).

(56) References Cited

OTHER PUBLICATIONS

Doty et al., "Hallux valgus and hypermobility of the first ray: facts and fiction," International Orthopaedics, vol. 37, 2013, pp. 1655-1660.

Dubovik et al., "Talonavicular Joint Arthrodesis and Medial Displacement Calcaneal Osteotomy for Treatment of Patients With Planovalgus Deformity" Traumatology and Orthopedics of Russia, vol. 18, No. 3, Sep. 30, 2012, pp. 83-88.

Easley et al., "Current Concepts Review: Hallux Valgus Part I: Pathomechanics, Clinical Assessment, and Nonoperative Management," Foot and Ankle International, vol. 28, No. 5, May 2007, pp. 654-659.

Easley et al., "Current Concepts Review: Hallux Valgus Part II: Operative Treatment," Foot and Ankle International, vol. 28, No. 6, Jun. 2007, pp. 748-758.

Easley et al., "What is the Best Treatment for Hallux Valgus?," Evidence-Based Orthopaedics—The Best Answers to Clinical Questions, Chapter 73, 2009, pp. 479-491.

EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.

Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.

Eustace et al., "Hallux valgus, first metatarsal pronation and collapse of the medial longitudinal arch—a radiological correlation," Skeletal Radiology, vol. 23, 1994, pp. 191-194.

Fallin et al., US Provisional Application Entitled Indexed Tri-Planar Osteotomy Guide and Method, U.S. Appl. No. 62/118,378, filed Feb. 19, 2015, 62 pages.

Fazal et al., "First metatarsophalangeal joint arthrodesis with two orthogonal two hole plates," Acta Orthopaedica et Traumatologica Turcica, vol. 52, 2018, pp. 363-366.

Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.

Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.

Ferrari et al., "A Radiographic Study of the Relationship Between Metatarsus Adductus and Hallux Valgus," The Journal of Foot and Ankle Surgery, vol. 42, No. 1, 2003, pp. 9-14.

Ferreyra et al., "Can we correct first metatarsal rotation and sesamoid position with the 3D Lapidus procedure?," Foot and Ankle Surgery, vol. 28, No. 3, Apr. 2022, pp. 313-318.

Fibretuff, "3D Printing, CNC Machining, Molding and Extruding Biocompatible material's with "bone like" Qualities for 3D Printing" https://fibretuff.us, Downloaded Feb. 24, 2023, pp. 22.

Fishco, "A Straightforward Guide to the Lapidus Bunionectomy, " Podiatry Today, Retrieved online from <https://www.hmpglobal-learningnetwork.com/site/podiatry/blogged/straightforward-guide-lapidus-bunionectomy>, dated Sep. 6, 2013, 5 pages.

Fishco, "Making the Lapidus Easy," The Podiatry Institute, Update 2014, Chapter 14, 2014, pp. 91-93.

Flavin et al., "Arthrodesis of the First Metatarsophalangeal Joint Using a Dorsal Titanium Contoured Plate," Foot & Ankle International, vol. 25, No. 11, Nov. 2004, pp. 783-787.

Fleming et al., "Results of Modified Lapidus Arthrodesis Procedure Using Medial Eminence as an Interpositional Autograft," The Journal of Foot & Ankle Surgery, vol. 50, 2011, pp. 272-275.

Fraissler et al., "Treatment of hallux valgus deformity," Efort Open Reviews, vol. 1, Aug. 2016, pp. 295-302.

Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.

Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, pp. 437-440.

Garthwait, "Accu-Cut System Facilitates Enhanced Precision," Podiatry Today, vol. 18, No. 6, Jun. 2005, 6 pages.

Gerard et al., "The Modified Lapidus Procedure," Orthopedics, vol. 31, No. 3, Mar. 2008, 7 pages.

Ghali et al., "The Management of Metatarsus Adductus et Supinatus," The Journal of Bone and Joint Surgery, vol. 66-B, No. 3, May 1984, pp. 376-380.

Giannoudis et al., "Hallux Valgus Correction," Practical Procedures in Elective Orthopaedic Surgery, Pelvis and Lower Extremity, Chapter 38, 2012, 22 pages.

Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.

Gotte, "Entwicklung eines Assistenzrobotersystems fr die Knieendoprothetik," Forschungsberichte, Technische Universitat Munchen, 165, 2002, 11 pages, including partial English Translation.

Gould et al., "A Prospective Evaluation of First Metatarsophalangeal Fusion Using an Innovative Dorsal Compression Plating System," The Journal of Foot & Ankle Surgery, vol. 60, 2021, pp. 891-896.

Gregg et al., "Plantar plate repair and Weil osteotomy for metatarsophalangeal joint instability," Foot and Ankle Surgery, vol. 13, 2007, pp. 116-121.

Greiner, "The Jargon of Pedal Movements," Foot & Ankle International, vol. 28, No. 1, Jan. 2007, pp. 109-125.

Grondal et al., "A Guide Plate for Accurate Positioning of First Metatarsophalangeal Joint during Fusion," Operative Orthopdie Und Traumatologie, vol. 16, No. 2, 2004, pp. 167-178 (Abstract Only).

Groves, "Functional Position Joint Sectioning: Pre-Load Method for Lapidus Arthrodesis," The Podiatry Institute, Update 2015, Chapter 6, 2015, pp. 23-29.

Groves, "Operative Report," St. Tammany Parish Hospital, Date of Procedure, Mar. 26, 2014, 2 pages.

Gutteck et al., "Comparative study of Lapidus bunionectomy using different osteosynthesis methods," Foot and Ankle Surgery, vol. 19, 2013, pp. 218-221.

Gutteck et al., "Is it feasible to rely on intraoperative X ray in correcting hallux valgus?," Archives of Orthopaedic and Trauma Surgery, vol. 133, 2013, pp. 753-755.

Hardy et al., "Observations on Hallux Valgus," The Journal of Bone and Joint Surgery, vol. 33B, No. 3, Aug. 1951,pp. 376-391.

Hatch et al., "Analysis of Shortening and Elevation of the First Ray With Instrumented Triplane First Tarsometatarsal Arthrodesis," Foot & Ankle Orthopaedics, vol. 5, No. 4, 2020, pp. 1-8.

Hatch et al., "Triplane Hallux Abducto Valgus Classification," The Journal of Foot & Ankle Surgery, vol. 57, No. 5, Sep./Oct. 2018, published online: May 18, 2018, pp. 972-981.

Hetherington et al., "Evaluation of surgical experience and the use of an osteotomy guide on the apical angle of an Austin osteotomy," The Foot, vol. 18, 2008, pp. 159-164.

Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.

Ho et al., "Hallux rigidus," Efort Open Reviews, vol. 2, Jan. 2017, pp. 13-20.

Hunt et al., "Locked Versus Nonlocked Plate Fixation for Hallux MTP Arthrodesis," Foot and Ankle International, vol. 32, No. 7, Jul. 2011, pp. 704-709.

Integra, "Integra Large Qwix Positioning and Fixation Screw, Surgical Technique," 2012, 16 pages.

Jackson III et al., "The Surgical Learning Curve for Modified Lapidus Procedure for Hallux Valgus Deformity," Foot & Ankle Specialist, Jul. 2021, 5 pages.

(56) References Cited

OTHER PUBLICATIONS

Jeuken et al., "Long-term Follow-up of a Randomized Controlled Trial Comparing Scarf to Chevron Osteotomy in Hallux Valgus Correction," Foot & Ankle International, vol. 37, No. 7, 2016, pp. 687-695.

Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.

Kim et al., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.

Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.

Klos et al., "Modified Lapidus arthrodesis with plantar plate and compression screw for treatment of hallux valgus with hypermobility of the first ray: A preliminary report," Foot and Ankle Surgery, vol. 19, 2013, pp. 239-244.

KLS Martin Group, "Individual Patient Solutions IPS Implants" , https://www.klsmartin.com/en-na/products/individual-patient-solutions/ips-implants/, Downloaded: Jun. 1, 2022, pp. 8.

Kurup et al., "Midfoot arthritis—current concepts review," Journal of Clinical Orthopaedics and Trauma, vol. 11, 2020, pp. 399-405.

La Reaux et al., "Metatarsus adductus and hallux abducto valgus: their correlation," The Journal of Foot Surgery, vol. 26, No. 4, Jul. 1987, pp. 304-308, Abstract Only.

Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.

Lapidus, "The Author's Bunion Operation From 1931 to 1959," Clinical Orthopaedics, vol. 16, 1960, pp. 119-135.

Latif et al., "First metatarsophalangeal fusion using joint specific dorsal plate with interfragmentary screw augmentation: Clinical and radiological outcomes," Foot and Ankle Surgery, vol. 25, 2019, pp. 132-136.

Le et al., "Tarsometatarsal Arthrodesis," Operative Techniques in Foot and Ankle Surgery, Section II, Chapter 40, 2011, pp. 281-285.

Lee et al., "Technique Tip: Lateral Soft-Tissue Release for Correction of Hallux Valgus Through a Medial Incision Using a Dorsal Flap Over the First Metatarsal," Foot & Ankle International, vol. 28, No. 8, Aug. 2007, pp. 949-951.

Li et al., "Evolution of Thinking of the Lapidus Procedure and Fixation," Foot and Ankle Clinics, vol. 25, No. 1, Mar. 2020, published online: Dec. 16, 2019, pp. 18 pages.

Lieske et al., "Implantation einer Sprunggelenktotalendo-prothese vom Typ Salto 2," Operative Orthopdie und Traumatologie, vol. 26, No. 4, 2014, pp. 401-413, including English Abstract on p. 403.

Little, "Joint Arthrodesis for Hallux Valgus," Clinics in Podiatric Medicine and Surgery, Hallux Abducto Valgus Surgery, updated Apr. 19, 2014, retrieved online from < https://www.footankleinstitute.com/first-metatarsophalangeal-joint-arthrodesis-in-the-treatment-of-hallux-valgus>, 7 pages.

Lopez et al., "Metatarsalgia: Assessment Algorithm and Decision Making," Foot and Ankle Clinics, vol. 24, No. 4, Dec. 2019, published online: Sep. 25, 2019, pp. 561-569.

MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.

Machacek Jr. et al., "Salvage of a Failed Keller Resection Arthroplasty," The Journal of Bone and Joint Surgery, vol. 86A, No. 6, Jun. 2004, pp. 1131-1138.

Magin, "Computernavigierter Gelenkersatz am Knie mit dem Orthopilot," Operative Orthopdie und Traumatologie, vol. 22, No. 1, 2010, pp. 63-80, including English Abstract on p. 64.

Magin, "Die belastungsstabile Lapidus-Arthrodese bei Hallux-valgus-Deformitt mittels IVP-Plattenfixateur (V-TEK-System)," Opera-tive Orthopdie und Traumatologie, vol. 26, No. 2, 2014, pp. 184-195, including English Abstract on p. 186.

Marshall et al., "The identification and appraisal of assessment tools used to evaluate metatarsus adductus: a systematic review of their measurement properties," Journal of Foot and Ankle Research, vol. 11, No. 25, 2018, 10 pages.

McAleer et al., "A systematic approach to the surgical correction of combined hallux valgus and metatarsus adductus deformities," The Journal of Foot & Ankle Surgery, May 21, 2021, 6 pages.

McAleer et al., "Radiographic Outcomes Following Triplanar Correction of Combined Hallux Valgus and Metatarsus Adductus Deformities," ACFAS Scientific Conference, Poster, Feb. 2022, 1 page.

McCabe et al., "Anatomical reconstruction of first ray instability hallux valgus with a medial anatomical TMTJ1 plate," Foot and Ankle Surgery, vol. 27, No. 8, Dec. 2021, pp. 869-873.

Mehtar et al., "Outcomes of bilateral simultaneous hallux MTPJ fusion," Foot and Ankle Surgery, vol. 27, 2021, pp. 213-216.

Michelangelo Bunion System, Surgical Technique ", Instratek Incorporated, publication date unknown, 4 pages."

Miller et al., "Variable Angle Locking Compression Plate as Alternative Fixation for Jones Fractures: A Case Series," Kansas Journal of Medicine, vol. 12, No. 2, May 2019, pp. 28-32.

Mini Joint Distractor, Arthrex, retrieved Dec. 19, 2014, from the Internet: <http://www.arthrex.com/foot-ankle/mini-joint-distractor/products>, 2 pages.

MiniRail System, Small Bone Innovations, Surgical Technique, 2010, 24 pages.

Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.

Mizuno et al., "Detorsion Osteotomy of the First Metatarsal Bone in Hallux Valgus," Japanese Orthopaedic Association, Tokyo, 1956; 30:813-819.

Modular Rail System: External Fixator, Smith & Nephew, Surgical Technique, 2013, 44 pages.

Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).

Moore et al., "Effect of Ankle Flexion Angle on Axial Alignment of Total Ankle Replacement," Foot and Ankle International, vol. 31, No. 12, Dec. 2010, pp. 1093-1098, (Abstract Only).

Mortier et al., "Axial Rotation of the First Metatarsal Head in a Normal Population and Hallux Valgus Patients," Orthopaedics and Traumatology: Surgery and Research, vol. 98, 2012, pp. 677-683.

Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.

Musculoskeletal Key "Arthrodesis of the Tarsmetatarsal Joint" https://musculoskeletalkey.com/arthrodesis-of-the-tarsometatarsal-joint/, Retrieved May 8, 2020, pp. 11.

Myerson, "Cuneiform-Metatarsal Arthrodesis," The Foot and Ankle, Chapter 9, 1997, pp. 107-117.

Nagy et al., "The AO Ulnar Shortening Osteotomy System Indications and Surgical Technique," Journal of Wrist Surgery, vol. 3, No. 2, 2014, pp. 91-97.

NexFix from Nexa Orthopedics, MetaFix I from Merete Medical, Inc. and the BioPro Lower Extremities from BioPro, found in Foot & Ankle International Journal, vol. 28, No. 1, Jan. 2007, 4 pages.

Nix et al., "Prevalence of hallux valgus in the general population: a systematic review and meta-analysis," Journal of Foot and Ankle Research, vol. 3, No. 21, 2010, 9 pages.

Novastep, "Pecaplasty Percutaneous Bunion Correction" Downloaded Jun. 29, 2022, pp. 24.

Novastep, "Pecaplasty Percutaneous Bunion Correction- Brochure Pecaplasty Targeting Guide" Downloaded Dec. 15, 2021, pp. 4.

Odenbring et al., "A guide instrument for high tibial osteotomy," Acta Orthopaedica Scandinavica, vol. 60, No. 4, 1989, pp. 449-451.

(56) References Cited

OTHER PUBLICATIONS

Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.

Instratek, "Michelangelo Bunion System, Surgical Technique", Instratek Incorporated, publication date unknown, 4 pages.

"Foot and Ankle Instrument Set," Smith & Nephew, 2013, 2 pages.

"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.

"Reconstructive Surgery of the Foot & Ankle," The Podiatry Institute, Update 2015, Conference Program, May 2015, 28 pages.

"Speed Continuous Active Compression Implant," BioMedical Enterprises, Inc., A120-029 Rev. 3, 2013, 4 pages.

"Visionaire: Patient Matched Cutting Blocks Surgical Procedure," Smith & Nephew, Inc., 2009, 2 pages.

Acumed "Acumed Osteotomy System" with partial English Translation, 2014, pp. 19.

Additive Orthopaedics, "The First and Only FDA Approved Patient Specific Talus Spacer", https://totaltalusreplacement.com, Downloaded: Mar. 4, 2022, pp. 11.

Aiyer et al. "Prevalence of Metatarsus Adductus in Patients Undergoing Hallux Valgus Surgery" Foot & Ankle International 2014, vol. 35(12), pp. 1292-1297.

Albano et al. "Biomechanical Study of Transcortical or Transtrabecular Bone Fixation of Patellar Tendon Graft With Bioabsorbable Pins in ACL Reconstruction in Sheep" Rev Bras Ortop. 2012, 47(1), pp. 43-49.

Alvine et al. "Peg and Dowel Fusion of the Proximal Interphalangeal Joint" Foot & Ankle vol. 1, No. 2, 1980 American Orthopaedic Foot Society, pp. 5.

Arthrex "Chevron Osteotomy" https://www.arthrex.com/foot-ankle/chevron-osteotomy, Retrieved Nov. 30, 2022, pp. 7.

Arthrex "Comprehensive Foot System" https://www.arthrex.com/resources/animation/8U3iaPvY6kO8bwFAwZF50Q/comprehensive-foot-system?referringTeam=foot_and_ankle, Published Aug. 27, 2013, pp. 3.

Arthrex, "Distal Tibia Allograft Workstation for Glenoid Bone Loss, Surgical Technique" Arthrex.com, 2018, pp. 8.

Baravarian, "Why the Lapidus Procedure is Ideal for Bunions" Podiatry Today, https://www.hmpgloballearningnetwork.com/site/podiatry/article/5542, May 2006 pp. 8.

Bauer et al. "Offset-V Osteotomy of the First Metatarsal Shaft in Hallux Abducto Valgus" Chapter 29, McGlamry's Comprehensive Textbook of Foot and Ankle Surgery, Fourth Edition, 2013, pp. 26.

Bednarz et al. "Modified Lapidus Procedure for the Treatment of Hypermobile Hallux Valgus" Foot & Ankle, American Orthopaedic Foot & Ankle Society, 2000, pp. 6.

Bennett et al. "Intraosseous Sliding Plate Fixation Used in Double Osteotomy Bunionectomy" Foot & Ankle International, 2019, vol. 40(1), pp. 85-88.

Biopro "Accu-Cut Osteotomy Guide System Accurate and consistent hallux valgus correction" Document Dates Sep. 16, 2019, pp. 2.

Boffeli et al. "Can We Abandon Saw Wedge Resection in Lapidus Fusion? A Comparative Study of Joint Preparation Techniques Regarding Correction of Deformity, Union Rate, and Preservation of First Ray Length" The Journal of Foot & Ankle Surgery, 58, 2019, pp. 1118-1124.

Bouaicha et al. "Fixation of Maximal Shift Scarf Osteotomy with Inside-Out Plating: Technique Tip" Foot & Ankle International, vol. 32, No. 5, May 2011, pp. 567-569.

Buda et al. "Effect of Fixation Type and Bone Graft on Tarsometatarsal Fusion" Foot & Ankle International 2018, vol. 39(12), pp. 1394-1402.

Carr et al. "Correctional Osteotomy for Metatarsus Primus Varus and Hallux Valgus*" The Journal of Bone and Joint Surgery, vol. 50-A, No. 7, Oct. 1968, pp. 1353-1367.

Catanese et al. "Measuring Sesamoid Position in Hallux Valgus When Is the Sesamoid Axial View Necessary?" Foot & Ankle Specialist, Downloaded Aug. 15, 2016, pp. 1-3.

Chesser et al. "New Advances With The Tarsometatarsal" Podiatry Today, vol. 30, Issue 10, Oct. 2017, pp. 28-36.

Chomej et al. "Lateralising DMMO (MIS) for simultaneous correction of a pes adductus during surgical treatment of a hallux valgus" Journal Pre-proof, The Foot, Accepted Jul. 16, 2020, pp. 33.

Cichero et al. "Different fixation constructs and the risk of non-union following first metatarsophalangeal joint arthrodesis" Foot and Ankle Surgery, 27, 2021, Accepted Oct. 15, 2020, pp. 789-792.

Coetzee et al., "Revision Hallux Valgus Correction," Operative Techniques in Foot and Ankle Surgery, Section I, Chapter 15, 2011, pp. 84-96.THROUGH. /A.R./.

Collan et al., "The biomechanics of the first metatarsal bone in hallux valgus: A preliminary study utilizing a weight bearing extremity CT," Foot and Ankle Surgery, vol. 19, 2013, pp. 155-161.

"Futura Forefoot Implant Arthroplasty Products," Tornier, Inc., 2008, 14 pages.

"Hat-Trick Lesser Toe Repair System, Foot and Ankle Technique Guide, Metatarsal Shortening Osteotomy Surgical Technique," Smith & Nephew, 2014, 16 pages.

"Hat-Trick Lesser Toe Repair System," Smith & Nephew, Brochure, Aug. 2014, 12 pages.

"Hoffmann II Compact External Fixation System", Stryker, Brochure, Literature No. 5075-1-500, 2006, 12 pages.

"Hoffmann II Micro Lengthener", Stryker, Operative Technique, Literature No. 5075-2-002, 2008, 12 pages.

"Hoffmann Small System External Fixator Orthopedic Instruments," Stryker, retrieved Dec. 19, 2014, from the Internet: < http://www.alibaba.com/product-detail/Stryker-Hoffmann-Small-System-External-Fixator_1438850129.html>, 3 pages.

Patient to Patient Precision, Accu-Cut, Osteotomy Guide System, BioPro, Foot & Ankle International Journal, vol. 23, No. 8, Aug. 2002, 2 pages.

Blomer "Problems and complications of knee endoprostheses from a manufacturer's point of view" Orthopade 200, 29, pp. 688-696, English Abstract.

"Prophecy Inbone Preoperative Navigation Guides", Wright Medical Technology, Inc., Nov. 2013, 6 pages.

"Rayhack Ulnar Shortening Generation II Low-Profile Locking System Surgical Technique," Wright Medical Technology, Inc., Dec. 2013, 20 pages.

Smith & Nephew scores a Hat-Trick with its entry into the high-growth hammer toe repair market, Smith & Nephew, Jul. 31, 2014, 2 pages.

"Lag Screw Target Bow," Stryker Leibinger GmbH & Co. KG, Germany 2004, 8 pages.

Anderson et al., "Uncemented STAR Total Ankle Protheses" Journal of Bone Joint Surgery America, Sep. 2004, Abstract of Article, pp. 6.

Coetzee et al., "The Lapidus Procedure: A Prospective Cohort Outcome Study," Foot & Ankle International, vol. 25, No. 8, Aug. 2004, pp. 526-531.

Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.

Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.

Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.

Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.

(56) References Cited

OTHER PUBLICATIONS

Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.

Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.

Claim Chart for U.S. Pat. No. 8,282,645 to Lawrence et al., entitled "Metatarsal Bone Implant Cutting Guide, " issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.

Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.

Tricot et al., "3D-corrective osteotomy using surgical guides for posttraumatic distal humeral deformity," Acta Orthopaedica Belgica, vol. 78, No. 4, 2012, pp. 538-542.

Vaida et al., "Effect on Foot Width With Triplanar Tarsometatarsal Arthrodesis for Hallux Valgus," Foot & Ankle Orthopaedics, vol. 5, No. 3, 2020, pp. 1-5.

Nyska, Synergy 3D MED, "Anatomical Model: Calcaneus" , 2022, pp. 3.

Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.

Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.

Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.

Otsuki et al., "Developing a novel custom cutting guide for curved per-acetabular osteotomy," International Orthopaedics (SICOT), vol. 37, 2013, pp. 1033-1038.

Park et al., "Comparative analysis of clinical outcomes of fixed-angle versus variable-angle locking compression plate for the treatment of Lisfranc injuries," Foot and Ankle Surgery, vol. 26, 2020, pp. 338-342.

Patel et al., "Modified Lapidus Arthrodesis: Rate of Nonunion in 227 Cases," The Journal of Foot & Ankle Surgery, vol. 43, No. 1, Jan./Feb. 2004, pp. 37-42.

Pentikainen et al., "Preoperative Radiological Factors Correlated to Long-Term Recurrence of Hallux Valgus Following Distal Chevron Osteotomy," Foot & Ankle International, vol. 35, No. 12, 2014, pp. 1262-1267.

Perler, "Cuboid Suspension in Charcot Reconstruction. Using 3D Imaging for Planning, Printing and Execution for Complex Deformity Correction" Downloaded Apr. 2021, pp. 4.

Peters et al., "Flexor Hallucis Longus Tendon Laceration as a Complication of Total Ankle Arthroplasty," Foot & Ankle International, vol. 34, No. 1, 2013, pp. 148-149.

Ray et al., "Hallux Valgus," Foot & Ankle Orthopaedics, vol. 4, No. 2, 2019, pp. 1-12.

Ray et al., "Multicenter Early Radiographic Outcomes of Triplanar Tarsometatarsal Arthrodesis With Early Weightbearing," Foot & Ankle International, vol. 40, No. 8, Aug. 1, 2019, published online: May 5, 2019, 7 pages.

Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.

Rx-Fix Mini Rail External Fixator, Wright Medical Technology, Brochure, Aug. 15, 2014, 2 pages.

Saltzman et al., "Prospective Controlled Trial of STAR Total Ankle Replacement Versus Ankle Fusion: Initial Results," Foot & Ankle International, vol. 30, No. 7, Jul. 2009, pp. 579-596.

Sammarco, "Surgical Strategies: Mau Osteotomy for Correction of Moderate and Severe Hallux Valgus Deformity," Foot & Ankle International, vol. 28, No. 7, Jul. 2007, pp. 857-864.

Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.

Santrock et al., "Hallux Valgus Deformity and Treatment: A Three-Dimensional Approach: Lapiplasty," Foot & Ankle Clinics, vol. 23, No. 2, 2018, pp. 281-295.

Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).

Schon et al., "Cuneiform-Metatarsal Arthrodesis for Hallux Valgus," The Foot and Ankle, Second Edition, Chapter 8, 2002, pp. 99-117.

Scranton Jr. et al., "Anatomic Variations in the First Ray: Part I. Anatomic Aspects Related to Bunion Surgery," Clinical Orthopaedics and Related Research, vol. 151, Sep. 1980, pp. 244-255.

Shima et al., "Operative Treatment for Hallux Valgus With Moderate to Severe Metatarsus Adductus," Foot & Ankle International, vol. 40, No. 6, 2019, pp. 641-647.

Shurnas et al., "Proximal Metatarsal Opening Wedge Osteotomy," Operative Techniques in Foot and Ankle Surgery, Section I, Chapter 13, 2011, pp. 73-78.

Siddiqui et al. "Fixation of Metatarsal Fracture With Bone Plate in a Dromedary Heifer," Open Veterinary Journal, vol. 3, No. 1, 2013, pp. 17-20.

Sidekick Stealth Rearfoot Fixator, Wright Medical Technology, Surgical Technique, Dec. 2, 2013, 20 pages.

Simons et al., "Short-Term Clinical Outcome of Hemiarthroplasty Versus Arthrodesis for End-Stage Hallux Rigidus," The Journal of Foot & Ankle Surgery, vol. 54, 2015, pp. 848-851.

Simpson et al., "Computer-Assisted Distraction Ostegogenesis by Ilizarov's Method," International Journal of Medical Robots and Computer Assisted Surgery, vol. 4, No. 4, Dec. 2008, pp. 310-320, (Abstract Only).

Small Bone External Fixation System, Acumed, Surgical Technique, Effective date Sep. 2014, 8 pages.

Smith et al., "Intraoperative Multiplanar Alignment System to Guide Triplanar Correction of Hallux Valgus Deformity," Techniques in Foot & Ankle Surgery, 2017, 8 pages.

Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.

Smith et al., "Understanding Frontal Plane Correction in Hallux Valgus Repair," Clinics in Podiatric Medicine and Surgery, vol. 35, 2018, pp. 27-36.

Sokoloff, "Lapidus Procedure," Textbook of Bunion Surgery, Chapter 15, 1981, pp. 277-287.

Stableloc External Fixation System, Acumed, Product Overview, Effective date Sep. 2015, 4 pages.

Stahl et al., "Derotation Of Post-Traumatic Femoral Deformities by Closed Intramedullary Sawing," Injury, vol. 37, No. 2, Feb. 2006, pp. 145-151, (Abstract Only).

Stamatis et al., "Mini Locking Plate as Medial Buttress for Oblique Osteotomy for Hallux Valgus," Foot & Ankle International, vol. 31, No. 10, Oct. 2010, pp. 920-922.

Stryker, "PROstep Minimally Invasive Surgery" https://www.stryker.com/us/en/foot-and-ankle/products/prostep.html, Downloaded Jun. 23, 2023, pp. 10.

Synergy 3D MED, "Anatomical Model: Calcaneus" Downloaded Mar. 2, 2023, pp. 2.

Synopsys, "Medical Image Segmentation with Machine Learning— Simpleware Automated Solution Modules" , https://www.synopsys.com/simpleware/software/auto-segmenter-modules.html#simpleware-as-ortho, 2022, pp. 12.

(56) References Cited

OTHER PUBLICATIONS

Talbot et al., "Assessing Sesamoid Subluxation: How Good is the AP Radiograph?," Foot and Ankle International, vol. 19, No. 8, Aug. 1998, pp. 547-554.

TempFix Spanning the Ankle Joint Half Pin and Transfixing Pin Techniques, Biomet Orthopedics, Surgical Technique, 2012, 16 pages.

Tornier Technology, "Tornier Blueprint 3D Planning + PSI" , https://www.wrightemedia.com/ProductFiles/Files/PDFs/CAW-8609_EN_HR_LE.pdf, Feb. 2017, pp. 12.

Total Ankle Institute, "Prophecy: Preoperative Navigation Guides" , https://www.totalankleinstitute.com/infinity-products/prophecy-preoperative-navigation-guides/, 2019, pp. 6.

Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.

Treace "'FastGrafter Autograft Harvesting System'" Downloaded from https://www.lapiplasty.com/surgeons/other-products/fastgrafter/, Dec. 4, 2024, pp. 8.

Treace Medical Concepts, "Adductoplasty Midfoot Correction System", https://www.lapiplasty.com/surgeons/other-products/adductoplasty-system/, Downloaded May 2, 2022, pp. 9.

Use for BME Speed Nitinol Staple Fixation for the Lapidus Procedure, "date unknown, 1 page."

Virzi et al. "Comprehensive Review of 3D Segmentation Software Tools for MRI Usable for Pelvic Surgery Planning", Journal of Digital Imaging (2020) 33, pp. 99-110.

Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.

Wendl et al., "Navigation in der Knieendoprothetik," OP-Journal, vol. 17, 2002, pp. 22-27, including English Abstract.

Whipple et al., "Zimmer Herbert Whipple Bone Screw System: Surgical Techniques for Fixation of Scaphoid and Other Small Bone Fractures," Zimmer, 2003, 59 pages.

Weber et al., "A Simple System for Navigation of Bone Alignment Osteotomies of the Tibia," International Congress Series, vol. 1268, Jan. 2004, pp. 608-613, (Abstract Only).

Wukich et al., "Hypermobility of the First Tarsometatarsal Joint," Foot and Ankle Clinics, vol. 10, No. 1, Mar. 2005, pp. 157-166.

Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.

Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.

Vitek, "Neue Techniken in der Fuchirurgie Das V-tek-System," ABW Wissenschaftsverlag GmbH, 2009, 11 pages, including English Abstract.

Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).

Weil et al., "Anatomic Plantar Plate Repair Using the Weil Metatarsal Osteotomy Approach," Foot & Ankle Specialist, vol. 4, No. 3, 2011, pp. 145-150.

Wienke et al., "Bone Stimulation for Nonunions: What the Evidence Reveals," Podiatry Today, vol. 24, No. 9, Sep. 2011, pp. 52-57.

Williams et al., "Metatarsus adductus: Development of a non-surgical treatment pathway," Journal of Paediatrics and Child Health, vol. 49, 2013, pp. E428-433.

Yasuda et al., "Proximal Supination Osteotomy of the First Metatarsal for Hallux Valgus," Foot and Ankle International, vol. 36, No. 6, Jun. 2015, pp. 696-704.

Walker et al., "The Role of First Ray Insufficiency in the Development of Metatarsalgia," Foot and Ankle Clinics, vol. 24, No. 4, Dec. 2019, published online: Sep. 5, 2019, pp. 641-648.

Weigelt et al., "Risk Factors for Nonunion After First Metatarsophalangeal Joint Arthrodesis With a Dorsal Locking Plate and Compression Screw Construct: Correction of Hallux Valgus Is Key," The Journal of Foot & Ankle Surgery, vol. 60, No. 6, Nov./Dec. 2021, pp. 1179-1183.

Wright Medical, "How Blueprint Works—from CT to 3D [CAW-9389]", https://www.wrightmeded.com/videos/how-blueprint-works-from-ct-to-3d-caw-9389, video time mark 32 seconds to 48 seconds, Dated May 26, 2022.

International Searching Authority, "International Search Report and Written Opinion", From Application No. PCT/US2023/025766, Mailed Sep. 20, 2023, pp. 9.

Nysak, M. , "Anatomical Model: Calcaneus", NYSKA, Synergy 3D Med, Anatomical Model: Calcaneus, last accessed Mar. 17, 2022, https://synergy3dmed. com/ 2022., 2022.

Perler, Adam , "Cuboid Suspension in Charcot Reconstruction", Perler, Adam, "Cuboid Suspension in Charcot Reconstruction" , Posted to website www.adamperler.com, Apr. 2021.

* cited by examiner

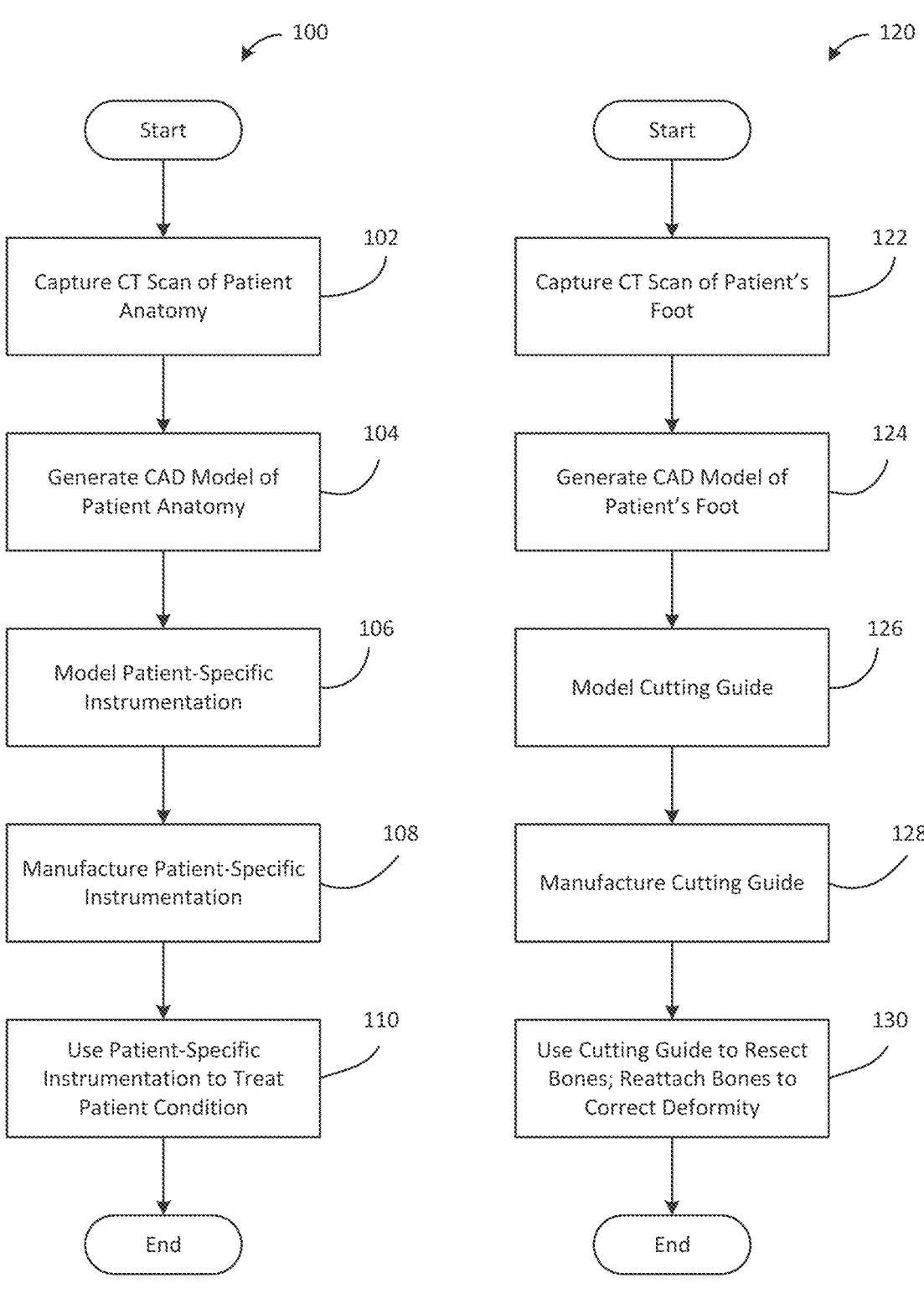
FIG. 1A          FIG. 1B

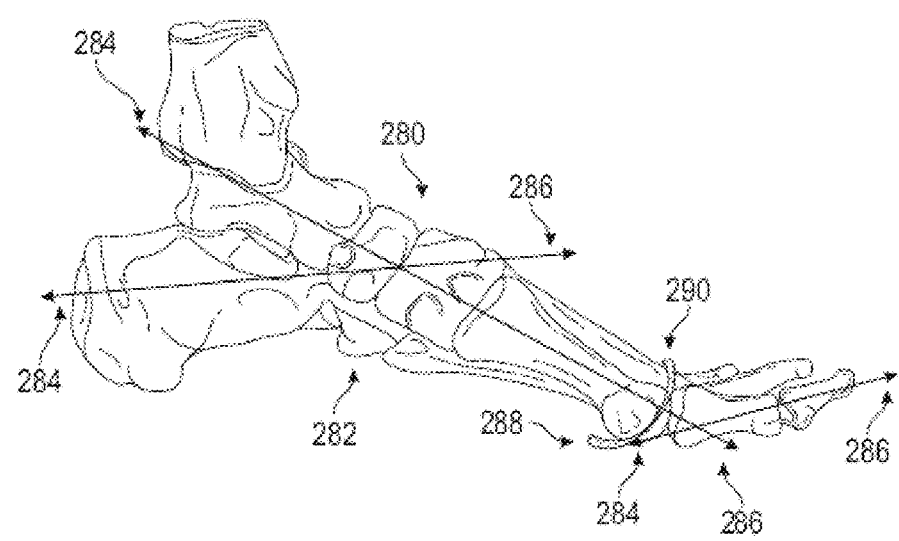
FIG. 2C
(PRIOR ART)
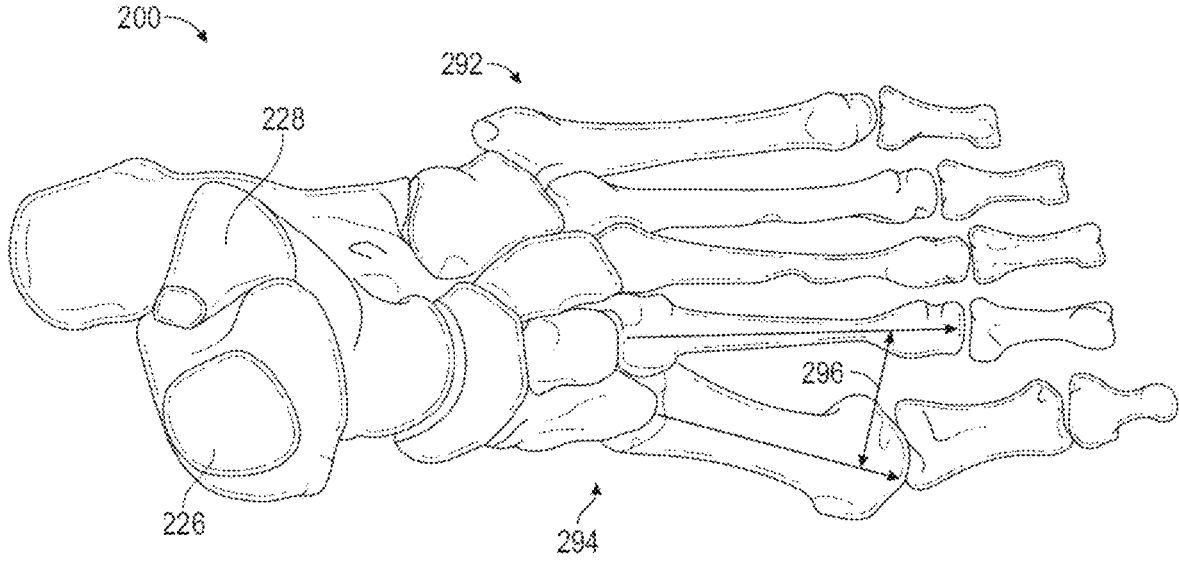
FIG. 2D
(PRIOR ART)

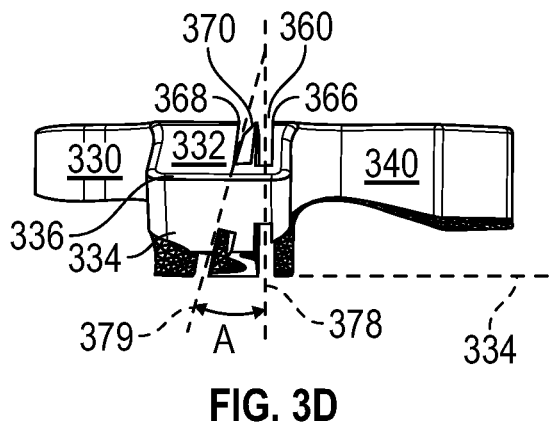
FIG. 3D
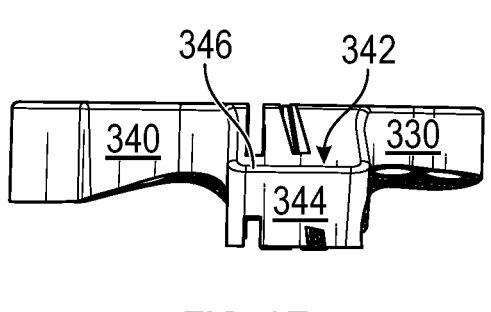
FIG. 3E
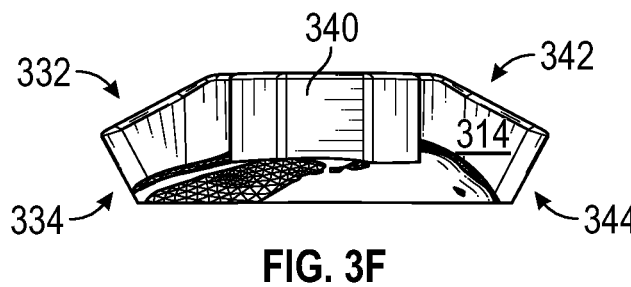
FIG. 3F
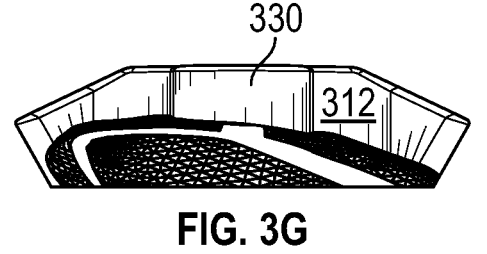
FIG. 3G
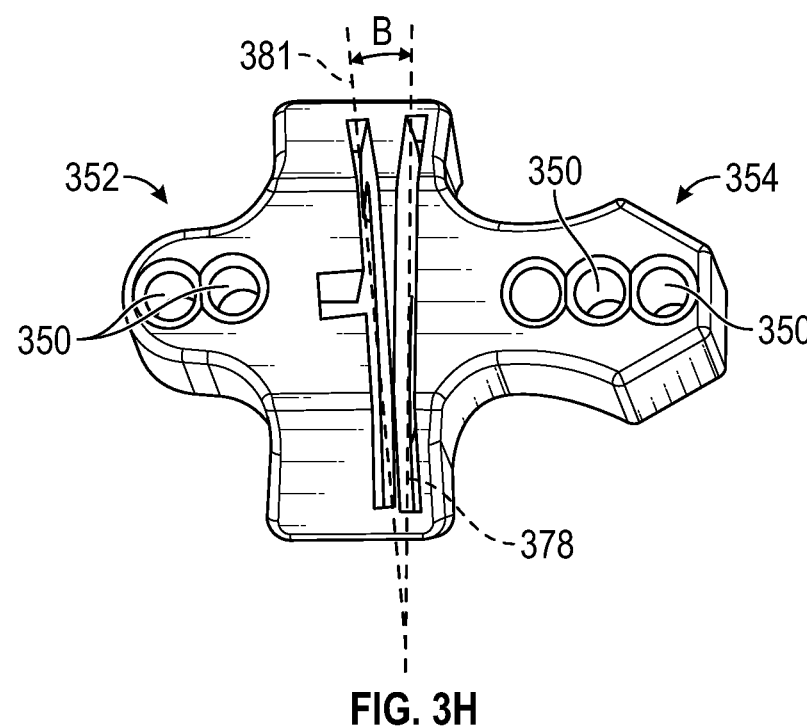
FIG. 3H

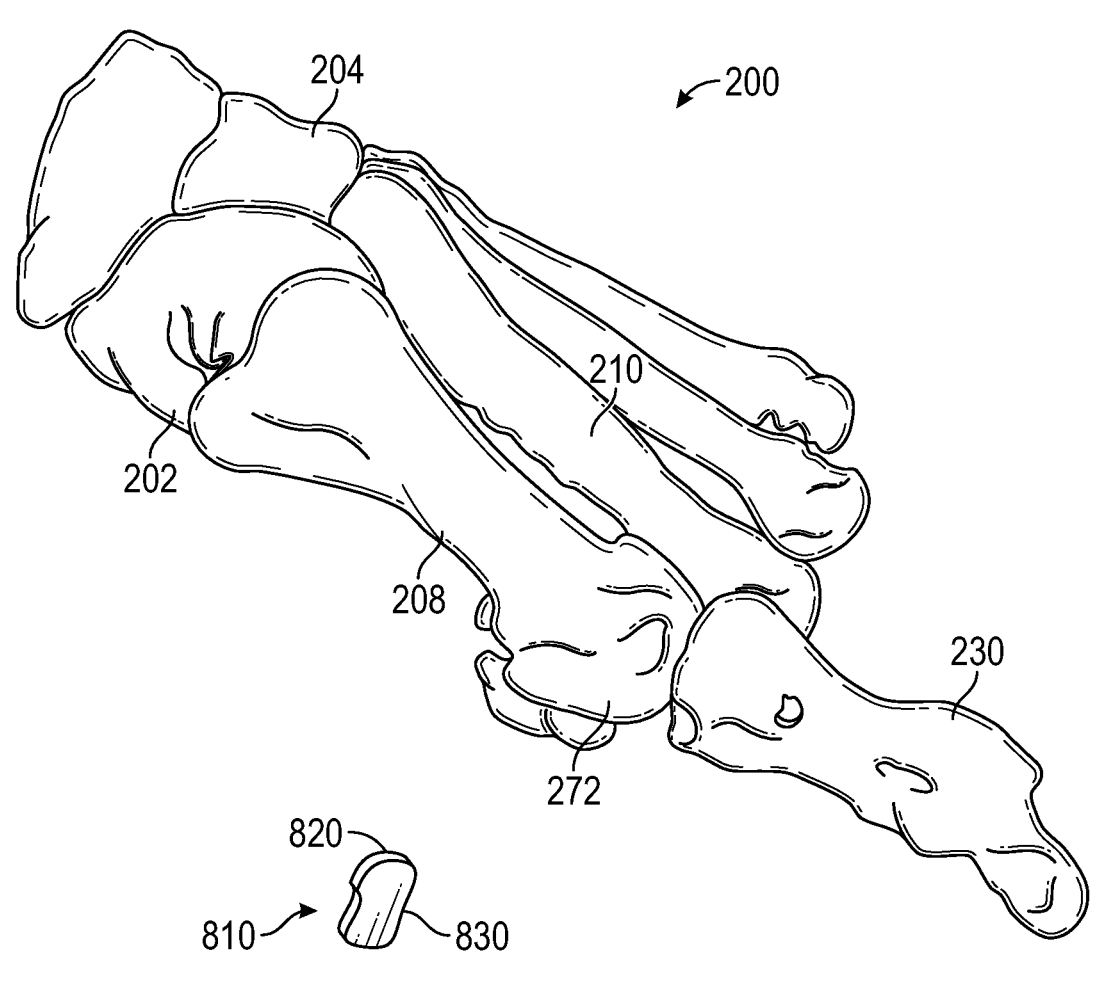
FIG. 8A
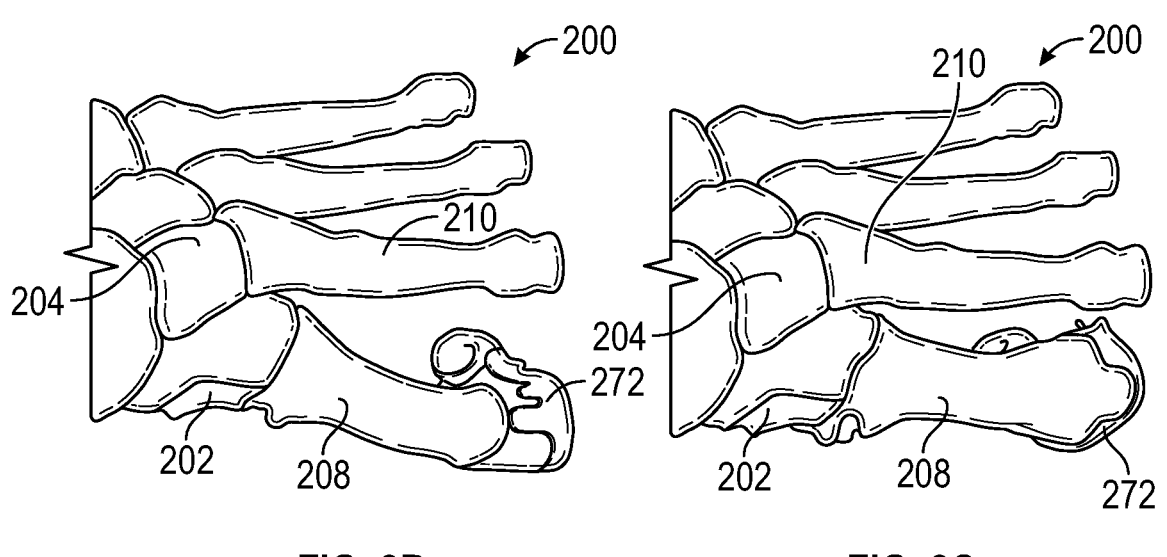
FIG. 8B                              FIG. 8C

1200

1204

Bone Model

1202

1210

Determine Anatomic Data

1220

Determine Deformity

1230

Provide Preliminary Cutting Guide Model

1240

Register Preliminary Cutting Guide Model to Bone Model

1250

Design Patient Specific Cutting Guide Model

1260

Manufacture Patient Specific Cutting Guide

1206

Patient Specific Cutting Guide

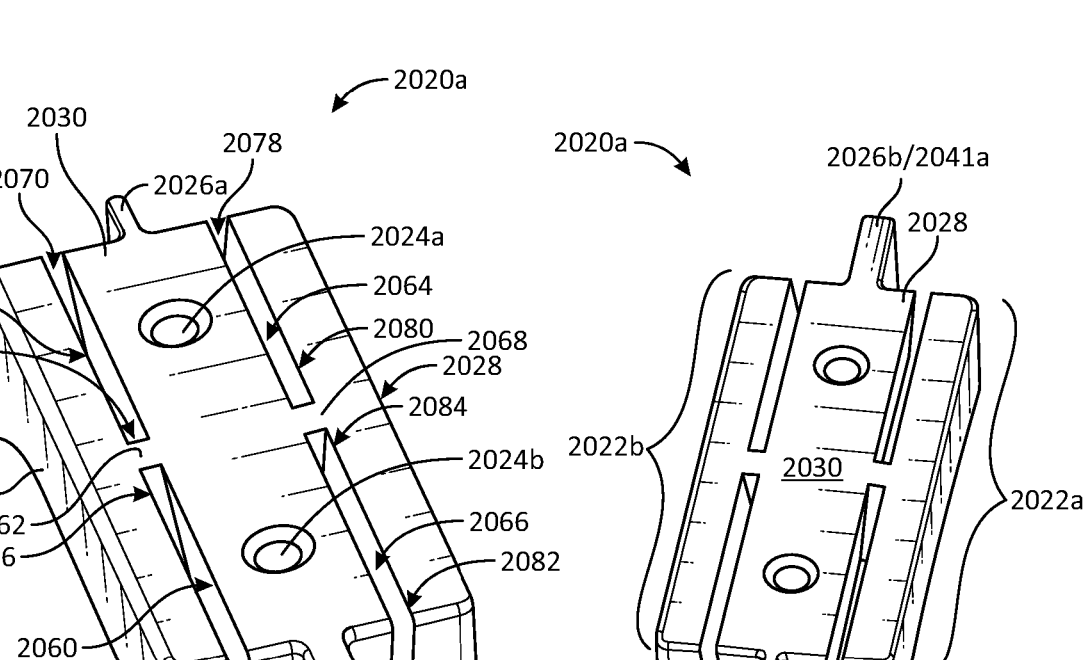
FIG. 21A             FIG. 21B
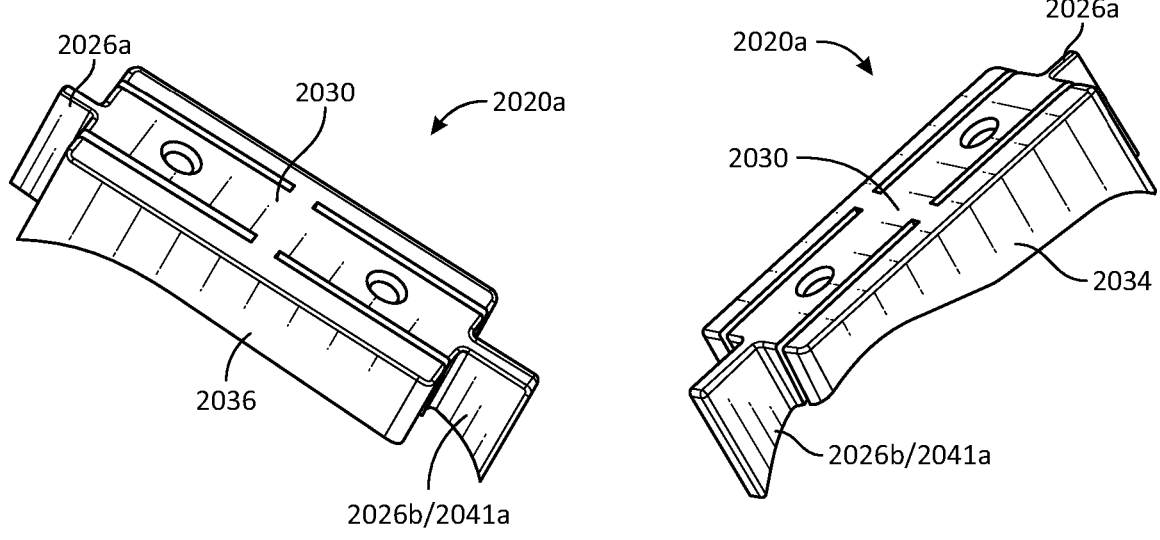
FIG. 21C             FIG. 21D

FIG. 21F          FIG. 21I          FIG. 21G

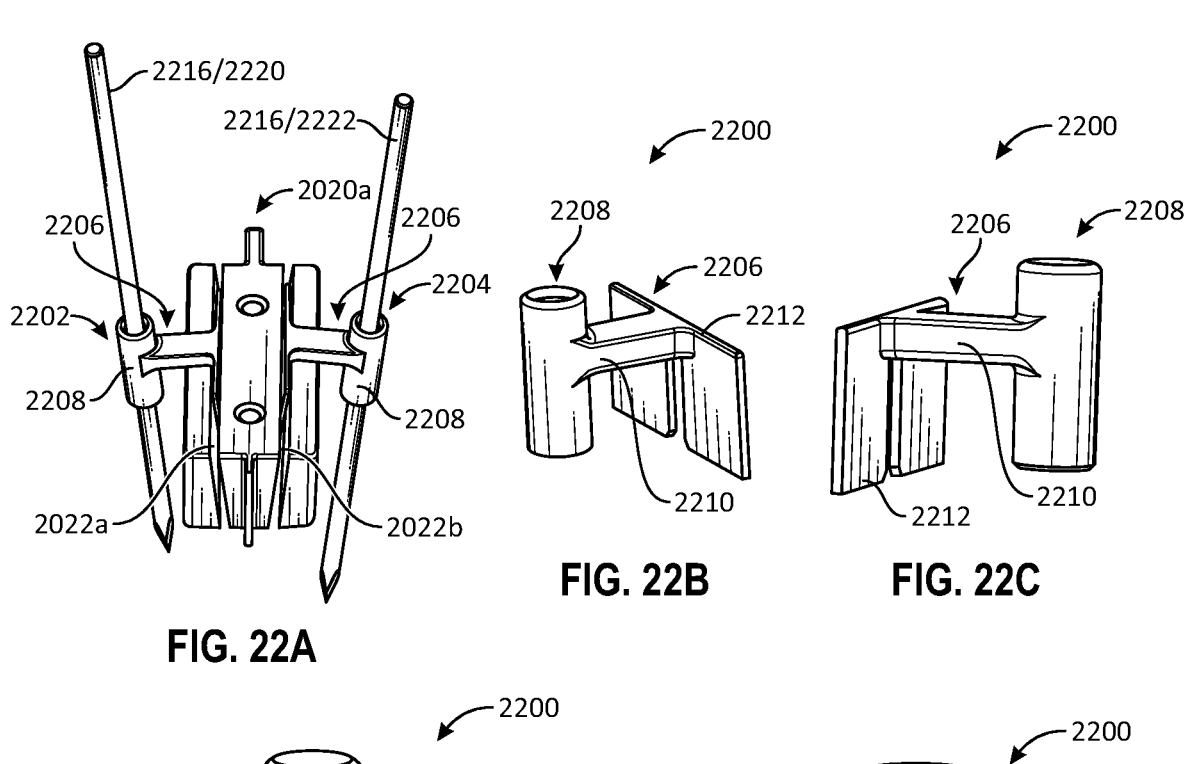
FIG. 22A
FIG. 22B
FIG. 22C
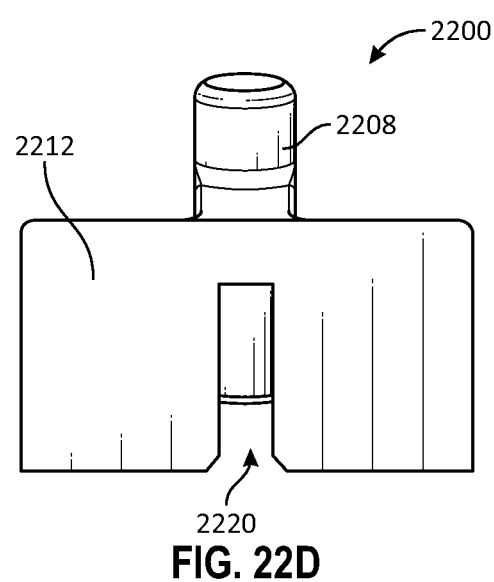
FIG. 22D
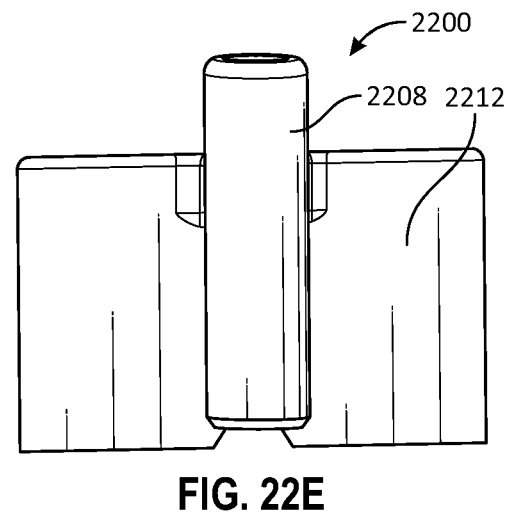
FIG. 22E
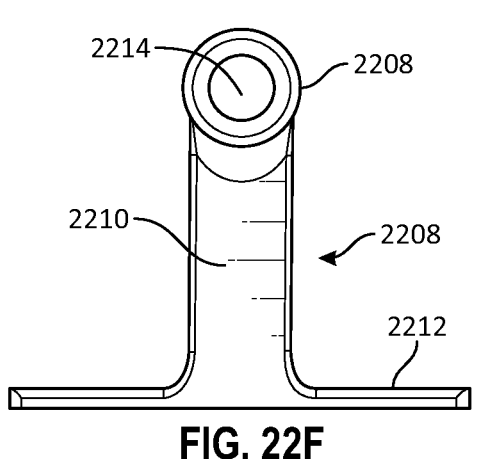
FIG. 22F
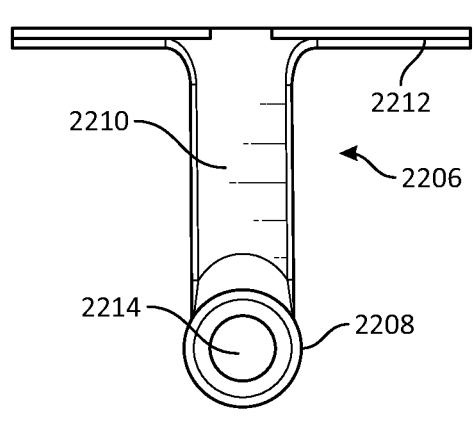
FIG. 22G

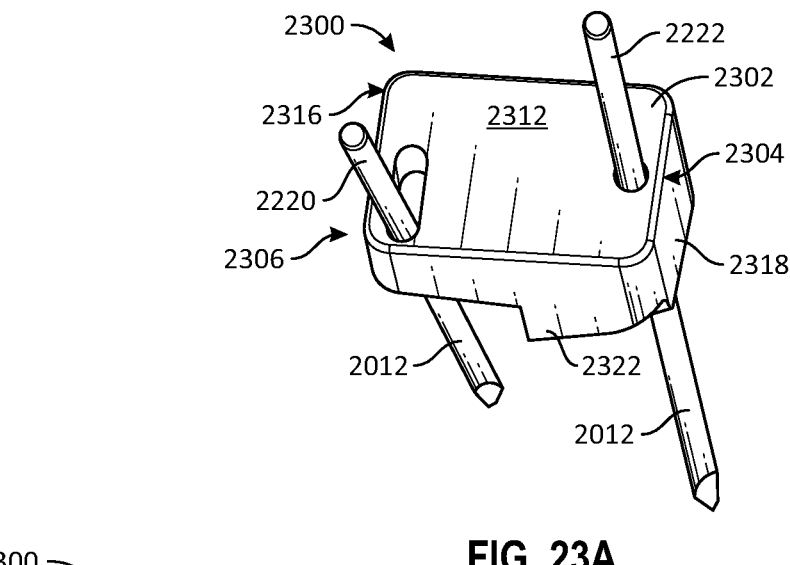
FIG. 23A
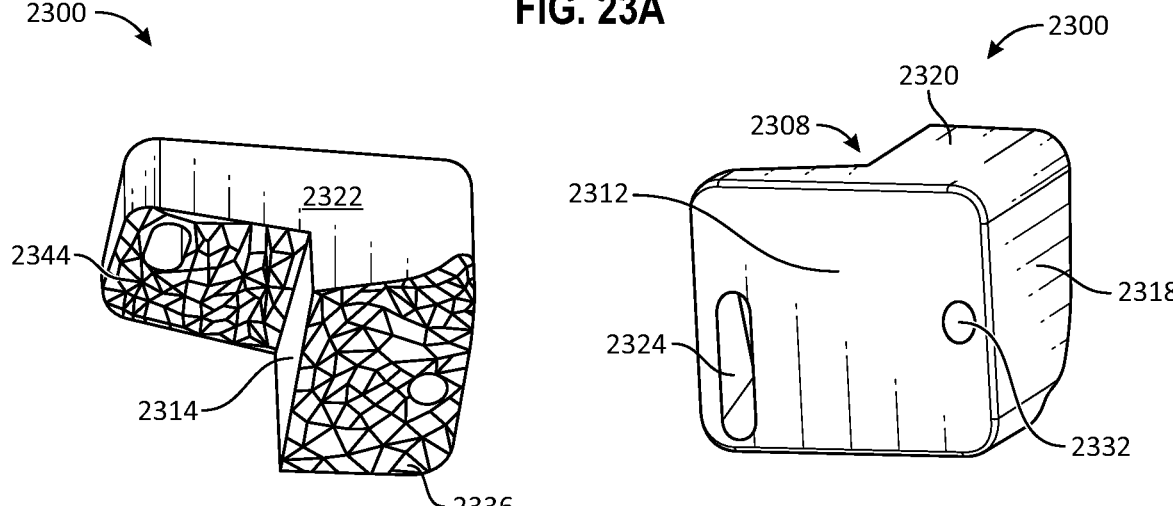
FIG. 23B　　　　　　　　FIG. 23C
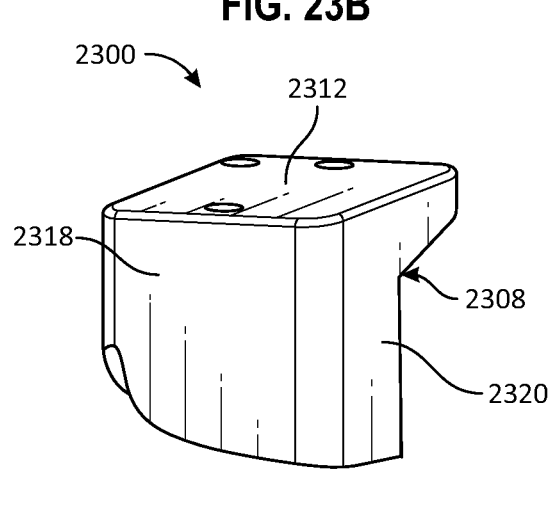
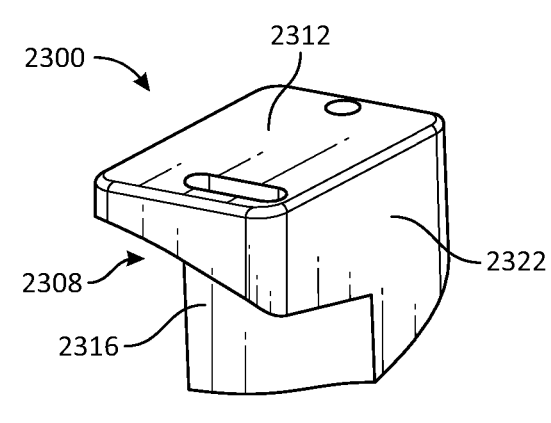
FIG. 23D　　　　　　　　FIG. 23E

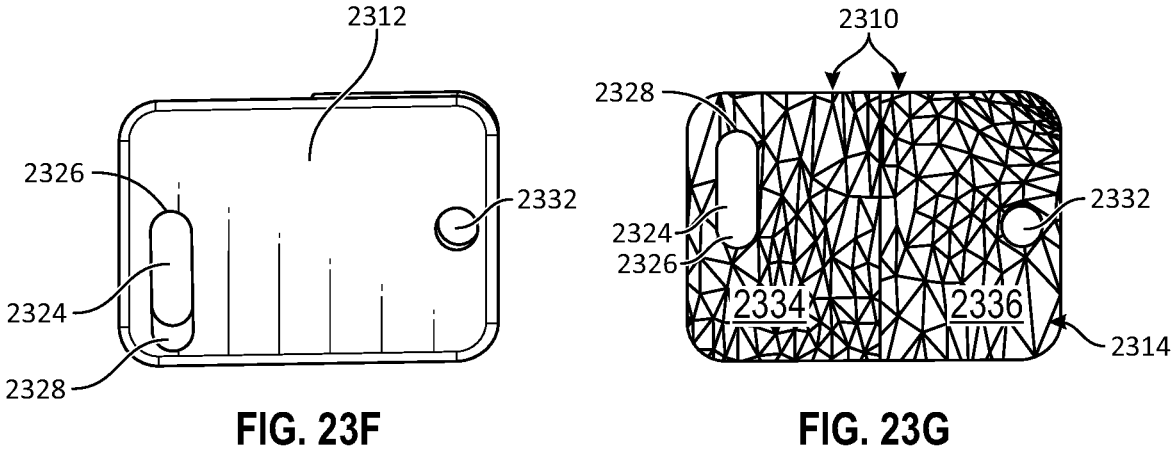
FIG. 23F
FIG. 23G
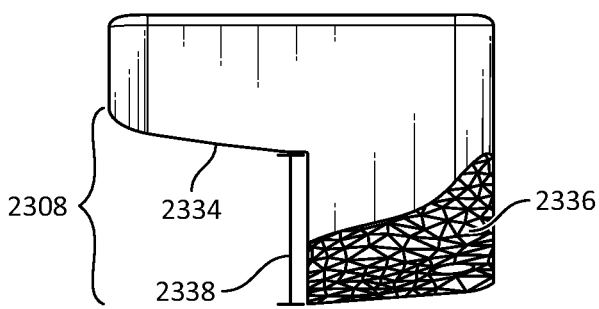
FIG. 23H

2400

| 2402 | Access a lateral surface of a calcaneus |

| 2404 | Position a resection guide onto the lateral surface, the resection guide comprising: a body; a posterior resection feature; an anterior resection feature; a first bone attachment feature; a second bone attachment feature; a plantar landmark registration feature; and a bone engagement surface |

| 2406 | Deploy a first fastener and a second fastener |

| 2408 | Insert the cutting tool into a posterior resection feature |

| 2410 | Insert the cutting tool into an anterior resection feature |

| 2412 | Engage a posterior pin guide with a posterior resection feature and deploying a posterior pin and engaging an anterior pin guide with an anterior resection feature and deploying an anterior pin |

| 2414 | Remove the posterior pin guide and the anterior pin guide and the resection guide |

| 2416 | Remove a wedge bone fragment by way of the first fastener and the second fastener |

| 2418 | Slide a positioning guide over the posterior pin and the anterior pin |

| 2420 | Slide the positioning guide along the posterior pin and anterior pin until the positioning guide contacts the posterior bone fragment and the anterior bone fragment |

| 2422 | Deploy fixation across an osteotomy between the posterior bone fragment and the anterior bone fragment |

FIG. 24A

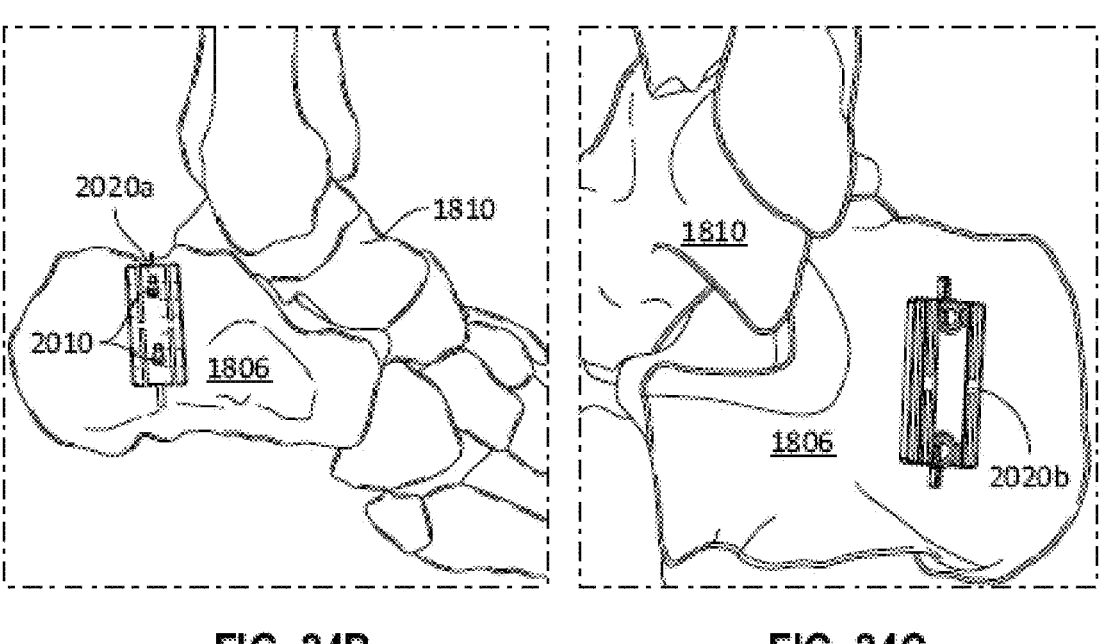
FIG. 24B                    FIG. 24C
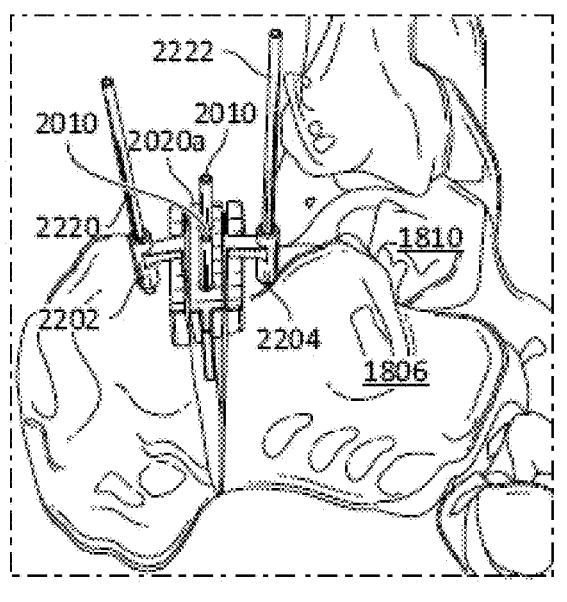
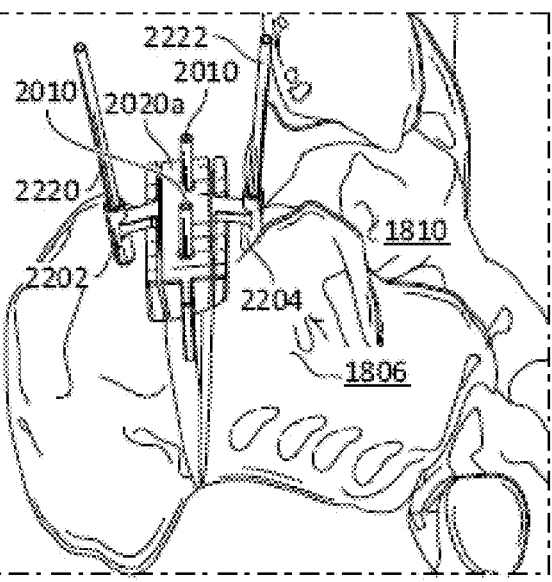
FIG. 24D                    FIG. 24E

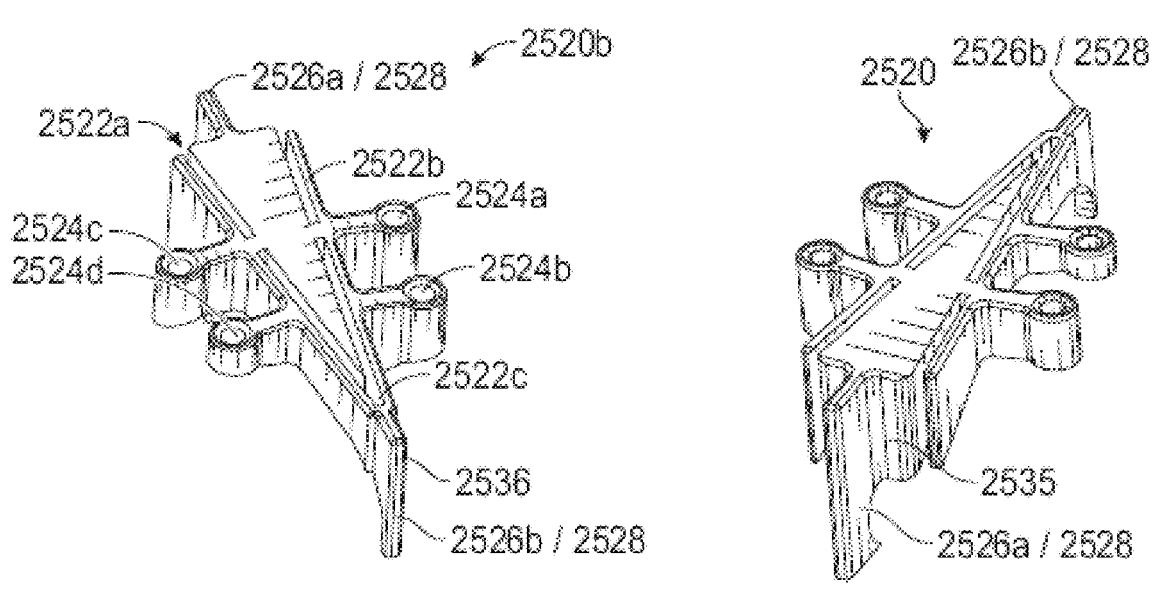
FIG. 27A          FIG. 27B
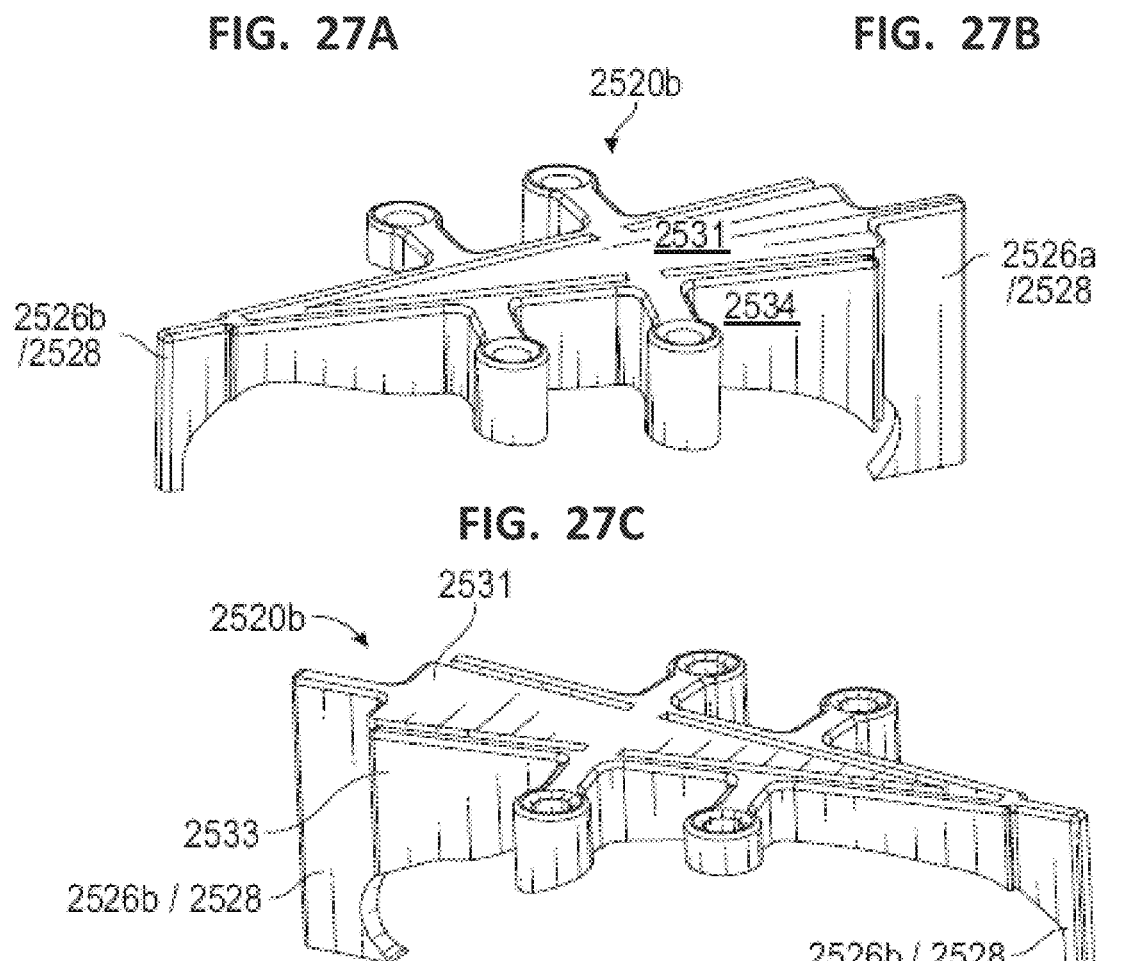
FIG. 27C
FIG. 27D

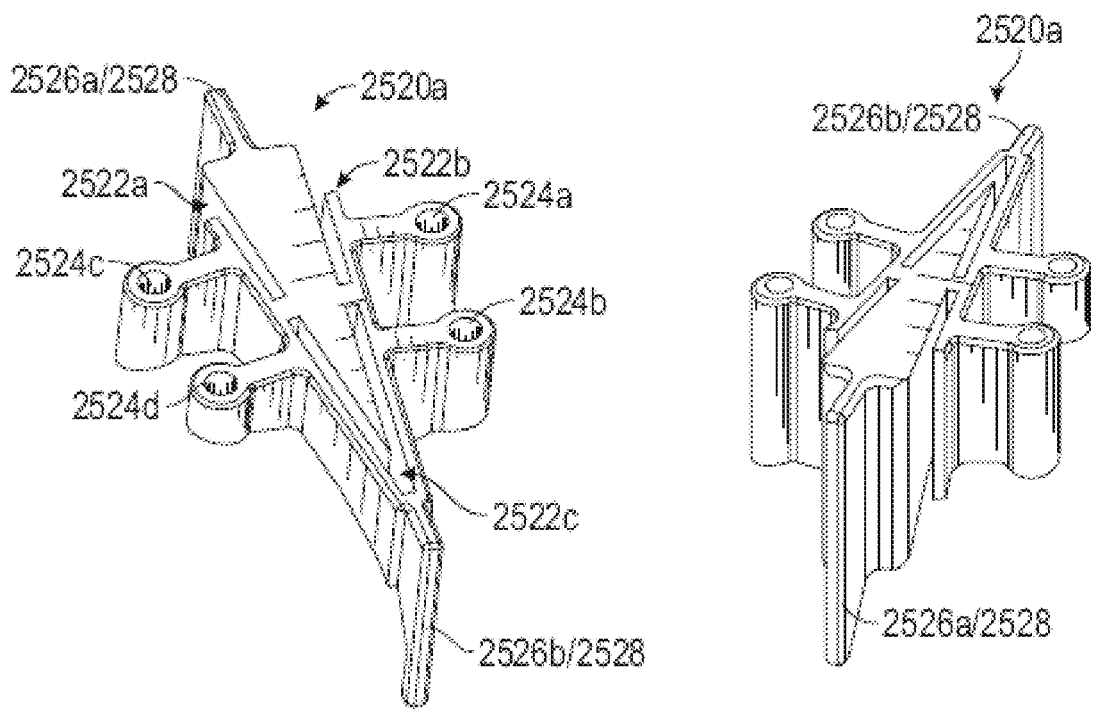
FIG. 28A                    FIG. 28B
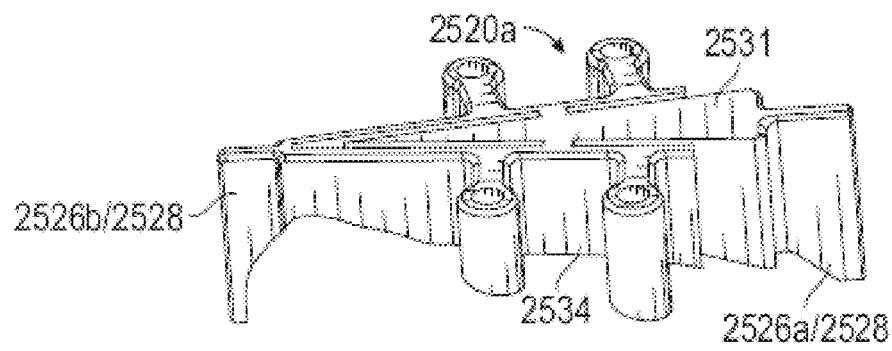
FIG. 28C
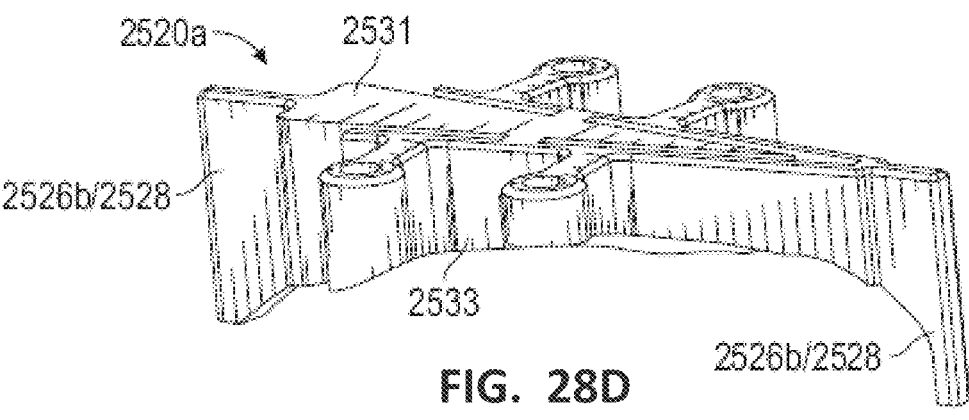
FIG. 28D

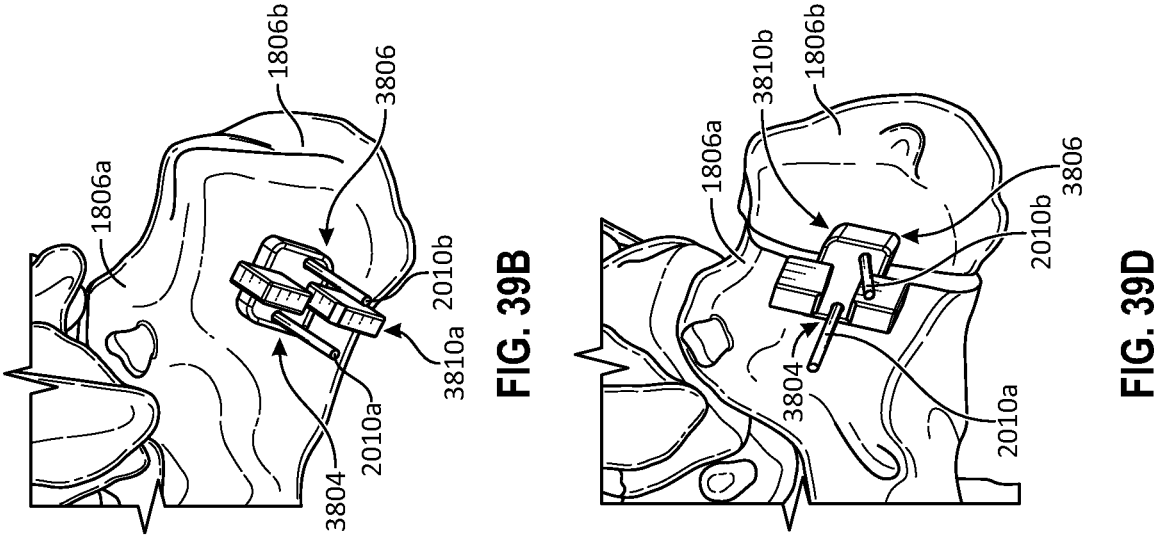
FIG. 39B
FIG. 39D
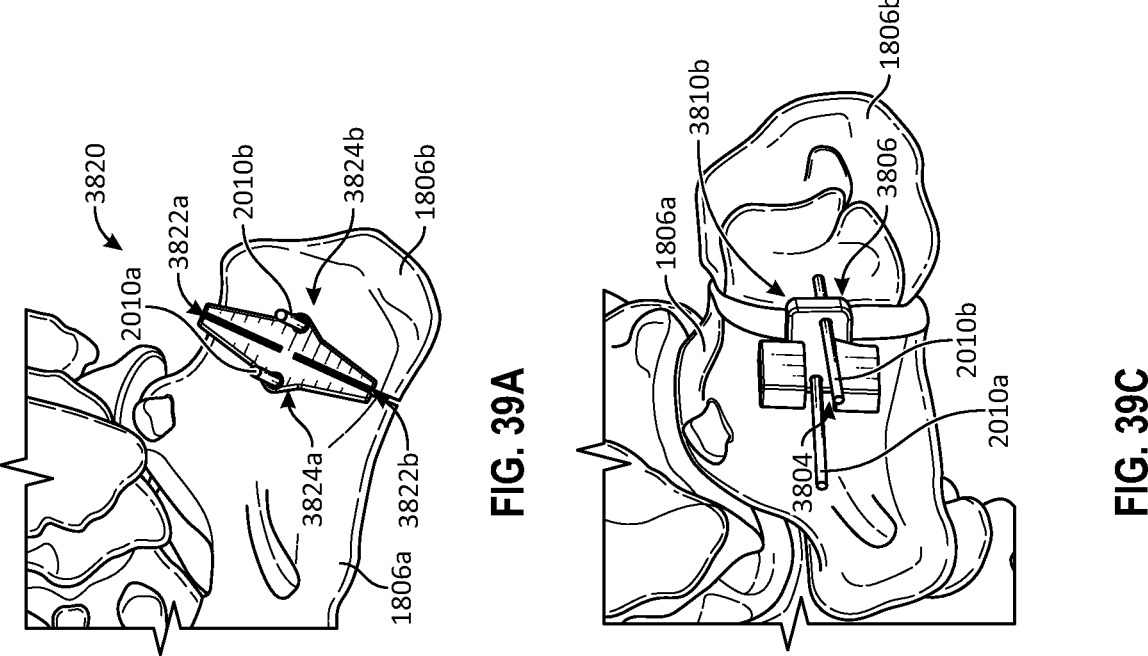
FIG. 39A
FIG. 39C

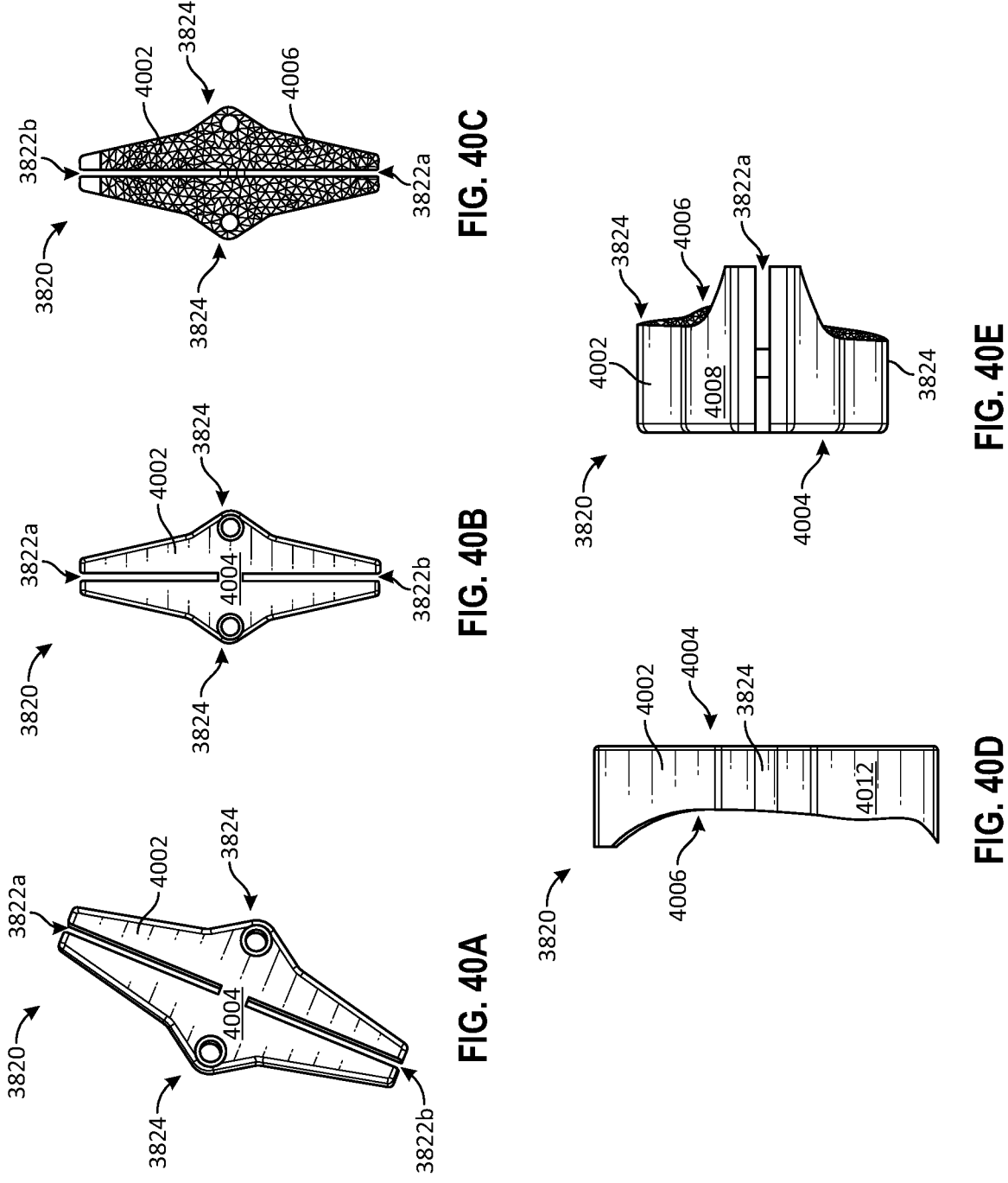

APPARATUS, SYSTEM, AND METHOD FOR GENERATING PATIENT-SPECIFIC IMPLANTS AND/OR INSTRUMENTATION FOR OSTEOTOMIES

CROSS-REFERENCE TO RELATED APPLICATIONS

This application claims the benefit of U.S. Provisional Application No. 63/353,317, filed Jun. 17, 2022, which is hereby incorporated by reference in its entirety.

TECHNICAL FIELD

The present disclosure relates to surgical devices, systems, instruments, and methods. More specifically, the present disclosure relates to patient-specific cutting guides and implants, and methods of designing and using the same.

BACKGROUND

Various bone conditions may be corrected using surgical procedures, in which one or more tendons, ligaments, and/or bones may be cut, replaced, repositioned, reoriented, reattached, fixated and/or fused. These surgical procedures can require a surgeon to properly locate, position, and/or orient one or more osteotomy cuts, fixation guides, fixators, bone tunnels, points of attachment for ends of grafts or soft tissue, and the like. Determining and locating an optimal location and trajectory for one or more steps of the surgical procedures and/or securing instruments that can guide or assist in steps of the surgical procedures such as performing osteotomies, deploying fixation, and the like, can be challenging, given conventional techniques and instruments. One of the challenges with conventional techniques is how to translate, map, or convert from a model of a patient's anatomy and/or virtual instrumentation to the real, physical world for performing a surgical procedure. Furthermore, surgical procedures can be extra challenging when working on anatomy such as bones of a patient's foot or hand which have much smaller bones that call for extra precision in comparison to larger bones such as a femur. What is needed is one or more devices or instruments to facilitate locating, aligning, orienting, planning, mapping from virtual models to physical anatomy, preparing for, initiating, executing, and/or completing such surgical procedures. In addition, what is needed is methods, apparatus, devices, implants and/or instrumentation that is customized to a specific patient such that precise and accurate adjustments and/or corrections can be made to meet the needs of each unique patient.

Wedge osteotomies can be challenging for a surgeon because in certain surgical procedures the surgeon may desire to preserve cortical bone opposite the osteotomy. Doing such osteotomies free-hand can be very challenging to get the desired angles, trajectories, in one or more planes, and still preserve cortical bone opposite the osteotomy. Existing solutions for guiding such orthopedic surgical procedures are inadequate and error prone.

SUMMARY

The various apparatus, devices, systems, and/or methods of the present disclosure have been developed in response to the present state of the art, and in particular, in response to the problems and needs in the art that have not yet been fully solved by currently available technology.

One general aspect of the present disclosure may include an osteotomy system that may include a resection guide having: a body having an anterior side, a posterior side, a medial side, a lateral side, a dorsal side, and a plantar side; a posterior resection feature configured to guide a cutting tool to form a first osteotomy in the bone, the posterior resection feature extending through the resection guide from the lateral side to the medial side along a first trajectory at least partially determined based on a bone model of at least a portion of the patient's foot, the bone model based on medical imaging of the patient's foot and configured to resemble the anatomy of the patient's foot; an anterior resection feature configured to guide a cutting tool to form a second osteotomy in the bone, the anterior resection feature extending through the resection guide from the lateral side to the medial side along a second trajectory at least partially determined based on the bone model; a bone attachment feature configured to secure the resection guide to the bone.

An osteotomy system that may also include at least one complementary component selected from the group having of: an alignment guide; a rotation guide; a compression guide; a correction guide; a positioning guide; a pin guide; and a fixation guide.

Implementations may also include one or more of the following features. A system where the first trajectory converges with the second trajectory at a vertex having a wedge angle, such that posterior resection feature and the anterior resection feature form a wedge osteotomy having a wedge bone fragment after formation of the first osteotomy and the second osteotomy, the wedge angle determined based, at least in part, on the bone model. A system where the bone attachment feature is configured to secure the resection guide to a portion of the bone that forms the wedge bone fragment after formation of the wedge osteotomy.

A system where the vertex is prepositioned to be between a medial cortex of the bone and the resection guide when the resection guide is designed for the patient's foot. A system where the medial side of the resection guide may include a bone engagement surface configured to register to a lateral surface of the bone, the bone engagement surface defined based a lateral surface of the bone model and a planned position of the resection guide on a lateral surface of the bone.

A system where the posterior resection feature may include: a posterior dorsal slot having an open dorsal end and a closed plantar end; a posterior plantar slot having an open plantar end and a closed dorsal end; a posterior bridge positioned between the posterior dorsal slot and the posterior plantar slot, the posterior bridge forming the closed plantar end of the posterior dorsal slot and the closed dorsal end of the posterior plantar slot; where the anterior resection feature may include: an anterior dorsal slot having an open dorsal end and a closed plantar end; an anterior plantar slot having an open plantar end and a closed dorsal end; an anterior bridge positioned between the anterior dorsal slot and the anterior plantar slot, the anterior bridge forming the closed plantar end of the anterior dorsal slot and the closed dorsal end of the anterior plantar slot.

A system where the at least one complementary component may include the pin guide having an arm configured to engage at least one of the posterior resection feature and the anterior resection feature, the arm connected to a bone engagement feature configured to receive a fastener. A system where the arm may include an opening configured to receive a bridge of at least one of the posterior resection feature and the anterior resection feature.

A system where at least one of the arm and the bone engagement feature may include a patient-specific feature defined based on the bone model. A system where the resection guide may include: a plantar landmark registration feature that extends from the plantar side of the resection guide; where the plantar landmark registration feature is configured to engage with a landmark of the bone. A system where the plantar landmark registration feature may include a bone engagement surface fabricated based on the bone model and the landmark of the bone may include a plantar surface of the bone.

A system where the at least one complementary component may include the positioning guide and where the positioning guide may include: a body having an anterior side, a posterior side, a medial side, a lateral side, a dorsal side, and a plantar side; an anterior alignment feature; a posterior alignment feature; and an offset feature on the medial side of the body, the offset feature configured to translate a posterior bone fragment relative to an anterior bone fragment, the posterior bone fragment and anterior bone fragment formed by way of one of the first osteotomy and the second osteotomy. A system where the positioning guide may include: a bone engagement surface on the medial side, the bone engagement surface configured to register to a lateral surface of the posterior bone fragment and the anterior bone fragment; and where the bone engagement surface is defined based on a lateral surface of the bone model and a planned reduced position of the posterior bone fragment and the anterior bone fragment.

One general aspect of the present disclosure may include an apparatus that may include a body having an anterior side, a posterior side, a medial side, a lateral side, a dorsal side, and a plantar side. An apparatus that may also include a posterior resection feature that extends from the lateral side to the medial side at a posterior angle, the posterior angle at least partially determined based on a calcaneus model derived from medical imaging of a calcaneus of a patient's foot, the calcaneus model configured to significantly resemble the anatomy of the patient's foot.

An apparatus that may furthermore include an anterior resection feature that extends from the lateral side to the medial side at an anterior angle, the anterior angle determined based on the calcaneus model and determined such that an osteotomy formed by way of the posterior resection feature and the anterior resection feature forms a wedge osteotomy having a wedge bone fragment determined based on the calcaneus model.

An apparatus that may in addition include a bone attachment feature configured to engage the wedge bone fragment after formation of the wedge osteotomy. An apparatus that may moreover include a plantar landmark registration feature that extends from the plantar side of the body and is configured to contact a plantar surface of the calcaneus. An apparatus that may also include a handle that extends from the dorsal side of the body. An apparatus that may furthermore include a bone engagement surface on the medial side of the body, the bone engagement surface configured to match a contour of the calcaneus when the body is positioned for use on the calcaneus.

Implementations may also include one or more of the following features. An apparatus where the posterior resection feature is configured to receive an arm of a posterior pin guide having an arm that connects a planar fin to a bone engagement feature having an opening and a posterior pin; and where the anterior resection feature is configured to receive an arm of an anterior pin guide having an arm that connects a planar fin to a bone engagement feature having an opening and an anterior pin; where the posterior pin guide is configured to guide the posterior pin into a posterior bone fragment parallel to an osteotomy formed using the posterior resection feature; and where the anterior pin guide is configured to guide the anterior pin into an anterior bone fragment substantially parallel to an osteotomy formed using the anterior resection feature.

An apparatus where the posterior pin deployed by way of the posterior pin guide and the anterior pin deployed by way of the anterior pin guide are configured to receive a positioning guide having: a body having an anterior side, a posterior side, a medial side, a lateral side, a dorsal side, and a plantar side; an anterior alignment feature; a posterior alignment feature; an offset feature on the medial side of the body, the offset feature configured to translate the posterior bone fragment relative to the anterior bone fragment; and a bone engagement surface on the medial side, the bone engagement surface configured to register to a lateral surface of the posterior bone fragment and the anterior bone fragment, the bone engagement surface defined based a lateral surface of the calcaneus model and a planned reduced position of the posterior bone fragment and the anterior bone fragment.

An apparatus where the posterior alignment feature may include a slot configured to receive the posterior pin, the slot having: a dorsal end; a plantar end; and a length between the dorsal end and the plantar end having a predetermined length based on the calcaneus model to permit an user to rotate the posterior bone fragment relative to the anterior bone fragment. An apparatus where the bone engagement surface extends to a medial side of the plantar landmark registration feature and the handle.

One general aspect of the present disclosure may include a method that may include accessing a lateral surface of a calcaneus. A method that may also include positioning a resection guide onto the lateral surface, the resection guide having: a body having an anterior side, a posterior side, a medial side, a lateral side, a dorsal side, and a plantar side; a posterior resection feature configured to guide a cutting tool to form a first osteotomy in the calcaneus, the posterior resection feature extending through the resection guide from the lateral side to the medial side along a first trajectory determined based on a calcaneus model of the calcaneus based on medical imaging of the patient's foot, the calcaneus model configured to match the anatomy of the patient's foot; an anterior resection feature configured to guide a cutting tool to form a second osteotomy that connects with the first osteotomy to form a wedge bone fragment from the calcaneus, the anterior resection feature extending through the resection guide from the lateral side to the medial side along a second trajectory determined based on the calcaneus model; a first bone attachment feature configured to engage the wedge bone fragment after formation of the wedge bone fragment; a second bone attachment feature configured to engage the wedge bone fragment after formation of the wedge bone fragment; a plantar landmark registration feature that extends from the plantar side of the body and is configured to contact a plantar surface of the calcaneus; and a bone engagement surface on the medial side of the body, the bone engagement surface configured to match a contour of the calcaneus when the body is positioned on the calcaneus.

A method that may furthermore include deploying a first fastener into the first bone attachment feature and a second fastener into the second bone attachment feature such that the first fastener and second fastener are parallel relative to each other and enter a portion of the calcaneus that will form the wedge bone fragment.

A method that may in addition include inserting the cutting tool into the posterior resection feature to a depth predefined in a preoperative plan designed based on the calcaneus model to form the first osteotomy.

A method that may moreover include inserting the cutting tool into the anterior resection feature to a depth predefined in a preoperative plan designed based on the calcaneus model to form the second osteotomy, the second osteotomy forming a posterior bone fragment and an anterior bone fragment.

A method that may also include engaging a posterior pin guide with the posterior resection feature and deploying a posterior pin into a bone attachment feature of the posterior pin guide and engaging an anterior pin guide with the anterior resection feature and deploying an anterior pin into a bone attachment feature of the anterior pin guide.

A method that may furthermore include removing the posterior pin guide and the anterior pin guide and the resection guide.

A method that may in addition include removing the wedge bone fragment by way of the first fastener and the second fastener.

A method that may moreover include sliding a positioning guide over the posterior pin and the anterior pin by passing the posterior pin through a posterior alignment feature and passing the anterior pin through an anterior alignment feature.

A method that may also include sliding the positioning guide along the posterior pin and anterior pin until the positioning guide contacts the posterior bone fragment and the anterior bone fragment.

A method that may furthermore include deploying fixation across an osteotomy between the posterior bone fragment and the anterior bone fragment.

Implementations may also include one or more of the following features. A method may include breaking a medial cortex of the calcaneus opposite the wedge bone fragment; and translating the posterior pin within the posterior alignment feature to rotate the posterior bone fragment to a position determined by a surgeon to remediate a condition of the patient's foot.

One general aspect of the present disclosure may include an osteotomy system that may include at least one fastener configured to engage a phalanx of a patient's foot. An osteotomy system that may also include a resection guide having: a body having an anterior side, a posterior side, a medial side, a lateral side, a dorsal side, and a plantar side; a posterior resection feature configured to guide a cutting tool to form a first osteotomy in the phalanx, a first trajectory for first osteotomy determined based on a bone model of the phalanx based on medical imaging of the patient's foot, the bone model configured to significantly resemble the anatomy of the patient's foot; an anterior resection feature configured to guide a cutting tool to form a second osteotomy in the phalanx, a second trajectory for second osteotomy determined based on the bone model; and a first bone attachment feature configured to secure the resection guide to the phalanx; a second bone attachment feature configured to secure the resection guide to the phalanx.

Implementations may also include one or more of the following features. A system where at least one of the first bone attachment feature and the second bone attachment feature are configured to form a guide hole for a fastener within the phalanx when the at least one of the first bone attachment feature and the second bone attachment feature are disengaged from the phalanx. A system where the first bone attachment feature is configured to form a first guide hole and the second bone attachment feature is configured to form a second guide hole and where the first guide hole is configured for a first leg of a bone staple and the second guide hole is configured for a second leg of the bone staple.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings in which:

FIG. 1A is a flowchart diagram depicting a method for correcting a bone condition, according to one embodiment.

FIG. 1B is a flowchart diagram depicting a method for correcting bunion deformity of the human foot, according to one embodiment.

FIG. 2C is a medial perspective view of bones of a foot.

FIG. 2D is a dorsal perspective view of bones of a foot.

FIGS. 3A-3H are top perspective, top perspective, bottom, front elevation, rear elevation, right, left, and alternative top perspective, views respectively, of a patient-specific cutting guide according to one embodiment.

FIG. 8A is a perspective view of the foot of FIG. 2, after resection of the first cuneiform and the first metatarsal, removal of the cutting guide, and placement of the first metatarsal to abut the first cuneiform, according to one embodiment.

FIGS. 8B and 8C are dorsal views of the foot of FIG. 2, before and after correction, respectively, according to one embodiment.

FIGS. 21A-21J illustrate views of a resection guide of the osteotomy system of FIG. 20, according to one embodiment.

FIGS. 22A-22G illustrate views of a pin guide or alignment guide of an osteotomy system, according to one embodiment.

FIGS. 23A-23H illustrate views of a positioning guide of an osteotomy system, according to one embodiment.

FIG. 24A is a flowchart diagram depicting a method remediating a bone condition present in a patient's foot, according to one embodiment.

FIGS. 24B-24G illustrates different stages of performing a surgical osteotomy procedure using an osteotomy system, according to one embodiment.

FIGS. 27A-27D illustrate views of a resection guide of an osteotomy system, according to one embodiment.

FIGS. 28A-28D illustrate views of a resection guide of an osteotomy system, according to another embodiment.

FIGS. 39A-39G illustrates different stages of performing a surgical osteotomy procedure using an osteotomy system of FIG. 38, according to one embodiment.

FIGS. 40A-40E illustrate views of a resection guide of an osteotomy system, according to one embodiment.

DETAILED DESCRIPTION

Figures 2A, 2B:
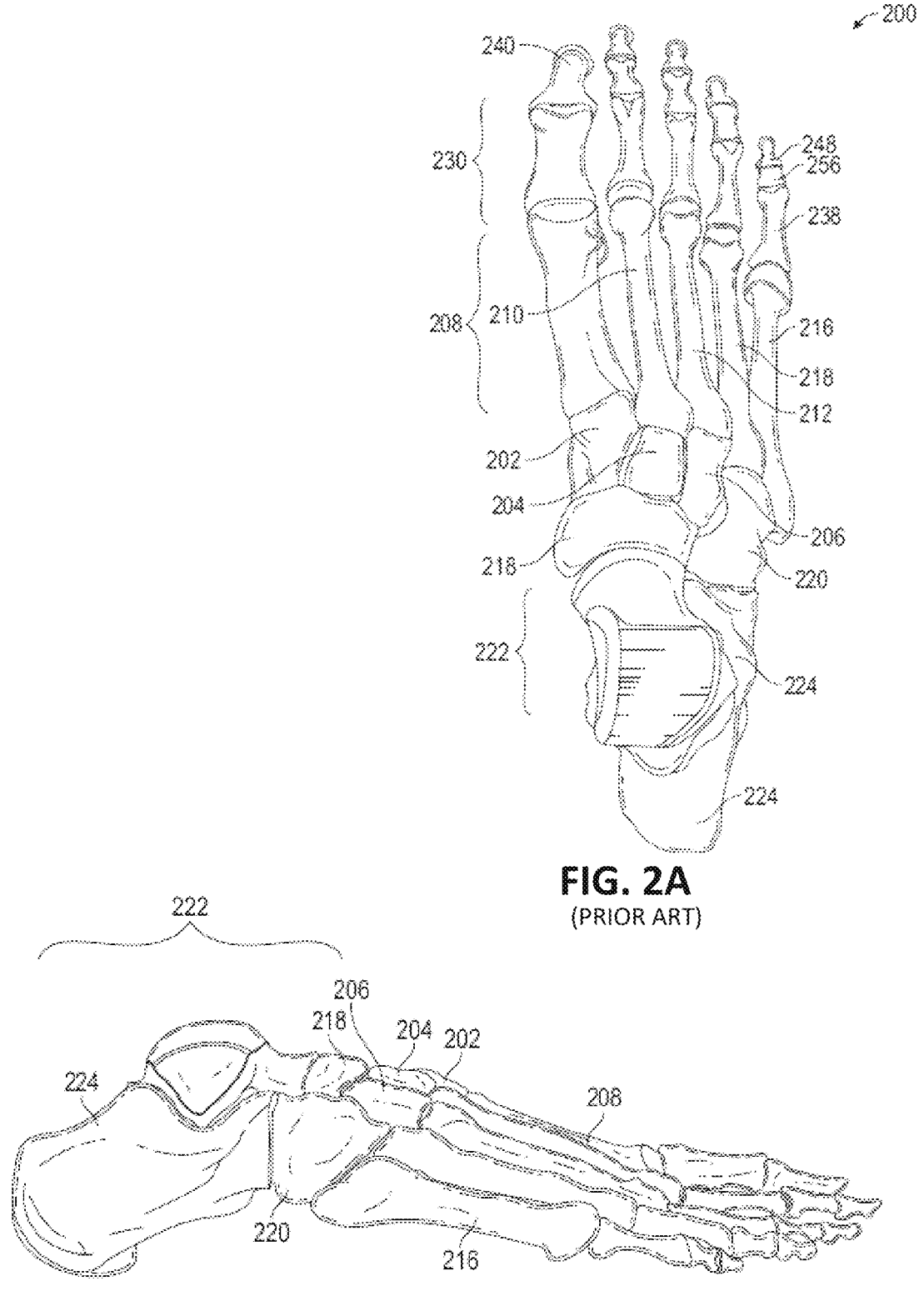
FIG. 2A is a dorsal perspective view of bones of a foot within a transverse plane.
FIG. 2B is a lateral perspective view of bones of a foot.

Exemplary embodiments of the disclosure will be best understood by reference to the drawings, wherein like parts are designated by like numerals throughout. It will be readily understood that the components, as generally described and illustrated in the Figures herein, could be arranged and designed in a wide variety of different configurations. Thus, the following more detailed description of the embodiments of the apparatus, system, and method is not intended to limit the scope of the disclosure but is merely representative of exemplary embodiments.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature can pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this disclosure. While these terms are commonly used to refer to the human body, certain terms are applicable to physical objects in general. A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body from the side which has a particular condition or structure. Proximal means toward the trunk of the body. Proximal may also mean toward a user, viewer, or operator. Distal means away from the trunk. Distal may also mean away from a user, viewer, or operator. Dorsal means toward the top of the foot or other body structure. Plantar means toward the sole of the foot or toward the bottom of the body structure.

Antegrade means forward moving from a proximal location/position to a distal location/position or moving in a forward direction. Retrograde means backward moving from a distal location/position to a proximal location/position or moving in a backwards direction. Sagittal refers to a midline of a patient's anatomy, which divides the body into left or right halves. The sagittal plane may be in the center of the body, splitting it into two halves. Prone means a body of a person lying face down. Supine means a body of a person lying face up.

"Patient-specific cutting guide" refers to a cutting guide designed, engineered, and/or fabricated for use with a specific patient. In one aspect, a patient-specific cutting guide is unique to a single patient and may include features unique to the patient such as a surface contour or other features.

"Patient specific" refers to a feature, an attribute, a characteristic, a structure, function, structure, device, guide, tool, instrument, apparatus, member, component, system, assembly, module, or subsystem or the like that is adjusted, tailored, modified, organized, configured, designed, arranged, engineered, and/or fabricated to specifically address the anatomy, physiology, condition, abnormalities, needs, or desires of a particular patient or surgeon serving the particular patient. In one aspect, a patient specific attribute or feature is unique to a single patient and may include features unique to the patient such as a number of cut channels, a number of bone attachment features, a number of bone engagement surfaces, a number of resection features, a depth of one or more cutting channels, an angle for one or more resection channels, a surface contour, component position, component orientation, a trajectory for an instrument, implant, or anatomical part of a patient, a lateral offset, and/or other features.

As used herein, a "condition" refers to a state of something with regard to its appearance, quality, or working order. In certain aspects, a condition may refer to a patient's state of health or physical fitness or the state of health or physical fitness of an organ or anatomical part of a patient. In certain embodiments, a condition may refer to an illness, defect, disease, or deformity of a patient or of an organ or anatomical part of a patient. (Search "condition" on wordhippo.com. WordHippo, 2021. Web. Accessed 8 Dec. 2021. Modified.)

"Bone condition" refers to any of a variety of conditions of bones of a patient. Generally, a bone condition refers to an orientation, position, and/or alignment of one or more bones of the patient relative to other anatomical structures of the body of the patient. Bone conditions may be caused by or result from deformities, misalignment, malrotation, fractures, joint failure, and/or the like. A bone condition includes, but is not limited to, any angular deformities of one or more bone segments in either the lower or upper extremities (for example, tibial deformities, calcaneal deformities, femoral deformities, and radial deformities). Alternatively, or in addition, "bone condition" can refer to the structural makeup and configuration of one or more bones of a patient. Thus bone condition may refer to a state or condition of regions, a thickness of a cortex, bone density, a thickness and/or porosity of internal regions (e.g. whether it is calcaneus or solid) of the bone or parts of the bone such as a head, a base, a shaft, a protuberance, a process, a lamina, a foramen, and the like of a bone, along the metaphyseal region, epiphysis region, and/or a diaphyseal region.

As used herein, "implant" refers to a medical device manufactured to replace a missing biological structure, support a damaged biological structure, or enhance an existing biological structure. Often medical implants are man-made devices, but implants can also be natural occurring structures. The surface of implants that contact the body may be made of, or include a biomedical material such as titanium, cobalt chrome, stainless steel, carbon fiber, another metallic alloy, silicone, polymer, Synthetic polyvinyl alcohol (PVA) hydrogels, biomaterials, biocompatible polymers such as PolyEther Ether Ketone (PEEK) or a polylactide polymer (e.g. PLLA) and/or others, or apatite, or any combination of these depending on what is functional and/or economical. Implants can have a variety of configurations and can be wholly, partially, and/or include a number of components that are flexible, semiflexible, pliable, elastic, supple, semi-rigid, or rigid. In some cases implants contain electronics, e.g. artificial pacemaker and cochlear implants. Some implants are bioactive, such as subcutaneous drug delivery devices in the form of implantable pills or drug-eluting stents. Orthopedic implants may be used to alleviate issues with bones and/or joints of a patient's body. Orthopedic implants can be used to treat bone fractures, osteoarthritis, scoliosis, spinal stenosis, discomfort, and pain. Examples of orthopedic implants include, but are not limited to, a wide variety of pins, rods, screws, anchors, spacers, sutures, all-suture implants, ball all-suture implants, self-locking suture implants, cross-threaded suture implants, plates used to anchor fractured bones while the bones heal or fuse together, and the like. (Search "implant (medicine)" on Wikipedia.com May 26, 2021. CC-BY-SA 3.0 Modified. Accessed Jun. 30, 2021.)

"Topographical" refers to the physical distribution of parts, structures, or features on the surface of, or within, an organ or other anatomical structure, or organism. (Search "define topographical" on google.com. Oxford Languages, Copyright 2022. Oxford University Press. Web., Modified. Accessed 15 Feb. 2022.)

As used herein, "preoperative plan" refers to a plan for performing a surgical procedure. Depending on the complexity of a surgery, a preoperative plan can be very simple and generic or very detailed and specific to a particular surgical procedure. In one aspect, a preoperative plan may include very detailed and specific step by step instructions for the surgical procedure. The instructions may be ordered according to a specific order for accomplishing a desired outcome. In certain embodiments, a preoperative plan may indicate which instruments, machines, systems, test, and/or personnel to use for the surgical procedure. A preoperative plan can take many forms and formats based on the needs and desires of the users of the preoperative plan. In one embodiment, the preoperative plan is a report that is displayed on a screen or that can be printed onto paper. In another embodiment, the preoperative plan may include instructions for operation planning software. In another embodiment, the preoperative plan may include instructions for surgical rehearsal tools, including software. In another embodiment, the preoperative plan may include instructions for operation planning using virtual reality or augmented reality software.

"Vertex" refers to a point at which lines, structures, trajectories, or pathways intersect. (Search "vertex" on wordhippo.com. WordHippo, 2023. Web. Modified. Accessed 13 Jun. 2023.)

As used herein, an "pin" refers to an elongated structure. In certain embodiments, a pin can be used to connect two structures or serve as a bearing between two structures. In certain embodiments, a pin can be configured to support a load (including a tension, compression, shear, torsion, and/or bending load). In certain embodiments, a pin may be a cylindrical structure that is thinner than connected structures. A pin can serve a variety of functions and may include a modifier identifying a particular function for example certain solutions may use alignment pins, attachment pins, securement pins, or the like. Pins may serve a temporary or permanent structural purpose. Pins can be used in a variety of devices, components, apparatus, and systems, including but not limited to, fixation plates, measurement instruments, pin guides, cutting guides, surgical instrumentation, and the like. A pin can serve as a fastener either temporarily or permanently. One example of a pin is a Kirschner wire ("K-wire"). A pin can have a variety of geometric cross-sectional shapes, including, but not limited to a circle, an ellipse, an ovoid, or other circular or semi-circular shape, as well as a rectangle, a square, or other polygon. A pin has two ends one end can be blunt and the other end may come to a point. A pin can be made from a variety of materials including metal, plastic, ceramic, wood, fiberglass, or the like. A pin may also be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others.

"Register" or "Registration" refers to an act of aligning, mating, contacting, engaging, or coupling one or more parts and/or surfaces of one object in relation to one or more parts and/or surfaces of another object. Often, the one or more parts and/or surfaces one object include protrusions and/or depressions that are the inverse or mirror configuration of protrusions and/or depressions of one or more parts and/or surfaces of the other object.

"Position" refers to a place or location. (Search "position" on wordhippo.com. WordHippo, 2022. Web. Modified. Accessed 9 Aug. 2022.) As used herein, "slot" refers to a narrow opening or groove. (search "slot" on Merriam-Webster.com. Merriam-Webster, 2021. Web. 4 Aug. 2021.

Modified.) As used herein, "end" refers to a part or structure of an area or span that lies at the boundary or edge. An end can also refer to a point that marks the extent of something and/or a point where something ceases to exist. An end can also refer to an extreme or last part lengthwise of a structure or surface. (search "end" on Merriam-Webster.com. Merriam-Webster, 2021. Web. 4 Aug. 2021. Modified.)

"Bone fragment" or "fragment" refers to a part of a bone that is normally part of another bone of a patient. A bone fragment may be partially or wholly separate from another bone of a patient due to a deformity, an osteotomy, a resection, and/or trauma. In one aspect, the bone that a bone fragment is normally part of, connected to, or joined with, is referred to as a parent bone.

"Cortex" refers to an area of bone that extends from an external surface of the bone towards a center part of the bone. The cortex is typically comprised of cortical bone.

As used herein, a "stop" refers to an apparatus, instrument, structure, member, device, component, system, or assembly structured, organized, configured, designed, arranged, or engineered to prevent, limit, impede, stop, or restrict motion or movement and/or operation of the another object, member, structure, component, part, apparatus, system, or assembly.

As used herein, a "fastener", "fixation device", or "fastener system" refers to any structure configured, designed, or engineered to join two structures. Fasteners may be made of a variety of materials including metal, plastic, composite materials, metal alloys, plastic composites, and the like. Examples of fasteners include, but are not limited to screws, rivets, bolts, nails, snaps, hook and loop, set screws, bone screws, nuts, posts, pins, thumb screws, and the like. Other examples of fasteners include, but are not limited to wires, Kirschner wires (K-wire), anchors, bone anchors, plates, bone plates, intramedullary nails or rods or pins, implants, sutures, soft sutures, soft anchors, tethers, interbody cages, fusion cages, and the like.

As used herein, a "fixation" or "fixation device" refers to an apparatus, instrument, structure, device, component, member, system, assembly, step, process, or module structured, organized, configured, designed, arranged, or engineered to connect two structures either permanently or temporarily. The two structures may be one or the other or both of manmade and/or biological tissues, hard tissues such as bones, teeth or the like, soft tissues such as ligament, cartilage, tendon, or the like. In certain embodiments, fixation is used as an adjective to describe a device or component or step in securing two structures such that the structures remain connected to each other in a desired position and/or orientation. Fixation devices can also serve to maintain a desired level of tension, compression, or redistribute load and stresses experienced by the two structures and can serve to reduce relative motion of one part relative to others. Examples of fixation devices are many and include both those for external fixation as well as those for internal fixation and include, but are not limited to pins, wires, Kirschner wires (K-wires), screws, anchors, bone anchors, plates, bone plates, intramedullary nails or rods or pins, implants, interbody cages, fusion cages, and the like.

In certain embodiments, the term fastener may refer to a fastener system that includes two or more structures configured to combine to serve as a fastener. An example of a fastener system is a rod or shaft having external threads and an opening or bore within another structure having corresponding internal threads configured to engage the external threads of the rod or shaft.

In certain embodiments, the term fastener may be used with an adjective that identifies an object or structure that the fastener may be particularly configured, designed, or engineered to engage, connect to, join, contact, or couple together with one or more other structures of the same or different types. For example, a "bone fastener" may refer to an apparatus for joining or connecting one or more bones, one or more bone portions, soft tissue and a bone or bone portion, hard tissue and a bone or bone portion, an apparatus and a bone or portion of bone, or the like.

In certain embodiments, a fastener may be a temporary fastener. A temporary fastener is configured to engage and serve a fastening function for a relatively short period of time. Typically, a temporary fastener is configured to be used until another procedure or operation is completed and/or until a particular event. In certain embodiments, a user may remove or disengage a temporary fastener. Alternatively, or in addition, another structure, event, or machine may cause the temporary fastener to become disengaged.

As used herein, "osteotomy" or "osteotomy procedure" or "surgical osteotomy" refers to a surgical operation in which one or more bones are cut to shorten or lengthen them or to change their alignment. The procedure can include removing one or more portions of bone and/or adding one or more portions of bone or bone substitutes. (Search "osteotomy" on Wikipedia.com Feb. 3, 22, 2021. CC-BY-SA 3.0 Modified. Accessed Feb. 15, 2022.) As used herein, "patient specific osteotomy procedure" refers to an osteotomy procedure that has been adjusted, tailored, modified, or configured to specifically address the anatomy, physiology, condition, abnormalities, needs, or desires of a particular patient. In certain aspects, one patient specific osteotomy procedure may be useable in connection with only one patient. In other aspects, one patient specific osteotomy procedure may be useable with a number of patients having a particular class of characteristics. In certain aspects, a patient specific osteotomy procedure may refer to a non-patient specific osteotomy procedure that includes one or more patient specific implants and/or instrumentation. In another aspects, a patient specific osteotomy procedure may refer to a patient specific osteotomy procedure that includes one or more patient specific implants, patient specific surgical steps, and/or patient specific instrumentation.

"Trajectory" refers to a path a body travels or a path configured for a body to travel through space. (Search "trajectory" on wordhippo.com. WordHippo, 2023. Web. Modified. Accessed 13 Jun. 2023.)

"Wedge osteotomy" refers to an osteotomy procedure in which one or more wedges are used as part of the procedure. Generally, wedge osteotomies can be of one of two types, open wedge and closing wedge. The type of osteotomy refers to how the procedure changes the relation between two parts of a bone involved in the osteotomy. In an open wedge osteotomy a wedge of bone or graft or other material is inserted in between two parts of a bone. Consequently, a wedge shape is "opened" in the bone. In a close/closed wedge osteotomy or closing wedge osteotomy a wedge of bone is removed from a bone. Consequently, a wedge shape formed in the bone is "closed."

As used herein, "anatomic data" refers to data identified, used, collected, gathered, and/or generated in connection with an anatomy of a human or animal. Examples of anatomic data may include location data for structures, both independent, and those connected to other structures within a coordinate system. Anatomic data may also include data that labels or identifies one or more anatomical structures. Anatomic data can include volumetric data, material composition data, and/or the like. Anatomic data can be generated based on medical imaging data or measurements using a variety of instruments including monitors and/or sensors. Anatomic data can be gathered, measured, or collected from anatomical models and/or can be used to generate, manipulate, or modify anatomical models.

A bone model or anatomic model of a patient's body or body part(s) may be generated by computing devices that analyze medical imaging images. Structures of a patient's body can be determined using a process called segmentation.

As used herein, "segmentation" or "image segmentation" refers the process of partitioning an image into different meaningful segments. These segments may correspond to different tissue classes, organs, pathologies, bones, or other biologically relevant structures. Medical image segmentation accommodates imaging ambiguities such as by low contrast, noise, and other imaging ambiguities.

Certain computer vision techniques can be used or adapted for image segmentation. For example, the techniques and or algorithms for segmentation may include, but are not limited to: Atlas-Based Segmentation: For many applications, a clinical expert can manually label several images; segmenting unseen images is a matter of extrapolating from these manually labeled training images. Methods of this style are typically referred to as atlas-based segmentation methods. Parametric atlas methods typically combine these training images into a single atlas image, while nonparametric atlas methods typically use all of the training images separately. Atlas-based methods usually require the use of image registration in order to align the atlas image or images to a new, unseen image.

Image registration is a process of correctly aligning images; Shape-Based Segmentation: Many methods parametrize a template shape for a given structure, often relying on control points along the boundary. The entire shape is then deformed to match a new image. Two of the most common shape-based techniques are Active Shape Models and Active Appearance Models; Image-Based Segmentation: Some methods initiate a template and refine its shape according to the image data while minimizing integral error measures, like the Active contour model and its variations; Interactive Segmentation: Interactive methods are useful when clinicians can provide some information, such as a seed region or rough outline of the region to segment. An algorithm can then iteratively refine such a segmentation, with or without guidance from the clinician. Manual segmentation, using tools such as a paint brush to explicitly define the tissue class of each pixel, remains the gold standard for many imaging applications. Recently, principles from feedback control theory have been incorporated into segmentation, which give the user much greater flexibility and allow for the automatic correction of errors; Subjective surface Segmentation: This method is based on the idea of evolution of segmentation function which is governed by an advection-diffusion model. To segment an object, a segmentation seed is needed (that is the starting point that determines the approximate position of the object in the image). Consequently, an initial segmentation function is constructed. With the subjective surface method, the position of the seed is the main factor determining the form of this segmentation function; and Hybrid segmentation which is based on combination of methods. (Search "medical image computing" on Wikipedia.com Jun. 24, 2021. CC-BY-SA 3.0 Modified. Accessed Jun. 24, 2021.)

As used herein, "medical imaging" refers to a technique and process of imaging the interior of a body for clinical analysis and medical intervention, as well as visual representation of the function of some organs or tissues (physiology). Medical imaging seeks to reveal internal structures hidden by the skin and bones, as well as to diagnose and treat disease. Medical imaging may be used to establish a database of normal anatomy and physiology to make possible identification of abnormalities. Medical imaging in its widest sense, is part of biological imaging and incorporates radiology, which uses the imaging technologies of X-ray radiography, magnetic resonance imaging, ultrasound, endoscopy, elastography, tactile imaging, thermography, medical photography, nuclear medicine functional imaging techniques as positron emission tomography (PET) and single-photon emission computed tomography (SPECT). Another form of X-ray radiography includes computerized tomography (CT) scans in which a computer controls the position of the X-ray sources and detectors. Magnetic Resonance Imaging (MRI) is another medical imaging technology. Measurement and recording techniques that are not primarily designed to produce images, such as electroencephalography (EEG), magnetoencephalography (MEG), electrocardiography (ECG), and others, represent other technologies that produce data susceptible to representation as a parameter graph vs. time or maps that contain data about the measurement locations. These technologies may be considered forms of medical imaging in certain disciplines. (Search "medical imaging" on Wikipedia.com Jun. 16, 2021. CC-BY-SA 3.0 Modified. Accessed Jun. 23, 2021.) Data, including images, text, and other data associated with medical imaging is referred to as patient imaging data. As used herein, "patient imaging data" refers to data identified, used, collected, gathered, and/or generated in connection with medical imaging and/or medical imaging data. Patient imaging data can be shared between users, systems, patients, and professionals using a common data format referred to as Digital Imaging and Communications in Medicine (DICOM) data. DICOM data is a standard format for storing, viewing, retrieving, and sharing medical images.

As used herein, "medical image computing" or "medical image processing" refers to systems, software, hardware, components, and/or apparatus that involve and combine the fields of computer science, information engineering, electrical engineering, physics, mathematics and medicine. Medical image computing develops computational and mathematical methods for working with medical images and their use for biomedical research and clinical care. One goal for medical image computing is to extract clinically relevant information or knowledge from medical images. While closely related to the field of medical imaging, medical image computing focuses on the computational analysis of the images, not their acquisition. The methods can be grouped into several broad categories: image segmentation, image registration, image-based physiological modeling, and others. (Search "medical image computing" on Wikipedia.com Jun. 24, 2021. CC-BY-SA 3.0 Modified. Accessed Jun. 24, 2021.) Medical image computing may include one or more processors or controllers on one or more computing devices. Such processors or controllers may be referred to herein as medical image processors. Medical imaging and medical image computing together can provide systems and methods to image, quantify and fuse both structural and functional information about a patient in vivo. These two technologies include the transformation of computational models to represent specific subjects/patients, thus paving the way for personalized computational models. Individualization of generic computational models through imaging can be realized in three complementary directions:

definition of the subject-specific computational domain (anatomy) and related subdomains (tissue types); definition of boundary and initial conditions from (dynamic and/or functional) imaging; and characterization of structural and functional tissue properties. Medical imaging and medical image computing enable in the translation of models to the clinical setting with both diagnostic and therapeutic applications. (Id.) In certain embodiments, medical image computing can be used to generate a bone model, a patient specific model, and/or a patent specific instrument from medical imaging and/or medical imaging data.

As used herein, "model" refers to an informative representation of an object, person or system. Representational models can be broadly divided into the concrete (e.g. physical form) and the abstract (e.g. behavioral patterns, especially as expressed in mathematical form). In abstract form, certain models may be based on data used in a computer system or software program to represent the model. Such models can be referred to as computer models. Computer models can be used to display the model, modify the model, print the model (either on a 2D medium or using a 3D printer or additive manufacturing technology). Computer models can also be used in environments with models of other objects, people, or systems. Computer models can also be used to generate simulations, display in virtual environment systems, display in augmented reality systems, or the like. Computer models can be used in Computer Aided Design (CAD) and/or Computer Aided Manufacturing (CAM) systems. Certain models may be identified with an adjective that identifies the object, person, or system the model represents. For example, a "bone" model is a model of a bone, and a "heart" model is a model of a heart. (Search "model" on Wikipedia.com Jun. 13, 2021. CC-BY-SA 3.0 Modified. Accessed Jun. 23, 2021.) Of course, a model may model a whole object or an entirety of the object or the model may model or represent a portion of the object. For example, a bone model may model a whole bone or a portion of the bone. As used herein, "additive manufacturing" refers to a manufacturing process in which materials are joined together in a process that repeatedly builds one layer on top of another to generate a three-dimensional structure or object. Additive manufacturing may also be referred to using different terms including: additive processes, additive fabrication, additive techniques, additive layer manufacturing, layer manufacturing, freeform fabrication, ASTM F2792 (American Society for Testing and Materials), and 3D printing. Additive manufacturing can build the three-dimensional structure or object using computer-controlled equipment that applies successive layers of the material(s) based on a three-dimensional model that may be defined using Computer Aided Design (CAD) software. Additive manufacturing can use a variety of materials including polymers, thermoplastics, metals, ceramics, biochemicals, and the like. Additive manufacturing may provide unique benefits, as an implant together with the pores and/or lattices can be directly manufactured (without the need to generate molds, tool paths, perform any milling, and/or other manufacturing steps).

As used herein, a "resection" refers to a method, procedure, or step that removes tissue from another anatomical structure or body. A resection is typically performed by a surgeon on a part of a body of a patient. (Search "surgery" on Wikipedia.com May 26, 2021. CC-BY-SA 3.0 Modified. Accessed May 26, 2021.) Resection may be used as a noun or a verb. In the verb form, the term is "resect" and refers to an act of performing, or doing, a resection. Past tense of the verb resect is resected.

As used herein, a "guide" refers to a part, component, member, or structure designed, adapted, configured, or engineered to guide or direct one or more other parts, components, or structures. A guide may be part of, integrated with, connected to, attachable to, or coupled to, another structure, device, or instrument. In one embodiment, a guide may include a modifier that identifies a particular function, location, orientation, operation, type, and/or a particular structure of the guide. Examples of such modifiers applied to a guide, include, but are not limited to, "pin guide" that guides or directs one or more pins, a "cutting guide" that guides or directs the making or one or more cuts, a placement, deployment, or insertion guide that guides or directs the placement, positioning, orientation, deployment, installation, or insertion of a fastener and/or implant, a "cross fixation guide" that guides deployment of a fastener or fixation member, an "alignment guide" that guides the alignment of two or more objects or structures, a "navigation guide" that guides a user in navigating a course or process or procedure such as a surgical procedure, a "resection guide" that serves to guide resection of soft or hard tissue, such as in an osteotomy, a "reduction guide" can serve to guide reduction of one or more bone segments or fragments, an "placement guide" that serves to identify how an object can be placed in relation to another object or structure, and the like. Furthermore, guides may include modifiers applied due to the procedure or location within a patient for which the guide is to be used. For example, where a guide is used at a joint, the guide may be referred to herein as an "arthrodesis guide." As used herein, "feature" refers to a distinctive attribute or aspect of something. (Search "feature" on google.com. Oxford Languages, 2021. Web. 20 Apr. 2021.) A feature may include a modifier that identifies a particular function or operation and/or a particular structure relating to the feature. Examples of such modifiers applied to a feature, include, but are not limited to, "attachment feature," "bone attachment feature," "securing feature," "protruding feature," "engagement feature," "offset feature," "alignment feature," "patient-specific feature," "disengagement feature," "resection feature", "guide feature", and the like.

"Fin" refers to an appendage to another structure. A fin can also refer to a thin, rigid component or structure used to stabilize, direct, and/or orient a connected structure. (Search "fin" on wordhippo.com. WordHippo, 2023. Web. Modified. Accessed 13 Jun. 2023.)

"Cutting tool" refers to any tool that can be used to cut or resect another object. In particular, a cutting tool can refer to a manual or power tool for cutting or resecting tissue of a patient. Examples of cutting tools include, but are not limited to, a burr, an oscillating saw, a reciprocating saw, a grater saw, a drill, a mill, a side-cutting burr, a pivoting burr, a pivoting resection guide, a pivoting drill bit, or the like.

As used herein, a "handle" or knob refers to a structure used to hold, control, or manipulate a device, apparatus, component, tool, or the like. A "handle" may be designed to be grasped and/or held using one or two hands of a user. In certain embodiments, a handle or knob may be an elongated structure. In one embodiment, a knob may be a shorter stubby structure.

"Contour" refers to an outline representing or bounding a shape or form of an object. Contour can also refer to an outside limit of an object, area, or surface of the object. (Search "contour" on wordhippo.com. WordHippo, 2023. Web. Modified. Accessed 13 Jun. 2023.)

Those of skill in the art will appreciate that a resection feature may take a variety of forms and may include a single feature or one or more features that together form the resection feature. In certain embodiments, the resection feature may take the form of one or more slots. Alternatively, or in addition, a resection feature may be referenced using other names including, but not limited to, channel, cut channels, and the like.

As used herein, "side" refers to a structure or part of a structure including, but not limited to: one of a longer bounding surfaces or lines of an object especially contrasted with the ends, a line or surface forming a border or face of an object, either surface of a thin object, a bounding line or structure of a geometric figure or shape, and the like. (search "side" on Merriam-Webster.com. Merriam-Webster, 2021. Web. 3 Aug. 2021. Modified.) A side can also refer to a geometric edge of a polygon (two-dimensional shape) and/or a face or surface of a polyhedron (three-dimensional shape). (Search "side" on Wikipedia.com Jul. 21, 2021. CC-BY-SA 3.0 Modified. Accessed Aug. 3, 2021.) Side can also refer to a location on a structure. For example, a side can be a location on a structure at, or near, a furthest position away from a central axis of the structure.

As used herein, the term "side" can include one or more modifiers that define and/or orient and/or distinguish the side of an object from others based on based on where and/or how the object is deployed within or in relation to a second object. For example, in the context of an implant for a patient, sides of the implant may be labeled based on where the sides are relative to the patient when the implant is deployed. As one example, an "anterior side" of an implant or instrument refers to a side that is anterior to other sides of the implant or instrument in relation to a patient when the implant or instrument is deployed in the patient. Similarly, As one example, an "medial side" of an implant or instrument refers to a side that is medial to other sides of the implant or instrument or faces the medial side of a patient when the implant or instrument is deployed in the patient. As another example, in the context of an instrument used with a patient, sides of the instrument may be labeled based on where the sides are when the instrument is being used for its purpose. As one example, a "front side" of an instrument refers to a side that is facing a user of the instrument when the instrument is in use. As another example, a "posterior side" is a side that faces or is on a posterior side of the implant or instrument when the device is deployed on or within a patient.

"Bridge" refers to a structure, apparatus, system, and/or construct that spans a divide or opening and/or connects one side of a divide or opening to another side. (Search "bridge" on wordhippo.com. WordHippo, 2023. Web. Modified. Accessed 13 Jun. 2023.)

As used herein, an "arm" refers to an elongated structure that extends from another structure such as a base or a body. In certain embodiments, an arm can be configured to support a load (including a tension, compression, shear, torsion, and/or bending load). In certain embodiments, an arm may comprise a generally planar structure. An arm can be a separate structure connected to, or integrated with, another structure. Based on how the arm connects to or extends from another structure, such as a base or body, the arm can resemble an arm of a human or animal in that the arm can be an appendage to another structure. An arm can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. An arm can be made from a variety of materials including, metal, plastic, ceramic, wood, fiberglass, or the like. One arm may be distinguished from another based on where the arm is positioned within a structure, component, or apparatus.

As used herein, an "opening" refers to a gap, a hole, an aperture, a port, a portal, a slit, a space or recess in a structure, a void in a structure, or the like. In certain embodiments, an opening can refer to a structure configured specifically for receiving something and/or for allowing access. In certain embodiments, an opening can pass through a structure. In such embodiments, the opening can be referred to as a window. In other embodiments, an opening can exist within a structure but not pass through the structure. In other embodiments, an opening can initiate on a surface or at an edge or at a side of a structure and extend into the structure for a distance, but not pass through or extend to another side or edge of the structure. In other embodiments, an opening can initiate on a surface or at an edge or at a side of a structure and extend into the structure until the opening extends through or extends to another side or edge of the structure. An opening can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. As used herein, the term "opening" can include one or more modifiers that define specific types of "openings" based on the purpose, function, operation, position, or location of the "opening." As one example, a "fastener opening" refers to an "opening" adapted, configured, designed, or engineered to accept or accommodate a "fastener."

The present disclosure discloses surgical systems and methods by which a bone condition, such as a deformity, may be corrected. Known methods of correcting bone conditions are often limited to a finite range of discretely sized instruments. A patient with an unusual condition, or anatomy that falls between instrument sizes, may not be readily treated with such systems.

Furthermore, patient-specific cutting guides may be used for various other procedures on the foot, or on other bones of the musculoskeletal system. Patient-specific cutting guides may be used for various procedures involving osteotomy, including but not limited to arthroplasty, fusion, and deformity correction procedures. According to one example, patient-specific cutting guides similar to the cutting guide 300 may be used for the metatarsophalangeal ("MTP") joint. A method similar to the method 100 may be employed.

In some embodiments, one or more articulating surfaces of a joint may be replaced and/or resurfaced. For example, for the MTP joint, a patient-specific cutting guide may be used to determine the angles of cuts on the distal metatarsal or the proximal phalanx in preparation for replacement or resurfacing of the metatarsal head and/or the proximal phalangeal base. Implants for either the metatarsal or the phalanx may be customized to match the patient's original anatomy, such as the curvature of the MTP joint. In other embodiments, an MTP joint may be fused through the use of patient-specific cutting guides. Patient-specific cutting guides may be used to treat (for example, via fusion, resurfacing, and/or arthroplasty) any joint in the body, using methods similar to the method 100.

According to other examples, patient-specific cutting guides may be used to carry out an Evans calcaneal osteotomy and/or a medializing calcaneal osteotomy.

Patient-specific instruments will be shown and described, in relation to an Evans calcaneal osteotomy, and a medializing calcaneal osteotomy.

FIG. 1A is a flowchart diagram depicting a method 100 for correcting a bone condition, according to one embodiment. The method 100 may be used for any of a wide variety of bone conditions, including but not limited to deformities, fractures, joint failure, and/or the like. Further, the method 100 may provide correction with a wide variety of treatments, including but not limited to arthroplasty, arthrodesis, fracture repair, and/or the like.

As shown, the method 100 may begin with a step 102 in which a CT scan (or another three-dimensional image, also referred to as medical imaging) of the patient's anatomy is obtained. The step 102 may entail capturing a scan of only the particular bone(s) to be treated, or may entail capture of additional anatomic information, such as the surrounding tissues. Additionally or alternatively, the step 102 may entail receiving a previously captured image, for example, at a design and/or fabrication facility. Performance of the step 102 may result in possession of a three-dimensional model of the patient's anatomy, or three-dimensional surface points that can be used to construct such a three-dimensional model.

After the step 102 has been carried out, the method 100 may proceed to a step 104 in which a CAD model of the patient's anatomy (including one or more bones) is generated. The CAD model may be one example of a bone model. The CAD model may be of any known format, including but not limited to SolidWorks, Catia, AutoCAD, or DXF. In some embodiments, customized software may be used to generate the CAD model from the CT scan. The CAD model may only include the bone(s) to be treated and/or may include surrounding tissues. In alternative embodiments, the step 104 may be omitted, as the CT scan may capture data that can directly be used in future steps without the need for conversion.

In one embodiment, the CAD model generated and/or patient-specific instrumentation, implants, and/or plan for conducting an operative procedure, may be enhanced by the use of advanced computer analysis system, machine learning, and/or automated/artificial intelligence. For example, these technologies may be used to revise a set of steps for a procedure such that a more desirable outcome is achieved.

In a step 106, the CAD model and/or CT scan data may be used to model patient-specific instrumentation that can be used to correct the condition, as it exists in the patient's anatomy. In some embodiments, any known CAD program may be used to view and/or manipulate the CAD model and/or CT scan, and generate one or more instruments that are matched specifically to the size and/or shape of the patient's bone(s). In some embodiments, such instrumentation may include a cutting guide that is attachable to one or more bones, with one or more resection features that facilitate resection of the one or more bones pursuant to a procedure such as arthroplasty or arthrodesis. In some embodiments, performance of the step 106 may include modelling an instrument with a bone apposition surface that is shaped to match the contour of a surface of the bone, such that the bone apposition surface can lie directly on the corresponding contour.

In a step 108, the model(s) may be used to manufacture patient-specific instrumentation and/or implants. This may be done via any known manufacturing method, including casting, forging, milling, additive manufacturing, and/or the like. Additive manufacturing may provide unique benefits, as the model may be directly used to manufacture the instrumentation and/or implants (without the need to generate molds, tool paths, and/or the like beforehand). Such instrumentation may optionally include a cutting guide with the bone apposition surface and one or more resection features as described above.

In addition to, or in the alternative to the step 108, the model(s) may be used to select from available sizes of implants and/or instruments and advise the surgeon accordingly. For example, where a range of cutting guides are available for a given procedure, analysis of the CAD data may facilitate pre-operative selection of the optimal cutting guide and/or optimal placement of the cutting guide on the bone. Similarly, if a range of implants may be used for a given procedure, analysis of the CAD data may facilitate pre-operative selection of the optimal implant(s). More particularly, properly-sized spacers, screws, bone plates, and/or other hardware may be pre-operatively selected.

Thus, the result of the step 108 may be provision, to the surgeon, of one or more of the following: (1) one or more patient-specific instruments; (2) one or more patient-specific implants; (3) an instrument, selected from one or more available instrument sizes and/or configurations; (4) an implant, selected from one or more available implant sizes and/or configurations; (5) instructions for which instrument(s) to select from available instrument sizes and/or configurations; (6) instructions for which implant(s) to select from available implant sizes and/or configurations; (7) instructions for proper positioning or anchorage of one or more instruments to be used in the procedure; and (8) instructions for proper positioning or anchorage of one or more implants to be used in the procedure. These items may be provided to the surgeon directly, or to a medical device company or representative, for subsequent delivery to the surgeon.

In a step 110, the manufactured instrumentation may be used in surgery to facilitate treatment of the condition. In some embodiments, this may entail placing the modelled bone apposition surface against the corresponding contour of the bone used to obtain its shape, and then using the resection feature(s) to guide resection of one or more bones. Then the bone(s) may be further treated, for example, by attaching one or more joint replacement implants (in the case of joint arthroplasty), or by attaching bone segments together (in the case of arthrodesis or fracture repair). Prior to completion of the step 110, the instrumentation may be removed from the patient, and the surgical wound may be closed.

As mentioned previously, the method 100 may be used to correct a wide variety of bone conditions. One example of the method 100 will be shown and described in connection with FIG. 1B, for correction of a bunion deformity of the foot.

In certain embodiments, one or more of a method, apparatus, and/or system of the disclosed solution can be used for training a surgeon to perform a patient-specific procedure or technique. In one embodiment, the CAD model generated and/or patient-specific instrumentation, implants, and/or plan for conducting an operative procedure can be used to train a surgeon to perform a patient-specific procedure or technique.

In one example embodiment, a surgeon may submit a CT scan of a patient's foot to an apparatus or system that implements the disclosed solution. Next, a manual or automated process may be used to generate a CAD model and for making the measurements and correction desired for the patient. In the automated process, advanced computer analysis system, machine learning and automated/artificial intelligence may be used to generate a CAD model and/or one or more patient-specific instruments and/or operation plans. For example, a patient-specific cutting guide may be fabricated that is registered to the patient's anatomy using a computer-aided machine (CAM) tool. In addition, a CAM tool may be used to fabricate a 3D structure representative of the patient's anatomy, referred to herein as a patient-specific synthetic cadaver. (e.g. one or more bones of a patient's foot). Next, the patient-specific cutting guide and the patient-specific synthetic cadaver can be provided to a surgeon who can then rehearse an operation procedure in full before going into an operating room with the patient.

In certain embodiments, the patient-specific cutting guide can be used to preposition and pre-drill a plate system for fixation purposes. Such plate systems may be optimally placed, per a CT scan, after a correction procedure for optimal fixation outcome. In another embodiment, the CAD model and/or automated process such as advanced computer analysis system, machine learning and automated/artificial intelligence may be used to measure a depth of the cut through the patient-specific cutting guide for use with robotics apparatus and/or systems which would control the depth of each cut within the guide to protect vital structures below or adjacent to a bone being cut. In another embodiment, the CAD model and/or automated process such as advanced computer analysis system, machine learning and automated/artificial intelligence may be used to define desired fastener (e.g. bone screw) length and/or trajectories through a patient-specific cutting guide and/or implant. The details for such lengths, trajectories, and components can be detailed in a report provided to the surgeon preparing to do a procedure.

FIG. 1B is a flowchart diagram depicting a method 120 for correcting bunion deformity of the human foot, according to one embodiment. The method 120 may be used to carry out an arthrodesis procedure by which the first metatarsocuneiform joint is removed and the first cuneiform and first metatarsal are secured together in a manner that properly aligns the first metatarsal, providing correction of the deformity.

As shown, the method 120 may begin with a step 122 in which a CT scan (or another three-dimensional image) of the patient's foot is obtained. The step 122 may entail capturing a scan of only the first cuneiform and first metatarsal, or may entail capture of additional anatomic information, such as the entire foot. Additionally or alternatively, the step 122 may entail receipt of previously captured image data. Capture of the entire foot in the step 122 may facilitate proper alignment of the first metatarsal with the rest of the foot (for example, with the second metatarsal). Performance of the step 122 may result in generation of a three-dimensional model of the patient's foot, or three-dimensional surface points that can be used to construct such a three-dimensional model.

After the step 122 has been carried out, the method 120 may proceed to a step 124 in which a CAD model of the relevant portion of the patient's anatomy is generated. The CAD model may optionally include the bones of the entire foot, like the CT scan obtained in the step 122. In alternative embodiments, the step 124 may be omitted in favor of direct utilization of the CT scan data, as described in connection with the step 104.

In a step 126, the CAD model and/or CT scan data may be used to model patient-specific instrumentation that can be used to correct the bunion deformity. Such instrumentation may include a cutting guide that is attachable to the first cuneiform and the first metatarsal, with two resection features that facilitate resection of the cuneiform and the metatarsal in preparation for arthrodesis. In some embodiments, performance of the step 126 may include modelling the cutting guide with a bone apposition surface that is shaped to match contours of the surfaces of the cuneiform and the metatarsal, such that the bone apposition surface can lie directly on the corresponding contours of the first cuneiform and the first metatarsal.

In a step 128, the model(s) may be used to manufacture patient-specific instrumentation and/or instruments. This may include manufacturing the cutting guide with the bone apposition surface and the resection features as described above. As in the step 108, the step 128 may additionally or alternatively involve provision of one or more instruments and/or implants from among a plurality of predetermined configurations or sizes. Further, the step 128 may additionally or alternatively involve provision of instructions for placement and/or anchorage of one or more instruments and/or instruments to carry out the procedure.

In a step 130, the manufactured cutting guide may be used in surgery to facilitate treatment of the condition. Specifically, the bone apposition surface of the cutting guide may be placed against the corresponding contours of the first cuneiform and the first metatarsal. The resection features (for example, slots) may then be positioned on either side of the joint between the first cuneiform and the first metatarsal to guide resection of the first metatarsal and the first cuneiform to remove the intervening joint. The cutting guide may then be removed, and the remaining portions of the first cuneiform and the first metatarsal may be placed to abut each other. The cutting guide may have been shaped such that the cuts made to the first cuneiform and the first metatarsal are properly oriented to bring the first metatarsal back into its proper orientation relative to the rest of the foot. The first cuneiform and the first metatarsal may be secured together using a bone plate or the like. The surgical wound may be closed to allow the foot to heal, and to allow the first cuneiform and the first metatarsal to fuse together.

The method 100 and the method 120 are merely exemplary. Those of skill in the art will recognize that various steps of the method 100 and the method 120 may be reordered, omitted, and/or supplemented with additional steps not specifically shown or described herein.

As mentioned previously, the method 120 is one species of the method 100; the present disclosure encompasses many different procedures, performed with respect to many different bones and/or joints of the body. Exemplary steps and instrumentation for the method 120 will further be shown and described in connection with FIGS. 2 through 7D. Those of skill in the art will recognize that the method 120 may be used in connection with different instruments; likewise, the instruments of FIGS. 2 through 7D may be used in connection with methods different from the method 100 and the method 120.

FIG. 2A is a perspective dorsal view of a foot 200. The foot 200 may have a medial cuneiform 202, an intermediate cuneiform 204, lateral cuneiform 206, a first metatarsal 208, a second metatarsal 210, third metatarsal 212, fourth metatarsal 214, fifth metatarsal 216, navicular 218, cuboid 220, talus 222, and calcaneus 224, among others. The medial cuneiform 202 and the intermediate cuneiform 204 may be joined together at a first metatarsocuneiform joint, and the first metatarsal 208 and the second metatarsal 210 may be joined together at a second metatarsocuneiform joint. The foot 200 includes a set of proximal phalanges numbered first through fifth (230, 232, 234, 236, 238) and a set of distal phalanges numbered first through fifth (240, 242, 244, 246, 248) and a set of middle phalanges numbered second through fifth (250, 252, 254, 256).

FIG. 2B is a perspective lateral view of a foot 200, with bones of the foot labeled.

FIG. 2C is a perspective medial view of a foot illustrating a dorsal side 280 and a plantar side 282. The foot 200, as illustrated, may have a tibia 226 and a fibula 228, among others. Dorsal refers to the top of the foot. Plantar refers to the bottom of the foot. Proximal 284 is defined as "closer to the primary attachment point". Distal 286 is defined as "further away from the attachment point". Plantarflex or plantarflexion 288 means movement toward the plantar side 282 of a foot or hand, toward the sole or palm. Dorsiflex or dorsiflexion means movement toward the dorsal side 278 of a foot or hand, toward the top. FIG. 2D is a perspective dorsal view of the foot 200. A transverse plane is the plane that shows the top of the foot. A lateral side 292 means a side furthest away from the midline of a body, or away from a plane of bilateral symmetry of the body. A medial side 294 means a side closest to the midline of a body, or toward a plane of bilateral symmetry of the body. For a Lapidus procedure, the intermetatarsal (IM) angle 296 is the angle to be corrected to remove the hallux valgus (bunion) deformity.

Figure 2E:
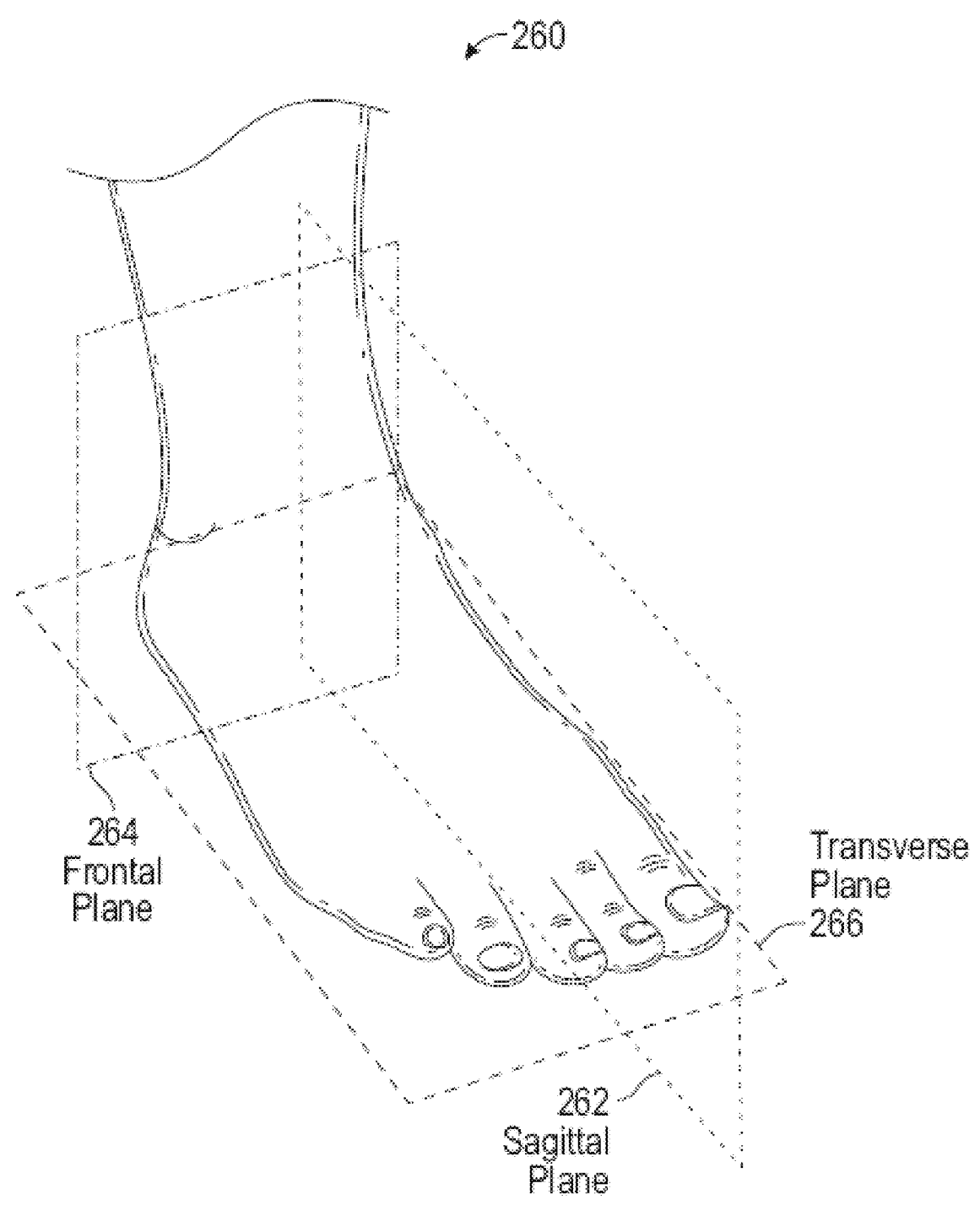
FIG. 2E is a view of a foot illustrating common planes of reference for a human foot.

FIG. 2E is a view of a foot illustrating common planes 260 of reference for a human foot. FIG. 2E illustrates a sagittal plane 262 that divides the foot into a right section and a left section half. The sagittal plane 262 is perpendicular to frontal or coronal plane 264 and the transverse plane 266. In the foot, the frontal plane 264 generally runs vertically through the ankle and the transverse plane 266 generally runs horizontally through the midfoot and toes of the foot.

Figure 2F:
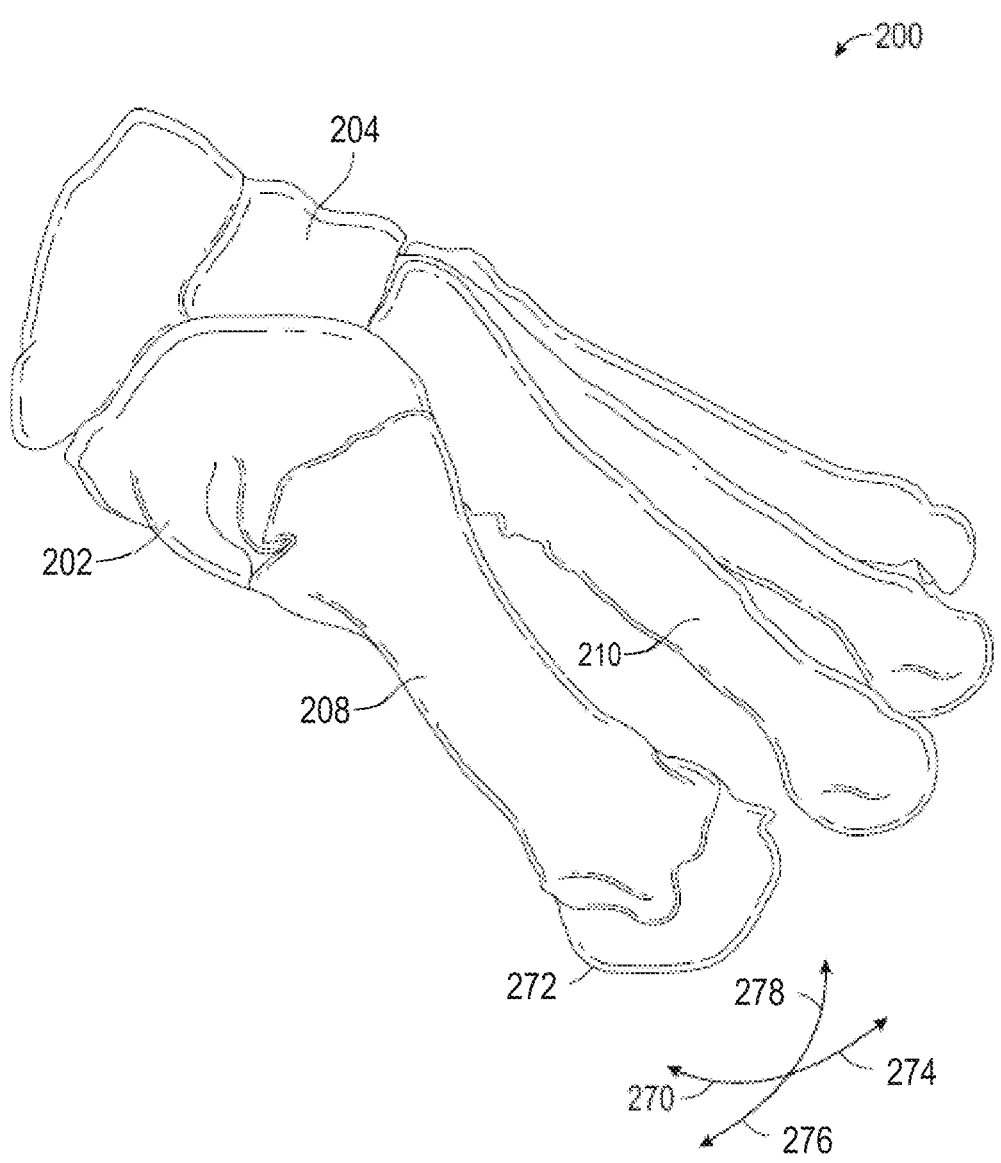
FIG. 2F is a perspective view of a portion of a foot with a bunion deformity to be treated through use of the apparatuses, systems, and/or methods of the present disclosure.
Figures 3A, 3B, 3C:
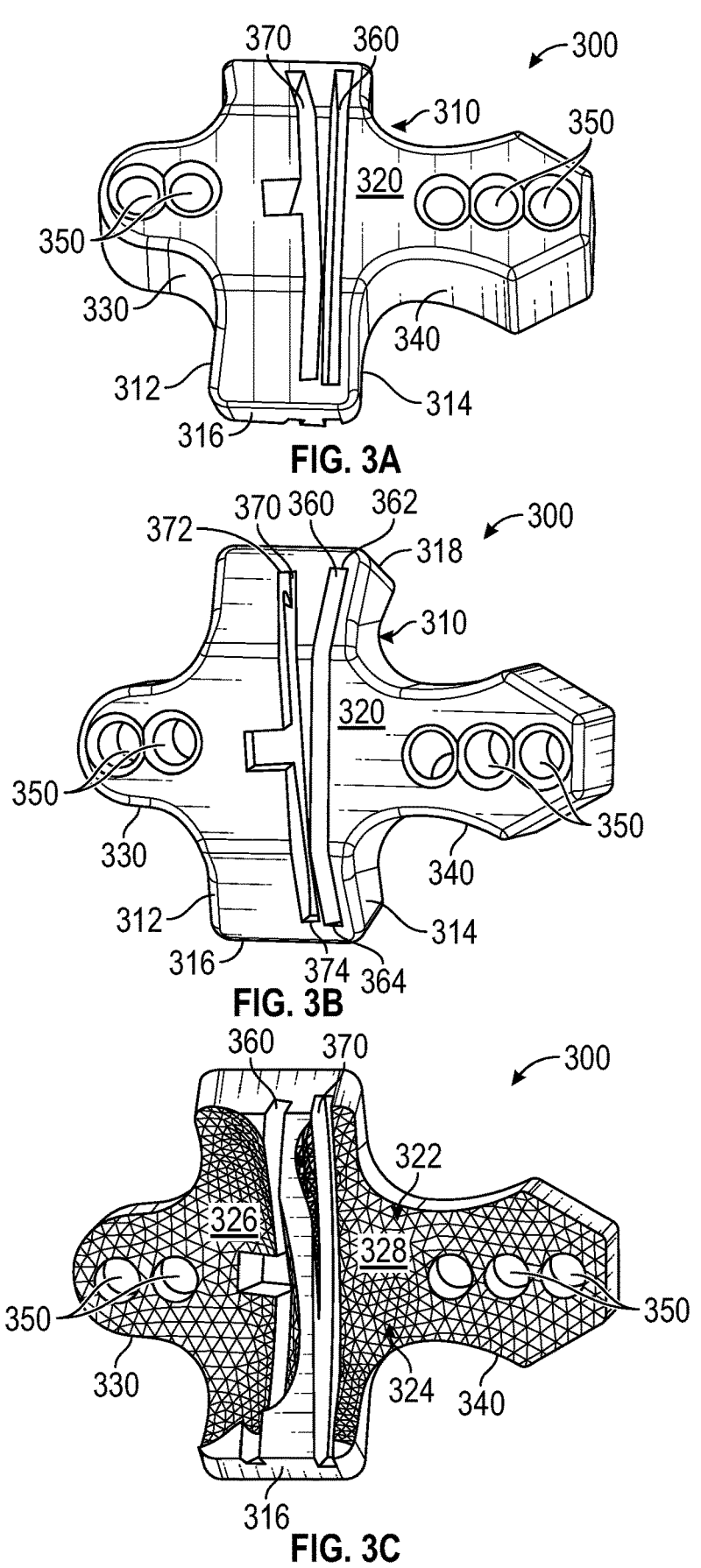

FIG. 2F is a perspective view of a portion of a foot 200 with a bunion deformity to be treated through use of the method 100 (and more specifically, the method 120) described above. The foot 200 may have a medial cuneiform 202, a intermediate cuneiform 202, a first metatarsal 208, and a second metatarsal 210. The medial cuneiform 202 and the first metatarsal 208 may be joined together at a first metatarsocuneiform joint, and the intermediate cuneiform 202 and the second metatarsal 210 may be joined together at a second metatarsocuneiform joint.

The first metatarsal 208 may be excessively angled in a medial direction 270 (i.e., toward the lower left-hand corner of the page), causing a painful protrusion at a distal end 272 of the first metatarsal 208, and further causing the phalanges (not shown) attached to the distal end 272 to be angled excessively in a lateral direction 274 (i.e., pointing toward the other phalanges of the foot, rather than pointing directly forward). The excessive medial angulation of the first metatarsal 208 may also result in an excessive gap between the first metatarsal 208 and the second metatarsal 210.

The first metatarsal 208 may further be offset in a plantar direction 276 or in a dorsal direction 290, relative to the remainder of the foot 200. Accordingly, the orientation of the first metatarsal 208 may need to be adjusted to move the distal end 272 in the lateral direction 274 and in the plantar direction 276 and/or in the dorsal direction 278.

Every deformity is different; accordingly, the degree of angular adjustment needed in each direction may be different for every patient. Use of a patient-specific cutting guide may help the surgeon obtain the optimal realignment in the lateral direction 274 and in the plantar direction 276 or the dorsal direction 278. Conversely, use of one of several differently-sized cutting guides may provide only approximate correction, as the surgeon may not have a guide that precisely matches the correction needed for the foot 200, and must thus choose the cutting guide that most closely provides the desired correction. Such differently sized cutting guides would not be contoured to fit the medial cuneiform 202 or the first metatarsal 208, thus introducing additional potential for error as the surgeon must properly align the selected cutting guide.

Thus, providing a patient-specific cutting guide may provide unique benefits. Specifically, the patient-specific cutting guide may provide precise correction of the deformity present in the foot 200 and may also reduce the likelihood of improper correction due to misalignment of the cutting guide on the foot 200. The optimal cut provided by such a cutting guide may further reduce the likelihood that additional procedures, such as attachment of the first metatarsal 208 to the second metatarsal 210 to each other with screws or the like, will be needed to provide the desired correction. Any such additional procedure carries its own added surgical burden and risk of failure. Thus, the use of patient-specific instrumentation may shorten surgery, accelerate recovery, and reduce the risk of complications.

FIGS. 3A-19H are top perspective, top perspective, bottom, front elevation, rear elevation, right, left, and alternative top perspective, respectively, of a patient-specific cutting guide, or cutting guide 300, according to one alternative embodiment.

The cutting guide 300 may be designed to facilitate resection of a first cuneiform near a distal end and a first metatarsal near a proximal end with planar cuts at the proper angles to provide dual-plane correction of the orientation of the first metatarsal relative to the first cuneiform, thereby providing correction in a lateral direction, in a plantar direction, and/or a dorsal direction.

As shown, the cutting guide 300 may have a body 310 with a monolithic construction and the general shape of a rectangular prism. As used herein, a "body" refers to a main or central part of a structure. The body may serve as a structural component to connect, interconnect, surround, enclose, and/or protect one or more other structural components. A body may be made from a variety of materials including, but not limited to, metal, plastic, ceramic, wood, fiberglass, acrylic, carbon, biocompatible materials, biodegradable materials or the like. A body may be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others. In one embodiment, a body may include a housing or frame or framework for a larger system, component, structure, or device. A body may include a modifier that identifies a particular function, location, orientation, operation, and/or a particular structure relating to the body. Examples of such modifiers applied to a body, include, but are not limited to, "inferior body," "superior body," "lateral body," "medial body," and the like.

The body 310 includes a proximal side 312, a distal side 314, a medial side 316, a lateral side 318, a superior side 320, and an inferior side 322. In the illustrated embodiment, the body 310 may also include a proximal arm 330 that extends from the body 310 and a distal arm 340 that extends from the body 310. The proximal side 312 is the side closest to the core of the patient when the cutting guide 300 is in use. The distal side 314 is the side furthest from the core of the patient when the cutting guide 300 is in use. The medial side 316 is the side facing medially when the cutting guide 300 is in use. The lateral side 318 is the side facing laterally when the cutting guide 300 is in use. The superior side 320 is the side facing up away from the bone(s) when the cutting guide 300 is in use. The inferior side 322 is the side facing down, facing, and/or contacting the bone(s) (e.g., contacting a surface of one or more bones) when the cutting guide 300 is in use.

The inferior side 322 may be custom contoured to match the shapes of one or more of the surfaces of the first cuneiform and/or the first metatarsal. In one embodiment, the inferior side 322 may include a bone engagement surface 324. The bone engagement surface 324 can be shaped to match a first surface of a first bone and a second surface of a second bone of a joint.

"Bone engagement surface" refers to a surface or other feature of an object, instrument, or apparatus, such as an implant that is oriented toward, faces, or contacts one or more bones of a patient. In one aspect, the bone engagement surface may abut, touch, or contact a surface of a bone. In another aspect, the bone engagement surface, or parts of the bone engagement surface, may be close to, but not abut, touch, or contact a surface of the bone. In certain aspects, the bone engagement surface can be configured to engage with a surface of one or more bones. Such a bone engagement surface may include projections and recesses that correspond to and match projections and recesses of the one or more bone surfaces. As used herein, matching projections and recesses means that a projection on one structure is of the substantially same size and shape as a corresponding recess of the other structure such that when the two structures are brought into contact or close proximity each projection of one structure seats/sits/fits within the recess of the other structure. A bone engagement surface may include flat parts of a side or surface, contoured parts of a side or surface, projections and/or recesses of a side or surface, or any combination of these. Such variations in the make-up and configuration of a bone engagement surface can exist within a single embodiment or separate embodiments. Said another way, a bone engagement surface is a surface that is the mirror inverse of a surface of the bone that the bone engagement surface abuts, touches, and/or contacts.

"Joint" or "Articulation" refers to the connection made between bones in a human or animal body which link the skeletal system to form a functional whole. Joints may be biomechanically classified as a simple joint, a compound joint, or a complex joint. Joints may be classified anatomically into groups such as joints of hand, elbow joints, wrist joints, axillary joints, sternoclavicular joints, vertebral articulations, temporomandibular joints, sacroiliac joints, hip joints, knee joints, articulations of foot, and the like. (Search "joint" on Wikipedia.com Dec. 19, 2021. CC-BY-SA 3.0 Modified. Accessed Jan. 20, 2022.)

In one example, the bone engagement surface 324 can be shaped such that the bone engagement surface 324 matches a surface of a cuneiform bone and a surface of a metatarsal bone of a tarsometatarsal ("TMT") joint. The bone engagement surface 324 can be so shaped because it is fabricated from a bone model of the patient's bones. The body 310 is configured, designed, and/or fabricated to seat transverse to a joint (e.g., a TMT joint) with the bone engagement surface 324 engaging a first surface of a first bone and a second surface of a second bone.

In one embodiment, the body 310 is configured to reside on the dorsal surfaces of the first cuneiform and the first metatarsal to provide proper alignment of the body 310 with the metatarsocuneiform joint (e.g., the joint between the first metatarsal and the medial cuneiform bone, aka a TMT joint). In another embodiment, the body 310 is configured to reside or sit between the medial surfaces and the dorsal surfaces, or on the medial surfaces of the first cuneiform and the first metatarsal to provide proper alignment of the body 310 with the metatarsocuneiform joint (e.g., the joint between the first metatarsal and the medial cuneiform bone) for an osteotomy.

In certain embodiments, the bone engagement surface 324 may include a cuneiform apposition portion 326 and a metatarsal apposition portion 328. As shown, the cuneiform apposition portion 326 may be contoured to match the contour of the surface of the first cuneiform on which it is to rest, and the metatarsal apposition portion 328 may similarly be contoured to match the contour of the surface of the first metatarsal on which it is to rest. (See FIG. 3C) Thus, the body 310 may have only one stable position and orientation relative to the first cuneiform and the first metatarsal during a surgical osteotomy for correcting the condition.

Advantageously, the fidelity of the patient imaging data enables the bone model, preliminary cutting guide model, and patient specific instrument (e.g., patient specific cutting guide, patient specific pin guide, patient specific alignment guide, etc.) to uniquely match a particular patient. Consequently, the bone engagement surface 324 can engage the surfaces of the bones of a joint in a single configuration. Such a close matching fit facilitates the surgical osteotomy.

FIG. 3D illustrates the cutting guide 300 from a view facing the medial side 316. FIG. 3E illustrates the cutting guide 300 from a view facing the lateral side 318. In certain embodiments, the cutting guide 300 may include one or more features that facilitate use of the cutting guide 300 while avoiding certain soft tissue in the vicinity of a joint. For example, the medial side 316 may include a medial superior surface 332 and a medial inferior surface 334 that meet at a medial edge 336. Advantageously, the medial inferior surface 334 may extend from inferior side 322 to the medial edge 336 at an angle such that the medial inferior surface 334 does not impinge soft tissue near the joint (e.g., near a medial end of the joint). In certain embodiments, the angle may range between about 80 and about 170 degrees. In another example, the lateral side 318 may include a lateral superior surface 342 and a lateral inferior surface 344 that meet at a lateral edge 346. Of course, the medial superior surface 332 may extend from the superior side 320 to the medial edge 336 at an angle. The angle of the medial superior surface 332 may enable use of the cutting guide 300 in tighter openings and thus minimize the size of incisions used for a procedure.

Advantageously, the lateral inferior surface 344 may extend from inferior side 322 to the lateral edge 346 at an angle such that the lateral inferior surface 344 does not impinge soft tissue near the joint (e.g., near a medial end of the joint). In certain embodiments, the angle may range between about 80 and about 170 degrees. Of course, the lateral superior surface 342 may extend from the superior side 320 to the lateral edge 346 at an angle. The angle of the lateral superior surface 342 may enable use of the cutting guide 300 in tighter openings and thus minimize the size of incisions used for a procedure.

The body 310 may further include resection features that guide a cutter to resect the first cuneiform and the first metatarsal in the manner needed to make the desired correction. For example, the resection features may be used to guide a planar cutting blade, an arcuate cutting blade, a drill or mill, a burr, and/or the like.

In the embodiment of FIGS. 3A through 3H, the resection features may guide a reciprocating planar blade, such as that of a surgical bone saw, that forms planar cuts in the first cuneiform and the first metatarsal. Various manual or powered tools may be used to form the planar cuts. In one embodiment, a sagittal bone saw can be used. In one example, the resection features may take the form of a first slot 360 and a second slot 370. The first slot 360 may include a lateral end 362 and a medial end 364. The second slot 370 may include a lateral end 372 and a medial end 374.

In one embodiment, the first slot 360 and the second slot 370 extend from the superior side 320 to the inferior side 322. In certain embodiments, the first slot 360 may extend from near the lateral side 318 to near the medial side 316. In other embodiments, one of, or both of, the first slot 360 and the second slot 370 may extend from one of the medial side 316 or the lateral side 318 of the body 310. In certain embodiments, the first slot 360 and second slot 370 intersect. In other embodiments, the first slot 360 and second slot 370 do not intersect.

Thus, upon desired positioning of the cutting guide 300, the second slot 370 may be positioned over at least a portion of the first cuneiform to facilitate resection of the first cuneiform, while the first slot 360 may be positioned over at least a portion of the first metatarsal to facilitate resection of the first metatarsal. In one embodiment, the second slot 370 is positioned near the distal end of the first cuneiform and the first slot 360 is positioned near the proximal end of the first metatarsal. The first slot 360 and second slot 370 together, with the bone engagement surface 324 overlying the first cuneiform and the first metatarsal, are positioned to guide resection of the first cuneiform and the first metatarsal during a surgical osteotomy for correcting a condition.

In alternative embodiments, a resection feature may be designed to guide a different type of cutter, such as a drill, mill, or side-cutting burr. In such embodiments, the resection feature may not be a slot, but may instead be a translatable or rotatable cutter retainer that guides translation and/or rotation of the cutter relative to the bone. In certain embodiments, two or more resection features may be replaced by a single resection feature sized to permit a surgeon to resect both a first cuneiform and a first metatarsal using a cutting guide 300.

In one embodiment, a first resection feature is configured to define a first cut surface that can be formed by resecting a first bone. A second resection feature is configured to define a second cut surface that can be formed by resecting a second bone. In such an embodiment, one or the other or both of the first cut surface and the second cut surface can be oriented according to one or more angles relative to landmarks on the bones or other anatomical structures.

Alternatively, or in addition, in certain embodiments, one or both of, the first resection feature and second resection feature may be positioned on, or in, the body 310 and/or have an orientation based on patient imaging data. The patient imaging data can be used to position and orient one, or both, of the first resection feature and second resection feature such that formation of one, or both, of the first cut surface and the second cut surface and fixation of the two cut surfaces against each other mitigates a condition of the patient. For example, as described in the present disclosure, patient imaging data can be used to generate bone models of bones of the patient. The bone models can be used to determine and/or define contours for a bone engagement surface 324, a position for a first slot 360, an orientation for a first slot 360, a position for a second slot 370, an orientation for a second slot 370, as well as other features and attributes of one or more patient specific instruments that can be used in a procedure.

"Cut surface" refers to a surface of an object that is created or formed by the removal of one or more parts of the object that includes the original surface. Cut surfaces can be created using a variety of methods, tools, or apparatuses and may be formed using a variety of removal actions, including, but not limited to, fenestrating, drilling, abrading, cutting, sawing, chiseling, digging, scrapping, and the like. Tools and/or methods used for forming a cut surface can include manual, mechanical, motorized, hydraulic, automated, robotic, and the like. In certain embodiments, the cut surface (s) are planar.

"Orientation" refers to a direction, angle, position, condition, state, or configuration of a first object, component, part, apparatus, system, or assembly relative to another object, component, part, apparatus, system, assembly, reference point, reference axis, or reference plane.

Figure 4:
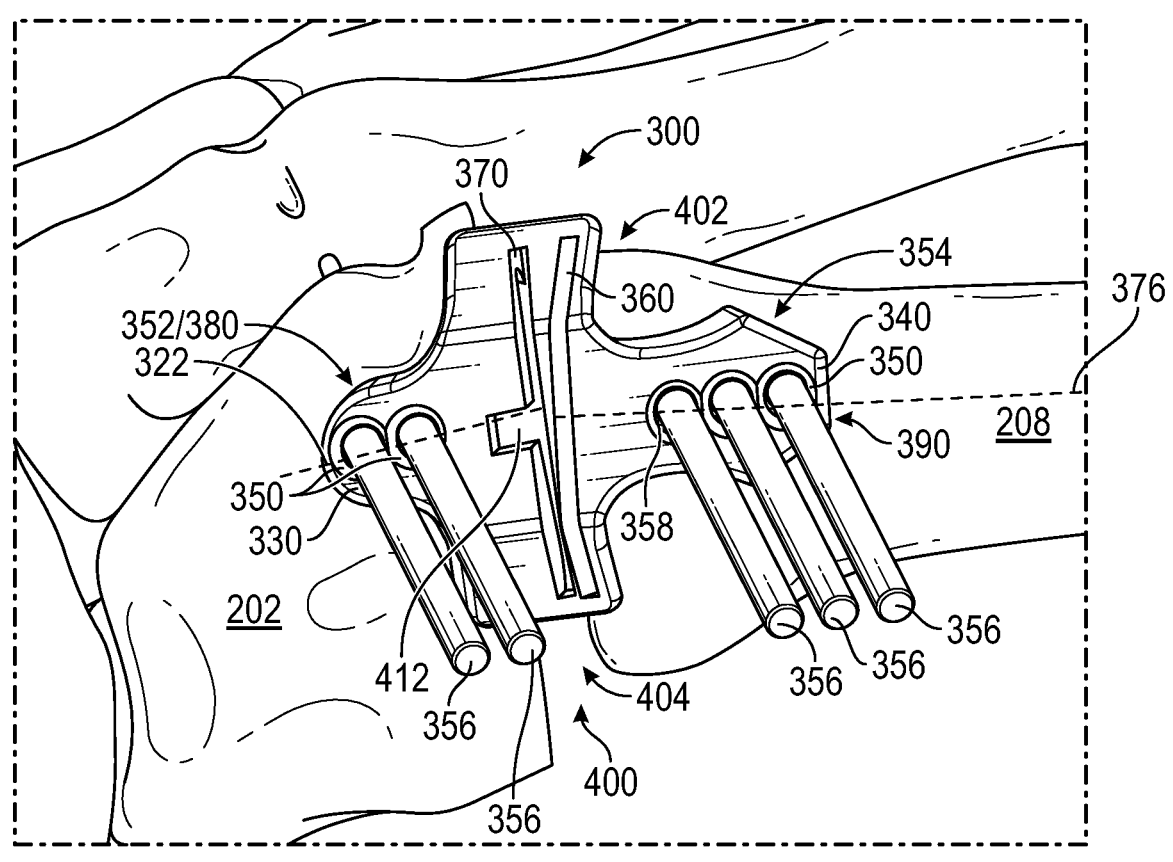
FIG. 4 illustrates a perspective view of a first cuneiform and a first metatarsal with one embodiment of a patient-specific cutting guide positioned over a tarsometatarsal ("TMT") joint.

FIG. 4 illustrates one embodiment of the cutting guide 300 secured to a first metatarsal 208 and a medial cuneiform 202. In the illustrated embodiment, the first resection feature may take the form of the first slot 360 and the second resection feature may take the form of the second slot 370. Referring now to FIGS. 4 and 3D, the position and/or angles (e.g., orientation) of one or both of the resection features based on patient imaging data is illustrated. In the illustrated embodiment, the first slot 360 is positioned between the distal side 314 and the second slot 370. The first slot 360 is oriented based on a desired angle for mitigating the condition of the patient. In one example, the first slot 360 is angled perpendicular to a longitudinal axis of the first metatarsal 208. This orientation of the first slot 360 enables the first cut surface to extend from the body 310 toward the bone to form a cut surface that is also perpendicular to the longitudinal axis 376 of one of the bones of a joint. "Longitudinal axis" refers to an axis of a structure, device, object, apparatus, or part thereof that extends from one end of a longest dimension to an opposite end. Typically, a longitudinal axis passes through a center of the structure, device, object, apparatus, or part thereof along the longitudinal axis. The center point used for the longitudinal axis may be a geometric center point and/or a mass center point. In the illustrated embodiment, the longitudinal axis 376 is the longitudinal axis of the first metatarsal 208.

In the illustrated embodiment, the second slot 370 is positioned between the proximal side 312 and the first slot 360. In addition in the illustrated embodiment, the second slot 370 is oriented based on a desired angle for mitigating the condition of the patient. In the illustrated embodiment, the orientation of the second slot 370 can be described in reference to a first angle A and a second angle B. FIG. 3D illustrates first angle A. In one embodiment, a second cut surface formed by resection using second slot 370 extends inferiorly away from a first cut surface formed by resection using first slot 360. Described another way, angle A is an angle between a first plane 378 that includes the first slot 360 and a first cut surface formed by resection using first slot 360 and a second plane that includes the second slot 370 and a second cut surface formed by resection using second slot 370, the second plane extending from the first plane toward the proximal side 312 of the body 310. In certain embodiments, angle A can range between about 4 degrees to about 18 degrees. In certain embodiments, angle A may start at 0 degrees and then increase to a positive number of degrees as illustrated or decrease to a negative number of degrees depending on how a surgeon may prescribe adjustments for a correction.

FIG. 3H illustrates second angle B. In one embodiment, a second cut surface formed by resection using second slot 370 extends posteriorly away from a first cut surface formed by resection using first slot 360. Described another way, in the illustrated embodiment, angle B is an angle between the first plane 378 that includes the first slot 360 and a first cut surface formed by resection using first slot 360 and a third plane 381 that includes the second slot 370 and a second cut surface formed by resection using second slot 370, the third plane 381 extending from the first plane toward the proximal side 312 of the body 310. In certain embodiments, angle B can range between about 0 degrees to about 35 degrees. In certain embodiments, angle B may start at 0 degrees and then increase to a positive number of degrees as illustrated or decrease to a negative number of degrees depending on how a surgeon may prescribe adjustments for a correction.

Those of skill in the art will appreciate that the position and orientation of the first slot 360 and second slot 370 and the corresponding cut surface a surgeon can form using these resection features can vary depending on the anatomical structures of the patient, the osteotomy procedure being performed, preferences of the surgeon, the nature of the condition, and the like. For example in the illustrated embodiment, the medial end 364 of the first slot 360 is closer to the medial end 374 of the second slot 370 than the lateral end 362 is in relation to the lateral end 372. In another embodiment, the lateral end 362 of the first slot 360 may be closer to the lateral end 372 of the second slot 370 than the medial end 364 is in relation to the medial end 374. Of course in another embodiment, the first slot 360 and second slot 370 may be configured such that a first distance between lateral end 362 and lateral end 372 and a second distance between medial end 364 and medial end 374 are substantially the same.

Referring to FIG. 3D, in one embodiment, anatomical data about the patient can be used to define other structures of the cutting guide 300 or other patient specific instruments. For example, anatomical data about the patient that can be captured in the patient imaging data (e.g., due to the fidelity of the technology providing the patient imaging data) can be used to define how deep a first resection feature and/or second resection feature is. Controlling the depth of the first resection feature and/or second resection feature can be used to manage how deep a surgeon's cutting instruments can reach within the first resection feature and/or second resection feature. Managing a depth for one or more resection features may be referred to as defining a patient specific height for the cutting guide 300.

For example, in one embodiment, patient imaging data can be used to define a distance between at a first top edge 366 of the first resection feature (e.g., first slot 360) and the first surface (e.g., a surface of a first bone such as a first metatarsal 208). Alternatively, or in addition, patient imaging data can be used to define a distance between at a second top edge 368 of the second resection feature (e.g., second slot 370) and the second surface (e.g., a surface of a second bone such as a medial cuneiform 202). Managing the distance between a first top edge 366 and/or second top edge 368 and a bone surface is one way to provide a stop within the cutting guide 300. The stop can serve to limit how deep a surgeon will resect hard tissue/soft tissue when using the cutting guide 300 for a procedure. If a surgeon resects until the resection instruments engages the stop, the surgeon can be assured that the resection extends to a desired depth (not too far and not too short).

As used herein, a "stop" refers to an apparatus, instrument, structure, member, device, component, system, or assembly structured, organized, configured, designed, arranged, or engineered to prevent, limit, impede, stop, or restrict motion or movement and/or operation of the another object, member, structure, component, part, apparatus, system, or assembly.

Referring to FIGS. 3H and 4, in one embodiment, the body 310, or one or more arms, may include one or more bone attachment features that facilitate attachment of the body 310 to the medial cuneiform 202 and/or first metatarsal 208. Such bone attachment features may include any of a wide variety of fasteners including, but not limited to, holes, spikes, fastening devices, and/or the like.

Effective connection of the cutting guide 300 to one or more bones across a joint can ensure that cut surfaces are formed in desired locations and orientation and mitigate removal of hard tissue and/or soft tissue outside in undesired locations.

Accordingly, the cutting guide 300 includes one or more bone attachment features. As embodied in FIGS. 3A through 3H, the bone attachment features may take the form of one or more holes 350 that extend from the inferior side 322 to the superior side 320 and/or one or more fixation devices. The holes 350 may be shaped to accommodate pins, K-wires, and/or other elongated bone fixation elements that can be anchored in the medial cuneiform 202 and/or the first metatarsal 208 to keep the cutting guide 300 in place.

FIG. 4 illustrates one example of a cutting guide 300 coupled to the bones using a proximal bone attachment feature 352 and a distal bone attachment feature 354. In the illustrated embodiment, the proximal bone attachment feature 352 includes at least hole 350 and a fastener and the distal bone attachment feature 354 includes at least hole 350 and a fastener. In FIG. 4 the fasteners are K-wires. Advantageously, the proximal bone attachment feature 352 and the distal bone attachment feature 354 each include at least two holes 350, each with a K-wire passing through the hole 350 and into bone facing the inferior side 322. Using two holes 350 and two fasteners ensures a stable coupling between the cutting guide 300 and the bone(s). Advantageously, in certain embodiments, the two holes 350 of the proximal bone attachment feature 352 and distal bone attachment feature 354 are align such that inserted K-wires are parallel to each other. Among other benefits, parallel K-wires of each of the proximal bone attachment feature 352 and distal bone attachment feature 354 prevent the cutting guide 300 from pivoting around one of the K-wires of a proximal bone attachment feature 352 or a distal bone attachment feature 354.

In the illustrated embodiment, the proximal arm 330 includes the proximal bone attachment feature 352 and the distal arm 340 includes the distal bone attachment feature 354. In one embodiment, the holes 350 of the proximal bone attachment feature 352 are aligned with each other and aligned perpendicular to a resection feature such as the second slot 370. The holes 350 of the distal bone attachment feature 354 may also be aligned with each other and aligned perpendicular to another resection feature such as the first slot 360. This means that the aligned holes 350 (and K-wires secured within them) of the distal bone attachment feature 354 will also be perpendicular to the cut surface formed using the first slot 360. This also means that the aligned holes 350 (and K-wires secured within them) of the proximal bone attachment feature 352 will also be perpendicular to the cut surface formed using the second slot 370. Consequently, at least one of the proximal bone attachment feature 352 and the distal bone attachment feature 354 can be used to position and orient a cut surface of the first metatarsal 208 and a cut surface of the medial cuneiform 202.

Returning to FIGS. 3A through 4, the body 310 may further have features that facilitate desired translation and orientation of the first metatarsal 208 and/or medial cuneiform 202 in order to fuse or join the two bones to complete the procedure. For example, in the illustrated embodiment, the cutting guide 300 may include at least one alignment feature. A second alignment feature may be integrated into the cutting guide 300 or the second alignment feature may be a separate feature from the cutting guide 300.

In the illustrated embodiment, the proximal bone attachment feature 352 serves as both a bone attachment feature and as an alignment feature, e.g., proximal alignment feature 380. In this manner, the proximal bone attachment feature 352 can provide both a bone attachment feature and an alignment feature in a single feature. In situations where a second bone of a joint, such as a first metatarsal 208, does not need to be rotated, translated, and/or re-oriented to mitigate a patient's condition, the distal bone attachment feature 354 may also serve as both a bone attachment feature and as an alignment feature, e.g., distal alignment feature 390.

Typically, in an osteotomy for a condition such as a hallux valgus, it is desirable to rotate the first metatarsal 208 to address the condition. The first metatarsal 208 may be rotated for example to reposition distal plantar sesamoids from a lateral orientation to a more plantar orientation. Research has shown that performing such re-orientation mitigates recurrence of a hallux valgus condition. In such situations, the distal bone attachment feature 354 may serve as a bone attachment feature and as a reference for the positioning of a distal alignment feature 390 that is separate from the cutting guide 300.

For example, in such instances, the distal bone attachment feature 354 may serve as a reference for placement of a distal alignment feature 390 (See FIG. 4A) that is parallel to the distal bone attachment feature 354 as measured along the longitudinal axis 376 of the first metatarsal 208. Subsequent to formation of a cut surface on the first metatarsal 208, the distal alignment feature 390 can be coupled to the first metatarsal 208 in parallel to the distal bone attachment feature 354 (e.g., by way of a pin guide). In certain embodiments, the distal alignment feature 390 can include two or more aligned holes and/or a pair of K-wires that enter the bone in parallel to each other. In addition, in such a situation, the proximal alignment feature 380 and the distal alignment feature 390 may not be aligned initially. Instead, the proximal alignment feature 380 and distal alignment feature 390 may be configured to align when the bone coupled to the distal alignment feature 390 is rotated. Fasteners 356 of the distal bone attachment feature 354 may be aligned with longitudinal axis 376 and perpendicular to first slot 360 by way of holes 350. Fasteners 356 of the proximal bone attachment feature 352 may be aligned with reference line 392 and perpendicular to second slot 370 by way of holes 350. The reference line 392 may not be aligned with the longitudinal axis 376.

FIG. 4 illustrates an example cutting guide 300 seated transverse to a tarsometatarsal ("TMT") joint 400. The TMT joint 400 includes a lateral end 402 and a medial end 404. In certain embodiments, such as the illustrated embodiment, the body 310 is configured to extend between the lateral end 402 and the medial end 404. In addition, the proximal arm 330 and the distal arm 340 may be aligned with each other.

Furthermore, in certain embodiments, the proximal arm 330 and the distal arm 340 may be positioned extending from the body 310 near the lateral end 402 (See FIG. 6). Said another way, the proximal arm 330 and the distal arm 340 may be positioned extending from the body 310 such that the arms extend over a dorsal surface of the medial cuneiform 202 and a dorsal surface of the first metatarsal 208. In another embodiment, the proximal arm 330 and the distal arm 340 may be positioned extending from the body 310 near the medial end 404.

FIG. 4 illustrates an example cutting guide 300 at a particular stage in an osteotomy procedure. In one embodiment, a surgeon has formed an incision transverse to a TMT joint 400 with a dorsal approach. In the illustrated embodiment, the cutting guide 300 may be configured (e.g., the bone engagement surface 324) to seat between the dorsal surface and medial surface of both the medial cuneiform 202 and the first metatarsal 208. The surgeon has also formed the incision down to the cortical bone surface of the medial cuneiform 202 and the first metatarsal 208. Further, the surgeon has cut, or moved to the side, soft tissue covering the cortical bone surface of the medial cuneiform 202 and the first metatarsal 208 sufficient to seat the bone engagement surface 324 onto the cortical bone surface of the medial cuneiform 202 and the first metatarsal 208.

A surgeon has deployed two or more fasteners 356 (e.g., K-wires) through the holes 350 of the proximal bone attachment feature 352 and the distal bone attachment feature 354. In certain embodiments, the distal bone attachment feature 354 and/or the proximal bone attachment feature 352 can include an additional hole 358 for another fastener 356. The additional hole 358 and fastener 356 can help keep the cutting guide 300 in place during resection and alignment operations. In certain embodiments, the additional hole 358 is aligned with two holes 350 of the distal arm 340, but need not be aligned.

Next, a surgeon can resect a distal articular surface of the medial cuneiform 202 and a proximal articular surface of the first metatarsal 208 by way of the second slot 370 and the first slot 360. After resection, the distal end of the medial cuneiform 202 includes a planar cut surface and the proximal end of the first metatarsal 208 includes a planar cut surface. FIG. 4 illustrates that the bone engagement surface 324 conforms to the surface of the two bones (e.g., medial cuneiform 202 and first metatarsal 208).

Figures 5A, 5B:
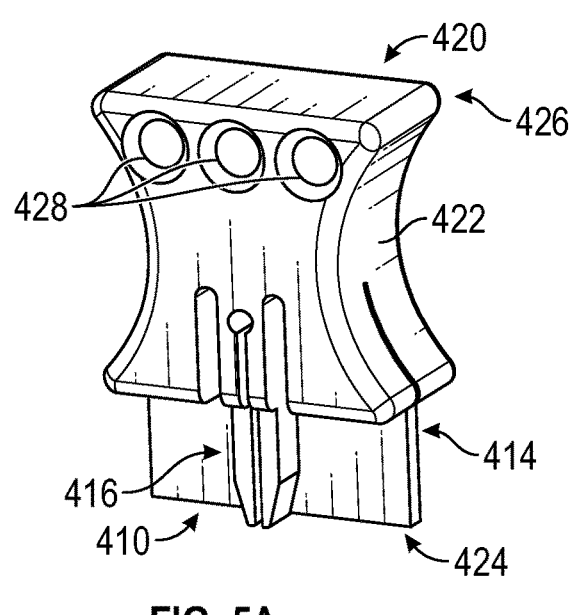
FIGS. 5A and 5B illustrate a perspective view of an alignment guide and of a first cuneiform and a first metatarsal with one embodiment of a patient-specific cutting guide according to one embodiment.

FIGS. 5A, 5B illustrate a perspective view of a first cuneiform and a first metatarsal with one embodiment of a patient-specific cutting guide. Prior to resection completed in the illustrated stage of FIG. 4, a surgeon may desire to check or confirm that the desired cutting guide is being used and that a selected cutting guide will provide a desired alignment between the bones of the foot after the resection and fixation steps.

Accordingly, in the illustrated embodiment, the cutting guide 300 may include one member of a coupler 410 configured to engage a corresponding member of the coupler coupled to an alignment guide 420. Those of skill in the art appreciate that various designs of a coupler may be used. In the illustrated embodiment, the coupler 410 includes an opening 412 (See FIG. 20) that may extend from the superior side 320 into the body 310 through to the inferior side 322 and a post 414. In one embodiment, the opening 412 may include one of the slots, such as second slot 370. The post 414 may include an engagement member 416.

In one embodiment, the opening 412 and the post 414 engage each other in a friction fit. For example, the post 414 may slide into the second slot 370 and the engagement member 416 may slide into the opening 412. In one embodiment, the engagement member 416 may include tabs that are biased outward and greater than a diameter of the opening 412 such that the tabs engage the opening 412 when inserted and release the opening when the tabs are pressed together.

The alignment guide 420 includes a body 422, an inferior end 424, and superior end 426 and one or more openings 428 near the superior end 426. The openings 428 may be aligned. A surgeon may use the alignment guide 420 by engaging the coupler 410 to couple the alignment guide 420 to the cutting guide 300. Next, a surgeon may insert one or more K-wires through the openings. The openings 428 and alignment guide 420 may be configured such that K-wires within the openings extend along an anterior-posterior axis and indicate the orientation and alignment of the medial cuneiform 202 and first metatarsal 208 once the osteotomy procedure is completed. A surgeon may compare this alignment with the orientation and alignment of other bones of the patient. In this manner, a surgeon can confirm that osteotomy procedure will accomplish the desired outcome once completed.

Figure 6A:
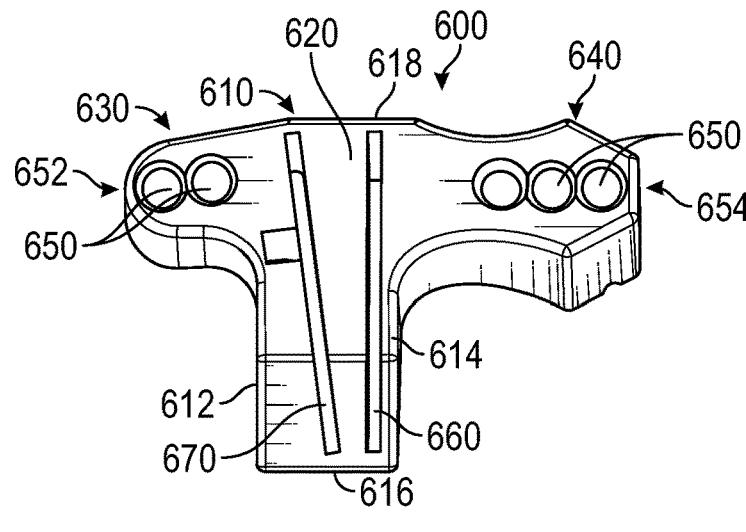
FIGS. 6A-6C are top perspective, top, bottom, views respectively, of a patient-specific cutting guide according to one embodiment.
Figure 6B:
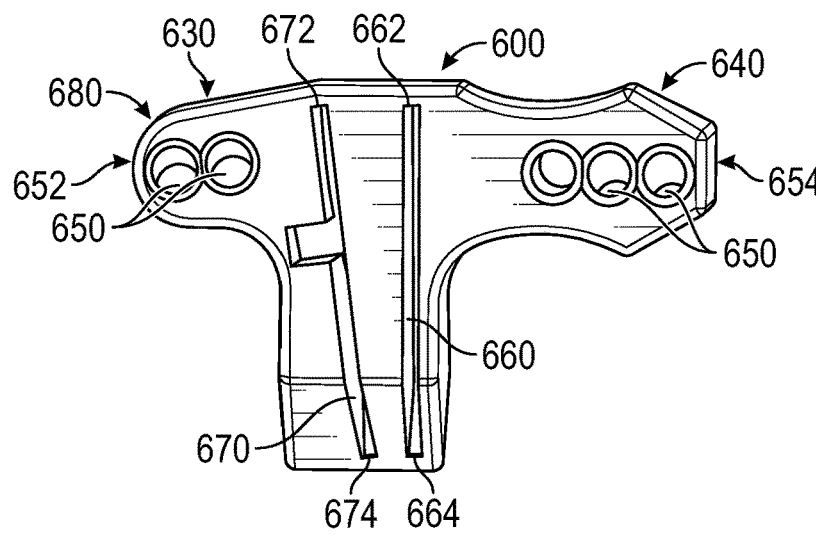
Figure 6C:
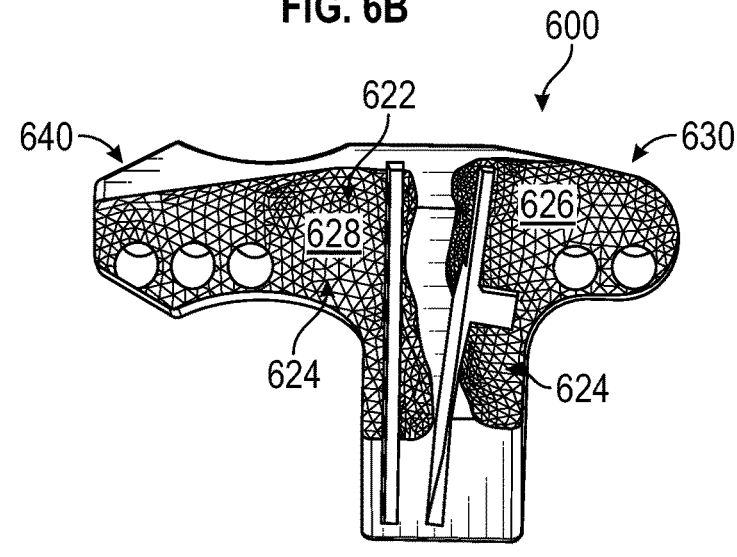

FIGS. 6A-6C are top perspective, top, bottom, respectively, of a patient-specific cutting guide 600 according to one embodiment. The cutting guide 600 may be designed to facilitate resection of a first cuneiform near a distal end and a first metatarsal near a proximal end with planar cuts at the proper angles to provide dual-plane correction of the orientation of the first metatarsal relative to the first cuneiform, thereby providing correction in a lateral direction, in a plantar direction, and/or a dorsal direction.

As shown, the cutting guide 600 may have a body 610 with a monolithic construction and the general shape of a rectangular shape. The body 610 includes a proximal side 612, a distal side 614, a medial side 616, a lateral side 618, a superior side 620, and an inferior side 622. In the illustrated embodiment, the body 610 may also include a proximal arm 630 that extends from the body 610 and a distal arm 640 that extends from the body 610. The proximal side 612 is the side closest to the core of the patient when the cutting guide 600 is in use. The distal side 614 is the side furthest from the core of the patient when the cutting guide 600 is in use. The medial side 616 is the side facing medially when the cutting guide 600 is in use. The lateral side 618 is the side facing laterally when the cutting guide 600 is in use. The superior side 620 is the side facing up away from the bone(s) when the cutting guide 600 is in use. The inferior side 622 is the side facing down, facing, and/or contacting the bone(s) (e.g., contacting a surface of one or more bones) when the cutting guide 600 is in use.

The inferior side 622 may be custom contoured to match the shapes of one or more of the surfaces of the first cuneiform and/or the first metatarsal. In one embodiment, the inferior side 622 may include a bone engagement surface 624. The bone engagement surface 624 can be shaped to match a first surface of a first bone and a second surface of a second bone of a joint.

In one example, the bone engagement surface 624 can be shaped such that the bone engagement surface 624 matches a surface of a cuneiform bone and a surface of a metatarsal bone of a tarsometatarsal ("TMT") joint. The bone engagement surface 624 can be so shaped because it is fabricated from a bone model of the patient's bones. The body 610 is configured, designed, and/or fabricated to seat transverse to a joint (e.g., a TMT joint) with the bone engagement surface 624 engaging a first surface of a first bone and a second surface of a second bone.

FIGS. 6A-6C includes similar components, parts, devices, apparatus, features, and aspects as those disclosed and described in relation to FIGS. 3A-19H, however the difference in FIGS. 6A-6C is that body 610, bone engagement surface 624, and/or one or more arms (e.g., proximal arm 630 and/or distal arm 640) are configured to couple to the bones and extend transverse to the joint, at least partially, if not completely, on the dorsal sides of the bones. Accordingly, the cutting guide 600 may be referred to as a dorsal cutting guide.

In addition, the cutting guide 600 may be configured to avoid contact with soft tissue such as nerves, tendons, blood vessels, and the like that may run along a medial and/or a lateral side of the first metatarsal 208. Accordingly, the cutting guide 600 may be fabricated to seat transverse to the TMT joint such that the bone engagement surface contacts a dorsal surface of the a first bone (e.g., medial cuneiform 202) and/or a second bone (e.g., first metatarsal 208). For example, the proximal arm 630 and/or distal arm 640 may be positioned more laterally than in other embodiments.

In the illustrated embodiment, the body 610 is configured to reside on the dorsal surfaces of the first cuneiform and the first metatarsal to provide proper alignment of the body 610 with the metatarsocuneiform joint (e.g., the joint between the first metatarsal and the medial cuneiform bone, aka a TMT joint). In another embodiment, the body 610 is configured to reside or sit between the medial surfaces and the dorsal surfaces for an osteotomy.

In certain embodiments, the bone engagement surface 624 may include a cuneiform apposition portion 626 and a metatarsal apposition portion 628. As shown, the cuneiform apposition portion 626 may be contoured to match the contour of the surface of the first cuneiform on which it is to rest, and the metatarsal apposition portion 628 may similarly be contoured to match the contour of the surface of the first metatarsal on which it is to rest. (See FIG. 6C) Thus, the body 610 may have only one stable position and orientation relative to the first cuneiform and the first metatarsal during a surgical osteotomy for correcting the condition.

Advantageously, the fidelity of the patient imaging data enables the bone model, preliminary cutting guide model, and patient specific instrument (e.g., patient specific cutting guide, patient specific pin guide, patient specific alignment guide, etc.) to uniquely match a particular patient. Consequently, the bone engagement surface 624 can engage the surfaces of the bones of a joint in a single configuration. Such a close matching fit facilitates the surgical osteotomy.

FIG. 6D illustrates the cutting guide 600 from a view facing the medial side 616. FIG. 6E illustrates the cutting guide 600 from a view facing the lateral side 618. In certain embodiments, the cutting guide 600 may include one or more features that facilitate use of the cutting guide 600 while avoiding certain soft tissue in the vicinity of a joint. For example, the medial side 616 may include a medial superior surface 632 and a medial inferior surface 634 that meet at a medial edge 636. Advantageously, the medial inferior surface 634 may extend from inferior side 622 to the medial edge 636 at an angle such that the medial inferior surface 634 does not impinge soft tissue near the joint (e.g., near a medial end of the joint). In certain embodiments, the angle may range between about 80 and 170 degrees. In another example, the lateral side 618 may include a lateral superior surface 642 and a lateral inferior surface 644 that meet at a lateral edge 646 (See FIG. 6E). Of course, the medial superior surface 632 may extend from the superior side 620 to the medial edge 636 at an angle. The angle of the medial superior surface 632 may enable use of the cutting guide 600 in tighter openings and thus minimize the size of incisions used for a procedure.

Advantageously, the lateral inferior surface 644 may extend from inferior side 622 to the lateral edge 646 at an angle such that the lateral inferior surface 644 does not impinge soft tissue near the joint (e.g., near a medial end of the joint). In certain embodiments, the angle may range between about 80 and 170 degrees. Of course, the lateral superior surface 642 may extend from the superior side 620 to the lateral edge 646 at an angle. The angle of the lateral superior surface 642 may enable use of the cutting guide 600 in tighter openings and thus minimize the size of incisions used for a procedure.

The body 610 may further include resection features that guide a cutter to resect the first cuneiform and the first metatarsal in the manner needed to make the desired correction. For example, the resection features may be used to guide a planar cutting blade, an arcuate cutting blade, a drill or mill, a burr, and/or the like.

In the embodiment of FIGS. 6A through 6C, the resection features may guide a reciprocating planar blade, such as that of a surgical bone saw, that forms planar cuts in the first cuneiform and the first metatarsal. Various manual or powered tools may be used to form the planar cuts. In one embodiment, a sagittal bone saw can be used. In one example, the resection features may take the form of a first slot 660 and a second slot 670. The first slot 660 may include a lateral end 662 and a medial end 664. The second slot 670 may include a lateral end 672 and a medial end 674.

In one embodiment, the first slot 660 and the second slot 670 extend from the superior side 620 to the inferior side 622. In certain embodiments, the first slot 660 may extend from near the lateral side 618 to near the medial side 616. In other embodiments, one of, or both of, the first slot 660 and the second slot 670 may extend from one of the medial side 616 or the lateral side 618 of the body 610. In certain embodiments, the first slot 660 and second slot 670 intersect. In other embodiments, the first slot 660 and second slot 670 do not intersect.

Thus, upon desired positioning of the cutting guide 600, the second slot 670 may be positioned over at least a portion of the first cuneiform to facilitate resection of the first cuneiform, while the first slot 660 may be positioned over at least a portion of the first metatarsal to facilitate resection of the first metatarsal. In one embodiment, the second slot 670 is positioned near the distal end of the first cuneiform and the first slot 660 is positioned near the proximal end of the first metatarsal. The first slot 660 and second slot 670 together, with the bone engagement surface 624 overlying the first cuneiform and the first metatarsal, are positioned to guide resection of the first cuneiform and the first metatarsal during a surgical osteotomy for correcting a condition.

In alternative embodiments, a resection feature may be designed to guide a different type of cutter, such as a drill, mill, or side-cutting burr. In such embodiments, the resection feature may not be a slot, but may instead be a translatable or rotatable cutter retainer that guides translation and/or rotation of the cutter relative to the bone. In certain embodiments, two or more resection features may be replaced by a single resection feature sized to permit a surgeon to resect both a first cuneiform and a first metatarsal using a single cutting guide 600.

In one embodiment, a first resection feature is configured to define a first cut surface that can be formed by resecting a first bone. A second resection feature is configured to define a second cut surface that can be formed by resecting a second bone. In such an embodiment, one or the other or both of the first cut surface and the second cut surface can be oriented according to one or more angles relative to landmarks on the bones or other anatomical structures.

Alternatively, or in addition, in certain embodiments, one or both of, the first resection feature and second resection feature may be positioned on, or in, the body 610 and/or have an orientation based on patient imaging data. The patient imaging data can be used to position and orient one, or both, of the first resection feature and second resection feature such that formation of one, or both, of the first cut surface and the second cut surface and fixation of the two cut surfaces against each other mitigates a condition of the patient. For example, as described in the present disclosure, patient imaging data can be used to generate bone models of bones of the patient. The bone models can be used to determine and/or define contours for a bone engagement surface 624, a position for a first slot 660, an orientation for a first slot 660, a position for a second slot 670, an orientation for a second slot 670, as well as other features and attributes of one or more patient specific instruments that can be used in a procedure.

FIG. 6 illustrates a perspective view of a first cuneiform and a first metatarsal with one embodiment of a patient-specific cutting guide positioned over a TMT joint. In the illustrated embodiment, the first resection feature may take the form of the first slot 660 and the second resection feature may take the form of the second slot 670. As with the embodiment of FIGS. 3A-19H and 20, the position and/or angles (e.g., orientation) of one or both of the resection features based on patient imaging data is illustrated. The first slot 660 is oriented based on a desired angle for mitigating the condition of the patient. In one example, the first slot 660 is angled perpendicular to a longitudinal axis 676 of the first metatarsal 208. This orientation of the first slot 660 enables the first cut surface to extend from the body 610 toward the bone to form a cut surface that is also perpendicular to the longitudinal axis 676 of one of the bones of a joint.

In the illustrated embodiment, the second slot 670 is positioned and oriented based on a desired angle for mitigating the condition of the patient. In the illustrated embodiment, the orientation of the second slot 670 can be described in reference to a first angle A and a second angle B, just as those angles are described above in relation to FIGS. 3D and 3H.

Those of skill in the art will appreciate that the position and orientation of the first slot 660 and second slot 670 and the corresponding cut surface a surgeon can form using these resection features can vary depending on the anatomical structures of the patient, the osteotomy procedure being performed, preferences of the surgeon, the nature of the condition, and the like.

Referring to FIGS. 6C and 23, in one embodiment, the body 610, or one or more arms, may include one or more bone attachment features that facilitate attachment of the body 610 to the medial cuneiform 202 and/or first metatarsal 208. Such bone attachment features may include any of a wide variety of fasteners including, but not limited to, holes, spikes, fastening devices, and/or the like. Effective connection of the cutting guide 600 to one or more bones across a joint can ensure that cut surfaces are formed in desired locations and orientation and mitigate removal of hard tissue and/or soft tissue outside in undesired locations.

Accordingly, the cutting guide 600 includes one or more bone attachment features. As embodied in FIGS. 6A through 6C, the bone attachment features may take the form of one or more holes 650 that extend from the inferior side 622 to the superior side 620 and/or one or more fixation devices. The holes 650 may be shaped to accommodate pins, K-wires, and/or other elongated bone fixation elements that can be anchored in the medial cuneiform 202 and/or the first metatarsal 208 to keep the cutting guide 600 in place.

FIG. 6 illustrates one example of a cutting guide 600 coupled to the bones using a proximal bone attachment feature 652 and a distal bone attachment feature 654. In the illustrated embodiment, the proximal bone attachment feature 652 includes at least hole 650 and a fastener and the distal bone attachment feature 654 includes at least hole 650 and a fastener. In FIG. 6 the fasteners are K-wires. Advantageously, the proximal bone attachment feature 652 and the distal bone attachment feature 654 each include at least holes 650, each with a K-wire passing through the hole 650 and into bone facing the inferior side 622. Using holes 650 and two fasteners ensures a stable coupling between the cutting guide 600 and the bone(s). Advantageously, in certain embodiments, the holes 650 of the proximal bone attachment feature 652 and distal bone attachment feature 654 are align such that inserted K-wires are parallel to each other. Among other benefits, parallel K-wires of each of the proximal bone attachment feature 652 and distal bone attachment feature 654 prevent the cutting guide 600 from pivoting around one of the K-wires of a proximal bone attachment feature 652 or a distal bone attachment feature 654.

In the illustrated embodiment, the proximal arm 630 includes the proximal bone attachment feature 652 and the distal arm 640 includes the distal bone attachment feature 654. In one embodiment, the holes 650 of the proximal bone attachment feature 652 are aligned with each other and aligned perpendicular to a resection feature such as the second slot 670 (see reference line 392). The holes 650 of the distal bone attachment feature 654 may also be aligned with each other and aligned perpendicular to another resection feature such as the first slot 660 (see reference line 394). This means that the aligned holes 650 (and K-wires secured within them) of the distal bone attachment feature 654 will also be perpendicular to the cut surface formed using the first slot 660. This also means that the aligned holes 650 (and K-wires secured within them) of the proximal bone attachment feature 652 will also be perpendicular to the cut surface formed using the second slot 670. Consequently, at least one of the proximal bone attachment feature 652 and the distal bone attachment feature 654 can be used to position and orient a cut surface of the first metatarsal 208 and a cut surface of the medial cuneiform 202. In certain embodiments, the proximal bone attachment feature 652 and distal bone attachment feature 654 may not be aligned with each other, the offset in the alignment may be the change in orientation of the bones of the joint desired to address the condition. It should be noted that the distal bone attachment feature 654 may be parallel to the longitudinal axis 676. In this manner, the distal bone attachment feature 654 can be used as a reference for positioning a distal alignment feature 690 on the first metatarsal 208.

Returning to FIGS. 3A through 4, the body 610 may further have features that facilitate desired translation and orientation of the first metatarsal 208 and/or medial cuneiform 202 in order to fuse or join the two bones to complete the procedure. For example, in the illustrated embodiment, the cutting guide 600 may include at least one alignment feature. A second alignment feature may be integrated into the cutting guide 600 or the second alignment feature may be a separate feature from the cutting guide 600.

In the illustrated embodiment, the proximal bone attachment feature 652 serves as both a bone attachment feature and as an alignment feature, e.g., proximal alignment feature 680. In this manner, the proximal bone attachment feature 652 can provide both a bone attachment feature and an alignment feature in a single feature. In situations where a second bone of a joint, such as a first metatarsal 208, does not need to be rotated, translated, and/or re-oriented to mitigate a patient's condition, the distal bone attachment feature 654 may also serve as both a bone attachment feature and as an alignment feature, e.g., distal alignment feature 690.

Typically, in an osteotomy for a condition such as a hallux valgus, it is desirable to rotate the first metatarsal 208 to address the condition. The first metatarsal 208 may be rotated for example to reposition distal plantar sesamoids from a lateral orientation to a more plantar orientation. Research has shown that performing such re-orientation mitigates recurrence of a hallux valgus condition. In such situations, the distal bone attachment feature 654 may serve as a bone attachment feature and as a reference for the positioning of a distal alignment feature 690 that is separate from the cutting guide 600.

For example, in such instances, the distal bone attachment feature 654 may serve as a reference for placement of a distal alignment feature 690 that is parallel to the distal bone attachment feature 654 as measured along the longitudinal axis 676 of the first metatarsal 208. Subsequent to formation of a cut surface on the first metatarsal 208, the distal alignment feature 690 can be coupled to the first metatarsal 208 in parallel to the distal bone attachment feature 654 (e.g., by way of a pin guide). In certain embodiments, the distal alignment feature 690 can include two or more aligned holes and/or a pair of K-wires that enter the bone in parallel to each other. In addition, in such a situation, the proximal alignment feature 680 and the distal alignment feature 690 may not be aligned initially. Instead, the proximal alignment feature 680 and distal alignment feature 690 may be configured to align when the bone coupled to the distal alignment feature 690 is rotated.

Figure 7:
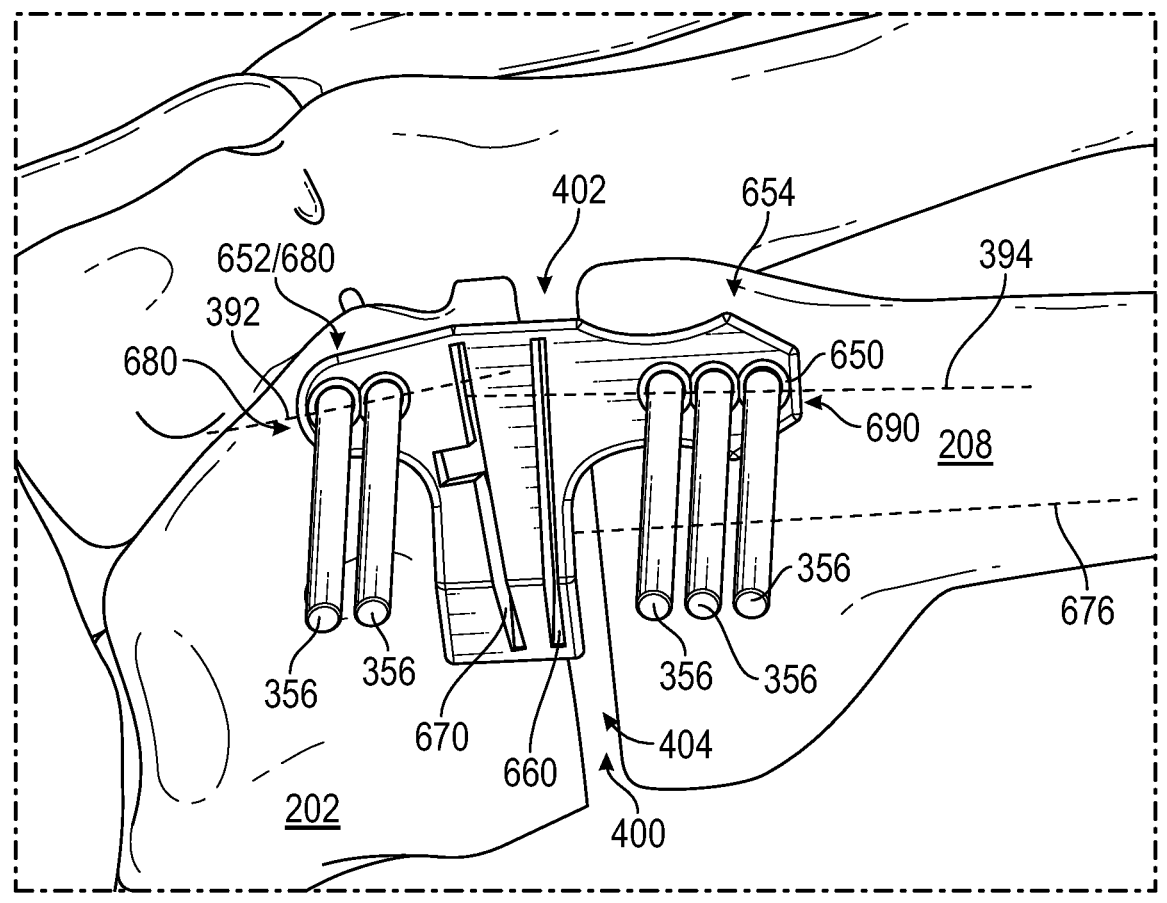
FIG. 7 illustrates a perspective view of a first cuneiform and a first metatarsal with one embodiment of a patient-specific cutting guide positioned over a TMT joint.

FIG. 7 illustrates an example cutting guide 600 seated transverse to a tarsometatarsal ("TMT") joint 400. The TMT joint 400 includes a lateral end 402 and a medial end 404. In certain embodiments, such as the illustrated embodiment, the body 610 is configured to extend between the lateral end 402 and the medial end 404. In this manner, the first slot 660 and second slot 670 extend along the TMT joint 400 in a lateral medial direction and are long enough that a surgeon can readily resect the respective ends of the respective bones of the joint. In addition, the proximal arm 630 and the distal arm 640 may be aligned with each other. In one embodiment, the proximal arm 630 and distal arm 640 may extend proximal to the lateral side 618 and/or proximal to the lateral end 402 of the joint (e.g., TMT joint 400).

Advantageously, the cutting guide 600 can be used with patients that have smaller bones and joints such as children or female patients. The cutting guide 600 fits directly on the dorsal surfaces of the bones of the joint. This placement can avoid contact with soft tissues that may run along the medial and/or lateral surfaces of the bones of the joint.

FIG. 7 illustrates that the cutting guide 600 can be secured to the bones using the proximal bone attachment feature 652 and/or distal bone attachment feature 654 each of which may include two or more fasteners 356. In certain embodiments, the fasteners 356 of the proximal bone attachment feature 652 are aligned with each other and perpendicular to the second slot 670. The fasteners 356 of the distal bone attachment feature 654 are aligned with each other and perpendicular to the first slot 660. The fit of the bone engagement surface 624 to the surfaces (dorsal in this embodiment) of the bones helps to secure the cutting guide 600 in place and ensure that resection of the bones using the first slot 660 and second slot 670 forms the desired cut surfaces for the procedure.

Those of skill in the art will appreciate that in various embodiments certain aspects may interface with one or more dorsal surfaces of each or both of the bones of a joint. The illustrated embodiments provide at least one example. In other embodiments, at least one of a cutting guide body, a proximal arm, a distal arm, and a bone engagement surface of a inferior surface of the body is configured to engage a dorsal surface of one or more of a first bone and a second bone.

It should be noted that the cutting guide 300 and/or cutting guide 600 may be configured to engage with a dorsal surface of one bone (e.g., a medial cuneiform 202) and a lateral surface of a second bone (e.g., a first metatarsal 208) of a joint (e.g., TMT joint 400). For example, where the patient has a hallux valgus condition, the first metatarsal 208 may have rotated about its longitudinal axis 376/676 such that the lateral surface of the first metatarsal 208 faces dorsal. Advantageously, the present disclosure accounts for this and the cutting guide 300/600 is configured to contact a dorsal surface on one bone and a lateral surface of the second bone (or proximal surface if the bone is rotated in the other direction). Furthermore, the proximal alignment feature 380/680 may engage with a dorsal surface of a proximal bone and the distal alignment feature 390/690 may engage with a dorsal surface of a distal bone, even though the distal bone has rotated.

Referring to FIGS. 4 and 7, in the illustrated embodiments, the proximal alignment feature 380/680 and distal alignment feature 390/690 may be in separate devices rather than being combined in a single device. FIGS. 4 and 7 show the proximal alignment feature 380/680 as part of the cutting guide 300/600.

FIG. 8A is a perspective view of a foot, after resection of the medial cuneiform 202 and the first metatarsal 208, removal of the cutting guide 300, and placement of the first metatarsal 208 to abut the medial cuneiform 202. As shown, the distal end 272 of the first metatarsal 208 may now be positioned much closer to the second metatarsal 210, in a more natural position. Further, FIG. 8A depicts a first proximal phalanx 230, which may now be properly oriented generally parallel to the other phalanges (not shown), rather than pointing in the lateral direction 274. If desired, further steps may be performed relative to the joint between the first metatarsal 208 and the first proximal phalanx 230 in order to place them in the proper relative orientation. The distal end 272 may also have been shifted in the plantar direction 276 or in the dorsal direction 278 from the position of FIG. 2. Thus, the desired dual-plane correction of the orientation of the first metatarsal 208 may be complete.

The first metatarsal 208 may be secured to the medial cuneiform 202, at least until proper bone in-growth has occurred between the medial cuneiform 202 and the first metatarsal 208. In some embodiments, a bone plate (not shown) or other fastener (not shown) may be used to secure the medial cuneiform 202 and the first metatarsal 208 together. Additional hardware (not shown) may be used to stabilize the position and/or orientation of the first proximal phalanx 230 relative to the first metatarsal 208, if desired. The surgical wound may be closed, and the foot 200 may be allowed to heal with the bunion deformity corrected.

FIGS. 8B and 8C are dorsal views of the foot 200, before and after correction, respectively. FIGS. 8B and 8C illustrate the correction of the angulation of the first metatarsal 208, by which the distal end 272 of the first metatarsal 208 is moved in the lateral direction 274. In some embodiments, an implant 810 may be inserted in the space between the first metatarsal 208 and the medial cuneiform 202 in order hold the first metatarsal 208 and the medial cuneiform 202 together and/or facilitate bony fusion between the first metatarsal 208 and the medial cuneiform 202.

In some embodiments, an implant 810 may be patient-specific. For example, the implant 810 may have a cuneiform-facing side 820 that is shaped and/or sized to be secured to the adjoining, resected surface of the medial cuneiform 202, and a metatarsal-facing side 830 that is shaped and/or sized to be secured to the adjoining, resected surface of the first metatarsal 208. As the resections made to the first metatarsal 208 and the medial cuneiform 202 may both planar, the cuneiform-facing side 820 and/or the metatarsal-facing side 830 may also be planar. However, the cuneiform-facing side 820 and/or the metatarsal-facing side 830 may advantageously each be shaped to match the profile of the resected surface of the medial cuneiform 202 and the first metatarsal 208, respectively.

This shaping may be accomplished by custom-designing the implant 810 for the patient, using the same models (for example, from CT scans) of the first metatarsal 208 and the medial cuneiform 202 that were used to generate the cutting guide 300. Thus, the implant 810 may have a shape that provides secure attachment and/or fusion between the first metatarsal 208 and the medial cuneiform 202 while avoiding proud edges or other protruding features that could otherwise interfere with surrounding tissues.

Figures 9A, 9B, 9C:
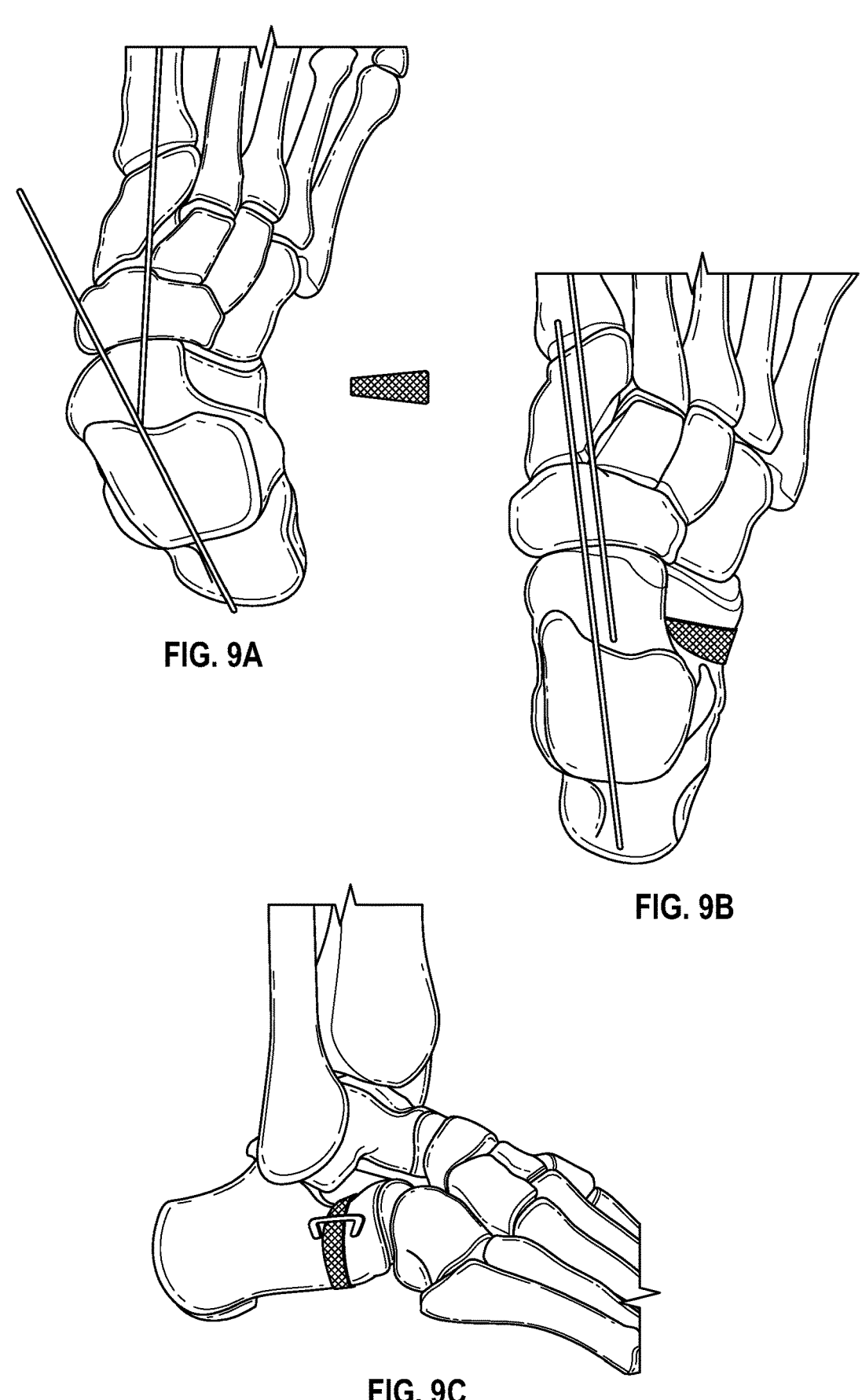
FIGS. 9A, 9B, and 9C are dorsal pre-operative, dorsal post-operative, and lateral post-operative views, respectively, of a foot treated with an Evans calcaneal osteotomy, according to one embodiment.

FIGS. 9A, 9B, and 9C are dorsal pre-operative, dorsal post-operative, and lateral post-operative views, respectively, of a foot treated with an Evans calcaneal osteotomy, according to one embodiment. Outward rotation of the foot may occur in patients with flatfoot. An Evans or lateral column lengthening procedure is sometimes performed for these patients. An incision is made on the outside of the foot, and the front half of the heel bone is cut. A bone wedge (typically either titanium or a bone-based graft) is then placed into the cut area of the heel bone. This wedge helps to "lengthen" the heel bone and rotate the foot back into its correct position. The wedge is usually kept in place using screws or a surgical staple.

Figure 10:
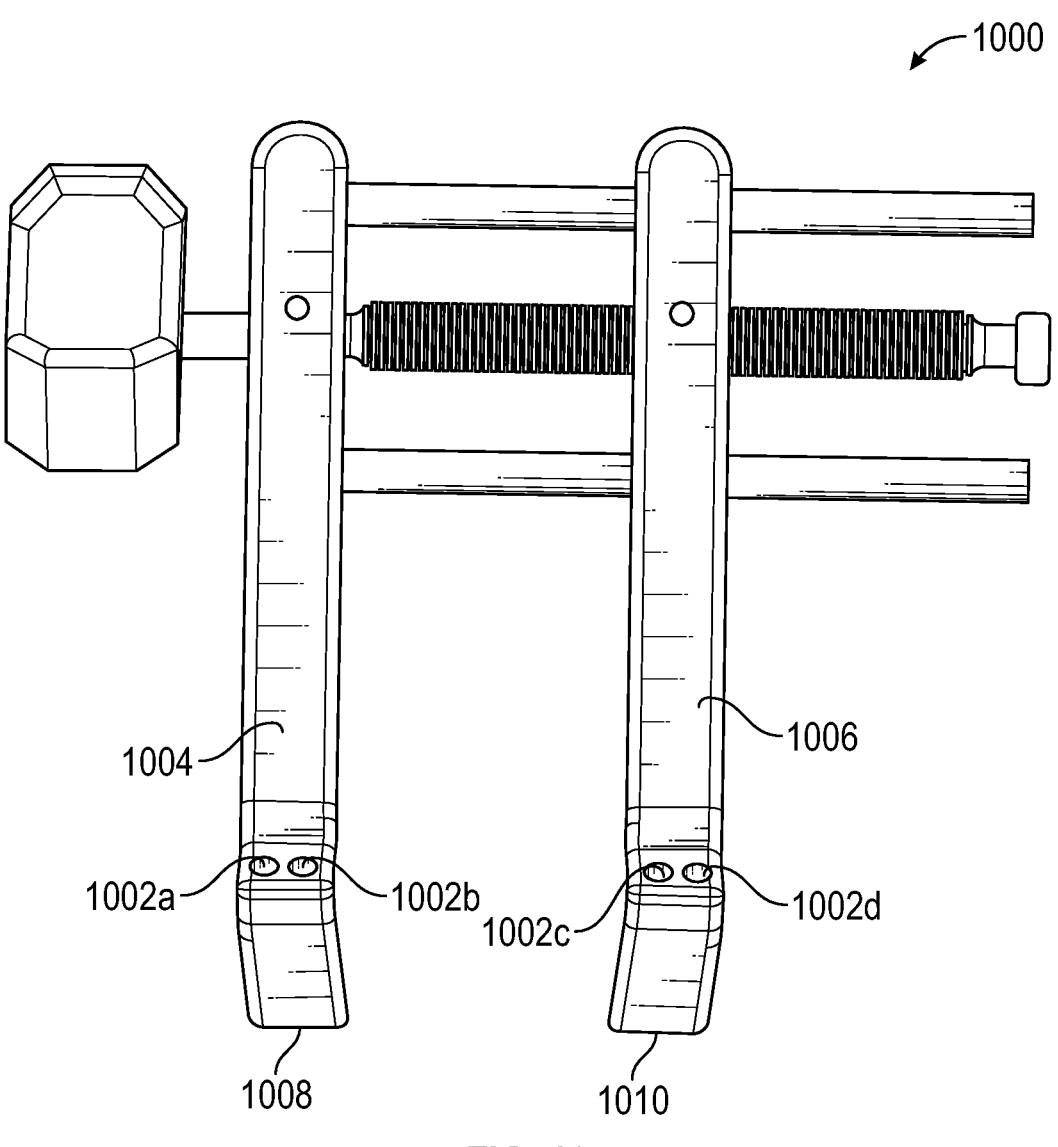
FIG. 10 illustrates an exemplary embodiment of a compressor/distractor that can be used with certain embodiments.

FIG. 10 illustrates an exemplary embodiment of a compressor/distractor 1000 that can be used with certain embodiments. The compressor/distractor 1000 can be used for one or both of distraction and compression. For example, the compressor/distractor 1000 can be used to distract the first metatarsal 208 relative to the medial cuneiform 202.

A user may slide holes 1002a,b over pins in one or both bones. This can cause a desired rotation and translation of the first metatarsal 208 relative to the medial cuneiform 202. When a user places the parallel compressor/distractor 1000 on over the pins this can force the cut faces of the two bones to become parallel. Advantageously, the cut faces of the two bones can be forced to become parallel because the position, orientation, and angles of the holes of alignment feature(s) can be predefined and customized for each patient when the cutting guide 600 is fabricated.

This alignment enables parallel compression of the two bones together using the parallel compressor/distractor 1000. Parallel compression enables more effective compression of the two bones together. Next, the space between the resected surfaces of the medial cuneiform 202 and the first metatarsal 208 is prepared for fusion. Then, the parallel compressor/distractor 1000 can be activated such that the medial cuneiform 202 and the first metatarsal 208 are fused together. The parallel compressor/distractor 1000 may include a first leg 1004 and a second leg 1006. At one end of each leg 1004/1006, the leg may include a toe 1008/1010 at its distal end. In one embodiment, the toes 1008/1010 are angled to point towards each other. The angled configuration of the legs 1004/1006 by way of the toes 1008/1010 may apply a torque force at the toes 1008/1010 which may further assist in pressing two bones connected to the parallel compressor/distractor 1000 together.

The present disclosure is not limited to cutting guides or extremity procedures. In some embodiments, patient-specific instrumentation may be used to correct a wide variety of bone conditions. Such conditions include, but are not limited to, any angular deformities from within one bone segment in either the lower or upper extremities (for example, tibial deformities, calcaneal deformities, femoral deformities, and radial deformities). The present disclosure may also be used to treat an interface between two bone segments (for example, the ankle joint, metatarsal cuneiform joint, lisfranc's joint, complex charcot deformity, wrist joint, knee joint, etc.). As one example, an angular deformity or segmental malalignment in the forefoot may be treated, such as is found at the metatarsal cuneiform level, the midfoot level such as the navicular cuneiform junction, hindfoot at the calcaneal cubiod or subtalar joint or at the ankle between the tibia and talar junction. Additionally, patient-specific instruments could be used in the proximal leg between two bone segments or in the upper extremity such as found at the wrist or metacarpal levels.

Artificial Neural Networks

Artificial Intelligence can utilize, for example, neural networks. Artificial neural networks (ANNs) can learn tasks based on examples, e.g. without task specific programming. ANNs can be based on a group of connected units or nodes, i.e. artificial neurons. Each connection between artificial neurons can generate a signal to be transmitted to another artificial neuron. One or more artificial neurons can receive the signal and process it and, for example, use it to initiate a task. The signal at a connection between artificial neurons can be a number, and the outputs can be calculated by various functions or algorithms, e.g. non-linear functions. Artificial neurons can have a weight assigned to them, which can amplify or de-emphasize their signal. Artificial neurons can be organized in layers, with different layers performing different kind of transformations. Artificial neural networks can utilize various techniques, processes and/or algorithms, e.g. backpropagation, parallel distributed processing, max-pooling, Hebbian learning, long term potentiation, support vector machines, and linear classifiers. ANNs can include recurrent neural networks and deep feedforward neural networks. ANNs can perform functions such as, for example, pattern recognition and machine learning. Components of ANNs can include neurons, connections and weights, propagation functions, and learning rules. Neurons can include an activation component, a threshold component, an activation function, and an output function. ANNs can define mathematical and other functions. ANNs can use predefined functions, e.g. hyperbolic tangent function, sigmoid function, softmax function or rectifier function.

ANNs can be used for learning. Learning can comprise using a number of observations to find a function which solves a predetermined or desired task in an optimal sense, e.g. an optimal outcome. Learning can be supervised learning, unsupervised learning and reinforcement learning. Supervised learning can use one or more sets of example pairs and the goal can be, for example, to find a function in an allowed class of functions that matches the examples. Pattern recognition, classification, and regression can be part of supervised learning. Supervised learning can use informational fuzzy networks, random forests, nearest neighbor algorithms, logistic model tree, and other algorithms. Supervised learning can use statistical classification, including, for example, decision trees, Bayesian networks, and/or linear classifiers.

In unsupervised learning, a set of data can be provided for example along with a cost function to be minimized, which can be a function of the data and the network output. The cost function can be dependent on the task and the properties of the parameters and observed variables or data. Unsupervised learning can be applied, for example, to pattern recognition, classification, and regression, general estimation problems, clustering, the estimation of statistical distributions, compression and filtering. Unsupervised learning can use one or more ANNs, expectation-maximization algorithms, data clustering, and the like. Association rule learning can use a priori algorithms, eclat algorithms, FP-growth algorithms, hierarchical clustering (e.g., single-linkage clustering and conceptual clustering), partitional clustering (e.g., K-means algorithm, fuzzy clustering), reinforcement learning (e.g., Monte Carlo method, Q-learning, temporal difference learning, and combinations thereof.

In reinforcement learning, data can be generated by an agent's interactions with one or more objects, e.g. a surgeon interacting with a patient. The agent, e.g. the surgeon, can perform an action, and the environment, e.g. a target tissue or a surgical site, can generate one or more observations and, for example, a cost according to some dynamics or parameters, e.g. a tissue removal or an infection risk. The objective can be to discover a treatment, treatment algorithm, treatment modification that can reduce or minimize a measure of the cost, e.g. an infection risk, a patient reported outcome measurement, a functional result. The parameters and dynamics of the environment, e.g. a surgical site, can be unknown, but can be estimated. The environment, e.g. a target tissue or a surgical site, can be modeled as a Markov decision process and actions, with possible probability distributions, e.g. a cost distribution, an observation distribution, and one or more transitions, and a policy or algorithm or solution can be defined as a conditional distribution over actions given one or more observations. Dynamic programming can be coupled with ANNs and applied to multidimensional nonlinear problems.

Learning can utilize one or more cost functions, e.g. the cost being an excellent or a poor clinical outcome. The cost function can yield information of how far a particular solution, e.g. a clinical treatment, treatment sequence or treatment algorithm or surgical technique, is from an optimal outcome, e.g. an excellent score in a patient reported outcome measure. ANNs can find the solution, e.g. a clinical treatment, treatment sequence or treatment algorithm or surgical technique, that yields the lowest cost, e.g. distance or amount away from an optimal outcome or excellent score in a patient reported outcome. The cost can be a function of the observations. The cost can be described as a statistic. A cost can be the mean squared error, which can try to minimize the average squared error between the network's output and one or more target values over example pair(s). A cost function can be selected or predetermined for a particular problem set, e.g. a clinical problem set or clinical observation data, e.g. pre-operative, intra-operative or post-operative data. AI can find and develop one or more optimal cost functions for a set of observational data and AI can refine the cost function as the size of the observational data set increases. (See U.S. Pat. No. 11,278,413 Para. 58-63).

Machine Learning

Machine learning can comprise supervised learning, semi-supervised learning, active learning, reinforcement learning or unsupervised learning. With supervised learning, the computer can receive example inputs and desired outputs, which can be provided from a database or using a learning tool; the objective is to learn one or more rules that map the inputs to the outputs. Semi-supervised learning can be different in that the computer can be given an incomplete training example input, optionally with some desired outputs missing. With active learning, the computer can only obtain training inputs for a limited set of examples, and the computer can optimize the choice of inputs to acquire labels for. With reinforcement learning, training data, e.g. inputs and desired outputs, can be given only as feedback to the program's actions in a dynamic environment, such as guiding a surgery. With unsupervised learning, no training input and/or output data are provided, leaving the computer and computer processor on its own to find structure in the inputs.

Machine learning can use processes such as, for example, classification, regression, clustering, density estimation, dimensionality reduction, and topic modeling. With classification, inputs can be divided into two or more classes, and, for example, the learning system can produce a model that assigns unseen inputs to one or more of these classes. Data can be classified, for example, into "excellent", "good", "acceptable" or "poor" outcome, e.g. clinical outcome. Numeric values or ranges of numeric values can be assigned to different classes, for example numeric values or ranges of numeric values from a patient reported outcome measurement, from a clinical reporting system, and/or from one or more electronic measurements. With regression, outputs can be continuous rather than discrete. Regression can be used, for example, when patient outcomes are continuous. With clustering, inputs can be divided into groups. The groups cannot be known beforehand; thus, with clustering learning can be unsupervised. With density estimation, the distribution of inputs in a given space or sample can be determined. With dimensionality reduction, inputs can be simplified by mapping them into a lower-dimensional space. With topic modeling, a machine learning system can be given a list of human language documents and can be tasked to find out which documents cover similar topics.

Developmental learning can include robotic learning, which can generate its own learning situations to acquire new skills through autonomous self-exploration and interaction, for example, with human teachers.

A goal of machine learning or deep learning can be to generalize from the experience. Generalization can be the ability of a learning machine or system to perform accurately on new, unseen inputs after having been trained on a training data set. Training examples can come from an unknown probability distribution and the learning machine or system can be tasked to build an input and output model that enables it to produce sufficiently accurate predictions with new inputs. Bounds or limits, e.g. probabilitistic bounds, on the performance, accuracy and reproducibility of machine learning can be determined. When machine learning is used for solving clinical problems, e.g. outcome prediction or treatment planning or modification, the bounds or limits of performance, accuracy and/or reproducibility of the machine learning system or learning machine can influence and/or determine the performance, accuracy, and/or reproducibility of the clinical application, e.g. outcome prediction or treatment planning or modification. Accuracy can include the assessment of true positives, true negatives, false positives and false negatives. Reproducibility can be precision. Performance of the machine learning system and/or learning machine can include other statistical measures known in the art for assessing the performance of a clinical system.

Learning systems including machine learning can use decision tree learning, association rule learning, artificial neural networks (ANNs), deep learning, inductive logic programming, support vector machines, clustering, Bayesian networks, reinforcement learning, representation learning, similarity and metric learning, sparse dictionary learning, biologic or genetic algorithms, rule based machine learning and learning classifier systems.

With decision tree learning, a decision tree can be used as a predictive model, which can map observations about one or more parameters to conclusions about the parameter's target value. With association learning, relations between variables or parameters can be identified in large databases. With ANNs, computations can be structured through an interconnected group of artificial neurons, processing information using a connected approach. ANNs can be non-linear data modeling took, using various statistical methods and approaches known in the art. Deep learning can employ multiple layers in an artificial neural network. Inductive logic programming (ILP) can utilize logic programming for rule learning, e.g. using a uniform representation for input examples, background knowledge, and hypotheses. Support vector machines (SVMs) can be a set of supervised learning methods used for classification and/or regression. A given a set of training examples can be marked as belonging to first category or a second category; an SVM training machine can build a model predicting whether a new input falls into the first or the second category.

Clustering can be the assignment of a set of observations into subsets, where data in each subset have similarities with regard to one or more parameters while data in different subsets can be dissimilar with regard to one or more parameters. Clustering techniques can provide information on similarity or dissimilarity, for example reflected in a similarity metric, a measurement of internal compactness or separation between different clusters. A Bayesian network can be a graphical model representing, for example, random variables and their conditional independencies. This can be shown in a directed acyclic graph. A Bayesian network can represent the probabilistic relationships between diseases and symptoms. A Bayesian network can be used to compute the probability(ies) of the presence of one or more disease.

With reinforcement learning, input and output pairs can never be presented; reinforcement learning can map a state, e.g. a clinical state of a patient, and can develop predictions, actions or treatment the system can make. With representation learning algorithms input information can be preserved but transformed to make it more useful, e.g. as a pre-processing step, prior to performing classification or predictions, allowing reconstruction of the inputs coming from the unknown data generating distribution.

Deep learning can utilize multiple levels of representation, e.g. in an ANN. Higher-level, e.g. more abstract, parameters or data can be defined as generating lower-level parameters or data. With similarity learning, the learning system or machine can be given pairs of data that are considered similar and pairs of less similar data. It can then learn a similarity function or a distance metric function that can predict if new objects are similar.

Rule-based machine can be identification and utilization of a set of relational rules that can represent the knowledge captured by the learning system. Learning classifier systems (LCS) can be a family of rule based machine learning algorithms or systems which can combine a discovery component with a learning component.

The accuracy of classification machine learning models can be evaluated using accuracy estimation techniques and statistical techniques and methods testing the accuracy, sensitivity, specificity, fake positive and false negative rates. Other statistical methods such as Receiver Operating Characteristic (ROC) and associated Area under the Curve (AUC) as well as Total Operating Characteristic (TOC) can be used. (See U.S. Pat. No. 11,278,413 Para. 64-75).

Deep Learning

Deep learning can include machine learning algorithms which can use multiple layers of non-linear processing units or elements. Each layer can use the output from a higher layer as input. Deep learning systems can work in a supervised setting, e.g. using one more classification systems. Deep learning systems can also work in an unsupervised setting, e.g. in the context of texture analysis or pattern recognition. Deep learning systems can learn multiple levels of representations that correspond to different levels of abstraction. The different levels can form an order or a hierarchy of concepts. The different layers of a deep learning system can reside in different layers of an artificial neural network, i.e. a deep neural network. They can include hidden layers in an ANN. Deep learning systems and deep ANNs can utilize Boltzmann machines. With deep learning systems, layers can correspond to layers of abstraction, e.g. across a deep neural network. Varying numbers of layers and layer sizes can provide different degrees of abstraction. Higher level, more complex concepts can be learned from lower level layers.

Deep neural networks (DNNs) can be one or more ANNs with multiple hidden layers between the input and output layers. DNNs can model complex non-linear relationships. DNNs can generate models where the object is expressed as a layered composition. DNNs can be feedforward networks in which data flows from the input layer to the output layer without looping back, DNNs can be recurrent neural networks or convolutional deep neural networks.

Deep learning algorithms can be applied to unsupervised learning tasks. This is an important benefit because unlabeled data can more abundant than labeled data. For example, in a clinical environment, a deep learning system with a multi-layered ANN can initially be trained using a classification of outcomes in a supervised fashion. As the data grow, the system can optionally learn in an unsupervised manner, for example by utilizing pattern recognition across large clinical datasets, which can include pre-operative, intra-operative and post-operative data. (See U.S. Pat. No. 11,278,413 Para. 76-79).

Classification

Classification can be a process of creating categories, in which data or objects can be recognized, differentiated or understood. A classification system can be an approach of accomplishing classification. Classification can be performed using mathematical classification, statistical classification, classification theorems, e.g. in mathematics, and attribute value systems. Classifications can be alphanumeric. Classifications can be single or multi-dimensional. Classifications can be single or multi-layered. Classifications can be color coded. An ANN can use a single classification system, e.g. in supervised learning. An ANN can use multiple classification systems. When multiple classification systems are used, they can reside in different layers of a DNN or deep learning system.

Classification can be the problem of identifying to which of a set of categories or sub-populations a new observation belongs; this can be determined, for example, using a training data set with observations whose category membership is known. For example, a diagnosis can be assigned to a patient as a category which can be described by measured data or characteristics such a heart rate, blood pressure, presence of absence of symptoms or combinations of symptoms. Classification can be a pattern recognition.

Individual observations or data can be divided into a set of quantifiable properties. These properties may be categorical, e.g. "a", "b", "c", "d" etc. or ordinal, e.g. "excellent", "very good", "good", "acceptable", "average", or "poor". They can be integer or real valued. Observations or data can also be classified using similarity or distance functions, e.g. based on earlier observations or data. An algorithm that implements classification can be a classifier, A classifier can sometimes also be a mathematical function, e.g. implemented by a classification algorithm, that can map input data to a category.

Data can be classified, for example, into "excellent", "good", "acceptable" or "poor" outcome, e.g. one or more clinical outcomes or clinical outcome variables. Numeric values or ranges of numeric values can be assigned to different classes, for example numeric values or ranges of numeric values from a patient reported outcome measurement, from a clinical reporting system, and/or from one or more electronic measurements.

Discriminative Vs. Generative Models and Networks

In machine learning, discriminative models can be distinguished from generative models.

1. Discriminative models are trained to learn the boundaries between classes. They model the conditional probability of a target variable Y (class), given an observation x: $P(Y|X=x)$ ("probability of Y given X=x"). Discriminative models describe the probability for classifying a given example x into a classy E Y. Discriminative models include, for example, logistic regression, conditional random fields, support vector machines, neural networks, random forests, or perceptrons.

Generative models model the distribution of individual classes. They can generate data and provide a statistical model of the joint probability distribution on X×Y, $P(X,Y)=P(X|Y)*P(Y)$, for an observable variable X and a target variable Y. Generative models include, for example, naïve Bayes models and Bayes networks, hidden Markov models, Boltzmann machines, variational autoencoders or generative adversarial networks (GAN).

In some embodiments, the computer system can use a trained artificial neural network (ANN) to determine the treatment plan. The ANN can implement a discriminative model. A discriminative model can be trained to classify the input data, i.e. the preoperative and/or intraoperative data and/or postoperative data, into different classes, wherein each class can represent a different treatment plan.

In some embodiments, the ANN can implement a generative model. Instead of assigning preoperative and/or intraoperative input data and/or postoperative data to an existing class, a generative model is trained to generate the treatment plan steps based on the input data.

In some embodiments, a generative and a discriminative network model can be combined into a generative adversarial network (GAN) to generate a treatment plan. Using a training data set of existing recorded treatment plans for a number of preoperative and/or intraoperative input data and/or postoperative data sets, in this situation, the generative network can be trained to generate a preferred treatment plan from the preoperative and/or intraoperative input data. The discriminative network can be trained to evaluate the generated treatment plan and to distinguish the generated treatment plan from the actual treatment plan of the training case. Thus, the discriminative network can force the generative network to improve its results. (See U.S. Pat. No. 11,278,413 Para. 80-91).

Figure 11:
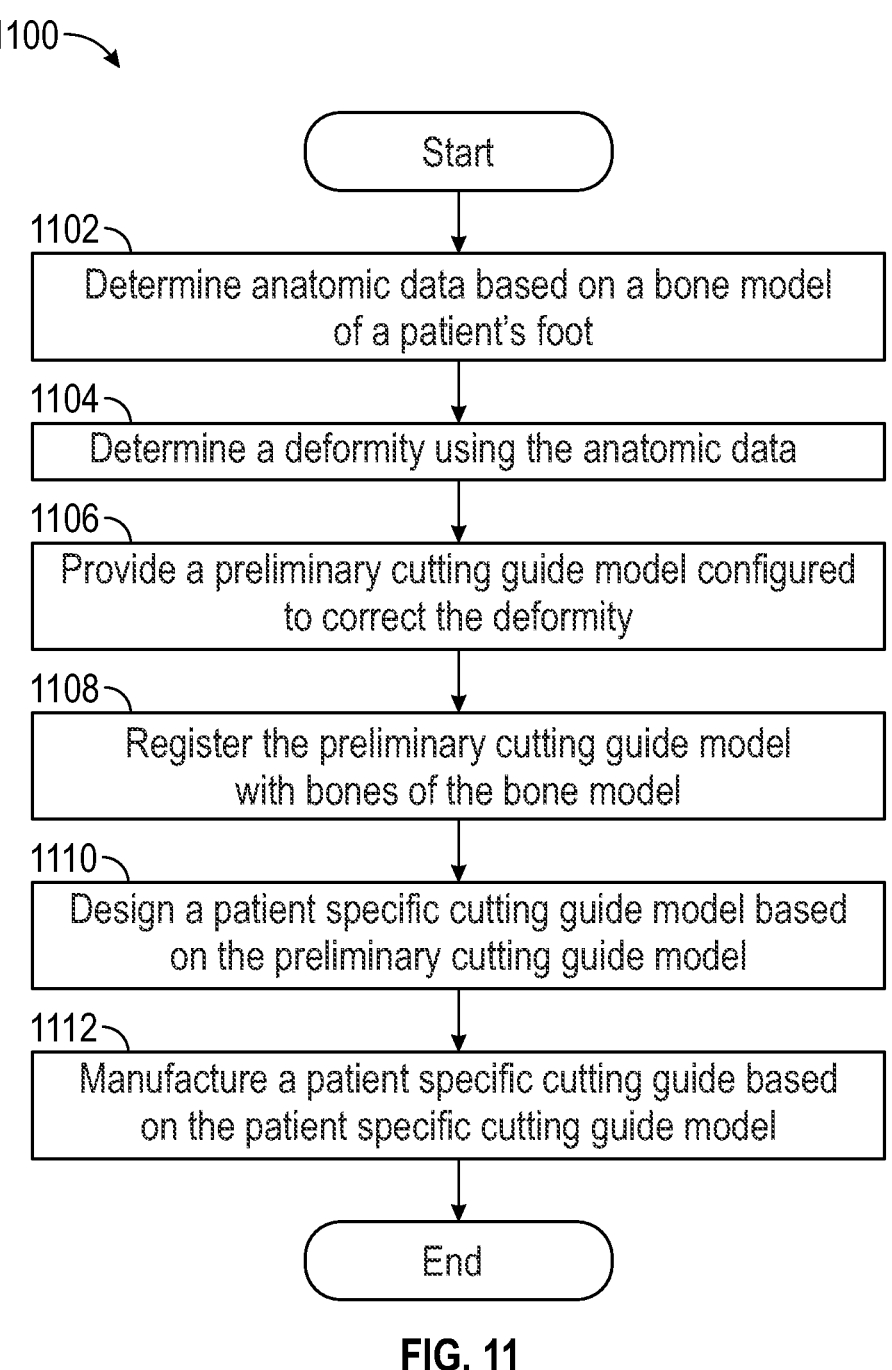
FIG. 11 is a flowchart diagram depicting a method 1100 for generating one or more patient specific instruments configured to correct a bone condition, according to one embodiment.

FIG. 11 illustrates a flowchart diagram depicting a method 1100 for generating one or more patient specific instruments configured to correct a bone condition, according to one embodiment. Prior to steps of the method 1100, a bone model (also referred to as CAD model above) is generated. The bone model may be generated using medical imaging of a patient's foot and may also be referred to as an anatomic model. The medical imaging image(s) may be used by computing devices to generate patient imaging data. The patient imaging data may be used to measure and account for orientation of one or more structures of a patient's anatomy. In certain embodiments, the patient imaging data may serve or be a part of anatomic data for a patient.

In one embodiment, the method 1100 begins after a bone model of a patient's body or body part(s) is generated. In a first step 1102, the method 1100 may review the bone model and data associated with the bone model to determine anatomic data of a patient's foot.

After step 1102, the method 1100 determine 1104 a deformity in the patient's anatomy using the anatomic data. In certain embodiments, the detection and/or identification of a deformity may employ advanced computer analysis system, expert systems, machine learning, and/or automated/artificial intelligence. As used herein, "artificial intelligence" refers to intelligence demonstrated by machines, unlike the natural intelligence displayed by humans and animals, which involves consciousness and emotionality. The distinction between artificial intelligence and natural intelligence categories is often revealed by the acronym chosen. 'Strong' AI is usually labelled as artificial general intelligence (AGI) while attempts to emulate 'natural' intelligence have been called artificial biological intelligence (ABI). Leading AI textbooks define the field as the study of "intelligent agents": any device that perceives its environment and takes actions that maximize its chance of achieving its goals. The term "artificial intelligence" can also be used to describe machines that mimic "cognitive" functions that humans associate with the human mind, such as "learning" and "problem solving". (Search "artificial intelligence" on Wikipedia.com Jun. 25, 2021. CC-BY-SA 3.0 Modified. Accessed Jun. 25, 2021.) Various kinds of deformities may be identified, such as a bunion. The deformities determined may include congenital as well as those caused by injury or trauma.

Next, the method 1100 proceeds and a preliminary cutting guide model is provided 1106 from a repository of template cutting guide models. A preliminary cutting guide model is a model of a preliminary cutting guide.

As used herein, "preliminary cutting guide" refers to a guide configured, designed, and/or engineered to serve as a template, prototype, archetype, or starting point for creating, generating, or fabricating a patient-specific cutting guide. In one aspect, the preliminary cutting guide may be used, as-is, without any further changes, modifications, or adjustments and thus become a patient-specific cutting guide. In another aspect, the preliminary cutting guide may be modified, adjusted, or configured to more specifically address the goals, objectives, or needs of a patient or a surgeon and by way of the modifications become a patient-specific cutting guide. The patient-specific cutting guide can be used by a user, such as a surgeon, to guide making one or more resections of a structure, such as a bone for a procedure. Accordingly, a preliminary cutting guide model can be used to generate a patient-specific cutting guide model. The patient-specific cutting guide model may be used in a surgical procedure to address, correct, or mitigate effects of the identified deformity and may be used to generate a patient-specific cutting guide that can be used in a surgical procedure for the patient.

In certain embodiments, the preliminary cutting guide model may be generated based on anatomic data and/or a bone model or a combination of these, and no model or predesigned structure, template, or prototype. Alternatively, or in addition, the preliminary cutting guide model may be, or may originate from, a template cutting guide model selected from a set of template cutting guide model. Each model in the set of template cutting guide models may include one or more cutting resection features positioned and/or sized and/or configured to fit for an average patient's foot. The template cutting guide model may subsequently be modified or revised by an automated process or manual process to generate the preliminary cutting guide model used in this disclosure.

As used herein, "template cutting guide" refers to a guide configured, designed, and/or engineered to serve as a template for creating, generating, or fabricating a patient-specific cutting guide. In one aspect, the template cutting guide may be used, as-is, without any further changes, modifications, or adjustments and thus become a patient-specific cutting guide. In another aspect, the template cutting guide may be modified, adjusted, or configured to more specifically address the goals, objectives, or needs of a patient or a surgeon and by way of the modifications become a patient-specific cutting guide. The patient-specific cutting guide can be used by a user, such as a surgeon, to guide making one or more resections of a structure, such as a bone for a procedure. Accordingly, a template cutting guide model can be used to generate a patient-specific cutting guide model. The patient-specific cutting guide model may be used in a surgical procedure to address, correct, or mitigate effects of the identified deformity and may be used to generate a patient-specific cutting guide that can be used in a surgical procedure for the patient.

"Repository" refers to any data source or dataset that includes data or content. In one embodiment, a repository resides on a computing device. In another embodiment, a repository resides on a remote computing or remote storage device. A repository may comprise a file, a folder, a directory, a set of files, a set of folders, a set of directories, a database, an application, a software application, content of a text, content of an email, content of a calendar entry, and the like. A repository, in one embodiment, comprises unstructured data. A repository, in one embodiment, comprises structured data such as a table, an array, a queue, a look up table, a hash table, a heap, a stack, or the like. A repository may store data in any format including binary, text, encrypted, unencrypted, a proprietary format, or the like.

Next, the method 1100 may register 1108 the preliminary cutting guide model with one or more bones of the bone model. This step 1108 facilitates customization and modification of the preliminary cutting guide model to generate a patient-specific cutting guide model from which a patient-specific cutting guide can be generated. The registration step 1108 combines two models and/or patient imaging data and positions both models for use in one system and/or in one model (e.g., model registration).

As used herein, "model registration" or "image registration" refers to a method, process, module, component, apparatus, and/or system that seeks to achieve precision in the alignment of two images. As used here, "image" may refer to either or both an image of a structure or object and another image or a model (e.g., a computer based model or a physical model, in either two dimensions or three dimensions). In the simplest case of image registration, two images are aligned. One image may serve as the target image and the other as a source image; the source image is transformed, positioned, realigned, and/or modified to match the target image. An optimization procedure may be applied that updates the transformation of the source image based on a similarity value that evaluates the current quality of the alignment. An iterative procedure of optimization may be repeated until a (local) optimum is found. An example is the registration of CT and PET images to combine structural and metabolic information. Image registration can be used in a variety of medical applications: Studying temporal changes; Longitudinal studies may acquire images over several months or years to study long-term processes, such as disease progression. Time series correspond to images acquired within the same session (seconds or minutes). Time series images can be used to study cognitive processes, heart deformations and respiration; Combining complementary information from different imaging modalities. One example may be the fusion of anatomical and functional information.

Since the size and shape of structures vary across modalities, evaluating the alignment quality can be more challenging. Thus, similarity measures such as mutual information may be used; Characterizing a population of subjects. In contrast to intra-subject registration, a one-to-one mapping may not exist between subjects, depending on the structural variability of the organ of interest. Inter-subject registration may be used for atlas construction in computational anatomy. Here, the objective may be to statistically model the anatomy of organs across subjects; Computer-assisted surgery: in computer-assisted surgery pre-operative images such as CT or MRI may be registered to intra-operative images or tracking systems to facilitate image guidance or navigation. There may be several considerations made when performing image registration: The transformation model. Common choices are rigid, affine, and deformable transformation models. B-spline and thin plate spline models are commonly used for parameterized transformation fields. Non-parametric or dense deformation fields carry a displacement vector at every grid location; this may use additional regularization constraints. A specific class of deformation fields are diffeomorphisms, which are invertible transformations with a smooth inverse; The similarity metric. A distance or similarity function is used to quantify the registration quality. This similarity can be calculated either on the original images or on features extracted from the images. Common similarity measures are sum of squared distances (SSD), correlation coefficient, and mutual information. The choice of similarity measure depends on whether the images are from the same modality; the acquisition noise can also play a role in this decision. For example, SSD may be the optimal similarity measure for images of the same modality with Gaussian noise. However, the image statistics in ultrasound may be significantly different from Gaussian noise, leading to the introduction of ultrasound specific similarity measures.

Multi-modal registration may use a more sophisticated similarity measure; alternatively, a different image representation can be used, such as structural representations or registering adjacent anatomy; The optimization procedure. Either continuous or discrete optimization is performed. For continuous optimization, gradient-based optimization techniques are applied to improve the convergence speed.

(Search "medical image computing" on Wikipedia.com Jun. 24, 2021. CC-BY-SA 3.0 Modified. Accessed Jun. 25, 2021.)

Next, the method 1100 may design 1110 a patient-specific cutting guide model based on the preliminary cutting guide model. The design step 1110 may be completely automated or may optionally permit a user to make changes to a preliminary cutting guide model or partially completed patient-specific cutting guide model before the patient-specific cutting guide model is complete. A preliminary cutting guide model and patient-specific cutting guide model are two examples of an instrument model. As used herein, "instrument model" refers to a model, either physical or digital, that represents an instrument, tool, apparatus, or device. Examples, of an instrument model can include a cutting guide model, a patient-specific cutting guide model, and the like. In one embodiment, a patient-specific cutting guide and a patient-specific cutting guide model may be unique to a particular patient and that patient's anatomy and/or condition.

The method 1100 may conclude by a step 1112 in which patient-specific cutting guide may be manufactured based on the patient-specific cutting guide model. Various manufacturing tools, devices, systems, and/or techniques can be used to manufacture the patient-specific cutting guide. As used herein, "manufacturing tool" or "fabrication tool" refers to a manufacturing or fabrication process, tool, system, or apparatus which creates an object, device, apparatus, feature, or component using one or more source materials. A manufacturing tool or fabrication tool can use a variety of manufacturing processes, including but not limited to additive manufacturing, subtractive manufacturing, forging, casting, and the like. The manufacturing tool can use a variety of materials including polymers, thermoplastics, metals, biocompatible materials, biodegradable materials, ceramics, biochemicals, and the like. A manufacturing tool may be operated manually by an operator, automatically using a computer numerical controller (CNC), or a combination of these techniques.

Figure 12:
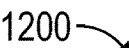
FIG. 12 illustrates an exemplary system configured to generate one or more patient specific instruments configured to correct a bone condition, according to one embodiment.

FIG. 12 illustrates an exemplary system 1200 configured to generate one or more patient specific instruments configured to correct a bone condition, according to one embodiment. "Bone condition" refers to any of a variety of conditions of bones of a patient. Bone conditions may be caused by or result from deformities, misalignment, malrotation, fractures, joint failure, and/or the like. A bone condition includes, but is not limited to, any angular deformities of one or more bone segments in either the lower or upper extremities (for example, tibial deformities, calcaneal deformities, femoral deformities, and radial deformities). "Malrotation" refers to a condition in which a part, typically a part of a patient's body has rotated from a normal position to an unnormal or uncommon position. The system 1200 may include an apparatus 1202 configured to accept, review, receive or reference a bone model 1204 and provide a patient-specific cutting guide 1206. In one embodiment, the apparatus 1202 is a computing device. In another embodiment, the apparatus 1202 may be a combination of computing devices and/or software components or a single software component such as a software application.

The apparatus 1202 may include a determination module 1210, a deformity module 1220, a provision module 1230, a registration module 1240, a design module 1250, and a manufacturing module 1260. Each of which may be implemented in one or more of software, hardware, or a combination of hardware and software.

The determination module 1210 determines anatomic data 1212 from a bone model 1204. In certain embodiments, the system 1200 may not include a determination module 1210 if the anatomic data is available directly from the bone model 1204. In certain embodiments, the anatomic data for a bone model 1204 may include data that identifies each anatomic structure within the bone model 1204 and attributes about the anatomic structure. For example, the anatomic data may include measurements of the length, width, height, and density of each bone in the bone model. Furthermore, the anatomic data may include position information that identifies where each structure, such as a bone is in the bone model 1204 relative to other structures, including bones. The anatomic data may be in any suitable format and may be stored separately or together with data that defines the bone model 1204.

In one embodiment, the determination module 1210 may use advanced computer analysis system such as image segmentation to determine the anatomic data. Alternatively, or in addition the determination module 1210 may use software and/or systems that implement one or more artificial intelligence methods (e.g., machine learning and/or neural networks) for deriving, determining, or extrapolating, anatomic data from the bone model. In one embodiment, the determination module 1210 may perform an anatomic mapping of the bone model 1204 to determine each unique aspect of the intended osteotomy procedure and/or bone resection and/or bone translation. The anatomic mapping may be used to determine coordinates to be used for an osteotomy procedure, position and manner of resections to be performed either manually or automatically or using robotic surgical assistance, a width for bone cuts, an angle for bone cuts, a predetermined depth for bone cuts, dimensions and configurations for resection instruments such as saw blades, milling bit size and/or speed, saw blade depth markers, and/or instructions for automatic or robotic resection operations.

The deformity module 1220 determines or identifies one or more deformities or other anomalies based on the anatomic data 1212. The deformity may include a deformity between two bones of a patient's foot as represented in the bone model 1204. In one embodiment, the deformity module 1220 may compare the anatomic data 1212 to a general model that is representative of most patient's anatomies and that does not have a deformity or anomaly. In one embodiment, if the anatomic data 1212 does not match the general model a deformity is determined. Various deformities may be detected including those that have well-known names for the condition and those that are unnamed.

The provision module 1230 is configured to provide a preliminary cutting guide model 1238. The provision module 1230 may use a variety of methods to provide the preliminary cutting guide model. In one embodiment, the provision module 1230 may generate preliminary cutting guide model. In the same or an alternative embodiment, the provision module 1230 may select a template cutting guide model for an osteotomy procedure configured to correct the deformity identified by the deformity module 1220. In one embodiment, the provision module 1230 may select a template cutting guide model from a set of template cutting guide models (e.g., a library, set, or repository of template cutting guide models).

The registration module 1240 registers the preliminary cutting guide model with one or more bones or other anatomical structures of the bone model 1204. As explained above, registration is a process of combining medical imaging data, patient imaging data, and/or one or more models such that the preliminary cutting guide model can be used with the bone model 1204.

The design module 1250 designs a patient-specific cutting guide (or patient-specific cutting guide model) based on the preliminary cutting guide model. The design operation of the design module 1250 may be completely automated, partially automated, or completely manual. A user may control how automated or manual the designing of the patient-specific cutting guide (or patient-specific cutting guide model) is.

The manufacturing module 1260 may manufacture a patient-specific cutting guide 1206 using the preliminary cutting guide model. The manufacturing module 1260 may use a patient-specific cutting guide model generated from the preliminary cutting guide model. The manufacturing module 1260 may provide the patient-specific cutting guide model to one or more manufacturing tools and/or fabrication tool. The patient-specific cutting guide model may be sent to the tools in any format such as an STL file or any other CAD modeling or CAM file or method for data exchange. In one embodiment, a user can adjust default parameters for the patient-specific cutting guide such as types and/or thicknesses of materials, dimensions, and the like before the manufacturing module 1260 provides the patient-specific cutting guide model to a manufacturing tool.

Effective connection of the cutting guide to one or more bones across a joint can ensure that cut surfaces are formed in desired locations and orientation and mitigate removal of hard tissue and/or soft tissue outside in undesired locations.

Figure 13:
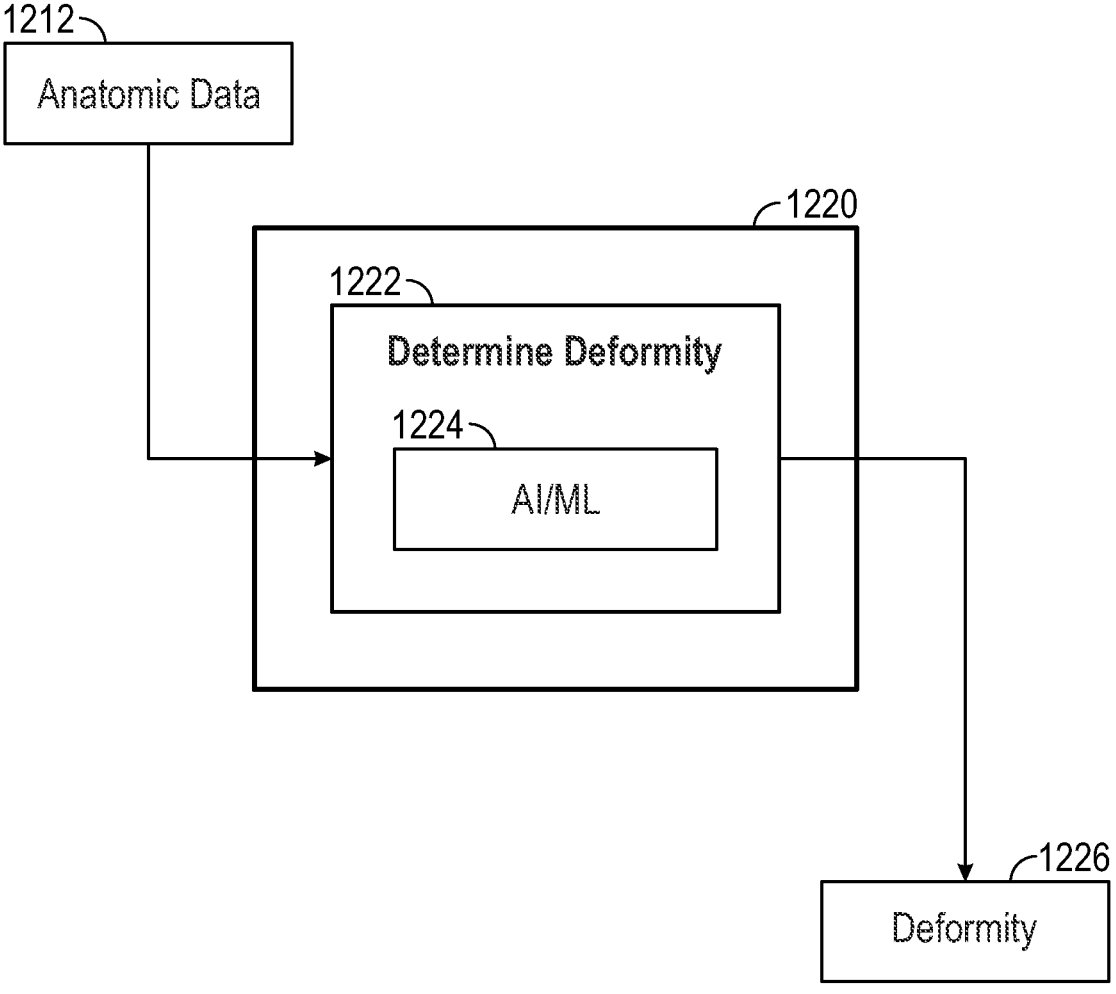
FIG. 13 illustrates an exemplary apparatus configured to determine a deformity, according to one embodiment.

FIG. 13 illustrates an exemplary deformity module 1220 configured to determine a deformity, according to one embodiment. The deformity module 1220 may detect one or more deformities and/or anomalies of a patient's anatomy by analyzing anatomic data 1212 and other inputs, such as a certain type or class of deformities to search for.

The deformity module 1220 may be completely automated, partially automated, or completely manual. A user may control how automated or manual the detection of the deformity is. The user may provide instructions to the deformity module 1220 to facilitate automatic or partially automated detection or determination of one or more deformities.

The deformity module 1220 may include a deformity detection module 1222. The deformity detection module 1222 may be configured for automated determination of a deformity. For example, in one embodiment, the deformity detection module 1222 includes an artificial intelligence or machine learning module 1224. The artificial intelligence or machine learning module 1224 is configured to implement one or more of a variety of artificial intelligence modules that may be trained for detecting an anomaly or deformity based on anatomic data 1212. In another embodiment, the deformity module 1220 may receive patient imaging data, a bone model, a CAD model or the like and use these inputs to determine deformities in the bones of a patient.

In one embodiment, the artificial intelligence or machine learning module 1224 may be trained using a large data set of anatomic data 1212 for healthy non-deformed bones and a large data set of anatomic data 1212 for deformed bones in which the deformity has been previously identified and labeled in the dataset. The artificial intelligence or machine learning module 1224 may implement, or use, a neural network configured according to the training such that as the artificial intelligence or machine learning module 1224 accepts the anatomic data 1212 for a particular patient, the artificial intelligence or machine learning module 1224 is able to determine what deformity 1226 exists in the patient's bones, when such a deformity 1226 exists.

Figure 14A:
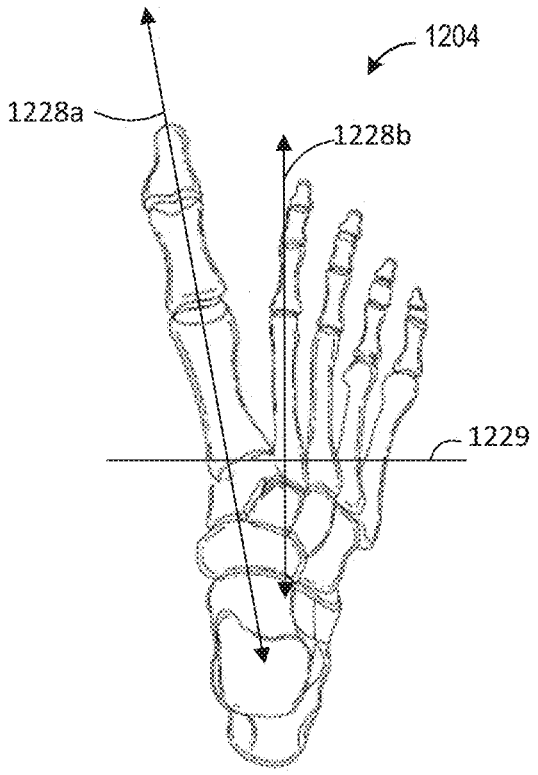
FIGS. 14A and 14B illustrates one example of a method for determining a deformity and a correction for the deformity, according to one embodiment.
Figure 14B:
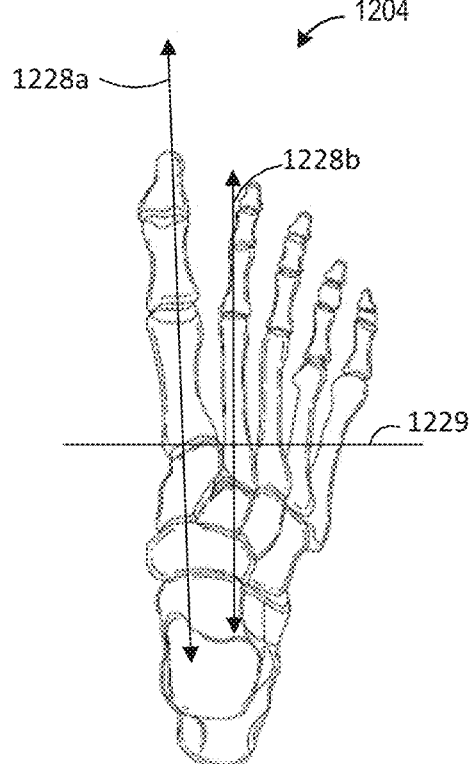

FIGS. 14A and 14B illustrates one example of a method for determining a deformity and a correction for the deformity, according to one embodiment. The deformity module 1220 may use a particular method for determining whether or not two or more bones have a deformity 1226. The deformity module 1220 may use one or more advanced computing techniques for determining the deformity 1226.

Referring now to FIG. 14A, in one embodiment, the deformity module 1220 starts by identifying a center longitudinal axis 1228*a*, 1228*b* (FIG. 14A shows two of the plurality of axes for clarity) for each bone in the bone model 1204. For example, the deformity module 1220 may identify the center longitudinal axis 1228*a* for a first metatarsal and the center longitudinal axis 1228*b* for the second metatarsal.

Next, the deformity module 1220 may identify a reference axis 1229 perpendicular with one of the center longitudinal axes 1228*a,b*, such as center longitudinal axis 1228*b*. The reference axis 1229 may be at or near a joint between bones of the bone model 1204. The deformity module 1220 may determine that a deformity 1226 exists if the center longitudinal axes 1228*a,b* are not parallel or are not parallel when measured with a predefined margin for error. FIG. 13A illustrates a bone model 1204 with a deformity 1226. The deformity 1226 is that the first metatarsal is not parallel or not sufficiently parallel to the second metatarsal at the joint between the first metatarsal and the medial cuneiform bones. Once the deformity 1226 is determined, the deformity module 1220 or apparatus 1202 may determine what steps, procedures, or instrumentation can be used to correct the deformity 1226. The deformity module 1220 may use a name, label, tag, or other identifier for a particular deformity 1226.

FIG. 14B illustrates the bone model 1204 of FIG. 14A after a corrective procedure and/or application of corrective implants may be performed. The center longitudinal axes 1228*a,b* are parallel, or sufficiently parallel, such that the deformity 1226 is not a problem for a patient.

Figure 15:
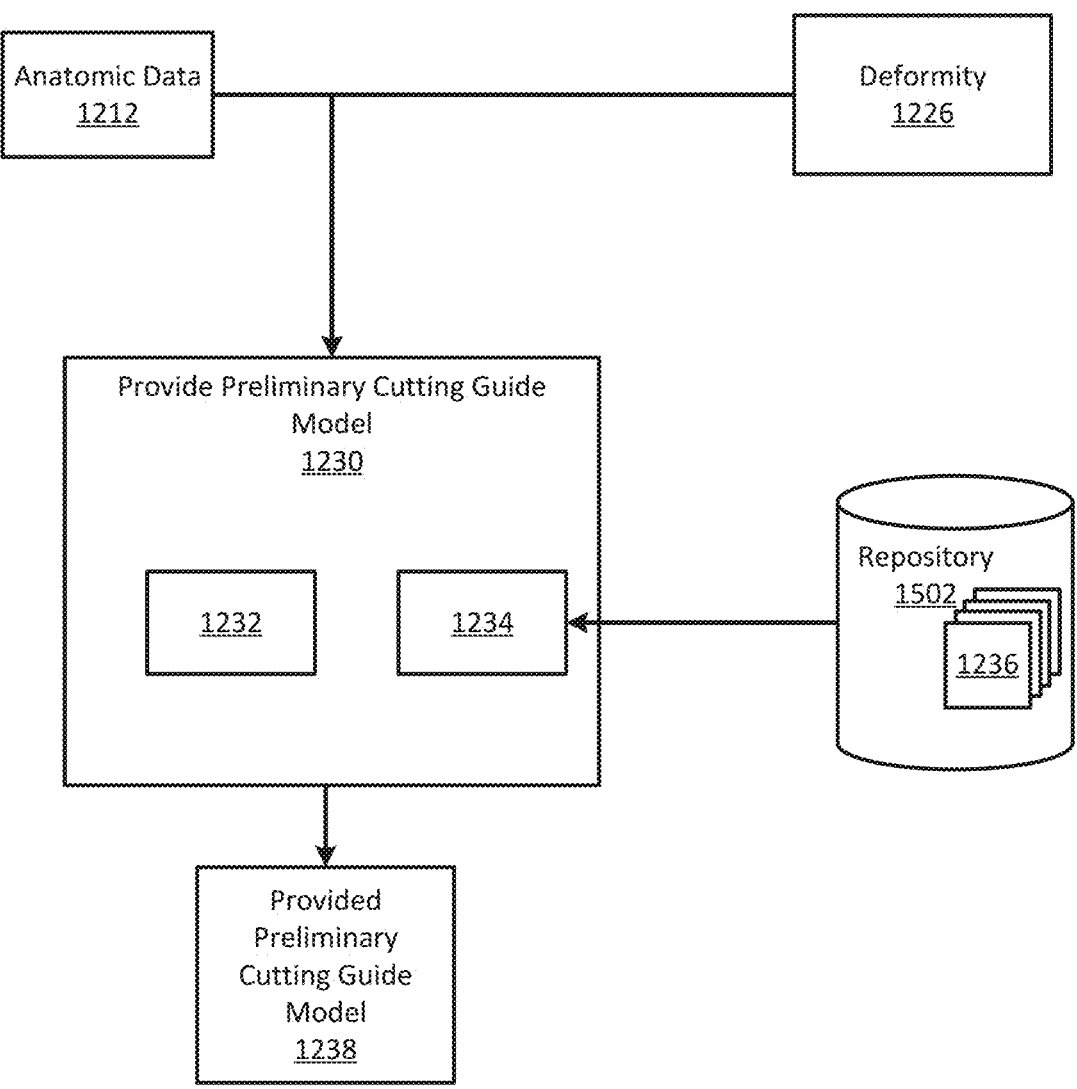
FIG. 15 illustrates an exemplary provision module configured to provide a preliminary cutting guide model, according to one embodiment.

FIG. 15 illustrates an exemplary provision module 1230 configured to provide a preliminary cutting guide model, according to one embodiment. The provision module 1230 may accept anatomic data 1212 and a designation, identifier, label, or name of a deformity 1226. In the illustrated embodiment, the provision module 1230 may generate a preliminary cutting guide model 1238 (e.g., generate from 'scratch') or the provision module 1230 may select a template cutting guide model 1236 automatically from a set of template cutting guide models 1236 stored in a repository 1502. The provision module 1230 may incorporate a variety of parameters in order to provision, generate, determine, or select a template cutting guide model 1236. For example, in addition to the anatomic data 1212, the provision module 1230 may include patient imaging data, deformity parameters for a variety of angular deformities (in all 3 planes) of the midfoot or hind foot and ankle where an osteotomy could be used, patient preferences, and/or surgeon input parameters.

In one embodiment, the provision module 1230 may include a generator 1232 and/or a selection module 1234. In one embodiment, the generator 1232 is configured to generate a preliminary cutting guide model 1238. In certain embodiments, the generator 1232 may generate or create the preliminary cutting guide model based on anatomic data and/or a bone model or a combination of these and no other inputs. (e.g. no model or predesigned structure, template, or prototype). Alternatively, or in addition, the generator 1232 may generate or create the preliminary cutting guide model using a standard set of features or components that can be combined to form the preliminary cutting guide model. The generated preliminary cutting guide model may subsequently be modified or revised by an automated process, and/or manual process, to generate the preliminary cutting guide model used in this disclosure.

The selection module 1234 may be configured to select a template cutting guide model 1236 for an osteotomy procedure configured to correct the deformity identified by the deformity module 1220. In one embodiment, the provision module 1230 may select a template cutting guide model 1236 from a set of template cutting guide models 1236 (e.g., a library, set, or repository of template cutting guide models 1236). In one embodiment, the template cutting guide model 1236 may include digital models. In another embodiment, the template cutting guide model 1236 may include physical models. In such an embodiment, the repository 1502 may be a warehouse or other inventory repository. Where the template cutting guide model 1236 are physical models, the systems, modules, and methods of this disclosure can be used and the physical model may be milled or machined (e.g., a CNC machine) to form a patient specific cutting guide that conforms to the bone surfaces of the patient.

Selection of a suitable template cutting guide model 1236 may be completely automated and/or may be partially automated and/or may depend on confirmation from a user before a generated preliminary cutting guide model or a proposed template cutting guide model 1236 becomes the preliminary cutting guide model 1238. In another embodiment, the selection module 1234 may facilitate a manual selection by a user of a template cutting guide model 1236 that would become the preliminary cutting guide model 1238. The selection module 1234 may use the anatomic data 1212 or the bone model 1204 or a combination of these to select a suitable template cutting guide model that would become the preliminary cutting guide model 1238.

In another embodiment, the generator 1232 may facilitate revisions or edits by a user of a generated cutting guide model that will become the preliminary cutting guide model 1238. The selection module 1234 may use the anatomic data 1212 or the bone model 1204 or a combination of these to select a suitable template cutting guide model that would become the preliminary cutting guide model 1238.

The repository 1502 may include any number of, and/or a variety of template cutting guide models 1236. The template cutting guide models 1236 may be distinguished based on a gender or age of the patient, which joint of a midfoot, hind foot, or ankle will be cut, which material will be used for the template cutting guide, and the like. The template cutting guide model 1236 may differ from each other in what degree of deformity correction the template cutting guide model 1236 is designed to provide. In addition, the template cutting guide models 1236 may be distinguished based how one or more features of the template cutting guide model 1236 are positioned, arranged, and/or configured relative to each other. For example in certain template cutting guide models 1236, the number, position, and/or configuration of alignment features and/or bone attachment features (e.g., holes) may vary based on needs or preferences of patients, the nature of the deformity, and/or surgeon preferences.

In certain embodiments, the template cutting guide models 1236 may vary in how the slots (e.g., resection features, See FIG. 6) for the cuts are positioned, angled, and oriented relative to each other and/or to a longitudinal axis of respective bones at a joint for use with the template cutting guide model 1236. For example in one template cutting guide model 1236 the slot 1352 for a resection of a metatarsal bone may be perpendicular to a longitudinal axis of the metatarsal bone and the slot 1350 may be angled relative to a longitudinal axis of the cuneiform or cuboid bone such that once the two bones are brought together the deformity is corrected. Alternatively, in another template cutting guide model 1236 the slot for a resection of a metatarsal bone may be angled relative to a longitudinal axis of the metatarsal bone and the slot 1350 may be perpendicular to a longitudinal axis of the cuneiform or cuboid bone such that once the two bones are brought together the deformity is corrected.

The selection module 1234 may be configured to automatically select a template cutting guide model 1236 and/or provide an automatic template cutting guide model 1236 recommendation that can be changed by a user, such as a surgeon. For example, in one embodiment, the provision module 1230 and/or selection module 1234 includes an artificial intelligence or machine learning module. The artificial intelligence or machine learning module is configured to implement one or more of a variety of artificial intelligence modules that may be trained for selecting a template cutting guide model 1236 based on anatomic data 1212 and/or other input parameters. In one embodiment, the artificial intelligence or machine learning module may be trained using a large data set of anatomic data 1212 for suitable template cutting guide models 1236 identified and labeled in the dataset by professionals for use to treat a particular deformity 1226. The artificial intelligence or machine learning module may implement, or use, a neural network configured according to the training such that as the artificial intelligence or machine learning module is able to select a suitable template cutting guide model 1236. The template cutting guide model 1236 selected by the selection module 1234 can become the preliminary cutting guide model 1238.

Figure 16:
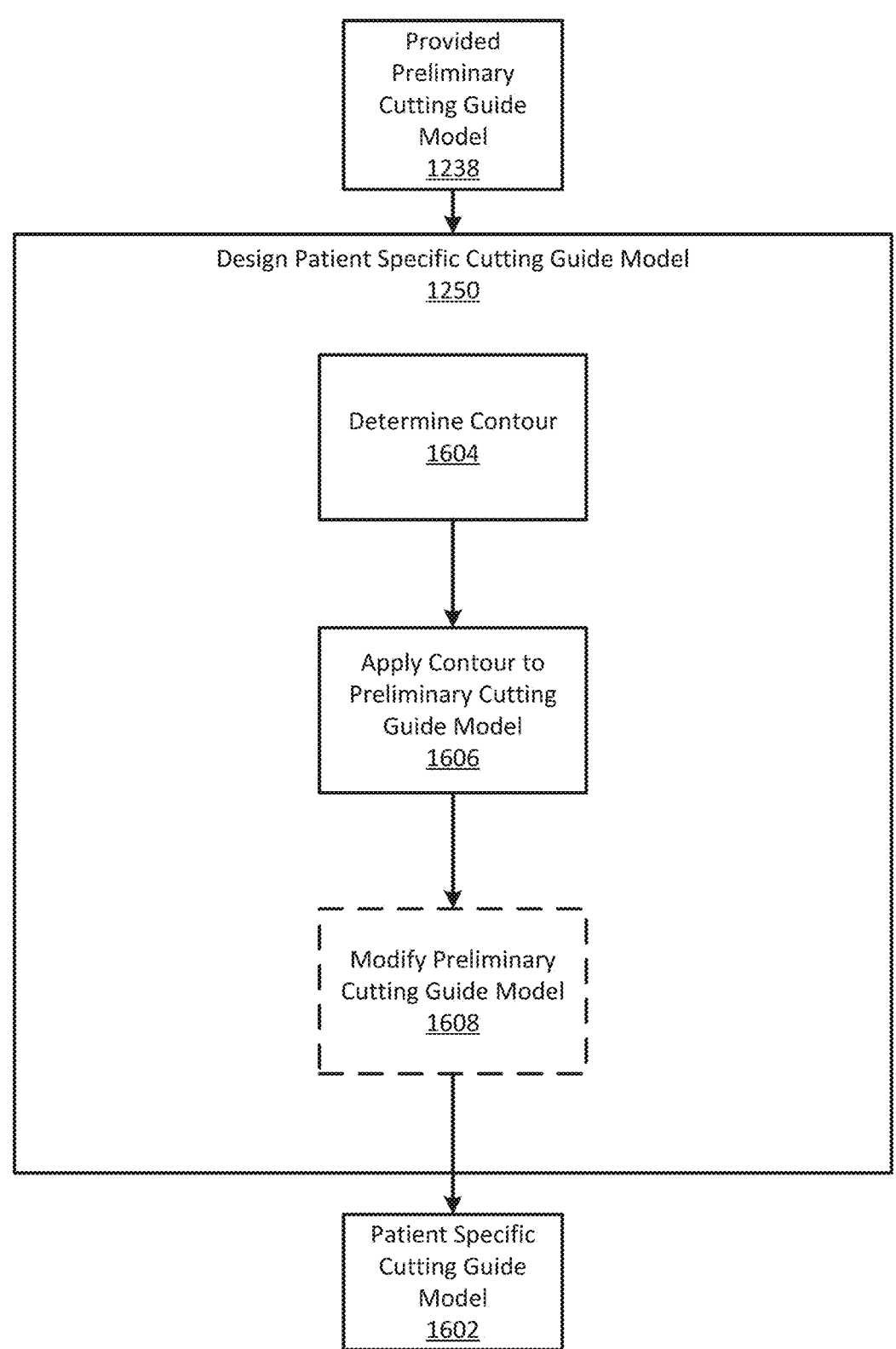
FIG. 16 illustrates an exemplary design module configured to design a patient specific cutting guide model, according to one embodiment.

FIG. 16 illustrates an exemplary design module 1250 configured to design a patient specific cutting guide model, according to one embodiment. The design module 1250 may accept a preliminary cutting guide model 1238 and generate a patient specific cutting guide model 1602. In one embodiment, the design module 1250 includes a contour module 1604, an application module 1606, and/or an optional modification module 1608.

Referring now to FIG. 16, the design module 1250 may modify the preliminary cutting guide model 1238 such that the bone-facing and/or bone-contacting surfaces of the preliminary cutting guide model 1238 match a contour of the surfaces and/or joint of bones of a joint that is to be resected using the preliminary cutting guide model 1238.

The contour module 1604 may determine a contour of the bones that will contact the preliminary cutting guide model 1238. The contour module 1604 may use a bone model 1204 and/or anatomic data 1212 to determine the contour. For example, the contour module 1604 may determine the shapes of the medial cuneiform 202 and/or the first metatarsal 208.

The application module 1606 may apply the contour to the provided preliminary cutting guide model 1238 to custom contour a bone apposition surface of the preliminary cutting guide model 1238 to match the shapes of the medial cuneiform 202 and/or the first metatarsal 208. Applying the contour to the preliminary cutting guide model 1238 may convert the preliminary cutting guide model 1238 to a patient specific cutting guide model 1602.

Generation of the contours of the cuneiform apposition portion 326 and the metatarsal apposition portion 328 of the preliminary cutting guide model 1238 may be performed relative easily in various CAD programs. In some embodiments, the shapes of the corresponding surfaces of the medial cuneiform 202 and the first metatarsal 208 may be obtained directly from the bone model 1204, anatomic data 1212, CAD models and/or CT scan data, and simply copied onto the preliminary cutting guide model 1238. Various operations may be used to copy surfaces from one object to another. Additionally or alternatively, various Boolean operations, such as a Boolean subtraction operation, may be used to remove material from a model for the body 310 of the preliminary cutting guide model 1238 with a shape that matches the surfaces of the medial cuneiform 202 and the first metatarsal 208.

In certain embodiments, the design module 1250 may include an optional module, such as a modification module 1608. The modification module 1608 may enable a user such as a technician or surgeon to make additional modifications to the design and configuration of the preliminary cutting guide model 1238. In one embodiment, the user can change any of the features, angles, configurations, or parameters of the preliminary cutting guide model 1238. For example, a surgeon may be aware of other concerns or anatomic deformities of a patient, for example on an opposite foot or in connection with a hip or other orthopedic joint which motivate the surgeon to adjust an angle of one of more resection features of the preliminary cutting guide model 1238.

Alternatively, or in addition, a user may use the modification module 1608 to modify a predefined osteotomy procedure. The user may add, remove, or modify steps and the instrumentation used in the osteotomy procedure to create a patient specific osteotomy procedure. In this manner, a user may configure features of a preliminary cutting guide model 1238 or modified preliminary cutting guide model and/or osteotomy procedure specific to a patient specific osteotomy procedure the surgeon is planning for the patient. As used herein, "patient specific osteotomy procedure" refers to an osteotomy procedure that has been adjusted, tailored, modified, or configured to specifically address the needs or desires or a particular patient. In certain aspects, one patient specific osteotomy procedure may be useable in connection with only one patient. In other aspects, one patient specific osteotomy procedure may be useable with a number of patients having a particular class of characteristics.

The user may review the preliminary cutting guide model 1238 and may adjustments or revisions or make no adjustments or revisions. The output of the modification module 1608 and/or the application module 1606 is a patient specific cutting guide model 1602.

Figure 17:
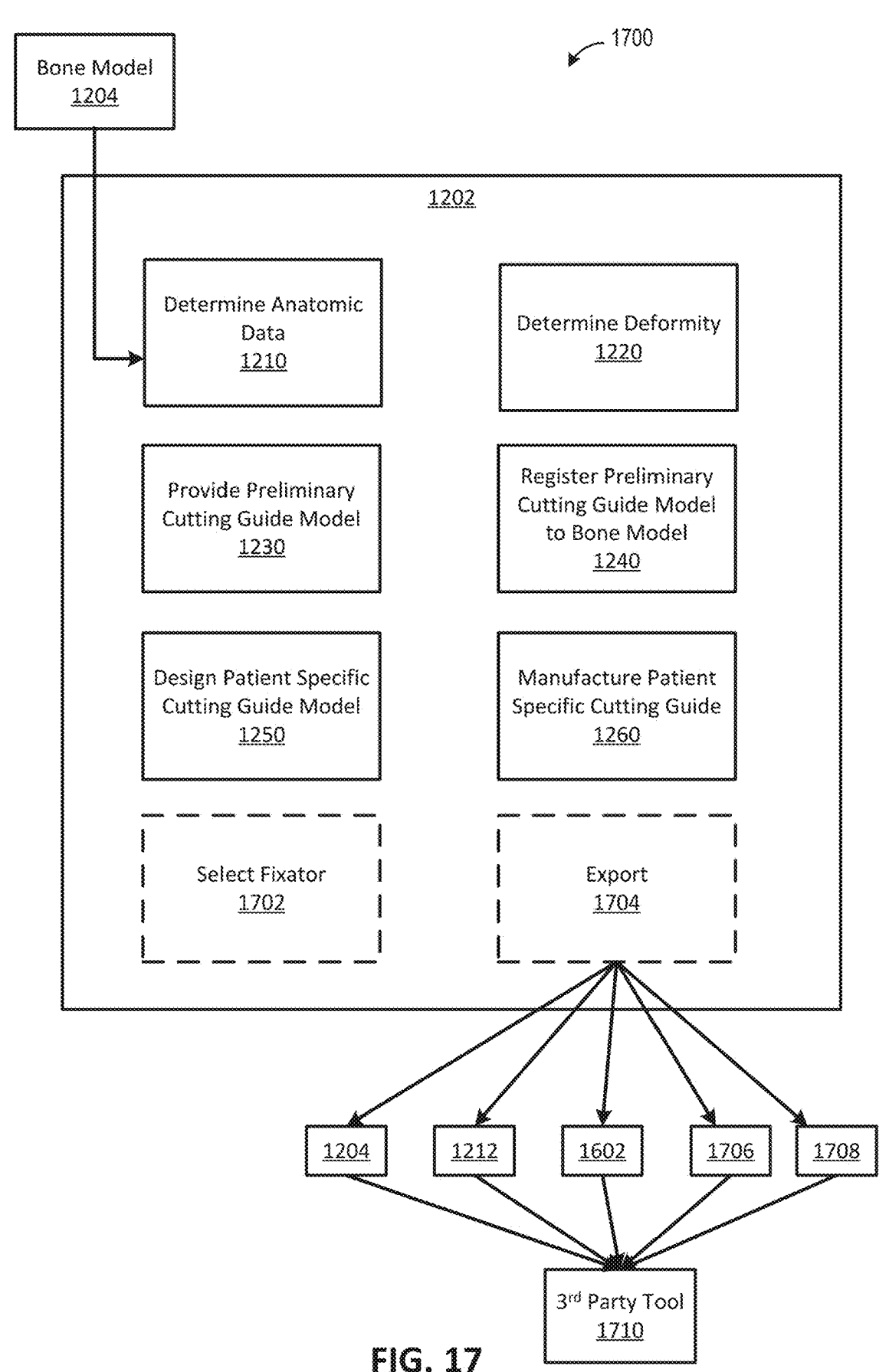
FIG. 17 illustrates an exemplary system configured to generate one or more patient specific instruments configured to correct a bone condition, according to one embodiment.

FIG. 17 illustrates an exemplary system 1700 configured to generate one or more patient specific instruments configured to correct a bone condition, according to one embodiment. The system 1700 may include similar components or modules to those described in relation to FIG. 12. In addition, the system 1700 may include a fixator selector 1702 and/or an export module 1704.

The fixator selector 1702 enables a user to determine which fixator(s) to use for an osteotomy procedure planned for a patient. In one embodiment, the fixator selector 1702 may recommend one or more fixators based on the bone model 1204, the deformity 1226 or input from a user or a history of prior osteotomy procedures performed to correct a particular deformity 1226. In one embodiment, the fixator selector 1702 selects a bone plate for fixation of two bones of the patient during an osteotomy procedure. The fixator selector 1702 may select a fixator model from a set of predefined fixator models or select a physical fixator from a set of fixators. The fixators may include a plate and associated accessories such as screws, anchors, and the like.

As used herein, a "fixator" refers to an apparatus, instrument, structure, device, component, member, system, assembly, or module structured, organized, configured, designed, arranged, or engineered to connect two bones or bone fragments or a single bone or bone fragment and another fixator to position and retain the bone or bone fragments in a desired position and/or orientation. Examples of fixators include both those for external fixation as well as those for internal fixation and include, but are not limited to pins, wires, Kirschner wires, screws, anchors, bone anchors, plates, bone plates, intramedullary nails or rods or pins, implants, interbody cages, fusion cages, and the like.

In one embodiment, the fixator selector 1702 includes an artificial intelligence or machine learning module. The artificial intelligence or machine learning module is configured to implement one or more of a variety of artificial intelligence modules that may be trained for selecting fixator(s) based on anatomic data 1212 and/or other input parameters. In one embodiment, the artificial intelligence or machine learning module may be trained using a large data set of anatomic data 1212 for suitable fixator(s) identified and labeled in the dataset by professionals for use to treat a particular deformity 1226. The artificial intelligence or machine learning module may implement, or use, a neural network configured according to the training such that as the artificial intelligence or machine learning module is able to select or recommend suitable fixator(s).

The export module 1704 is configured to enable exporting of a patient specific cutting guide model 1602 for a variety of purposes including, but not limited to, fabrication/manufacture of a patient specific cutting guide 1206 and/or fixator(s), generation of a preoperative plan, generation of a physical bone model matching the bone model 1204, and the like. In one embodiment, the export module 1704 is configured to export the bone model 1204, anatomic data 1212, a patient specific cutting guide model 1602, a preoperative plan 1706, a fixator model 1708, or the like. In this manner the custom instrumentation and/or procedural steps for an osteotomy procedure can be used in other tools. The preoperative plan 1706 may include a set of step by step instructions and/or recommendations for a surgeon or other staff in performing an osteotomy procedure such as patient specific osteotomy procedure. The preoperative plan 1706 may include images and text instructions and may include identification of instrumentation to be used for different steps of the osteotomy procedure. The instrumentation may include the patient specific cutting guide 1206 and/or one or more fixators. In one embodiment, the export module 1704 may provide a fixator model which can be used to fabricate a fixator for the osteotomy procedure.

The exports (1204, 1212, 1602, 1706, and 1708) may be inputs for a variety of 3rd party tools 1710 including a manufacturing tool, a simulation tool, a virtual reality tool, an augmented reality tool, an operative procedure simulation tool, a robotic assistance tool, and the like. A surgeon can then use these tools when performing an osteotomy procedure or for rehearsals and preparation for the osteotomy procedure. For example, a physical model of the bones, patient specific cutting guide 1206, and/or fixators can be fabricated, and these can be used for a rehearsal operative procedure. Alternatively, a surgeon can use the bone model 1204, preliminary cutting guide model 1238, and/or a fixator model to perform a simulated osteotomy procedure using an operative procedure simulation tool.

Figure 18:
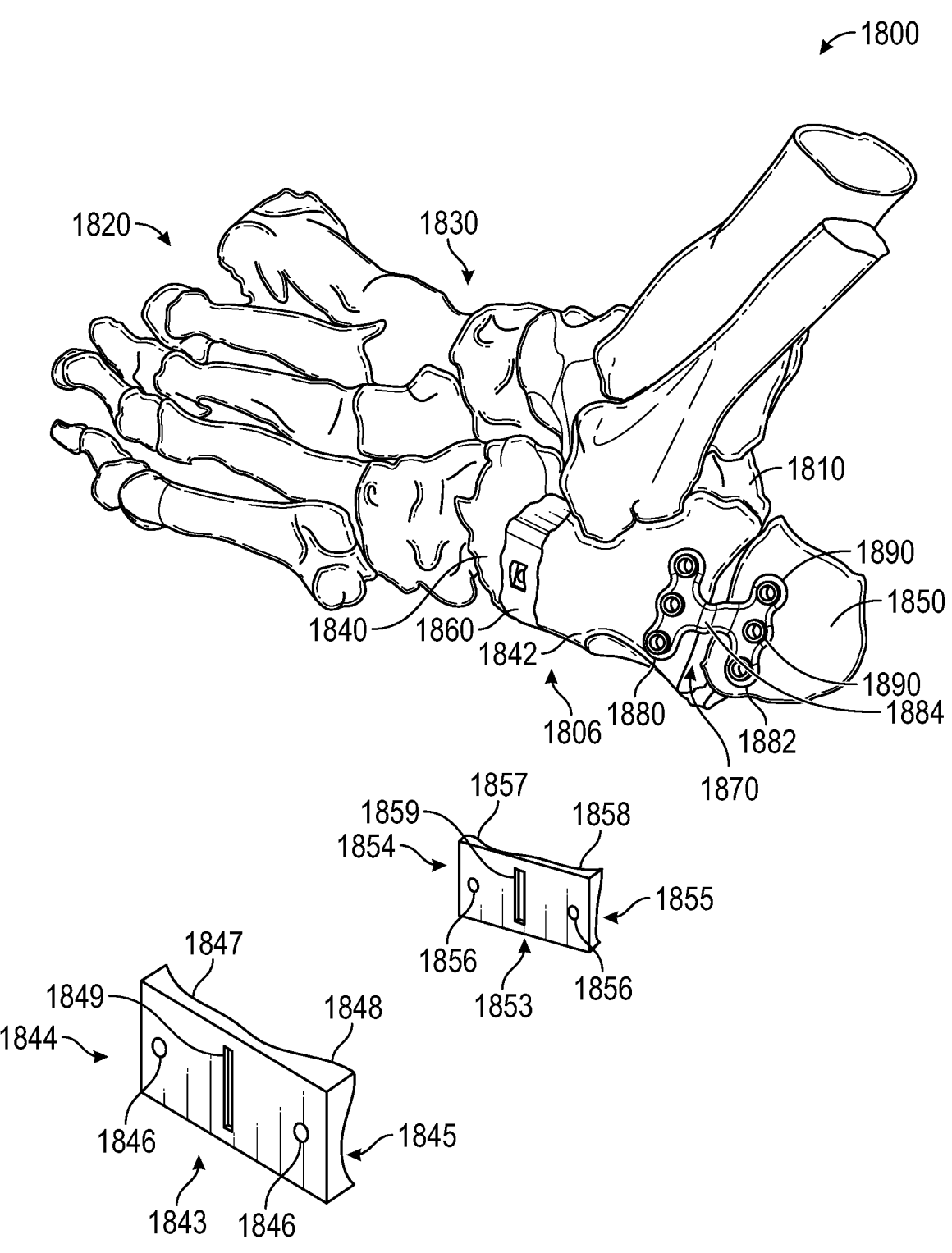
FIG. 18 is a rear, perspective view of a foot, after performance of an Evans calcaneal osteotomy and a medializing calcaneal osteotomy, according to one embodiment.

FIG. 18 is a rear, perspective view of a foot 1800, after performance of an Evans calcaneal osteotomy and a medializing calcaneal osteotomy with patient-specific instruments and/or implants, according to one embodiment. The foot 1800 may have a calcaneus 1806 and a talus 1810, in addition to the metacarpals 1820 and cuneiforms 1830. Pursuant to the Evans calcaneal osteotomy, an anterior portion of the calcaneus 1806 may be cut along the medial-lateral direction to separate a first bone segment 1840 of the calcaneus 1806 from a second bone segment 1842 of the calcaneus 1806. The second bone segment 1842 may be reoriented medially, relative to the first bone segment 1840, such that a heel 1850 of the calcaneus 1806 is moved medially, simulating a natural, healthy arch in the foot 200.

The cut between the first bone segment 1840 and the second bone segment 1842 may be carried out virtually (for example, in CAD) on a model of the calcaneus 1806 obtained from a CT scan or other imaging of the patient's foot. Thus, the optimal realignment of the posterior end of the calcaneus 1806 can be obtained. If desired, a patient-specific cutting guide, or cutting guide 1843, may be generated in order to facilitate resection of the calcaneus 1806.

As shown, the cutting guide 1843 may have a first end 1844 and a second end 1845, each of which has a bone attachment feature 1846. The bone attachment features 1846 may be used to secure the first end 1844 and the second end 1845 to the first bone segment 1840 and the second bone segment 1842, respectively. The first end 1844 may have a first bone engagement surface 1847 that is shaped to match a corresponding contour on the first bone segment 1840, and the second end 1845 may have a second bone engagement surface 1848 that is shaped to match a corresponding contour on the second bone segment 1842. Thus, the cutting guide 1843 may naturally lie flush with the surface of the calcaneus 1806, in the optimal position on the calcaneus 1806 to facilitate resection of the calcaneus 1806 to divide the first bone segment 1840 from the second bone segment 1842. The cutting guide 1843 may have a resection feature 1849, such as a slot, that can be used to guide a cutter to form a single cut between the first bone segment 1840 and the second bone segment 1842.

After the cut has been made to split the calcaneus 1806 into the first bone segment 1840 and the second bone segment 1842, the surgeon may angle the second bone segment 1842 relative to the first bone segment 1840 in the predetermined (previously modeled) relative orientation. This reorientation between the first bone segment 1840 and the second bone segment 1842 may leave a wedge-shaped gap between the first bone segment 1840 and the second bone segment 1842. In order to maintain the desired relative orientation, an implant 1860 with a wedge shape may be inserted into the gap and secured to the first bone segment 1840 and the second bone segment 1842. The implant 1860 may be fabricated specifically for the patient, since the precise angulation and position of the realignment may also be patient specific. As shown, the implant 1860 may have exterior surfaces that are contoured to match the contours of the adjoining portions of the first bone segment 1840 and the second bone segment 1842. Thus, the implant 1860 may provide secure fixation, while not protruding beyond the adjoining surfaces of the first bone segment 1840 and the second bone segment 1842. Thus, the implant 1860 may be devoid of proud edges or other protrusions that could otherwise interfere with motion between the calcaneus 1806 and the talus 1810, or with surrounding soft tissues, thus interfering with the patient's post-operative gait. "Soft tissue" refers to tissue of a patient (i.e., human or animal). Examples of soft tissue include but are not limited to skin, ligament, tendon, fascia, fat muscle, fibrous tissue, blood vessels, lymph vessels, brain tissue, and/or nerves.

The implant 1860 may be made of any biocompatible material, including but not limited to Titanium and alloys thereof, stainless steel, PEEK, and/or the like. The implant 1860 may be formed by any method known in the art, including but not limited to forging, casting, milling, additive manufacturing, and/or the like. In some embodiments, the implant 1860 may have an interior void that can be filled with bone graft or other material designed to promote boney in-growth between the cut surfaces of the first bone segment 1840 and the second bone segment 1842. In alternative embodiments, the implant 1860 may have a mesh and/or lattice structure that facilitates such boney in-growth, which structure may be formed via additive manufacturing.

As mentioned previously, a medializing calcaneal osteotomy may optionally be performed in addition to or in place of the Evans calcaneal osteotomy. As shown, the heel 1850 may be cut from the remainder of the second bone segment 1842 and may be displaced medially. This displacement may also help to restore normal gait and tendon function in the foot 200, particularly when coupled with the Evans calcaneal osteotomy. The proper displacement of the heel 1850 relative to the remainder of the second bone segment 1842 may be determined based on analysis of the CAD models from scans of the foot 200. If desired, the model of the calcaneus 1806 may be divided and manipulated in CAD to simulate the repositioning of the heel 1850 pursuant to the medializing calcaneal osteotomy. Thus, the alignment of the heel 1850 relative to the remainder of the foot 200 can easily be assessed and optimized prior to surgery.

Such preoperative alignment and planning may be particularly useful where multiple procedures, such as the Evans calcaneal osteotomy and the medializing calcaneal osteotomy, are combined for a single patient. Without such planning, it may be difficult to properly assess the effect of the combined procedures on the patient's anatomy. For example, the effect of the Evans calcaneal osteotomy, and that of the medializing calcaneal osteotomy, is to shift the heel 1850 medially. The combined shift may be difficult to assess in the operating room but may be much more easily and accurately gauged via manipulation of the modeled anatomy.

In some embodiments, one or more additional procedures may be carried out, in addition to or in the alternative to those of FIG. 9. For example, in addition to or in the alternative to the Evans calcaneal osteotomy and the medializing calcaneal osteotomy, a cotton osteotomy (medial cuneiform opening wedge osteotomy) and/or a first metatarsal midfoot osteotomy may be performed. Patient-specific cutting guides may be designed, fabricated, and surgically used to facilitate any of these procedures through the presence of bone engagement surfaces that are shaped to rest on the particular bony surfaces adjacent to the osteotomy.

As in the case of the Evans calcaneal osteotomy, a custom cutting guide, or cutting guide 1853, may be generated to help the surgeon obtain the correction that was previously modeled and/or planned using the computer models of the patient's foot. The cutting guide 1853 may have a structure and function similar to that of the cutting guide 1843 used for the Evans calcaneal osteotomy. Such a cutting guide may have contoured surfaces that match the contours of the adjoining boney surfaces of the remainder of the second bone segment 1842 and/or the heel 1850.

More specifically, the cutting guide 1853 may have a first end 1854 and a second end 1855, each of which has a bone attachment feature 1856. The bone attachment features 1856 may be used to secure the first end 1854 and the second end 1855 to the second bone segment 1842 and the heel 1850, respectively. The first end 1854 may have a first bone engagement surface 1857 that is shaped to match a corresponding contour on the second bone segment 1842, and the second end 1855 may have a second bone engagement surface 1858 that is shaped to match a corresponding contour on the heel 1850. Thus, the cutting guide 1853 may naturally lie flush with the surface of the calcaneus 1806, in the optimal position on the calcaneus 1806 to facilitate resection of the calcaneus 1806 to divide the second bone segment 1842 from the heel 1850. The cutting guide 1853 may have a resection feature 1859, such as a slot, that can be used to guide a cutter to form a single cut between the second bone segment 1842 and the heel 1850.

In order to maintain the heel 1850 in the proper position relative to the remainder of the second bone segment 1842, a bone plate 1870 may be secured to the heel 1850 and to the remainder of the second bone segment 1842. The bone plate 1870 may include a first end 1880 secured to the remainder of the second bone segment 1842, a second end 1882 secured to the heel 1850, and an intermediate portion 1884 that extends from the first end 1880 to the second end 1882, and provides the desired medial shift between the first end 1880 and the second end 1882. The first end 1880 and the second end 1882 may be secured to the remainder of the second bone segment 1842 and to the heel 1850, respectively, through the use of screws 1890.

Like the implant 1860, the bone plate 1870 may be made of any known biocompatible material, through the use of any manufacturing process known in the art. In some embodiments, the bone plate 1870 may also be fabricated specifically for the foot, enabling the bone plate 1870 to precisely maintain the desired level of correction. When made specifically for the foot in combination with each other, the implant 1860 and the bone plate 1870 may provide a highly predictable, precise, and customizable level of correction of the flat foot deformity.

Advantageously in certain embodiments, the present disclosure can be used to prepare a preoperative plan, one or more instruments, implants, or guides, including implants and/or guides that are patient-specific, and/or to perform one or more osteotomies on any body part of a patient.

FIG. 18 illustrates a couple of examples of osteotomies that can be performed. In particular, the present disclosure can be used to perform wedge osteotomies.

Figure 19:
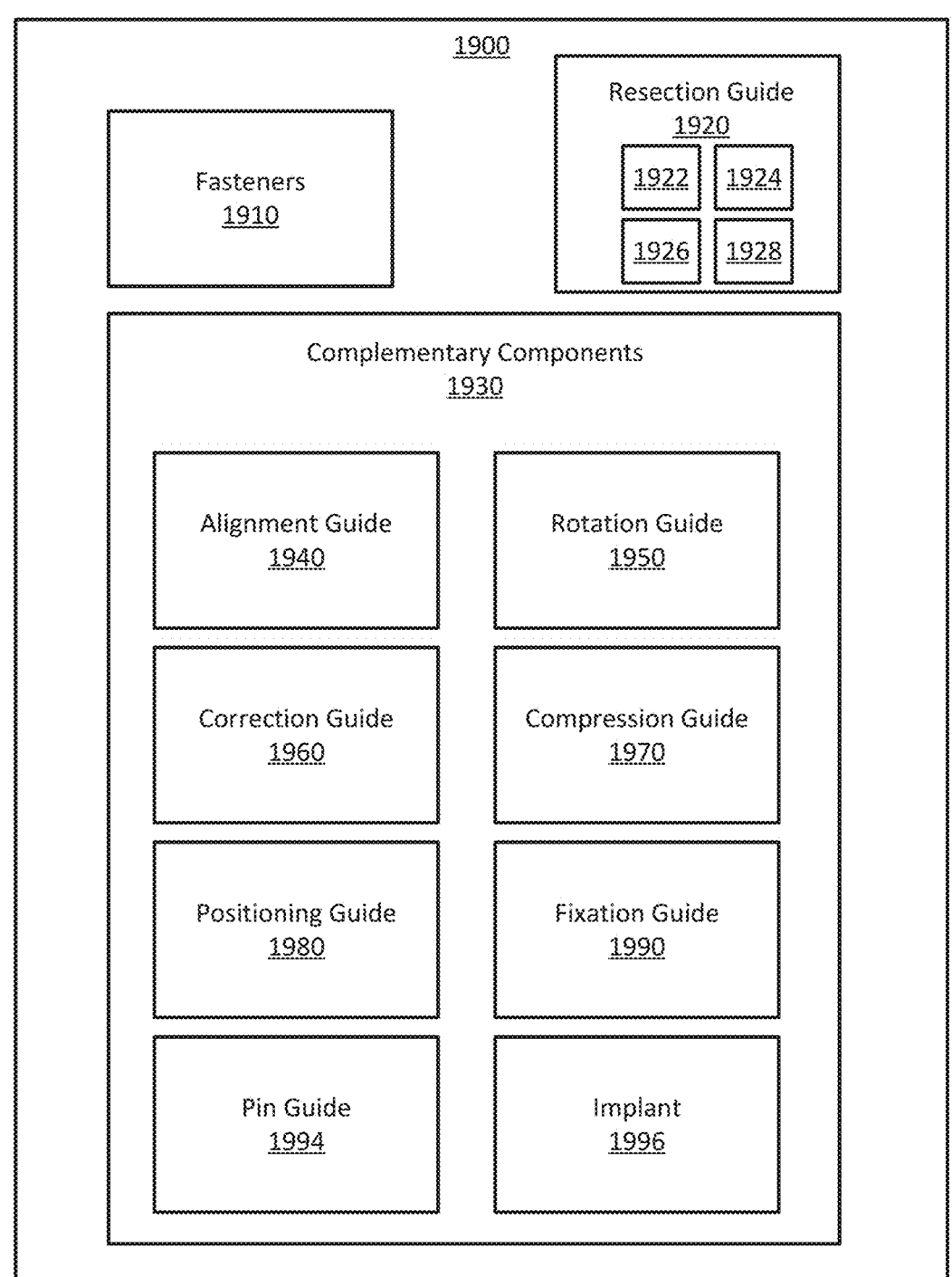
FIG. 19 illustrates an exemplary osteotomy system, according to one embodiment.

FIG. 19 illustrates an exemplary osteotomy system 1900, according to one embodiment. The osteotomy system 1900 can include one or more fasteners 1910, one or more resection guides 1920, and one or more complementary components 1930. While an osteotomy system 1900 can be used for any osteotomy procedure, one or more features, components, and/or aspects of the osteotomy system 1900 may be particularly suited for a wedge osteotomy, an Evans osteotomy, a Kouts osteotomy, or the like.

In certain embodiments, the one or more fasteners 1910 can include both one or more permanent fasteners and one or more temporary fasteners. Typically, the fasteners 1910 may be used during a variety of different steps of procedure. Temporary fasteners are often used because they can securely hold bone or parts of bones well steps of the procedure are conducted. A common temporary fastener that can be used with osteotomy systems 1900 is a K-wire, also referred to as a pin.

The one or more resection guides 1920 assist a surgeon in performing different resection steps for an osteotomy procedure. In certain embodiments, a resection guide 1920 includes one or more resection features 1922 and one or more bone attachment features 1924. The resection features 1922 can take a variety of forms and/or embodiments. Similarly, the bone attachment features 1924 can take a variety of forms and/or embodiments. The resection features 1922 provide a guide for a surgeon using a cutting tool to resect a bone, one or more bones, or other tissues of a patient. The bone attachment features 1924 serve to secure the resection guide 1920 to one or more bones and/or one or more other structures. Often, a bone attachment features 1924 can include a hole in the resection guide 1920 together with a temporary fastener such as a K-wire or pin.

In certain embodiments, a resection guide 1920 may include one or more bone engagement surfaces 1926 and/or one or more landmark registration features 1928. "Landmark registration features" refers to a structure configured to engage with a feature, aspect, attribute, or characteristic of a first object to orient and/or position a second object that includes the landmark registration feature with respect to the first object. A variety of structures can serve as a landmark registration feature. For example, a landmark registration feature may include a protrusion, a projection, a tuberosity, a cavity, a void, a divot, a tab, an extension, a hook, a curve, or the like. Similarly, a variety of structures can serve as a landmark that engages with a landmark registration feature. For example, in the context of a bone, a landmark may include head, neck, condyle, epicondyle, tuberosity, tubercle, crest, spine, process, trochanter, linea, fossa, foramen, notch, groove or sulcus, a protrusion, a projection, a tuberosity, a cavity, a void, a divot, a tab, an extension, a hook, a curve, a surface of a bone such as a medial surface, a lateral surface, an anterior surface, a posterior surface, a plantar surface, or the like.

In certain embodiments, the bone engagement surface 1926 are patient-specific—contoured to match a surface of one or more bones the resection guide 1920 contacts during the osteotomy procedure. Alternatively, or in addition, the bone engagement surface 1926 may not be patient-specific and may, or may not, contact a bone surface during use of the resection guide 1920. Those of skill in the art appreciate that one or more sides of any of the members of the osteotomy system 1900 may include one or more bone engagement surfaces 1926. Consequently, one or more sides of the fasteners 1910, the resection guide(s) 1920, the complementary components 1930, one or more pin guides 1994, and/or the implants 1996 may include one or more bone engagement surfaces 1926.

The complementary components 1930 serve to assist a surgeon during one or more steps of an osteotomy procedure. Those of skill in the art appreciate that a number of components can serve as complementary components 1930. Examples of complementary components 1930 include, but are not limited to, an alignment guide 1940, a rotation guide 1950, a correction guide 1960, a compression guide 1970, a positioning guide 1980, a fixation guide 1990, one or more pin guides 1994, and one or more implants 1996. In general, the complementary components 1930 serve to assist a surgeon in performing the function included in the name of the complementary component 1930. Thus, an alignment guide 1940 can help a surgeon align bones, parts of bones, or other parts of a patient as part of an osteotomy procedure. A rotation guide 1950 can help a surgeon rotate one or more bones, parts of bones, or other parts of a patient as part of an osteotomy procedure.

A correction guide 1960 can help a surgeon position and/or orient one or more bones, parts of bones, or other parts of a patient as part of an osteotomy procedure in order to reduce the bone, bones, bone parts, or other parts and/or in order to correct a position and/or orientation of the bone, bones, bone parts, or other parts. A compression guide 1970 can help a surgeon compress one or more bones, parts of bones, or other parts of a patient together or against an implant as part of an osteotomy procedure. A positioning guide 1980 can help a surgeon position one or more bones, parts of bones, or other parts of a patient as part of an osteotomy procedure. In certain embodiments, the positioning guide 1980 may be designed and fabricated to be patient-specific. The patient-specific aspects can include a patient-specific bone engagement surface, a predefined angle for reorienting one or more bone or bone parts within one or more planes, a predefined position for bone attachment features 1924 or fasteners 1910, or the like. Alternatively, or in addition, the positioning guide 1980 may be selected from a kit, collection, or repository of a number of positioning guides 1980: each having a different configuration for one or more aspects/attributes of the positioning guide 1980. For example, each member of the repository/kit may include a different positioning angle (repositioning or correction angle), the angles may differ by 2 degrees for example. In such an embodiment, each positioning guide 1980 may not be patient-specific to a particular patient, but may provide the desired amount of positioning to meet the goals of the surgeon. In certain embodiments, a preoperative plan generated based on the present disclosure may include a recommendation for the positioning guide 1980 to be used, even if the recommended positioning guide 1980 is not patient-specific to the particular patient.

A fixation guide 1990 can help a surgeon in completing one or more temporary or permanent fixation steps for one or more bones, parts of bones, or other parts of a patient as part of an osteotomy procedure. One or more pin guides 1994 serve to guide a surgeon in deployment of one or more pins (e.g., K-wires) for use in a surgical procedure. In one embodiment, the one or more pin guides 1994 may engage with, and/or reference for position and/or trajectory off of one or more resection guides 1920 and/or any of the complementary components 1930. In one embodiment, one or more pin guides 1994 may be configured to enable (or facilitate) deployment of one or more pins at a predefined distance, offset, and/or trajectory relative to another component of the osteotomy system 1900 and/or one or more osteotomies formed during a surgical procedure. In another embodiment, one or more pin guides 1994 may be configured to enable (or facilitate) deployment of one or more pins at a patient-specific distance, offset, and/or trajectory relative to another component of the osteotomy system 1900 and/or one or more osteotomies formed during a surgical procedure. The patient-specific distance, offset, and/or trajectory may be predetermined to satisfy the needs of a patient and/or a surgeon.

One example of a complementary components 1930 may include the compressor/distractor 1000. The compressor/distractor 1000 can be used to compress or distract bones or parts of bones involved in an osteotomy procedure.

Advantageously, the osteotomy system 1900 can help a surgeon overcome one or more of the challenges in performing an osteotomy procedure, particularly on bones of a foot of a patient, such as on the forefoot, midfoot, or hindfoot. One challenge during an osteotomy procedure can be maintaining control of and/or position and/or orientation of a bone, one or more bones, and/or bone pieces/fragments, particular once a resection is performed. Advantageously, the fasteners 1910, resection guide 1920, and/or complementary components 1930 can be configured to assist in overcoming this challenge.

Advantageously, the osteotomy system 1900 can help a surgeon in positioning, placing, and/or orienting a resection guide accurately. Modern techniques may include preoperative planning, simulation, or even practice using computer models, virtual reality systems, augmented reality systems or the like. However, simulations and models are still different from positioning a resection guide on a patient's bone, joint, or body part during the procedure. The osteotomy system 1900 can include a number of features to assist the surgeon with the positioning. In one embodiment, the resection guide 1920 can include one or more landmark registration features 1928.

Advantageously, the osteotomy system 1900 can help a surgeon in securing guides of the osteotomy system 1900, such as a resection guide, as well as how to readily remove the guide (e.g., resection guide) without disturbing a reduction, shifting, reorienting, or repositioning one or more bones or parts of bones while removing the guide. In certain embodiments, the osteotomy system 1900 is configured to permit removal of a guide while keeping temporary fasteners in place for use in subsequent steps of an osteotomy procedure. Alternatively, or in addition, the osteotomy system 1900 facilitates positioning of temporary fasteners during one step of the wedge osteotomy procedure for use in a subsequent step of the wedge osteotomy procedure. Removal of a guide during an osteotomy procedure can be particularly challenging where translation and/or rotation of the bones involved in the wedge osteotomy procedure is required for the success of the wedge osteotomy procedure. Advantageously, the osteotomy system 1900 accommodates translation and/or rotation of the bones during the wedge osteotomy procedure while facilitating a successful outcome for the wedge osteotomy procedure.

Advantageously, the components of the osteotomy system 1900 can be specifically designed for a particular patient. Alternatively, or in addition, the components of the osteotomy system 1900 can be specifically designed for a class of patients. Each of the components of the osteotomy system 1900 can be designed, adapted, engineered and/or manufactured such that each feature, attribute, or aspect of the component is specifically designed to address one or more specific indications present in a patient. Advantageously, the cuts made for the osteotomy procedure can be of a size, position, orientation, and/or angle that provides from an optimal osteotomy with minimal risk of undesirable resection. In one embodiment, the components of the osteotomy system 1900 can be configured such that an osteotomy is performed that enables a correction in more than one plane in relation to the parts of the body of the patient. For example, cut channels in a resection guide 1920 can be oriented and configured such that when the bones are fused/fixated the correction results from translation, rotation, and/or movement of bones or bone parts in two or more planes (e.g., sagittal and transverse).

In certain embodiments, the components of the osteotomy system 1900 may be made as small as possible to minimize the amount of soft tissue that is opened in the patient for the osteotomy procedure. Alternatively, or in addition, walls and/or sides of the components may be beveled and/or angled to avoid contact with other hard tissue or soft tissues in the operating field for the osteotomy procedure.

Those of skill in the art will appreciate that for certain wedge osteotomy procedure a complementary components 1930 may not be needed or a given complementary components 1930 may be optional for use in the wedge osteotomy procedure. Similarly, those of skill in the art will appreciate that certain features of the fasteners 1910, resection guides 1920, and/or complementary components 1930 can be combined into one or more of apparatus or devices or may be provided using a plurality of separate devices.

Dwyer Osteotomy

Figure 20:
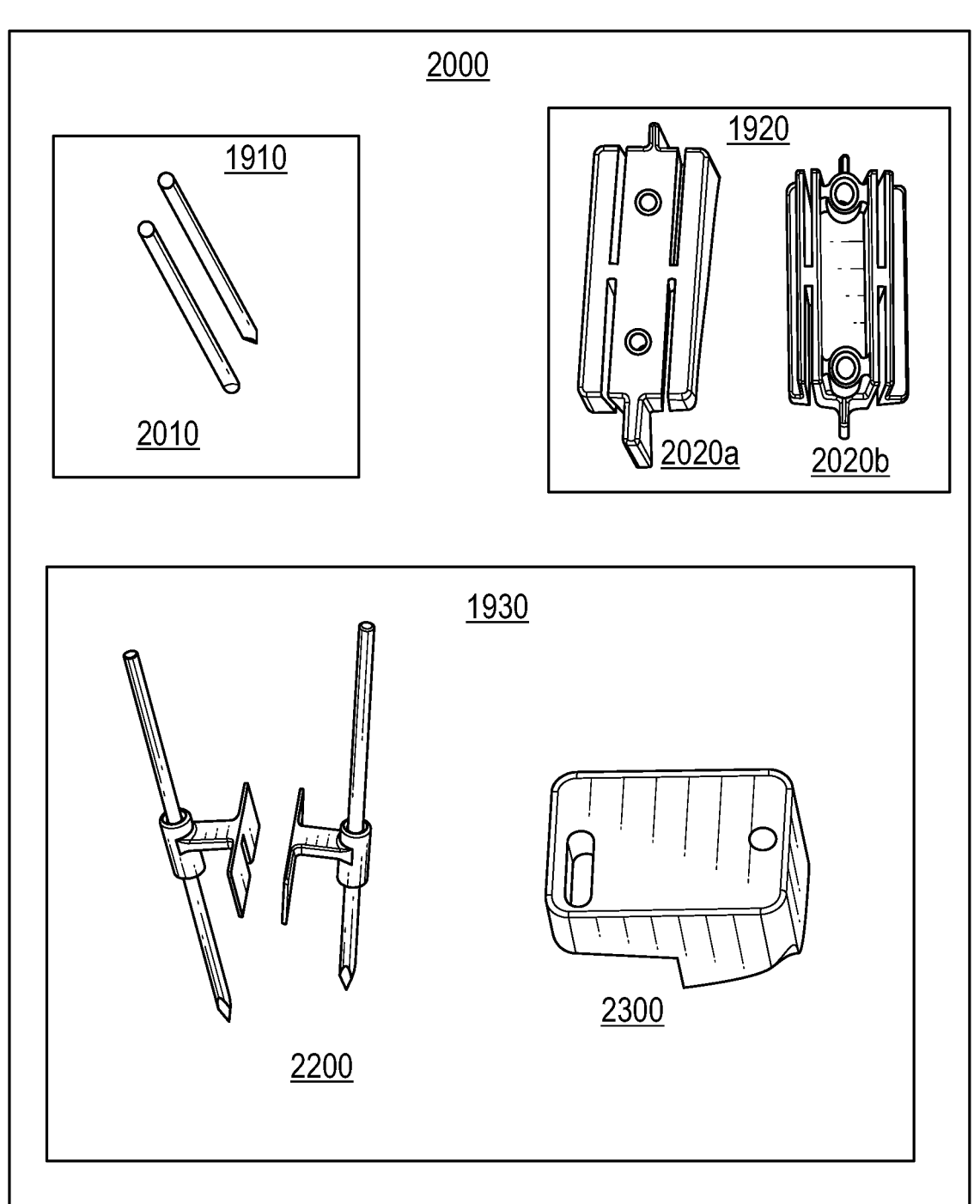
FIG. 20 illustrates an exemplary osteotomy system for a Dwyer osteotomy, according to one embodiment.

FIG. 20 illustrates an exemplary osteotomy system 2000 for a Dwyer osteotomy, according to one embodiment. In one embodiment, an osteotomy system 2000 may include a resection guide 2020 (two embodiments 2020*a*, 2020*b*) and at least one complementary component 1930. In such an embodiment, the resection guide 2020 and/or the at least one complementary component 1930 may include a patient-specific feature. In one embodiment, the osteotomy system 2000 includes at least one complementary component 1930 selected from a group of complementary components 1930. Examples of members of the group, include, but are not limited to, an alignment guide, a rotation guide, a compression guide, a correction guide, a positioning guide, a pin guide, a fixation guide, and the like. One or more of the guides that are included in the at least one complementary component 1930 can include a patient-specific feature, including but not limited to, a bone engagement surface, a bone attachment feature, a resection feature, a landmark registration feature, a handle, or the like.

In certain embodiments, a single complementary component 1930 may be configured to perform functions of two or more other components in the group of at least one complementary component 1930. The other components may be combined because of aspects identified in one or more bone models of one or more bones of a patient and may be combined to form a patient-specific component. Alternatively, or in addition, other components may be combined to reduce the number of instruments used or required for a surgical procedure and/or to reduce the number of steps in a surgical procedure. Furthermore in certain embodiments, osteotomy system 2000 may be configured and designed first in a virtual environment together with a surgical technique that minimizes the number of complementary component 1930 used or needed and/or the number of steps in the surgical technique. For example, the resection guide 2020 and/or at least one fastener 2010 and/or complementary component 1930 may cooperate with each other to provide instruments (that may or may not include patient-specific aspects) and a surgical technique that provides a favorable outcome for the patient and places a least amount of pressure on the surgeon.

In the illustrated embodiment, the osteotomy system 2000 includes at least one fastener 2010, a resection guide 2020 (two embodiments 2020*a*, 2020*b*), one or more pin guides 2200, and a positioning guide 2300.

FIGS. 21A-21J illustrate views of a resection guide 2020 of the osteotomy system of Figure according to one embodiment. In one embodiment, the resection guide 2020*a* includes one or more resection features 2022 (e.g., posterior resection feature 2022*a*, anterior resection feature 2022*b*), one or more bone attachment features 2024 (e.g., first bone attachment feature 2024*a*, second bone attachment feature 2024*b*), one or more handles 2026 (e.g., handles 2026*a,b*), a body 2028, and a bone engagement surface 2033.

FIG. 21A illustrates a perspective plantar-posterior view of one embodiment of a resection guide 2020*a* that includes posterior resection feature 2022*a*, anterior resection feature 2022*b*. The illustrated embodiment includes two resection features 2022 and two bone attachment features 2024.

The body 2028 includes a lateral side 2030, a medial side 2032, an anterior side 2034, a posterior side 2036, a dorsal side 2038, and a plantar side 2040. See FIGS. 21A-21I. Generally, the sides of the body 2028 refer to the direction the sides face when a resection guide 2020 is in use. The medial side 2032 faces the bone of the patient and in the medial direction relative to the patient. The lateral side 2030 faces away from the patient and in the lateral direction. The anterior side 2034 faces in the anterior direction and the posterior side 2036 faces in the posterior direction relative to the patient.

Resection features 2022 facilitate performing an osteotomy on a bone of a patient. The resection features 2022 may serve as a template or guide for manipulating a cutting tool to create the osteotomy. In one embodiment, the resection features 2022 guide a cutting tool along a predetermined trajectory to cut into and/or through the bone.

FIG. 21B illustrates an embodiment of a resection guide 2020*a* that includes a posterior resection feature 2022*a* and an anterior resection feature 2022*b*. FIG. 21B illustrates a perspective dorsal-posterior view of one embodiment of a resection guide 2020*a*. In certain embodiments, the posterior resection feature 2022*a* and anterior resection feature 2022*b* may be parallel to each other at a surface of the lateral side 2030 of the body 2028. Alternatively, or in addition, the posterior resection feature 2022*a* and anterior resection feature 2022*b* may be non-parallel with respect to each other at the surface of the lateral side 2030 of the body 2028.

FIG. 21C illustrates a posterior perspective view of a resection guide 2020*a*.

FIG. 21D illustrates an anterior perspective view of a resection guide 2020*a*.

Referring to FIGS. 21C and 21D, the resection guide 2020*a* may include one or more one or more bone attachment features 2024. The one or more bone attachment features 2024 secure the resection guide 2020*a* to the bone for one or more osteotomies. In one embodiment, a single bone attachment feature 2024 may be sufficient to secure the resection guide 2020*a* for a surgical procedure.

In the illustrated embodiment, a bone attachment feature 2024 is embodied in the form of an opening that extends from the lateral side 2030 to the medial side 2032. The opening is sized to receive and securely engage (e.g., by way of a friction fit) with a fastener 2010 deployed through the opening and into the bone. In one embodiment, a single bone attachment feature 2024. In another embodiment, a bone attachment feature 2024 may be made up of two or more bone attachment features (e.g., bone attachment feature 2024*a* and bone attachment feature 2024*b*) In the illustrated embodiment, the bone attachment features 2024 includes a first bone attachment feature 2024*a* and a second bone attachment feature 2024*b*. Using two bone attachment features 2024 can be advantageous because two bone attachment features 2024 secured to the bone can prevent the resection guide 2020*a* from rotating about one single bone attachment feature 2024.

One challenge in performing an osteotomy may be in how to control bone fragments formed by the osteotomy. Great effort is made to perform a surgical procedure with the smallest incisions to reduce the disruption of tissue and expedite healing and recovery. However, such efforts may increase the challenges of controlling bone fragments formed by the osteotomy. For example, suppose the resection guide 2020*a* is used for a wedge osteotomy. Upon successful completion of the osteotomy, a wedge bone fragment may be created below the resection guide 2020*a*. Advantageously in the illustrated embodiment, at least one bone attachment feature 2024 is positioned between the posterior resection feature 2022*a* and the anterior resection feature 2022*b*. Consequently, when an osteotomy using both the posterior resection feature 2022*a* and the anterior resection feature 2022*b* is completed, the resulting wedge bone fragment remains secured to the at least one bone attachment feature 2024. Of course, a fastener 2010 for the at least one bone attachment feature 2024 may extend into the bone to a depth such that the fastener 2010 does not interfere with completion of the wedge osteotomy. After the wedge osteotomy a surgeon can remove the wedge bone fragment, if desired, using the fastener 2010.

In the illustrated embodiment, the bone attachment features 2024 are aligned with each other. In another embodiment, the bone attachment features 2024 may be unaligned with each other. In certain embodiments, the bone attachment features 2024 are configured such that fasteners 2010 that used with the bone attachment features 2024 are parallel to each other. In this way, the resection guide 2020*a* can be readily slid off of the fasteners 2010 while the fasteners 2010 remain in the bone. Advantageously, the remaining fasteners 2010 can be reused in subsequent steps of a surgical procedure.

Those of skill in the art will appreciate that the one or more bone attachment features 2024 may be implemented in a variety of ways and/or with a variety of structures. For example, in one embodiment that a bone attachment features 2024 may be embodied as one or more prongs, pins, or spikes extending from the medial side 2032 of the resection guide 2020*a*. The pins, prongs or spikes may be driven into the bone by way of a mallet. Of course, other embodiments for the bone attachment feature 2024 may have a different configuration and still fall within the scope of the present disclosure.

In certain embodiments, the resection guide 2020*a* can include one or more handles 2026. The handle 2026 can facilitate positioning and/or placement of the resection guide 2020*a*. In certain embodiments, the resection guide 2020*a* may not include handles 2026. Instead, a user may grasp the body 2028 for positioning. Alternatively, or in addition, the handle 2026 may be relatively straight and may be aligned with a longitudinal axis of the resection guide 2020*a* such that handle 2026 can be used as a visual guide for a surgeon to confirm the positioning, placement, and/or orientation of the resection guide 2020*a* on a bone of the patient. Of course, other aspects of the resection guide 2020*a* may serve the same or similar functions as a handle 2026, such that a dedicated handle 2026 may not be needed.

Furthermore, handle 2026 may serve more than one function or purpose. In certain embodiments, one or more of the handles 2026 can serve as both a handle used by a user to position/orient the resection guide 2020*a* and/or as a landmark registration feature.

A landmark registration feature serves to assist a surgeon in mapping or converting from a position of a model of a resection guide 2020 one a model of one or more bones of a patient in a virtual environment and/or in a preoperative plan to an actual physical position on one or more bones of a patient during a procedure. In the illustrated embodiment, the resection guide 2020*a* includes at least one landmark registration feature.

In particular, the resection guide 2020 may include a plantar landmark registration feature 2041*a*. In another embodiment, the resection guide 2020 may include a dorsal landmark registration feature 2041*b*. See for example, FIG. 21E. Alternatively, or in addition, the resection guide 2020 can include a landmark registration feature 2041 that extends from any side of the resection guide 2020.

The landmark registration feature 2041 is configured to engage with landmarks on the bone of the patient. Advantageously, the landmark registration feature 2041 can provide a surgeon with confidence and assurance in the placement and positioning of the resection guide 2020*a* on the bone because the landmark registration feature 2041 engages with one or more particular landmarks on the bone (e.g., a projection or a depression or cavity). The landmark registration features 2041 is one feature that assists a surgeon in transferring a position of an instrument model relative to a bone model of the patient to an instrument positioned on the actual bone of the patient during a surgical procedure.

Alternatively, or in addition, the landmark registration feature 2041 can include a bone engagement surface 2043 that can further facilitate registration of the landmark registration feature 2041 and/or resection guide 2020*a* with the bone. In this manner, a surgeon can be assured intraoperatively that the resection guide 2020*a* is being positioned in accordance with a preoperative plan. In one embodiment, the bone engagement surface 2043 is fabricated based on a bone model of the bone the bone engagement surface 2043 is to engage. In certain embodiments, the bone engagement surface 2043 is shaped to accept a surface of a bone placed in contact with the resection guide 2020*a*. Alternatively, or in addition, the bone engagement surface 2043 of the landmark registration feature 2041 may be shaped to include a contour that resembles, substantially resembles, and/or matches a surface of a bone model of a bone that the resection guide 2020*a* is to be used with for a surgical procedure (e.g., a patient's bone). The bone engagement surface 2043 may be formed with, a part of, and/or similar to the bone engagement surface 2033 of the resection guide 2020*a*.

In certain embodiments, the landmark registration feature 2041 can be shaped like a hook to engage a plantar/inferior surface of bone or a dorsal/superior surface of bone. Alternatively, or in addition, the resection guide 2020*a* may include a landmark registration feature 2041 on each end (inferior/plantar landmark registration feature 2041*a* and superior/dorsal landmark registration feature 2041*b*), together the landmark registration features 2041 can engage one or more landmarks of a surface of the bone such that the surgeon can accurately position and register the resection guide 2020*a* to the bone. Of course, a resection guide 2020*a* can include a plurality of landmark registration features 2041. In one embodiment, one or more landmark registration features 2041 can engage a plantar side of a calcaneus 224 and/or a dorsal side of the calcaneus 224.

In the illustrated embodiment, a plantar landmark registration feature 2041*a* extends from the plantar side 2040. Advantageously, the landmark registration feature 2041 is configured to engage with one or more landmarks for bone of a patient. Advantageously, because the resection guide 2020*a* is defined in relation to one or more bones of a patient using a model of the one or more bones and a model of the resection guide 2020*a*, the size, shape, length and width of the landmark registration feature 2041 can be defined to facilitate engagement between the landmark registration feature 2041 and a landmark such as a dorsal surface of the bone. Furthermore, whether or not the resection guide 2020*a* includes a landmark registration feature 2041 may be a patient-specific feature.

Like the body 2028, the plantar landmark registration feature 2041*a* and the handle 2026*a* may also include a medial side 2032, the body 2028 and the plantar landmark registration feature 2041*a* may both have the same medial side 2032. In one embodiment, the bone engagement surface 2033 may include the bone engagement surface 2043 (See FIGS. 21E, 21F). Said another way, the bone engagement surface 2033 may extend beyond the medial side 2032 of the body 2028 to include a medial side of the plantar landmark registration feature 2041*a* and the handle 2026*a*.

In certain embodiments, the posterior resection feature 2022*a* and anterior resection feature 2022*b* may extend from the lateral side 2030 to the medial side 2032. Advantageously, a depth of the posterior resection feature 2022*a* and/or anterior resection feature 2022*b* through the body 2028 is long enough to guide a cutting tool and keep the cutting tool oriented along a trajectory defined by an opening of the resection features 2022. Advantageously, the present disclosure enables a osteotomy system 2000 that assists a surgeon in managing a depth of an osteotomy in the bone.

Figure 21E:
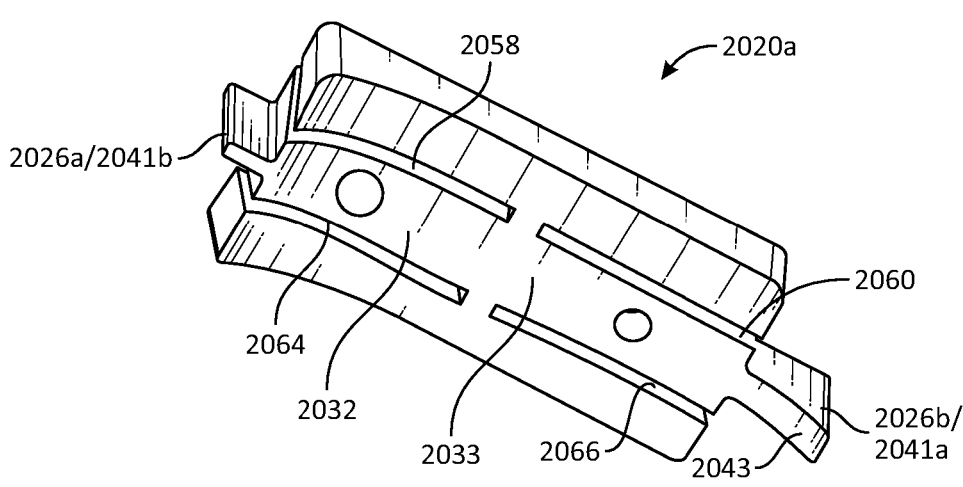

FIG. 21E illustrates a medial side 2032 perspective view of a resection guide 2020*a*. In the illustrated embodiment, the medial side 2032 includes a bone engagement surface 2033. In one embodiment, the bone engagement surface 2033 is configured to contact and/or engage with a surface of a bone of a patient. In one embodiment, periosteum on the bone is elevated and/or stripped around the area of the bone where the resection guide 2020*a* is to be positioned. The periosteal elevation exposes the bone surface for engagement by the bone engagement surface 2033. Advantageously, the bone engagement surface 2033 is configured to substantially conform to the surface of the bone. Alternatively, or in addition, the bone engagement surface 2033 is configured to partially conform to the surface of the bone.

Alternatively, or in addition, the bone engagement surface 2033 is configured to receive the surface of the bone, where the resection guide 2020*a* is to be placed. Specifically, a user, based on a prescription and/or in consultation with a surgeon, may determine a planned position for a resection guide 2020*a* on a lateral surface of a bone of the patient. The user may then reflect this planned position using a model of the bone of the patient and a model of the resection guide 2020*a*. Because the model of the bone of the patient is a highly accurate representation, the bone engagement surface 2033 defined on the medial side 2032 of the model of the resection guide 2020*a* accurately includes the features and aspects of the surface of the bone of the patient. Examples of features and aspects of a bone that the bone engagement surface 2033 can include, but are not limited to, a tuberosity, tubercle, crest, spine, process, trochanter, linea, fossa, foramen, notch, groove or sulcus, a protrusion, a projection, a tuberosity, a cavity, a void, a divot, a tab, an extension, a hook, a curve, or the like of the surface of the bone model, but in a reverse or inverse configuration. For example, where a cavity is on a surface of the bone model (and the bone of the patient) a protrusion exists on the bone engagement surface 2033 exists that fits into the cavity.

In one embodiment, the bone engagement surface 2033 is configured to register to a lateral surface of a bone of a patient. In certain embodiments, the bone engagement surface 2033 is defined based, at least in part, on a lateral surface of a bone model of a bone of a patient's foot. Advantageously, the bone engagement surface 2033 is a negative contoured surface that resembles, substantially resembles, and/or matches a surface of the bone model contacting a model of the resection guide 2020*a*, when the model of the resection guide 2020*a* is positioned as desired on the bone model. In one embodiment, registration of a bone engagement surface 2033 means that each feature or aspect of the bone engagement surface 2033 engages, mates, and/or fits within a corresponding feature or aspect of the surface of the bone of the patient. For example, where the bone surface includes a protrusion, the bone engagement surface 2033 includes a recess configured to accept and engage with that protrusion.

As mentioned herein, the bone model used to determine, or at least partially determine, the shape, size, and/or configuration of the bone engagement surface 2033 is based on medical imaging of at least a portion of the patient's foot and is configured to resemble, significantly resemble, and/or match the anatomy of the patient's foot.

FIG. 21F is a medial side view of a resection guide 2020*a*.

FIG. 21G is a lateral side view of a resection guide 2020*a*.

Figure 21H:
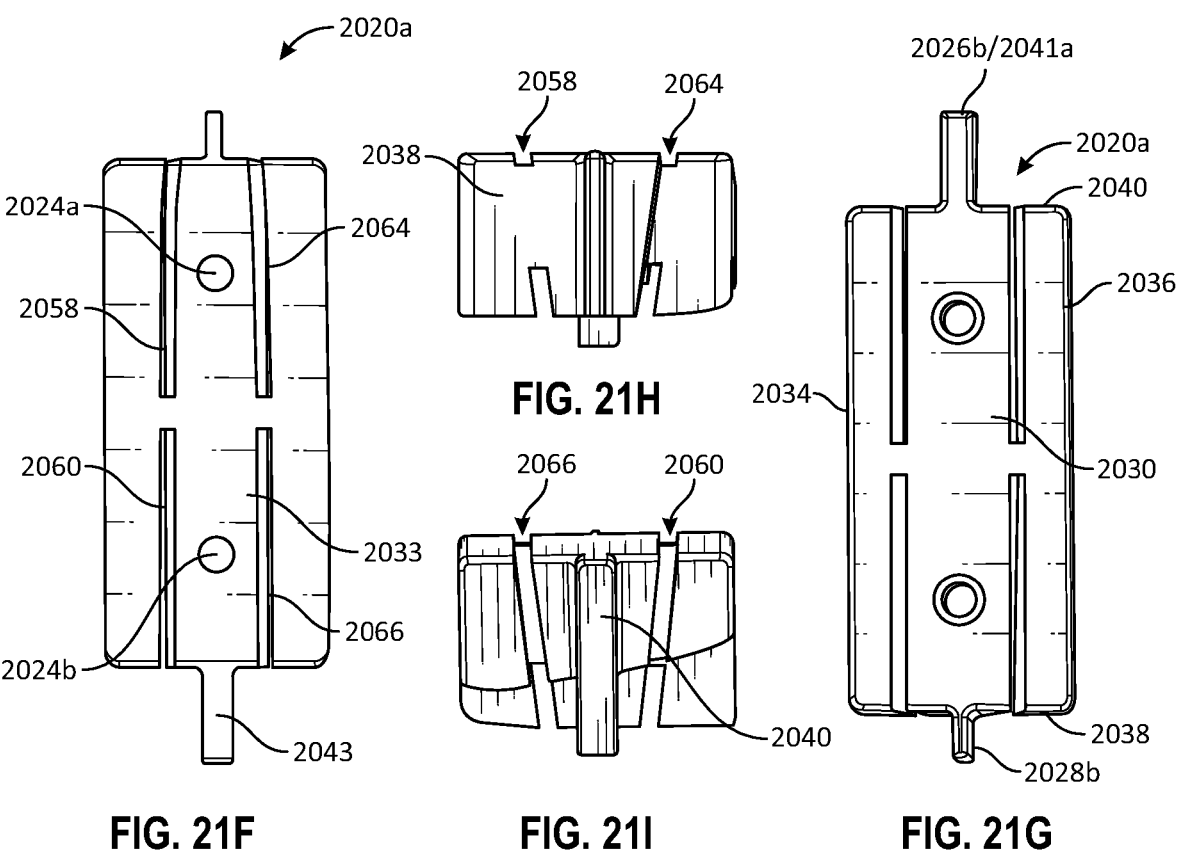

FIG. 21H is a dorsal side view of a resection guide 2020*a*.

FIG. 21I is a plantar side view of a resection guide 2020*a*.

Figure 21J:
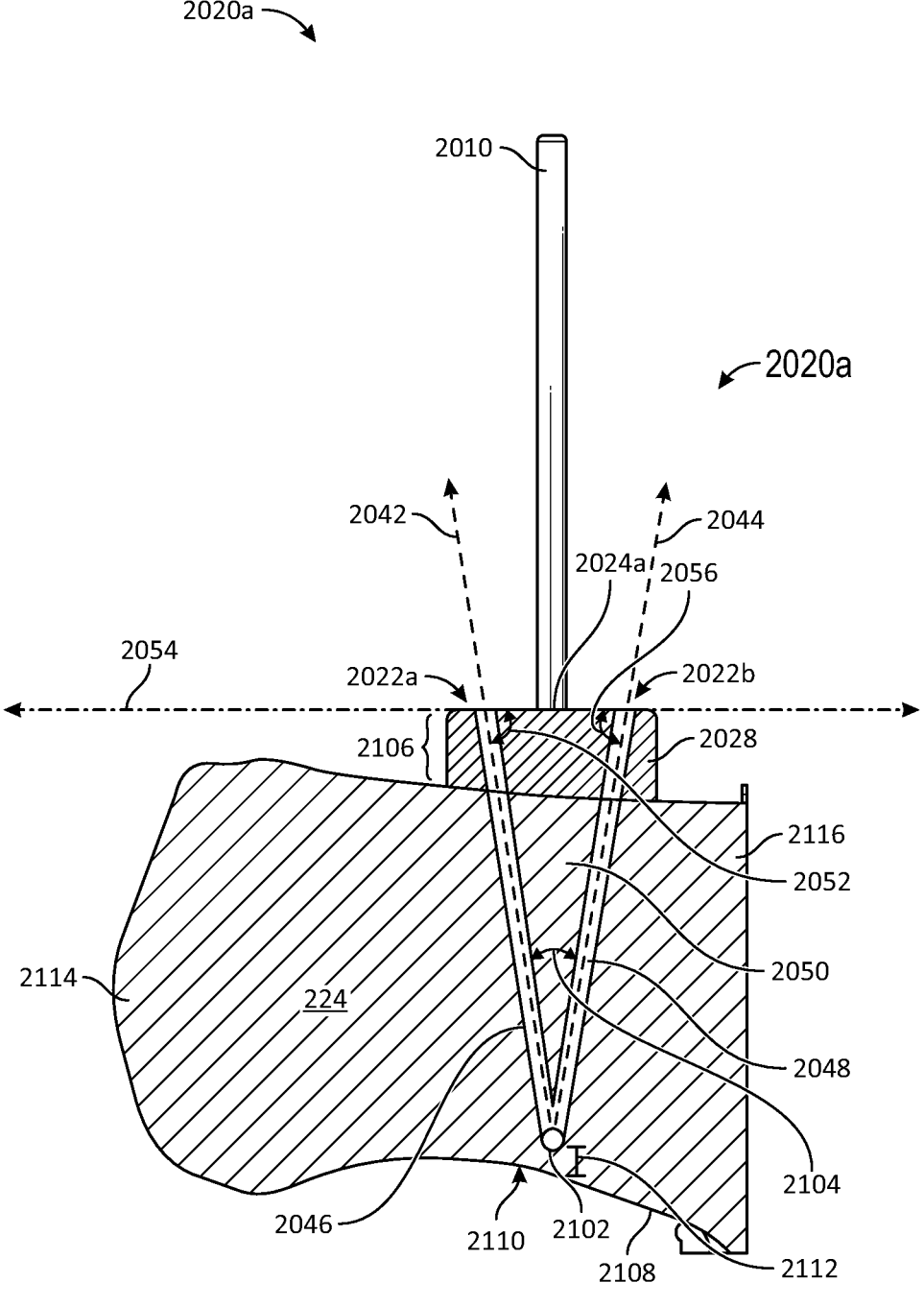

FIG. 21J illustrates a cross section view of the resection guide 2020*a* positioned on a bone (e.g., a calcaneus) of a patient. A surgeon has created a first osteotomy using the posterior resection feature 2022*a* and a second osteotomy using the anterior resection feature 2022*b*.

Referring now to FIGS. 21J, 21A, and 21B, in the illustrated embodiment, the posterior resection feature 2022*a* comprises an opening that starts on the lateral side 2030 and extends to the medial side 2032. The opening of the posterior resection feature 2022*a* extends through the body 2028 along a first trajectory 2042. In the illustrated embodiment, the anterior resection feature 2022*b* comprises an opening that starts on the lateral side 2030 and extends to the medial side 2032. The opening of the anterior resection feature 2022*b* extends through the body 2028 along a second trajectory 2044.

The opening of the posterior resection feature 2022*a* and/or the opening of the anterior resection feature 2022*b* has a width and/or length large enough to accommodate, or accept, a cutting element of a cutting tool. In one embodiment, the opening of the posterior resection feature 2022*a* is configured to guide and/or enable a cutting tool to form a first osteotomy 2046 into, and/or through, the bone. Advantageously, the first osteotomy 2046 tracks, follows, and/or is aligned with the first trajectory 2042. In one embodiment, the opening of the anterior resection feature 2022*b* is configured to guide and/or enable a cutting tool to form a second osteotomy 2048 into, and/or through, the bone. Advantageously, the second osteotomy 2048 tracks, follows, and/or is aligned with the second trajectory 2044. Thus, a surgeon operating the cutting tool within the opening of the posterior resection feature 2022*a* and the anterior resection feature 2022*b* can readily form a first osteotomy 2046 and a second osteotomy 2048 that matches a design that may have been set out in a model of the resection guide 2020*a* and/or a model of the patient's bone(s).

In one embodiment, the first trajectory 2042 may be determined and/or defined to be a patient-specific feature. Similarly, the second trajectory 2044 may be determined and/or defined to be a patient-specific feature. Advantageously, using the apparatus, methods, and/or systems of the present disclosure a user may determine and/or at least partially determine the first trajectory 2042 and/or the second trajectory 2044 based on a bone model of at least a portion a bone of the patient that is to receive one or more osteotomies. The bone model of at least a portion of the bone can be derived from and/or based on medical imaging of a patient's foot. In certain embodiments, the bone model used to determine, or at least partially determine, the first trajectory 2042 and/or the second trajectory 2044 is configured to resemble, substantially resemble, or match the anatomy of the patient's foot.

As used herein, in certain embodiments, partial determination of the first trajectory 2042 and/or the second trajectory 2044 based on a bone model may mean that the bone model for the a bone of a patient that will receive the osteotomies is used together with other imaging data, anatomic data, patient imaging data, patient data, information from a prescription from a doctor, information about surgeon preferences, measurement data taken from the bone model or medical imaging, or the like may also be used to determine the first trajectory 2041 and/or the second trajectory 2044.

In one embodiment, the posterior resection feature 2022a extends through the resection guide 2020 from the lateral side 2030 to the medial side 2032 along the first trajectory 2042. The first trajectory 2042 is at least partially determined based on a bone model of at least a portion of a bone of a patient's foot. The bone model is based on medical imaging of the patient's foot and is configured to resemble, significantly resemble, and/or match the anatomy of the patient's foot. Alternatively, or in addition, the anterior resection feature 2022b extends through the resection guide 2020 from the lateral side 2030 to the medial side 2032 along the second trajectory 2044. The second trajectory 2044 is at least partially determined based on a bone model of at least a portion of a bone of a patient's foot. The bone model is based on medical imaging of the patient's foot and is configured to resemble, significantly resemble, and/or match the anatomy of the patient's foot.

Those of skill in the art will appreciate that the first trajectory 2042 and the second trajectory 2044 can define a path for the osteotomies formed using the posterior resection feature 2022a and/or anterior resection feature 2022b. Alternatively, or in addition, where a surgical procedure plans to perform a wedge osteotomy, the first trajectory 2042 and the second trajectory 2044 can predefine the size, shape, and configuration of a wedge fragment formed by the osteotomy.

In one embodiment, a surgeon may desire to perform a wedge osteotomy. In this embodiment, the resection guide 2020a is designed such that the first trajectory 2042 converges with the second trajectory 2044 at a vertex 2102 having a wedge angle 2104, such that posterior resection feature 2022a and the anterior resection feature 2022b form a wedge osteotomy comprising a wedge bone fragment 2050 after formation of the first osteotomy 2046 and the second osteotomy 2048, the wedge angle 2104 determined based, at least in part, on the bone model 1204. Advantageously, the various aspects of the design of the resection guide 2020a and/or an accompanying surgical technique and/or complementary components 1930 can be done prior to fabrication of one or more components of the osteotomy system 2000. Thus, a surgeon can define or adjust the position of the vertex 2102, the number of degrees for the wedge angle 2104, a height 2106 of the body 2028, and the like. Of course, certain of these aspects may be predefined for a surgeon and/or recommendations made to a surgeon. Alternatively, or in addition, certain of these aspects may be patient-specific while others may be standard based on experience and/or established practice for a particular procedure.

In certain embodiments, a surgeon and/or a technician, working with the surgeon, may determine the size, shape, and/or configuration of a wedge bone fragment 2050 to be removed from the bone. Furthermore, a surgeon and/or a technician can determine whether to perform an osteotomy that forms a wedge bone fragment 2050 or an osteotomy that enables an opening wedge osteotomy or an osteotomy that does not include a wedge (closing or opening). The type of osteotomy to be performed can determine whether or not the first trajectory 2042 and/or second trajectory 2044 converge and/or the size of the posterior angle 2052 and/or anterior angle 2056.

In one embodiment, a surgeon can also determine, preoperatively, whether the vertex 2102 will be inside the bone or outside the bone. For example, the surgeon may decide to have the vertex 2102 outside the bone a distance away from a medial surface 2108 of the bone (e.g., calcaneus 224). The position of the vertex 2102 may depend on the surgical procedure, surgeon preference, a surgeon's planned correction, or the like. In such an embodiment, the first trajectory 2042 may converge with the second trajectory 2044 at a vertex 2102 outside the bone and spaced a distance from the medial cortex 2110 of the bone.

In another instance, a surgeon may determine to have the vertex 2102 between the medial cortex 2110 of the bone and the resection guide 2020a when the resection guide 2020a is in use for a surgical procedure. Alternatively, or in addition, a surgeon may determine to have the vertex 2102 between a medial cortex 2110 of the bone and the resection guide 2020a when the resection guide 2020a is designed for a patient's foot. In certain osteotomies, a surgeon may desire that the vertex 2102 is positioned within the bone and offset from the medial cortex 2110 by a predetermined offset 2112. Advantageously, using embodiments of the present disclosure a surgeon can determine and/or adjust the size of the predetermined offset 2112.

A surgeon may desired to position the vertex 2102 between the medial cortex 2110 of the bone and the resection guide 2020a when the resection guide 2020a is in use for a surgical procedure such that the first osteotomy 2046 and the second osteotomy 2048 leave bone between the vertex 2102 and the medial cortex 2110 intact. This intact bone may serve to keep a posterior bone fragment 2114 connected to an anterior bone fragment 2116. Depending on the surgical procedure planned, a surgeon may desire to keep this bone intact to serve as a "living hinge" which can be used to close the wedge osteotomy. Of course, different surgeons may have different sizes they want for predetermined offset 2112. Alternatively, or in addition, the size of the predetermined offset 2112 may be based at least in part on how the patient presents for the procedure or preparation and planning for the procedure.

Advantageously, the present disclosure enables the thickness/size of the predetermined offset 2112 to be predetermined, to be patient-specific, as well as the determination of whether or not to have a predetermined offset 2112. As described, a surgeon may preposition the vertex 2102 to be within the bone or outside the bone.

In certain embodiments, the position of the vertex 2102 may be customized to a particular patient. The vertex 2102 position may be patient-specific. Alternatively, or in addition, the position of the vertex 2102 may be set at a default predetermined offset 2112, such as one millimeter. In another embodiment, the position of the vertex 2102 may be predetermined, for example due to the type of osteotomy being performed.

In one embodiment, the position of the vertex 2102 may be fixed due to the type of osteotomy to be performed. Those of skill in the art will appreciate that with a fixed position of the vertex 2102 and based on a thickness of the bone at the location for the osteotomy, the size of the wedge angle 2104 can directly impact the width of the body 2028. Those of skill in the art will appreciate that the size of the wedge angle 2104 can vary depending on the needs of the patient, surgeon preferences, anatomical data, or the like. In one embodiment, the wedge angle 2104 may range from between about 5.0 degrees to about 45.0 degrees. In one embodiment, the wedge angle 2104 is about 13.4 degrees. In another embodiment, the wedge angle 2104 is about 18.3 degrees. Advantageously, a user or surgeon can define and/or adjust the wedge angle 2104 in a tool that views and/or edits parameters for the bone model and/or for a model of the resection guide 2020. In one embodiment, the wedge angle 2104 is determined based on the bone model.

FIG. 21J also illustrates a one fastener 2010 secured within a first bone attachment feature 2024*a*. The first bone attachment feature 2024*a* secures the resection guide 2020 to a portion of the bone during an osteotomy. The bone attachment feature 2024 secures the resection guide 2020*a* to a portion of the bone that forms the wedge bone fragment 2050 after formation of a wedge osteotomy. As described herein, the osteotomy system 2000 may include a second bone attachment feature 2024*b* that can be used to secure the resection guide 2020*a* to the bone. In one embodiment, the first bone attachment feature 2024*a* and second bone attachment feature 2024*b* include fasteners 2010 that enter the bone in parallel to each other, to facilitate removal of the resection guide 2020*a* while leaving the fasteners 2010 in the bone. In the illustrated embodiment, the fasteners 2010 in the first bone attachment feature 2024*a* and second bone attachment feature 2024*b* both enter the portion of the bone that becomes the wedge bone fragment 2050. With the fasteners 2010 in the wedge bone fragment 2050, the wedge bone fragment 2050 can be readily manipulated and/or removed during a surgical procedure.

Advantageously, embodiments of the present disclosure enable a user (e.g., a technician, and/or a surgeon) to visualize and work with the bone model as well as a model of the resection guide 2020 before the resection guide 2020 is fabricated. Accordingly, a user can identify and measure the effects of one or more osteotomies formed using the resection guide 2020 along the first trajectory 2042 and/or the second trajectory 2044. In addition, a user can change the first trajectory 2042, the second trajectory 2044, the positions of the posterior resection feature 2022*a* and/or the anterior resection feature 2022*b* relative to each other (in one, two, or three planes), and a variety of other aspects of the resection guide 2020 and/or the osteotomy system 2000 before instruments are fabricated and used on patient. Thus, a user can design and/or revise the resection guide 2020 and its characteristics and features to accomplish a customized surgical procedure and/or outcome for the patient.

Referring back to FIGS. 11, 12, and/or 17, the embodiments of the present disclosure may use one or more bone models (e.g., bone model 1204) in determining, partially determining, and/or as a factor in identifying, positioning, selecting, orienting, and/or defining components of the osteotomy systems. Those of skill in the art will appreciate that the accuracy of and/or fidelity of the bone model can vary depending on the technology and/or equipment used to capture and/or process the medical imaging. Consequently, in one embodiment, the accuracy and fidelity and/or quality of the medical imaging and/or processing to generate a three dimensional bone model may result in a bone model having each of the same features as the corresponding bone of a patient such that bone model 1204 may match or substantially may match the anatomy of a patient's foot. In another embodiment, the accuracy and fidelity and/or quality of the medical imaging and/or processing to generate a three dimensional bone model may be such that the accuracy, fidelity, and/or quality may be less than the highest. In such an instance, the bone model 1204 may resemble or significantly resemble the anatomy of a patient's foot. This may mean that certain features and/or aspects are exactly the same while others are similar but not actually the same as corresponding features on bone(s) of the patient.

Furthermore, those of skill in the art will appreciate that the bone model 1204 may model a portion of a single bone of a patient. Alternatively, or in addition, the bone model 1204 may model all or substantially all of a single bone of a patient. Alternatively, or in addition, the bone model 1204 may model a plurality of bones of a patient.

Referring now to FIG. 21J, the resection guide 2020*a* can be used for a surgical procedure on a calcaneus 224, or another bone, of a patient. The resection guide 2020*a* may include at least one bone attachment feature. In one embodiment, a user may secure the resection guide 2020*a* to the calcaneus 224 by deploying at least one fastener 2010 through the at least one bone attachment feature and into the calcaneus 224.

In the illustrated embodiment, the resection guide 2020*a* includes a posterior resection feature 2022*a* and an anterior resection feature 2022*b*. The posterior resection feature 2022*a* is configured to guide a cutting tool to form a first osteotomy 2046. The anterior resection feature 2022*b* is configured to guide a cutting tool (which may be the same cutting tool) to form a second osteotomy 2048.

The posterior resection feature 2022*a* extends through the resection guide 2020*a* from the lateral side 2030 to the medial side 2032 along the first trajectory 2042. The first trajectory 2042 is at least partially determined based on a calcaneus model of at least a portion of a calcaneus of a patient's foot. The calcaneus model is based on medical imaging of the patient's foot and is configured to resemble, significantly resemble, and/or match the anatomy of the patient's foot. Alternatively, or in addition, the anterior resection feature 2022*b* extends through the resection guide 2020 from the lateral side 2030 to the medial side 2032 along the second trajectory 2044. The second trajectory 2044 is at least partially determined based on the calcaneus model of at least a portion of the calcaneus 224 of the patient's foot.

In the illustrated embodiment, the second osteotomy 2048 connects with the first osteotomy 2046 to form a wedge bone fragment 2050. Advantageously, the wedge bone fragment 2050 is connected to the at least one fastener 2010. This connection enables a surgeon to readily remove and/or manipulate the wedge bone fragment 2050, as needed.

In certain embodiments, a posterior resection feature 2022*a* may extend from a lateral side 2030 to a medial side 2032 at a posterior angle 2052, the posterior angle 2052 may be an angle measured in degrees from an axis 2054 parallel to a lateral side 2030 of the body 2028 to the first trajectory 2042. An anterior resection feature 2022*b* may extend from a lateral side 2030 to a medial side 2032 at an anterior angle 2056, the anterior angle 2056 may be an angle measured in degrees from the axis 2054 to the second trajectory 2044.

The posterior angle 2052 may be determined, at least partially, based on a calcaneus model derived from medical imaging of a calcaneus of a patient's foot. In one embodiment, the calcaneus model is configured to significantly resemble the anatomy of the patient's foot. The anterior angle 2056 may be determined based on the calcaneus model. Furthermore, the anterior angle 2056 may be determined such that an osteotomy formed by way of the posterior resection feature 2022*a* and the anterior resection feature 2022*b* forms a wedge osteotomy. The wedge osteotomy includes a wedge bone fragment 2050. In certain embodiments, the wedge bone fragment 2050 may be determined, at least partially, based on the calcaneus model.

Referring still to FIG. 21J, in one embodiment, the resection guide 2020a includes at least one bone attachment feature that may be configured to receive at least one fastener 2010. The fastener 2010 may engage a portion of the calcaneus before formation of the wedge osteotomy. Advantageously, the fastener 2010 may extend into the calcaneus such that the fastener 2010 does not interfere with the wedge osteotomy, but the fastener 2010 also engages the wedge bone fragment 2050 after formation of the wedge osteotomy.

Those of skill in the art will appreciate that the posterior resection feature 2022a and/or anterior resection feature 2022b can have a variety of different designs and may be similar to each other or different from each other. In the illustrated embodiment, the resection features 2022 have a similar mirrored configuration, one for the posterior resection feature 2022a and one for the anterior resection feature 2022b. Generally, resection features 2022 include openings that may also be referred to as slots, channels, or the like. Likewise, the posterior resection feature 2022a and/or anterior resection feature 2022b may have the same or similar or different opening configurations.

In the illustrated embodiment, the posterior resection feature 2022a includes a posterior dorsal slot 2058, a posterior plantar slot 2060, and a posterior bridge 2062. In certain embodiments, the posterior dorsal slot 2058 and a posterior plantar slot 2060 have a similar height, width, and depth. The anterior resection feature 2022b includes an anterior dorsal slot 2064, an anterior plantar slot 2066, and an anterior bridge 2068. In certain embodiments, the anterior dorsal slot 2064 and an anterior plantar slot 2066 have a similar height, width, and depth.

The posterior dorsal slot 2058 may include an open dorsal end 2070 and a closed plantar end 2072. The posterior plantar slot 2060 may include an open plantar end 2074 and a closed dorsal end 2076. The anterior dorsal slot 2064 may include an open dorsal end 2078 and a closed plantar end 2080. The anterior plantar slot 2066 may include an open plantar end 2082 and a closed dorsal end 2084. In the illustrated embodiment, the posterior bridge 2062 is positioned between the posterior dorsal slot 2058 and the posterior plantar slot 2060. In one embodiment, the posterior bridge 2062 may form the closed plantar end 2070 of the posterior dorsal slot 2058 and the closed dorsal end 2074 of the posterior plantar slot 2060. In one embodiment, the anterior bridge 2068 is positioned between anterior dorsal slot 2064 and the anterior plantar slot 2066. The anterior bridge 2068 can form the closed plantar end 2080 of the anterior dorsal slot 2064 and the closed dorsal end 2084 of the anterior plantar slot 2066.

Advantageously, the resection features 2022 can be positioned, sized, and/or oriented to enable a surgeon to resect any particular shape in the bone for the osteotomy procedure. In the illustrated embodiment, the resection features 2022 are configured to direct a cutting tool at an angle into the bone such that a wedge is resected. Advantageously, the size, shape, and angle of the wedge can be predefined and can be determined preoperatively and can be patient-specific. In this manner, the resection guide 2020a serves to provide for a patient-specific osteotomy procedure. Alternatively, or in addition, the resection features 2022 can be configured to enable a surgeon to readily resect in a plantar direction and/or a dorsal direction. In the illustrated embodiment, the resection features 2022 include an opening on one end to permit the surgeon to position a cutting tool to make desired cuts that can extend all the way to dorsal and/or plantar surfaces of the bone.

Advantageously, the illustrated embodiment the resection features 2022 include open ends (e.g., open dorsal end 2070, open plantar end 2074, open dorsal end 2078, and open plantar end 2082). The open ends end able a surgeon to manipulate or tilt a cutting tool from a normal orientation relative to the slot to an angled position that moves the cutting tool out past the perimeter of the resection guide 2020a. For example, a surgeon can insert a cutting tool in posterior dorsal slot 2058 and cut bone below the posterior dorsal slot 2058. In addition, the surgeon can angle the cutting tool in a plantar direction and the posterior dorsal slot 2058 guides the cutting tool to cut outside the perimeter of the resection guide 2020a. In particular, moving the cutting tool in a plantar direction enables a cutting blade of the cutting tool to cut bone dorsal to, but still aligned with the posterior dorsal slot 2058. In this manner, the surgeon can create an osteotomy that extends dorsally beyond a dorsal cortex of the bone. Similarly, and in like manner, the open plantar end 2074, open dorsal end 2078, and/or open plantar end 2082 enable the surgeon to form an osteotomy that reaches to the other dorsal and/or plantar surfaces of the bone. These open ends allow the resection guide 2020 to be smaller (not as long along its longitudinal axis) such that smaller incisions are needed for use.

In the illustrated embodiment, the posterior bridge 2062 is aligned horizontally with the anterior bridge 2068. However, those of skill in the art will appreciate that the posterior bridge 2062 and anterior bridge 2068 may be unaligned in other embodiments. Furthermore, those of skill in the art appreciate that the posterior resection feature 2022a and/or anterior resection feature 2022b may have a variety of configurations, including a single slot with a closed plantar end and an opposite open dorsal end, a single slot with an open plantar end and an opposite closed dorsal end, a single slot with a closed plantar end and a closed opposite dorsal end, or the like.

Referring still to FIG. 21J, the resection guide 2020a can include a plantar landmark registration feature 2041a and a handle 2026 (not shown due to cross section, see FIGS. 22A-221), the a plantar landmark registration feature 2041a extends from a plantar side 2040 of the body 2028 and is configured to contact a plantar surface of the calcaneus 224. Alternatively, or in addition, the resection guide 2020a can include a bone engagement surface 2033 on the medial side 2032 of the body 2028. The bone engagement surface 2033 is configured to resemble, substantially resemble, or match a contour of the calcaneus when the body 2028 is positioned on the calcaneus 224. In one embodiment, the resection guide 2020a may include a handle 2026 that extends from a dorsal side 2038 of the body 2028.

FIGS. 22A-22G illustrate views of a pin guide of an osteotomy system, such as osteotomy system 2000, according to one embodiment. In one embodiment, the osteotomy system 2000 may include at least one complementary component 1930. The complementary component 1930 may include one or more pin guides 2200. In certain embodiments, the complementary component 1930 may include a posterior pin guide 2202 and an anterior pin guide 2204. In one embodiment, a single pin guide 2200 may be used as both the posterior pin guide 2202 and the anterior pin guide 2204. Using a single pin guide 2200 may promote re-use and/or may facilitate fabrication of pin guides 2200. Alternatively, or in addition, the posterior pin guide 2202 may be configured differently from the anterior pin guide 2204.

The pin guide 2200 serves to position and/or orient one or more pins for deployment into bone of a patient. Advantageously, the pin guide 2200 may be designed using a model of the bone and/or a model of other components of the osteotomy system 2000. In particular, a pin guide 2200 may enable fasteners 2010 in another component such as the resection guide 2020 to be parallel with each other and one or more fasteners 2010 to be deployed into a bone at a non-parallel angle relative to each other. Pins in the bone at non-parallel angles can be used for reduction and/or compression and/or fixation during a step of a surgical procedure.

In the illustrated embodiment, the posterior pin guide 2202 and the anterior pin guide 2204 may be similar. Advantageously, a user or surgeon can define the posterior pin guide 2202 and the anterior pin guide 2204 to be patient-specific. For example, one pin guide 2200 may have a default or standard configuration and the other pin guide (e.g., the posterior pin guide 2202 and/or the anterior pin guide 2204) may have a different, customized, and/or patient-specific configuration.

In one embodiment, the osteotomy system 2000 includes a resection guide 2020a configured to cooperate with the one or more pin guides 2200 to position one or more pins. FIG. 22A illustrates a resection guide 2020a with two pin guides 2200 (e.g., a posterior pin guide 2202 and an anterior pin guide 2204). A pin guide 2200 may include an arm 2206 configured to engage at least one of a posterior resection feature 2022a and an anterior resection feature 2022b. The arm 2206 may be connected to a bone engagement feature 2208 configured to receive a fastener such as a pin or K-wire.

The arm 2206 engages a resection feature 2022 and connects the bone engagement feature 2208 to the resection feature 2022. In one embodiment, the arm 2206 includes an opening 2220 sized and/or configured to receive a bridge (e.g., posterior bridge 2062 and/or anterior bridge 2068) of a resection feature 2022 (e.g., a posterior resection feature 2022a and/or an anterior resection feature 2022b). In certain embodiments, the arm 2206 may engage the resection feature 2022 by sliding the opening 2220 over the bridge. Alternatively, or in addition, another part of the arm 2206 may slide down into one or more openings of a resection feature 2022. In one embodiment, the opening 2220 may include a closed end that includes two corners that meet at right angles. Similarly, a top surface of the bridge (e.g., posterior bridge 2062 and/or anterior bridge 2068) may be rectangular such that top edges of the bridge engage the two corners of the opening 2220 when the arm 2206 is engaged with a bridges as desired or, when the arm 2206 is fully engage with the resection feature 2022.

The bone engagement feature 2208 can serve to guide and/or position a pin during deployment into a bone. In certain embodiments, each of the pin guides 2200 include an arm 2206 and a bone engagement feature 2208. The arm 2206 may include a body 2210 and a coupler 2212. The body 2210 connects the coupler 2212 and the bone engagement feature 2208.

The bone engagement feature 2208 can be implemented using a hole 2214 and a fastener 2216. Advantageously, pin guides 2200 (e.g., a posterior pin guide 2202 and an anterior pin guide 2204) enable a fastener 2216 to be deployed where needed for a surgical procedure. In the illustrated embodiment, fasteners 2216 may be needed in a posterior bone fragment 2114 and/or in an anterior bone fragment 2116 for one or more steps of a surgical procedure.

In the illustrated embodiment, the pin guides 2200 (e.g., a posterior pin guide 2202 and an anterior pin guide 2204) serve to enable deployment of fasteners 2216 a distance, such as a predetermined distance from a posterior side 2036 and/or an anterior side 2034 of a resection guide 2020. The fasteners 2216 engage with the holes 2214 and the holes 2214 and arm 2206 cooperate to direct the fasteners 2216 into the bone in a desired position and/or angle. The fastener 2216 may engage the hole 2214 in a friction fit. In certain embodiments, once a fastener 2216 is deployed through a hole 2214, the pin guide 2200 may be removed by leaving the fastener 2216 in place and sliding the pin guide 2200 up and off of the fastener 2216.

The coupler 2212 enables the pin guide 2200 to be connected and/or disconnected from a complementary component 1930. The complementary component 1930 may serve as a reference or guide for the placement, positioning, and/or orientation of fasteners 2216 into bone and/or bone fragments during a surgical procedure. Those of skill in the art will appreciate that the coupler 2212 may be implemented using a variety of configurations.

In the illustrated embodiment, the coupler 2212 is implemented as a fin 2218 that includes an opening 2220. The opening 2220 may be sized and/or configured to receive a bridge (e.g., posterior bridge 2062 and/or anterior bridge 2068) of a resection feature 2022. In certain embodiments, the coupler 2212 may engage the resection feature 2022 by sliding the opening 2220 over the bridge. Alternatively, or in addition, the fin 2218 may slide down into one or more openings of a resection feature 2022 and secure the orientation and/or position of the pin guide 2200.

In another embodiment, the coupler 2212 may couple or connect to a different structure of a complementary component 1930. For example, in one embodiment, the coupler 2212 may couple to one or more fasteners 2010 deployed in a resection guide 2020.

FIG. 22B is a perspective view of one example pin guide 2200. FIG. 22B illustrates that the coupler 2212 (or fin 2218) may extend from the body 2210 parallel to the bone engagement feature 2208. FIG. 22C is a perspective view.

FIG. 22D is a distal side view of one example pin guide 2200. FIG. 22D illustrates one embodiment of a coupler 2212 and/or a fin 2218 with an opening 2220. FIG. 22E is a proximal side view of one example pin guide 2200.

FIG. 22F is a superior side view of one example pin guide 2200. FIG. 22F illustrates the hole 2214. In one embodiment, the hole 2214 extends from one end of the bone engagement feature 2208 to the other end. FIG. 22G is an inferior side view of one example pin guide 2200.

Referring now to FIG. 22A, in one embodiment, while the coupler 2212 and bone engagement feature 2208 may extend from the body 2210 in parallel, a fastener 2216 deployed using the pin guide 2200 may deploy at a non-perpendicular angle in relation to the bone. In the illustrated embodiment, this is because as the pin guide 2200 engages with the resection feature 2022 (e.g., posterior resection feature 2022a and/or anterior resection feature 2022b) the coupler 2212 can assume the same angle in relation to the body 2028 as the opening of the resection feature 2022. Consequently, the fastener 2216 deployed using the bone engagement feature 2208 enters the bone at substantially the same angle as an opening of the resection feature 2022. Since the angle of the opening of the resection feature 2022 can be patient-specific, the angle of deployment for one or more fasteners 2216 can also be patient-specific.

Those of skill in the art will appreciate that varies aspects of the pin guide 2200 can be configured and/or customized to meet the needs of a particular patient, surgeon for a surgical procedure. Alternatively, or in addition, at least one of the arm 2206 and the bone engagement feature 2208 can include one or more patient-specific features. These patient-specific features may be defined at least in part based on a bone model of the bone the pin guide 2200 will be used with. For example, a distance of a fastener 2216 from an osteotomy can be controlled and/or set by defining a length of the body 2210. An angle of entry for a fastener 2216 can be controlled by way of an angle of a resection feature 2022 and/or an angle of a coupler 2212 and/or a fin 2218 relative to an angle of a bone engagement feature 2208 used for deployment of the fastener 2216. Advantageously, each of these angles, configurations, aspects, and/or features can be customized and designed in a model of the pin guide 2200 before the pin guide 2200 is fabricated for use. These angles, configurations, aspects, and/or features may be patient-specific features for a pin guide 2200.

Referring still to FIG. 22A, in one embodiment, the resection guide 2020a includes a posterior resection feature 2022a and an anterior resection feature 2022b. The osteotomy system 2000 may include a posterior pin guide 2202 and an anterior pin guide 2204. The posterior resection feature 2022a is configured to receive an arm 2206 of the posterior pin guide 2202 and the anterior resection feature 2022b is configured to receive an arm 2206 of the anterior pin guide 2204. The posterior pin guide 2202 includes an arm 2206 that connects a planar fin (e.g., fin 2218) to a bone engagement feature 2208 that includes an opening, such as hole 2214, and a posterior pin 2220. The anterior pin guide 2204 includes an arm 2206 that connects a planar fin (e.g., fin 2218) to a bone engagement feature 2208 that includes an opening, such as hole 2214, and an anterior pin 2222.

In the embodiment of FIG. 22a, the posterior pin guide 2202 is configured to guide the posterior pin 2220 into a posterior bone fragment 2114 (See FIG. 21J) parallel to an osteotomy (e.g., first osteotomy 2046) formed using the posterior resection feature 2022a. The anterior pin guide 2204 is configured to guide the anterior pin 2222 into an anterior bone fragment 2116 (See FIG. 21J) parallel to an osteotomy (e.g., second osteotomy 2048) formed using the anterior resection feature 2022b. Alternatively, or in addition, the anterior pin guide 2204 is configured to guide the anterior pin 2222 into an anterior bone fragment 2116 (See FIG. 21J) substantially parallel to an osteotomy (e.g., second osteotomy 2048) formed using the anterior resection feature 2022b. The anterior pin 2222 may be deployed at an angle that is not parallel to the osteotomy (e.g., second osteotomy 2048) such that when the osteotomy is reduced a predetermined degree of compression is applied to the cut faces of the osteotomy.

Advantageously, fasteners 2216 (e.g., posterior pin 2220 and/or anterior pin 2222) deployed using the pin guide(s) 2200 may be used for subsequent steps in a surgical procedure. In one embodiment, the osteotomy system 2000 may include a positioning guide 2300 as one of the complementary components 1930. In one embodiment, for example, a posterior pin 2220 deployed by way of a posterior pin guide 2202 and an anterior pin 2222 deployed by way of an anterior pin guide 2204 are configured to receive a positioning guide 2300. In certain embodiments, depending on how various components of the osteotomy system 2000 are designed and/or fabricated a positioning guide 2300 may serve to position a posterior bone fragment 2114 and/or an anterior bone fragment 2116, reduce an osteotomy, and/or compress two bone fragments together. Alternatively, or in addition, the positioning guide 2300 may also serve as a correction guide, a rotation guide, an alignment guide, and/or the like.

The positioning guide 2300 may be similar in form and/or function to the positioning guide 1980 described herein.

Alternatively, or in addition, the positioning guide 2300 may be configured differently. In one embodiment, the positioning guide 2300 facilitates positioning one or more bones, bone fragments, implants, and/or instruments for one or more steps of a surgical procedure.

FIGS. 23A-23G illustrate views of a positioning guide 2300 of an osteotomy system, according to one embodiment. In one embodiment, the positioning guide 2300 includes a body 2302, an anterior alignment feature 2304, and a posterior alignment feature 2306. In another embodiment, the positioning guide 2300 includes the body 2302, the anterior alignment feature 2304, the posterior alignment feature 2306, and an offset feature 2308. In another embodiment, the positioning guide 2300 includes the body 2302, the anterior alignment feature 2304, the posterior alignment feature 2306, the offset feature 2308, and a bone engagement surface 2310.

The body 2302 may include a lateral side 2312, a medial side 2314, a posterior side 2316, an anterior side 2318, a dorsal side 2320, and a plantar side 2322. FIGS. 23A-23H illustrate different views of one embodiment of a positioning guide 2300 and the sides of the body 2302.

The posterior alignment feature 2306 and/or anterior alignment feature 2304 assist a surgeon in aligning and/or positioning and/or orienting a first bone fragment (e.g., posterior bone fragment 2114) and a second bone fragment (e.g., anterior bone fragment 2116). In one embodiment, the surgeon seeks to reduce an osteotomy and bring the first bone fragment and second bone fragment in contact with each other to encourage the two bone fragments to grow together and heal an osteotomy closed. The posterior alignment feature 2306 and/or anterior alignment feature 2304 give a surgeon a secure, reliable, and stable tool to control and/or manipulate the bone fragments, which now may be mostly separated (but for a living hinge, opposite segment of cortical bone) or completely separated.

In one embodiment, the posterior alignment feature 2306 may include the posterior pin 2220 and the anterior alignment feature 2304 may include the anterior pin 2222. Together with the posterior pin 2220 and the anterior pin 2222, the posterior alignment feature 2306 and/or anterior alignment feature 2304 give a surgeon "handles" for translating and/or rotating the bone fragments. In another embodiment, the posterior alignment feature 2306 is independent of the posterior pin 2220 and the anterior alignment feature 2304 is independent of the anterior pin 2222.

In the illustrated embodiment, the posterior alignment feature 2306 may be embodied as a slot 2324 that includes a dorsal end 2326, a plantar end 2328, and a length 2330 between the dorsal end 2326 and the plantar end 2328. The slot 2324 may be configured to receive a posterior pin 2220.

In one embodiment, the length 2330 is patient-specific and may be determined prior to fabricating the positioning guide 2300. In one embodiment, the length 2330 is a predetermined length based on a bone model (e.g., a model of a calcaneus 224). The predetermined length may be set or defined to permit a user such as a surgeon to rotate a first bone fragment (e.g., posterior bone fragment 2114) relative to a second bone fragment (e.g., anterior bone fragment 2116). In certain embodiments, a prescription may include a number of degrees of rotation a surgeon desires for a posterior bone fragment 2114 and a system or apparatus may translate that number of degrees into the predetermined length for the length 2330.

The anterior alignment feature 2304 may be embodied as a hole 2332 or opening that extends from the lateral side 2312 to the medial side 2314.

In one embodiment, the slot 2324 and/or the hole 2332 may extend through the body 2302 perpendicular to a planar surface of the lateral side 2312. Alternatively, or in addition, one or the other, or both of the slot 2324 and/or the hole 2332 may extend through the body 2302 at an angle that is not perpendicular to a planar surface of the lateral side 2312. Advantageously, the embodiments of the present disclosure enable a user or surgeon to specifically design the positioning guide 2300 with a desired angle relationship for the slot 2324 and/or the hole 2332 through the body 2302.

During use of the positioning guide 2300, a surgeon may slide the slot 2324 over the posterior pin 2220 and the anterior pin 2222 over the hole 2332. As the positioning guide 2300 slides down the pins (e.g., posterior pin 2220 and anterior pin 2222) the distance between the slot 2324 and the hole 2332 longitudinally may reduce the osteotomy and bring the two bone fragments into contact with each other. Initially, the posterior pin 2220 may be near the dorsal end 2326. A surgeon can then move the posterior pin 2220 toward the plantar end 2328 to rotate the bone fragment engaged by the posterior pin 2220 about its longitudinal axis. The surgeon determines whether the posterior pin 2220 should be moved to near the plantar end 2328, remain near the dorsal end 2326, or some position in between. With the bone fragments connected to the posterior pin 2220 and/or the anterior pin 2222 translated, reduced, and/or rotated, surgeon can then connect the two bone fragments using temporary or permanent fixation hardware and/or techniques. In such an example, a surgeon can predefine (e.g., the length 2330 and/or the slot 2324) how much rotation is desired and/or adjust the amount of rotation intraoperatively to achieve a desired orientation during the surgery.

In another embodiment, the anterior alignment feature 2304 may include a slot 2324 and the posterior alignment feature 2306 may include a hole 2332. Alternatively, or in addition, both the anterior alignment feature 2304 and the posterior alignment feature 2306 may each include slot 2324. Alternatively, or in addition, both the anterior alignment feature 2304 and the posterior alignment feature 2306 may each include hole 2332.

Referring to FIGS. 23B, 23G, and 23H, in one embodiment, a positioning guide 2300 may include a bone engagement surface 2310. The bone engagement surface 2310 may be on the medial side 2314 of the body 2302. The bone engagement surface 2310 may be configured to register to a lateral surface of the posterior bone fragment 2114 and the anterior bone fragment 2116. In certain embodiments, this can mean that the bone engagement surface 2310 contacts and/or engages with the lateral surface of the bone fragments. In particular, recesses of the bone engagement surface 2310 engage with protrusions on the lateral surface and protrusions of the bone engagement surface 2310 engage with recesses on the lateral surface.

In the illustrated embodiment, the positioning guide 2300 serves to reduce the osteotomy and bring two bone fragments together for fixation and eventual fusion. Accordingly, the bone engagement surface 2310 can be configured to account for a portion of each of the bone fragments (e.g., posterior bone fragment 2114 and anterior bone fragment 2116) after one or more of these bone fragments has been translated and/or rotated to a position below the positioning guide 2300. Advantageously, in certain embodiments, the bone engagement surface 2310 can be defined, at least in part, based a lateral surface of a one or more bone models of bones involved in a surgical procedure. In addition, the bone engagement surface 2310 can be defined, at least in part, based on a planned reduced position of a posterior bone fragment 2114 and/or an anterior bone fragment 2116. The planned reduced position may represent a desired final position of the bone fragment prior to fixation. Advantageously, the bone engagement surface 2310 is configured to resemble, substantially resemble, and/or match the surface of the bone fragments in this condition. In certain embodiments, the bone engagement surface 2310 may engage the lateral surface of the bone fragments such that a surgeon can "feel" the positioning guide 2300 register into place and "feel" that the positioning guide 2300 is in the position planned before the surgical procedure.

For example, suppose the bone is a calcaneus 224 and the surgical procedure and/or surgeon plans to retain the position of that anterior bone fragment 2116 and to translate and/or rotate the posterior bone fragment 2114 to correct a deformity. For example, a surgeon may perform the osteotomy of the calcaneus 224 to correct a varus deformity of the calcaneus 224. Consequently, the surgeon can plan to perform a superolateral (upward and lateral) translation of the posterior bone fragment 2114. Alternatively, or in addition, the surgeon may plan to rotate the posterior bone fragment 2114 to address a bone condition of the patient. Advantageously, the osteotomy system 2000 enables a surgeon to preplan the procedure and visualize how the procedure can address the condition. Furthermore, a surgeon can define a bone engagement surface 2310 for the positioning guide 2300 that will engage with the surfaces of the posterior bone fragment 2114 and/or the anterior bone fragment 2116 which will confirm intraoperatively that the bone fragments are in the predefined positions relative to each other. Advantageously, the bone engagement surface 2310 is defined, at least in part, based a lateral surface of a calcaneus model of the calcaneus 224. In addition, the bone engagement surface 2310 is defined, at least in part, based on a planned reduced position of the posterior bone fragment 2114 and/or the anterior bone fragment 2116.

In certain embodiments, where, for example, the positioning guide 2300 includes an offset feature 2308, the bone engagement surface 2310 may include a posterior surface 2334 and an anterior surface 2336. The posterior surface 2334 is configured to engage a surface of a posterior bone fragment 2114 and the anterior surface 2336 is configured to engage a surface of an anterior bone fragment 2116. Advantageously, one or both of the posterior surface 2334 and/or anterior surface 2336 can be configured to include a contour that resembles, substantially resembles, and/or matches a contour of a lateral surface of a posterior bone fragment 2114 and/or anterior bone fragment 2116 after one or the other or both of the bone fragments (e.g., posterior bone fragment 2114 and/or anterior bone fragment 2116) are positioned in preparation for fixation of the bone fragments.

Referring to FIGS. 23C, 23D, 23E, and 23H, in certain embodiments, the positioning guide 2300 includes an offset feature 2308. The offset feature 2308 may also be referred to as a translation feature. The offset feature 2308 may be a structure that translates on bone or bone fragment in relation to another. In one embodiment, the offset feature 2308 can be used to translate a posterior bone fragment 2114 in relation to an anterior bone fragment 2116. Those of skill in the art will appreciate that the offset feature 2308 may drive one bone fragment in one direction while the other bone fragment remains stationary, may pull one bone fragment in one direction while the other bone fragment remains stationary, may pull one bone fragment in one direction while driving the other bone fragment in another direction, may drive one bone fragment in one direction while driving the other bone fragment in another direction, may drive both bone fragments in the same direction, or the like.

In one embodiment, the offset feature 2308 may include an offset distance 2338. The offset distance 2338 may determine how much translation is provided between two bone fragments. In one embodiment, the offset distance 2338 can range from about 0 millimeters (i.e., no translation) to about 10 millimeters. Advantageously, the magnitude of the offset distance 2338 can be set using a model of one or more bones of the patient and/or a model of the positioning guide 2300. In this manner, the offset feature 2308 and/or the offset distance 2338 can be a patient-specific feature that can be defined based, at least in part on a model of a bone of a patient. A surgeon, or other user, can define the offset distance 2338 based on a desired about of translation.

Alternatively, or in addition, a plurality of positioning guide 2300 (either with or without a bone engagement surface 2310, which may also be patient-specific or may not be patient-specific) may be fabricated and provided to a surgeon for possible use during a surgical procedure. The plurality of positioning guides 2300 may be provided in a kit. In one embodiment, each positioning guide 2300 in the kit may include a standard and/or default offset distance 2338. For example, the offset distance 2338 may vary by 5 millimeters between positioning guides 2300 in the kit.

In this manner, a surgeon may use one positioning guide 2300 initially, may then check the translation and/or alignment and/or results and may opt to change to another different positioning guide 2300, for example, one having a different offset feature 2308 and/or offset distance 2338. In this manner, a surgeon may try different positioning guides 2300 intraoperatively until a positioning guide 2300 is found that provides a desired amount of translation and/or rotation and/or reduction and/or compression for two bones and/or bone fragments of a patient.

In one embodiment, the offset feature 2308 may be activated by sliding the positioning guide 2300 down along a posterior pin 2220 and an anterior pin 2222 until a medial side 2314 contacts a first bone fragment. Next, the positioning guide 2300 may be pressed against a bone and/or a pin may be pulled in an opposite direction from the direction the positioning guide 2300 is pressed until a second bone fragment engages the medial side 2314. In this manner, the offset feature 2308 can facilitate positioning of two bone fragments prior to fixation. In one embodiment, the offset feature 2308 is configured to translate a posterior bone fragment 2114 relative to an anterior bone fragment 2116. The posterior bone fragment 2114 and anterior bone fragment 2116 may be formed by way of a first osteotomy 2046 or a second osteotomy 2048.

Advantageously, the offset feature 2308 can be designed prior to fabrication of the positioning guide 2300 and may include two offset surfaces of the medial side 2087. The amount of offset and/or configuration can be predefined and approved by a surgeon before fabrication of the positioning guide 2300. In one embodiment, the positioning guide 2300 may also include one or more drill guides for pilot holes or anchor holes for one or more fasteners of a fixation assembly. For example, holes extending from the lateral side 2086 to the medial side 2087 may be used for drill pilot holes and/or K-wires for deployment of bone screws and/or a bone plate.

FIG. 24A is a flowchart of an example method 2400. In some implementations, one or more method steps of FIG. 24A may be performed by a surgeon using one or more of the systems, apparatuses, and/or components described herein.

As shown in FIG. 24A, method 2400 may include accessing a lateral surface of a calcaneus (block 2402). For example, a surgeon may access a lateral surface of a calcaneus, by using conventional surgical approaches to access the bone and/or to perform a periosteal elevation.

As also shown in FIG. 24A, method 2400 may include positioning a resection guide onto the lateral surface of the calcaneus. The resection guide may include: a body having an anterior side, a posterior side, a medial side, a lateral side, a dorsal side, and a plantar side; a posterior resection feature configured to guide a cutting tool to form a first osteotomy in the calcaneus, the posterior resection feature extending through the resection guide from the lateral side to the plantar medial side along a first trajectory determined based on a calcaneus model of the calcaneus based on medical imaging of the patient's foot, the calcaneus model configured to match the anatomy of the patient's foot; an anterior resection feature configured to guide a cutting tool to form a second osteotomy that connects with the first osteotomy to form a wedge bone fragment from the calcaneus, the anterior resection feature extending through the resection guide from the lateral side to the plantar medial side along a second trajectory determined based on the calcaneus model; a first bone attachment feature configured to engage the wedge bone fragment after formation of the wedge bone fragment; a second bone attachment feature configured to engage the wedge bone fragment after formation of the wedge bone fragment; a plantar landmark registration feature that extends from the plantar side of the body and is configured to contact a plantar surface of the calcaneus; and a bone engagement surface on the medial side of the body, the bone engagement surface configured to match a contour of the calcaneus when the body is positioned on the calcaneus (block 2404). For example, a surgeon may position a resection guide onto the lateral surface, the resection guide, as described herein.

As further shown in FIG. 24A, method 2400 may include deploying a first fastener into the first bone attachment feature and a second fastener into the second bone attachment feature such that the first fastener and second fastener are parallel relative to each other and enter a portion of the calcaneus that will form the wedge bone fragment (block 2406). For example, a surgeon may deploy a first fastener into the first bone attachment feature and a second fastener into the second bone attachment feature such that the first fastener and second fastener are parallel relative to each other and enter a portion of the calcaneus that will form the wedge bone fragment, as described herein.

As also shown in FIG. 24A, method 2400 may include inserting the cutting tool into the posterior resection feature to a depth predefined in a preoperative plan designed based on the calcaneus model to form the first osteotomy (block 2408). For example, a surgeon may insert the cutting tool into the posterior resection feature to a depth predefined in a preoperative plan designed based on the calcaneus model to form the first osteotomy, as described above.

As further shown in FIG. 24A, method 2400 may include inserting the cutting tool into the anterior resection feature to a depth predefined in a preoperative plan designed based on the calcaneus model to form the second osteotomy, the second osteotomy forming a posterior bone fragment and an anterior bone fragment (block 2410). For example, a surgeon may insert the cutting tool into the anterior resection feature to a depth predefined in a preoperative plan designed based on the calcaneus model to form the second osteotomy, the second osteotomy forming a posterior bone fragment and an anterior bone fragment, as described herein.

As also shown in FIG. 24A, method 2400 may include engaging a posterior pin guide with the posterior resection feature and deploying a posterior pin into a bone attachment feature of the posterior pin guide and engaging an anterior pin guide with the anterior resection feature and deploying an anterior pin into a bone attachment feature of the anterior pin guide (block 2412). For example, a surgeon may engage a posterior pin guide with the posterior resection feature and deploy a posterior pin into a bone attachment feature of the posterior pin guide and engage an anterior pin guide with the anterior resection feature and deploy an anterior pin into a bone attachment feature of the anterior pin guide, as described herein.

As further shown in FIG. 24A, method 2400 may include removing the posterior pin guide and the anterior pin guide and the resection guide (block 2414). For example, a surgeon may remove the posterior pin guide and the anterior pin guide and the resection guide, as described herein.

As also shown in FIG. 24A, method 2400 may include removing the wedge bone fragment by way of the first fastener and the second fastener (block 2416). For example, a surgeon may remove the wedge bone fragment by way of the first fastener and the second fastener, as described herein.

As further shown in FIG. 24A, method 2400 may include sliding a positioning guide over the posterior pin and the anterior pin by passing the posterior pin through a posterior alignment feature and passing the anterior pin through an anterior alignment feature (block 2418). For example, a surgeon may slide a positioning guide over the posterior pin and the anterior pin by passing the posterior pin through a posterior alignment feature and passing the anterior pin through an anterior alignment feature, as described herein.

As also shown in FIG. 24A, method 2400 may include sliding the positioning guide along the posterior pin and anterior pin until the positioning guide contacts the posterior bone fragment and the anterior bone fragment (block 2420). For example, a surgeon may slide the positioning guide along the posterior pin and anterior pin until the positioning guide contacts the posterior bone fragment and the anterior bone fragment, as described herein.

As further shown in FIG. 24A, method 2400 may include deploying fixation across an osteotomy between the posterior bone fragment and the anterior bone fragment (block 2422). For example, a surgeon may deploy fixation across an osteotomy between the posterior bone fragment and the anterior bone fragment, as described herein.

FIGS. 24B-24G illustrates different stages of performing a surgical osteotomy procedure (e.g., a Dwyer osteotomy) using certain embodiments of the osteotomy system 2000 and/or the method 2400, according to one embodiment. Typically, a preferred approach for a Dwyer osteotomy is on the lateral side of the calcaneus 1806. In the illustrated embodiment, the surgical procedure creates a wedge osteotomy. According to one embodiment, a surgeon may access a lateral surface of the calcaneus 1806 (block 2402, FIG. 24A).

Next a surgeon may position a resection guide 2020 such as resection guide 2020a on the lateral surface in a position predetermined using a calcaneus model of the patient's calcaneus 1806. In certain embodiments, the step of positioning can include seating or registration of the resection guide 2020 to a surface of the calcaneus 1806 (a bone). The resection guide 2020 may be configured, for example, as one of the embodiments described herein.

Once positioned, a surgeon may deploy a first fastener 2010 into a first bone attachment feature 2024a and a second fastener into second bone attachment feature 2024b such that the first fastener and second fastener are parallel relative to each other and enter a portion of the calcaneus that will form a wedge bone fragment. (block 2406)

FIG. 24B illustrates the resection guide 2020a secured to the calcaneus 1806 by way of fasteners 2010. FIG. 24C illustrates the resection guide 2020b (an alternative embodiment, fasteners 2010 omitted) positioned on a calcaneus 1806 of a foot.

Next, a surgeon may insert a cutting tool into a posterior resection feature 2022a and an anterior resection feature 2022b and form a wedge bone fragment 2050. (blocks 2408 and 2410). In certain embodiments, the osteotomy system 2000 may include a guide for managing how deep a surgeon cuts into the calcaneus 1806 using the cutting tool. In one embodiment, the depth may be recommended in a preoperative plan and a surgeon may configure the cutting tool to indicate when that depth is reached. Alternatively, or in addition, the resection guide 2020 may include a stop that prevents cutting below the recommended depth. For example, the resection guide 2020 may have a height 2106 that is such that the lateral side 2030 of the resection guide 2020 may serve as a stop to prevent cutting beyond a particular depth. Alternatively, or in addition, a separate structure may be provided with the osteotomy system 2000 and/or the resection guide 2020 to serve as a stop to control cutting depth into a bone.

Next, a surgeon may engage a posterior pin guide 2202 with the posterior resection feature 2022a and an anterior pin guide 2204 with the anterior resection feature 2022b. in addition, the surgeon may deploy a posterior pin 2220 into the posterior pin guide 2202 and an anterior pin 2222 into the anterior pin guide 2204. (block 2412)

FIG. 24D illustrates a stage in the surgical osteotomy procedure (e.g., a Dwyer osteotomy) in which a wedge resection has been performed. The wedge bone fragment 2050 is not shown for clarity. The pin guides 2200 include the posterior pin 2220 and the anterior pin 2222 (because these pins serve to engage a posterior bone fragment 2114 and an anterior bone fragment 2116 of the calcaneus 1806 after the resection and/or for subsequent repositioning of the bone fragments of the calcaneus 1806.

FIG. 24E illustrates a closer view of the stage in the surgical osteotomy procedure (e.g., a Dwyer osteotomy) of FIG. 24D. Note that in certain embodiments, the wedge cut from the bone may not extend to the opposite side of the bone. Instead approximately a 1-3 mm section of bone can be left on the other side of the bone from the osteotomy. This section can facilitate handling of the bone fragments of the calcaneus 1806 during the surgical osteotomy procedure (e.g., a Dwyer osteotomy). In certain embodiments, this remaining portion can be used as a living hinge to keep the two bone fragments together during a fixation step or during one or more steps of the surgical osteotomy procedure. In one embodiment, for example where a surgeon plans to rotate one bone fragment in relation to the other, the method 2400 may further include breaking a medial cortex 2110 opposite a wedge bone fragment 2050. Now, with the bone fragments separated, a surgeon may translate a posterior pin 2220 within a posterior alignment feature 2306 of a positioning guide 2300 to rotate a posterior bone fragment 2114 to a position determined by a surgeon to remediate a condition of the patient's foot. For example, a surgeon may seek to achieve rectus alignment for a patient's foot, this may include structural realignment of the calcaneus 1806 from a calcaneal varus or valgus deformity to a rectus alignment. The ability to translate and/or rotate the posterior bone fragment 2114 in relation to the anterior bone fragment 2116 enables such repositioning and correction.

Figure 24F:
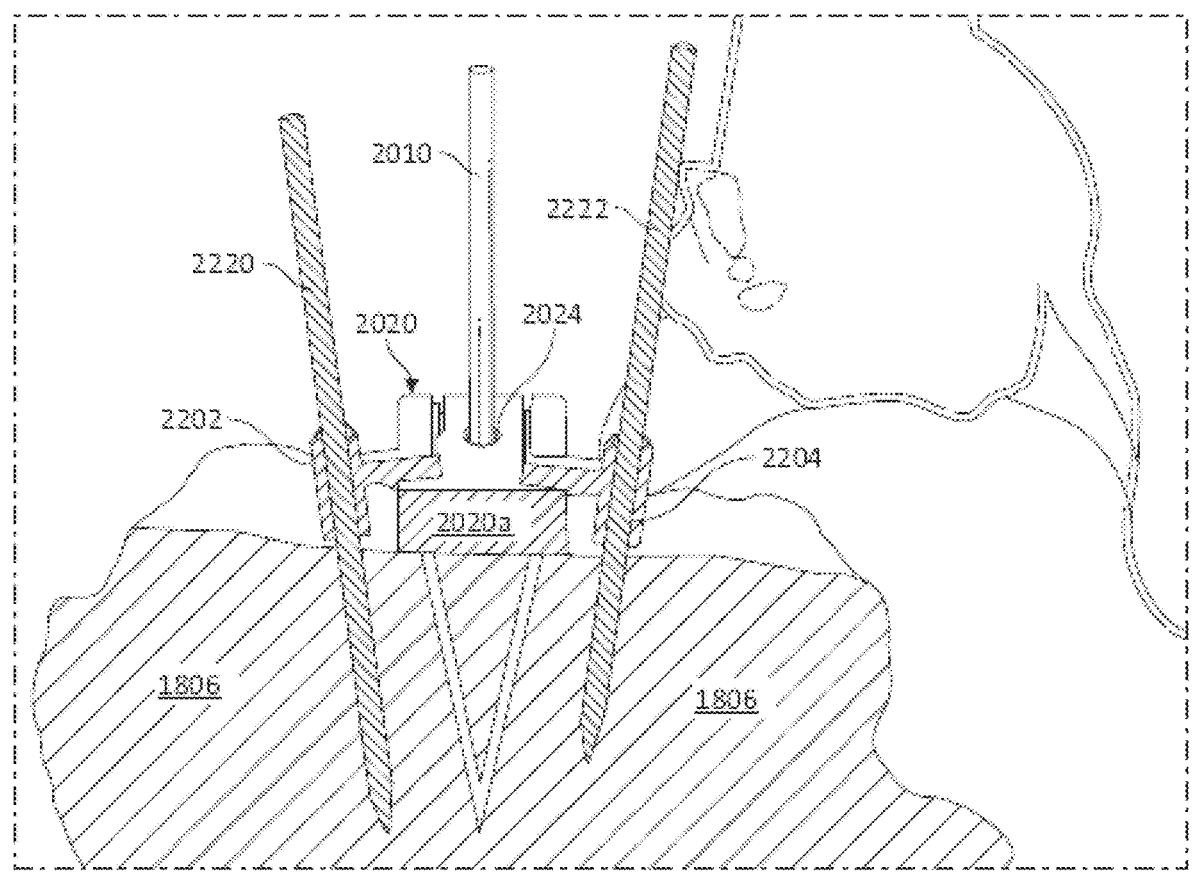

FIG. 24F illustrates a cross section view from an inferior side of the calcaneus 1806 looking upward. FIG. 24F includes the resection guide 2020*a* of FIG. 21D taken along a line along an anterior-posterior direction through the resection guide 2020*a*, a posterior pin guide 2202, anterior pin guide 2204, posterior pin 2220, and anterior pin 2222.

FIG. 24F illustrates that the resection guide 2020*a* can be configured to resect a particular shape from the bone, such as a wedge shape. Furthermore, the resection guide 2020*a* can be configured to resect a shape specific and unique to a particular patient. Said another way, the dimensions of the wedge bone fragment 2050 can be patient-specific.

Advantageously, resection features 2022 of the resection guide 2020*a* can be configured to enable a surgeon using a cutting tool to separate the resected bone (e.g., wedge bone fragment 2050) from the patient bone (e.g., calcaneus 1806) while leaving in a part of the bone on the medial side, the medial cortex 2110. Advantageously, bone attachment features 2024 can be positioned within a perimeter of the resection features 2022 of the resection guide 2020*a*. Having the bone attachment features 2024 within the perimeter of the of the lateral side of the resection guide 2020*a* can provide secure engagement of a resected part (e.g., a wedge bone fragment 2050) of the bone once resection is complete. This can facilitate removal and/or repositioning of the wedge bone fragment 2050. In addition, fasteners 2010 used together with the bone attachment features 2024 can extend perpendicular to a surface of the resection guide 2020*a* and/or parallel to each other which can then facilitate removal of the resection guide 2020*a* after forming one or more osteotomies. Alternatively, or in addition, bone attachment features 2024 within the perimeter of the lateral side of the resection guide 2020*a* can facilitate minimally invasive surgery (MIS) procedures because this positioning of the bone attachment features 2024 can enable the resection guide 2020 to be smaller in size.

FIG. 24F illustrates that one or more resection features 2022 of the resection guide 2020*a* can be used to position additional fasteners that can be used later in an osteotomy procedure to reposition bone or bone parts of the patient (e.g., parts of the calcaneus 1806). In FIG. 24F, a first osteotomy and a second osteotomy have been performed and a bone wedge fragment is connected to the one or more fasteners 2010 but separated from the calcaneus 1806.

In one embodiment, an arm 2206 of a pin guide 2200 can be placed into a resection feature 2022 at a predefined position. The arm 2206 may extend at a predefined distance and/or angle such that a fastener 2010 inserted through a hole 2214 near one end of the arm 2206 will engage the bone (e.g. calcaneus 1806) or part of a bone at a desired position and/or angle. Advantageously, even though the fasteners 2010 may engage the bone, calcaneus 1806, at a variety of angles, the pin guides 2200 may be separate components such that they can be readily removed as the osteotomy procedure (e.g., wedge osteotomy procedure) proceeds to subsequent steps. Of course, in certain embodiments, the pin guides 2200 may be integrated with the resection guide 2020. Separate pin guides 2200 may be desirable to facilitate removal of the resection guide 2020 and/or pin guides 2200 during a procedure.

In certain embodiments, it may be desirable to position the fasteners 2010 within the pin guides 2200 and relative to each other such that the fasteners 2010 are aligned in an anterior to posterior direction. In this manner, the original position of the parts of the bone (e.g. calcaneus 1806) can be maintained and used for subsequent steps of the osteotomy procedure (e.g., wedge osteotomy procedure).

After the stage illustrated in FIG. 24E, a surgeon may remove the posterior pin guide 2202, anterior pin guide 2204, and the resection guide 2020. (block 2414) Then, a surgeon may remove the wedge bone fragment 2050 using, for example, the one or more fasteners 2010. (block 2416) Then, a surgeon may slide a positioning guide 2300 over the posterior pin 2220 and the anterior pin 2222 until the positioning guide 2300 contacts the posterior bone fragment 2114 and the anterior bone fragment 2116. (block 2420) In certain embodiments, this action of sliding the positioning guide 2300 to contact bone fragments can cause the osteotomy to be reduced and/or can cause the bone fragments to be translated and/or rotated relative to each other.

Figure 24G:
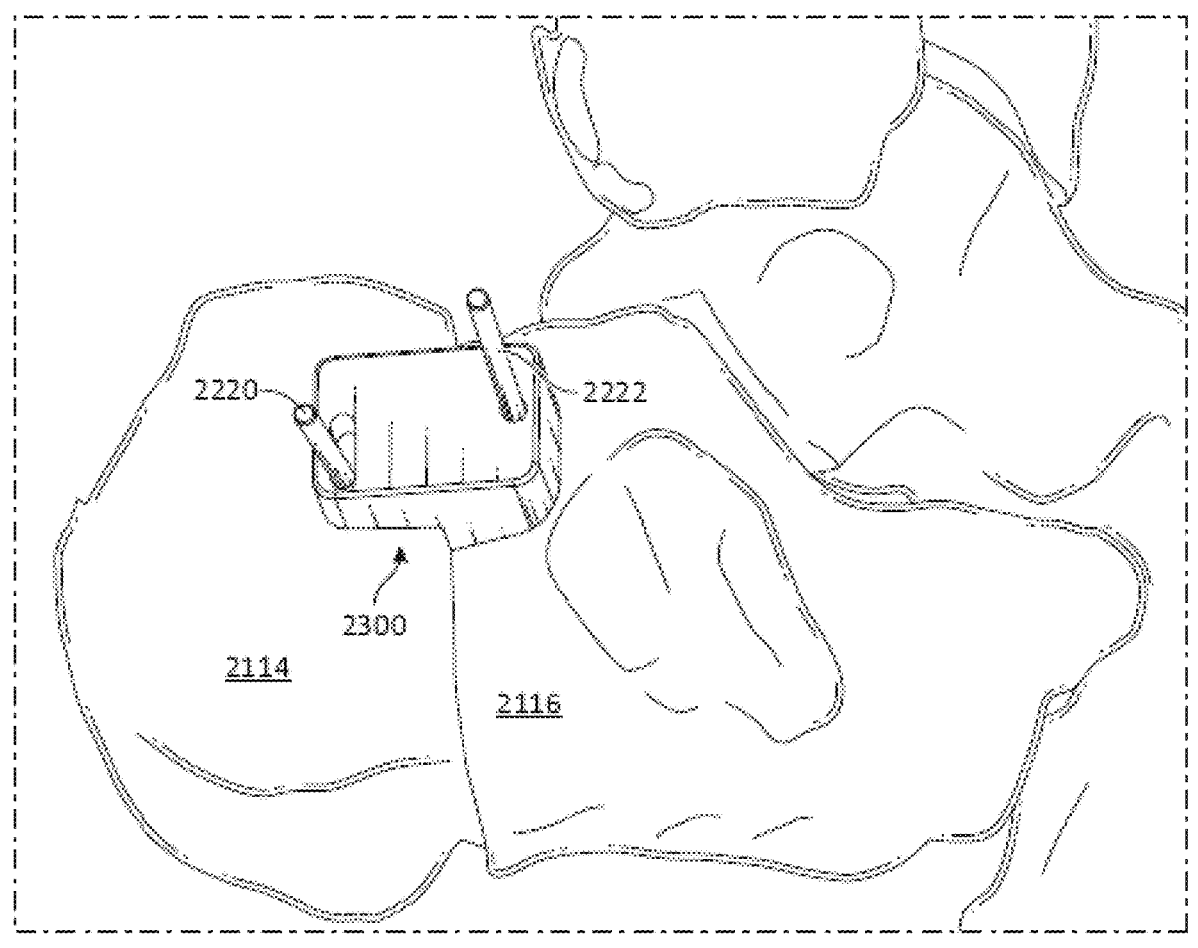

FIG. 24G illustrates a stage in the surgical osteotomy procedure (e.g., a Dwyer osteotomy) of FIG. 24E. The resection guide 2020*a* and pin guides 2200 have been removed. The additional fasteners 2012 in the pin guides 2200 remain engaged with the calcaneus 1806. A positioning guide 2300 has been deployed. In certain embodiments, a medial cortex 2110 opposite the osteotomy may be broken by a surgeon (e.g., manually). Alternatively, or in addition, the resection guide 2020*a* can be configured to enable resection through the bone to the medial surface 2108 of the calcaneus 1806.

In certain embodiments, the positioning guide 2300 can facilitate translation and/or rotation of two parts of a bone or two bones of a patient. In the illustrated embodiment, the action of positioning guide 2300 on the fasteners 2012 can cause the posterior bone fragment 2114 to translate relative to the anterior bone fragment 2116. In certain embodiments, the positioning guide 2300 can include an offset feature (translation feature) that facilitates positioning the posterior bone fragment 2114 with a desired translation and/or orientation relative to the anterior bone fragment 2116. In addition, in certain embodiments, one or more of the pin guides 2200 (e.g., an anterior pin guide 2204 and a posterior pin guide 2202) may permit rotation of one part of the bone in relation to the other part or another landmark.

After the stage of an osteotomy procedure illustrated in FIG. 24G, a surgeon may temporarily or permanently fixate the posterior bone fragment 2114 and the anterior bone fragment 2116. In one embodiment, a surgeon may deploy fixation across an osteotomy between the posterior bone fragment 2114 and the anterior bone fragment 2116.

The surgeon may use a variety of fasteners including a staple, a plate, one or more K-wires for temporary fixation, or the like. In one embodiment, the posterior pin 2220 and/or anterior pin 2222 may be designed to provide pilot holes and/or anchor holes for one or more fasteners of a fixation assembly, device, system, or apparatus.

Zadik Osteotomy

Figure 25:
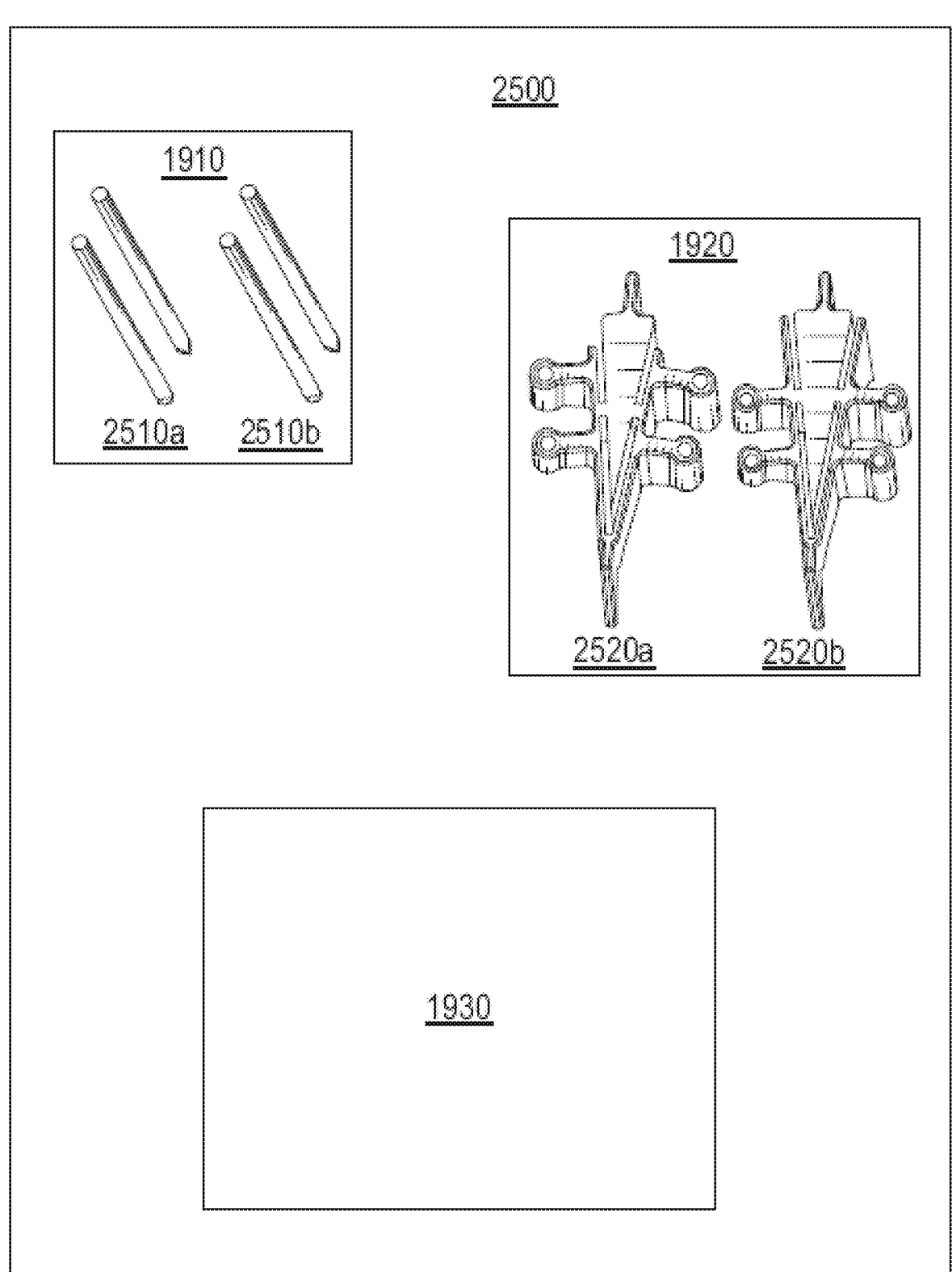
FIG. 25 illustrates an exemplary osteotomy system for a Zadik osteotomy, according to one embodiment.

FIG. 25 illustrates an exemplary osteotomy system 2500 for a Zadik osteotomy, according to one embodiment. The osteotomy system 2500 can include two or more fasteners 2510 (2510*a*, 2510*b*), a resection guide 2520 (two embodiments 2520*a*, 2520*b*), and one or more complementary components 1930. While specific embodiments of complementary components 1930 are not specifically shown here in relation to the osteotomy system 2500, those of skill in the art will appreciate that complementary components 1930 similar in feature, purpose, design, implementation, configuration, and purpose as those described in relation to the wedge osteotomy system 2000 can be used for the osteotomy system 2500. Thus, the osteotomy system 2500 can include one or more alignment guides 1940, rotation guides 1950, correction guides 1960, compression guides 1970, positioning guides 1980, fixation guides 1990, one or more pin guides 1994, and/or implants 1996.

Figure 26A:
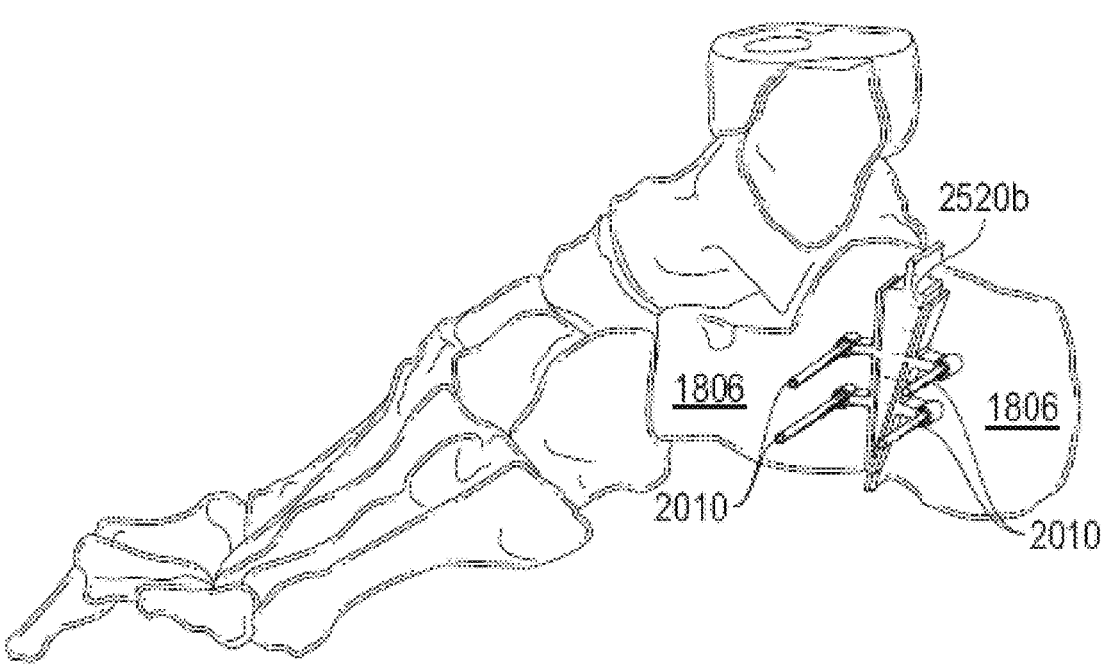
FIGS. 26A-26B illustrates different stages of performing a surgical osteotomy procedure using the osteotomy system of FIG. 25, according to one embodiment.
Figure 26B:
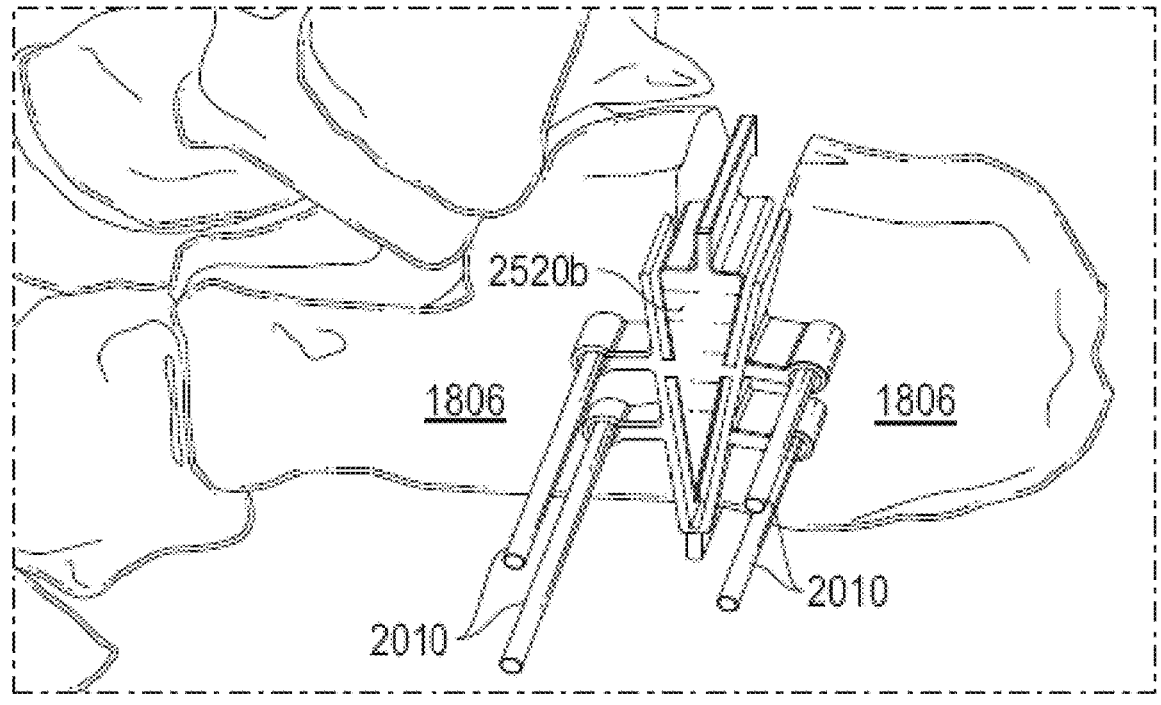

FIGS. 26A-26B illustrates different stages of performing a surgical osteotomy procedure (e.g., a Zadik osteotomy) using the osteotomy system of FIG. 25, according to one embodiment. Typically, the preferred approach for a Zadik osteotomy is on the lateral side of the calcaneus 1806. FIG. 26A illustrates the resection guide 2520*b* secured to the calcaneus 1806 by way of fasteners 2010.

FIG. 26B illustrates a closer view of the stage in the surgical osteotomy procedure (e.g., a Zadik osteotomy) of FIG. 26A with the resection guide 2520*b* positioned on a calcaneus 1806 of a foot. FIG. 26B illustrates a stage in the surgical osteotomy procedure (e.g., a Zadik osteotomy) in which a wedge resection has been performed. Fasteners 2012 can serve to engage the proximal and distal parts of the calcaneus 1806 after the resection and/or for subsequent repositioning of the proximal and distal parts of the calcaneus 1806.

Note that FIG. 26B illustrates a wedge cut that extends to the opposite side of the bone. Alternatively, or in addition, in certain embodiments, instead of the wedge extending to the opposite side approximately a 1-3 mm section of bone may be left on the other side (medial side) of the bone. This section can facilitate handling of the parts of the calcaneus 1806 during the surgical osteotomy procedure (e.g., a Zadik osteotomy). In certain embodiments, the remaining portion can be used as a living hinge to keep the two parts of the bone together during a fixation step or during one or more steps of the surgical osteotomy procedure.

FIGS. 27A-27D illustrate views of a resection guide of an osteotomy system, according to one embodiment. The resection guide 2520 of osteotomy system 2500 can include some or all of the same or substantially the same features, aspects, and/or components as the resection guide 2020. Accordingly, the resection guide 2520 can or may include one or more resection features 2522 (e.g., resection features 2522*a-c*), one or more bone attachment features 2524 (e.g., bone attachment features 2524*a-d*), one or more handles 2526 (e.g., handles 2026*a,b*), one or more bone engagement surfaces 2530, and one or more landmark registration features 2528 (e.g., landmark registration feature 2528*a,b*). Similarly, features of the resection guide 2520 (e.g., resection features 2522, bone attachment features 2524, handles 2526, landmark registration features 2528, and bone engagement surfaces 2530) may be the same, similar, or substantially similar to those of the resection guide 1920 or resection guide 2020 described above. Of course the features of the resection guide 2520 may be configured to facilitate the particular osteotomy procedure (e.g., Zadik).

In one embodiment, the resection features 2522 may be positioned and oriented such that resecting along the resection features 2522 will enable resection of a wedge shape from the bone. Advantageously, the resection features 2522 can be positioned and oriented such that the wedge enables a repositioning of parts of the bone in two or more planes (biplanar; e.g., sagittal and transverse). Of course, the resection features 2522 can also be positioned and oriented such that the resection cuts made are within a single plane, and may angle toward each other to form a wedge resection.

In addition, the resection guide 2520*a* includes a lateral side 2531, a medial side 2532, a proximal side 2533, a distal side 2534, a superior side 2535, and an inferior side 2536. Generally, the sides of the resection guide 2520 refer to the direction the sides face when the resection guide 2520 is in use. In certain embodiments, one or more of the handles

2526 can serve as both a handle used by a user to position the resection guide 2520*b* and/or as a landmark registration feature 2528. The landmark registration feature 2528 can provide the same features, advantages, and/or benefits as the landmark registration feature 2041 described herein.

FIGS. 28A-28D illustrate views of a resection guide 2520*a* of an osteotomy system, according to another embodiment. The resection guide 2520*a* may be similar to the resection guide 2520*b* described above, except that the resection guide 2520*a* may include differences in the resection features 2522. For example, FIG. 28A illustrates that the resection feature 2522*a* and resection features 2522*b* may not include an outer wall that extends as far as the outer wall of the resection guide 2520*b*.

Figure 29A:
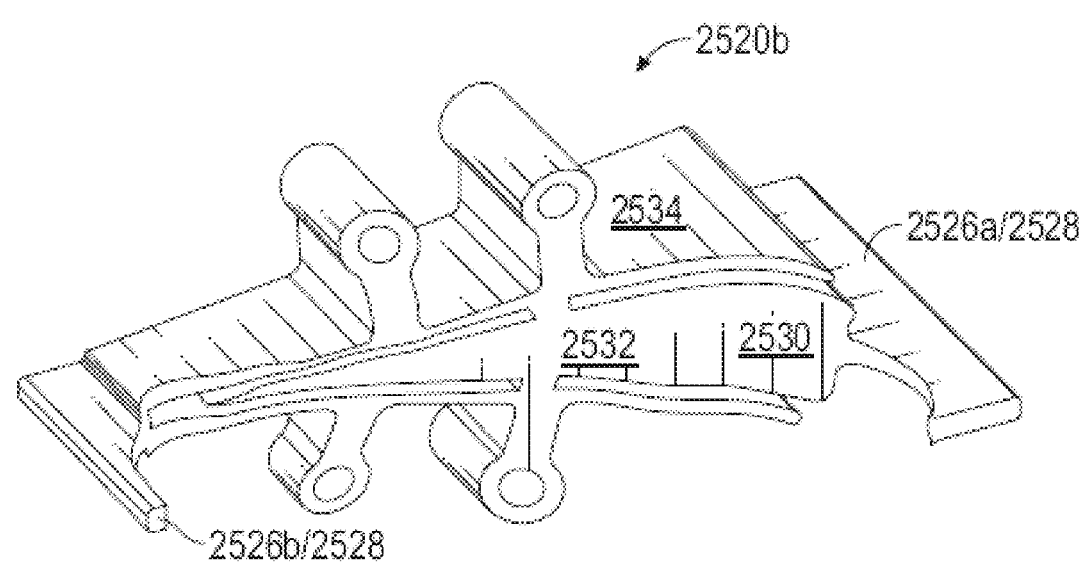
FIGS. 29A-29B illustrate views of the resection guide of FIGS. 27A-27D, according to another embodiment.
Figure 29B:
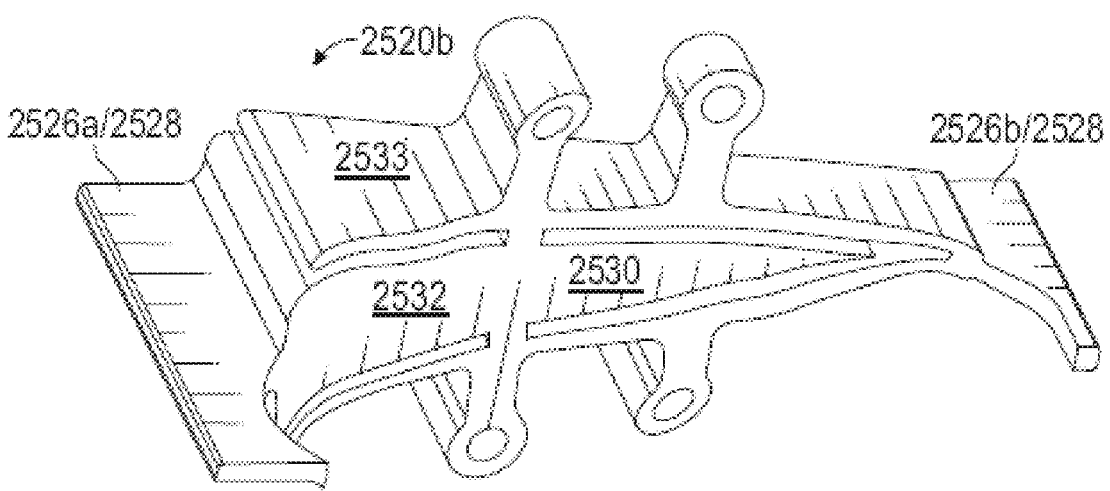

FIGS. 29A-29B illustrate views of the resection guide of FIGS. 27A-27D, according to another embodiment. These figures illustrate the medial side 2532 and the bone engagement surface 2530.

Z Osteotomy

Figure 30:
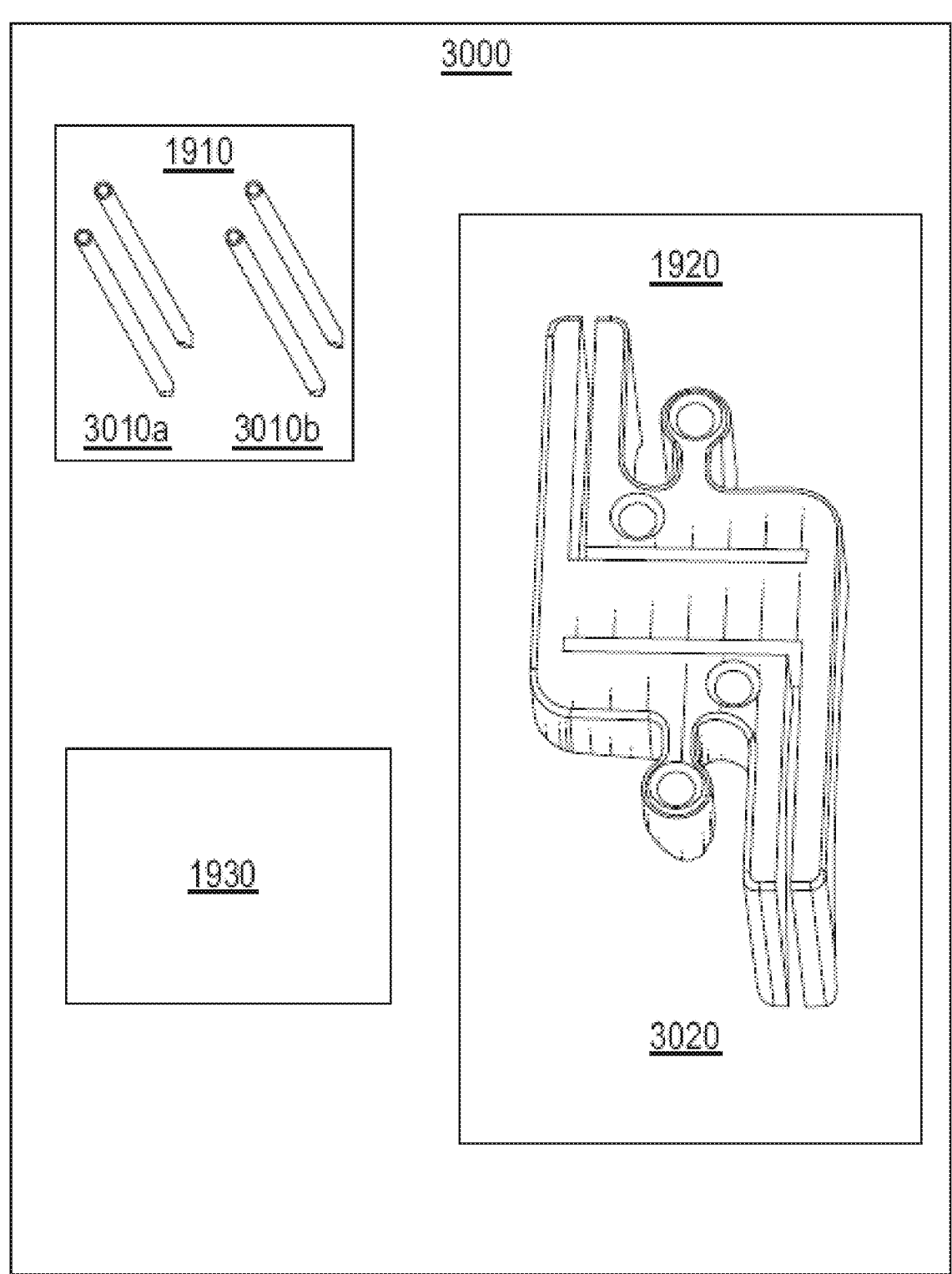
FIG. 30 illustrates an exemplary osteotomy system for a Z osteotomy, according to one embodiment.

FIG. 30 illustrates an exemplary osteotomy system 3000 for a Z osteotomy, according to one embodiment. The osteotomy system 3000 can include two or more fasteners 3010 (3010*a*, 3010*b*), a resection guide 3020, and one or more complementary components 1930. While specific embodiments of complementary components 1930 are not specifically shown here in relation to the osteotomy system 3000, those of skill in the art will appreciate that complementary components 1930 similar in feature, purpose, design, implementation, configuration, and purpose as those described in relation to the wedge osteotomy system 2000 can be used for the osteotomy system 3000. Thus, the osteotomy system 3000 can include one or more alignment guides 1940, rotation guides 1950, correction guides 1960, compression guides 1970, positioning guides 1980, fixation guides 1990, one or more pin guides 1994, and/or implants 1996.

Figure 31:
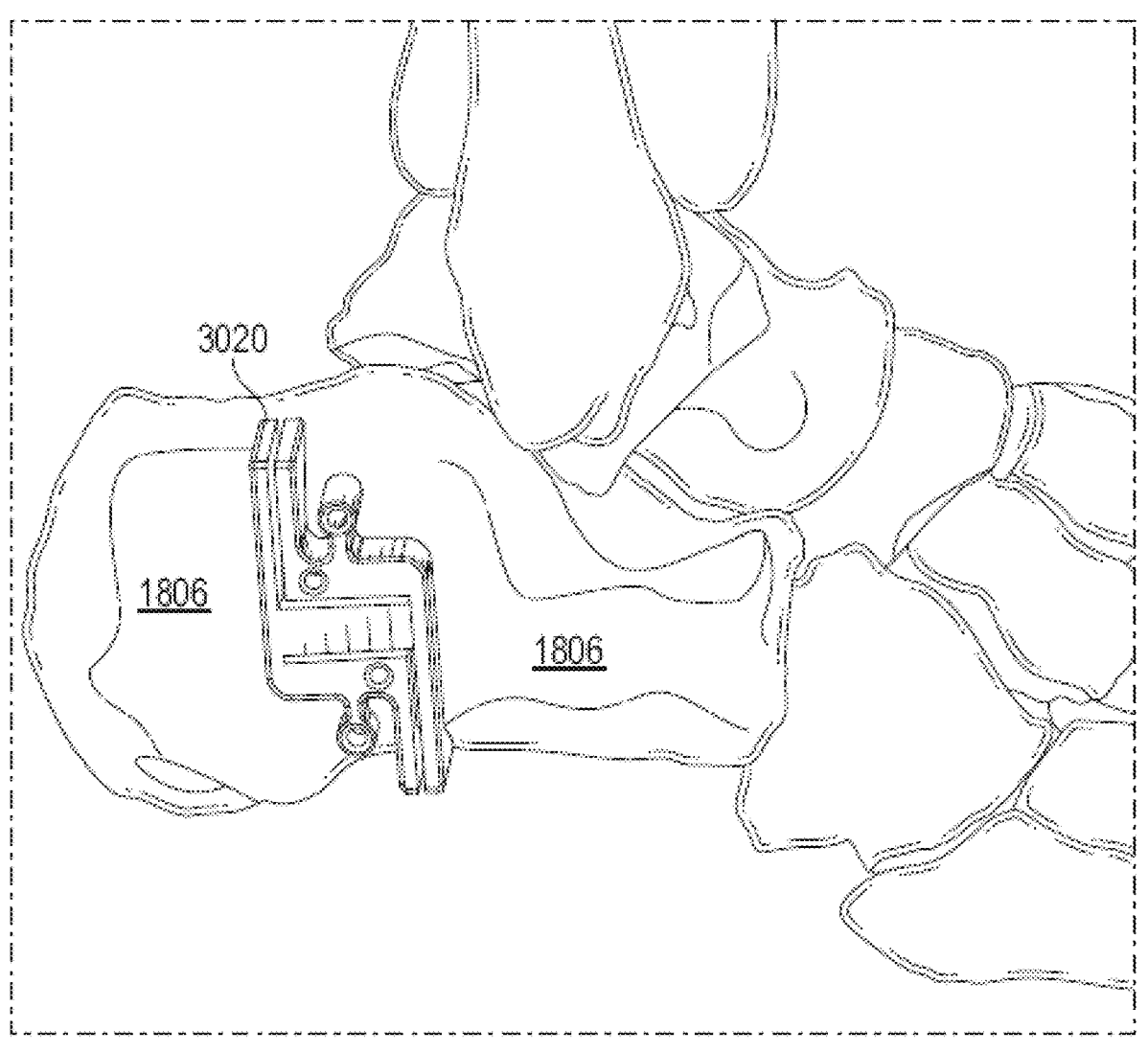
FIG. 31 illustrates a stage of performing a surgical osteotomy procedure using an osteotomy system, according to one embodiment.

FIG. 31 illustrates a stage of performing a surgical osteotomy procedure (e.g., a Z osteotomy) using the osteotomy system of FIG. 30, according to one embodiment. Typically, the preferred approach for a Z osteotomy is on the lateral side of the calcaneus 1806. FIG. 31 illustrates the resection guide 3020 positioned on the calcaneus 1806, the resection guide 3020 may be secured to the calcaneus 1806 by way of fasteners 3010.

FIGS. 32A-32F illustrate views of a resection guide of an osteotomy system, according to one embodiment. The resection guide 3020 can include some or all of the same or substantially the same features, aspects, and/or components as the resection guide 2020. Accordingly, the resection guide 3020 can or may include one or more resection features 3022 (e.g., resection features 3022*a,b*), one or more bone attachment features 3024 (e.g., bone attachment features 3024*a-d*), one or more handles 3026 (e.g., handles 3026*a,b*), one or more bone engagement surfaces 3030, and one or more landmark registration features 3028 (e.g., landmark registration feature 3028*a,b*). Similarly, features of the resection guide 3020 (e.g., resection features 3022, bone attachment features 3024, handles 3026, landmark registration features 3028, and bone engagement surfaces 3030) may be the same, similar, or substantially similar to those of the resection guide 1920, resection guide 2020, and/or resection guide 2520 described above. Of course, the features of the resection guide 3020 may be configured to facilitate the particular osteotomy procedure (e.g., Z).

In addition, the resection guide 3020 includes a lateral side 3031, a medial side 3032, a proximal side 3033, a distal side 3034, a superior side 3035, and an inferior side 3036.

Generally, the sides of the resection guide 3020 refer to the direction the sides face when the resection guide 3020 is in use. In certain embodiments, one or more of the handles 3026 can serve as both a handle used by a user to position the resection guide 3020 and/or as a landmark registration feature 3028. The landmark registration feature 3028 can provide the same features, advantages, and/or benefits as the landmark registration feature 2042 described above.

Figures 32A, 32B, 32C, 32D:
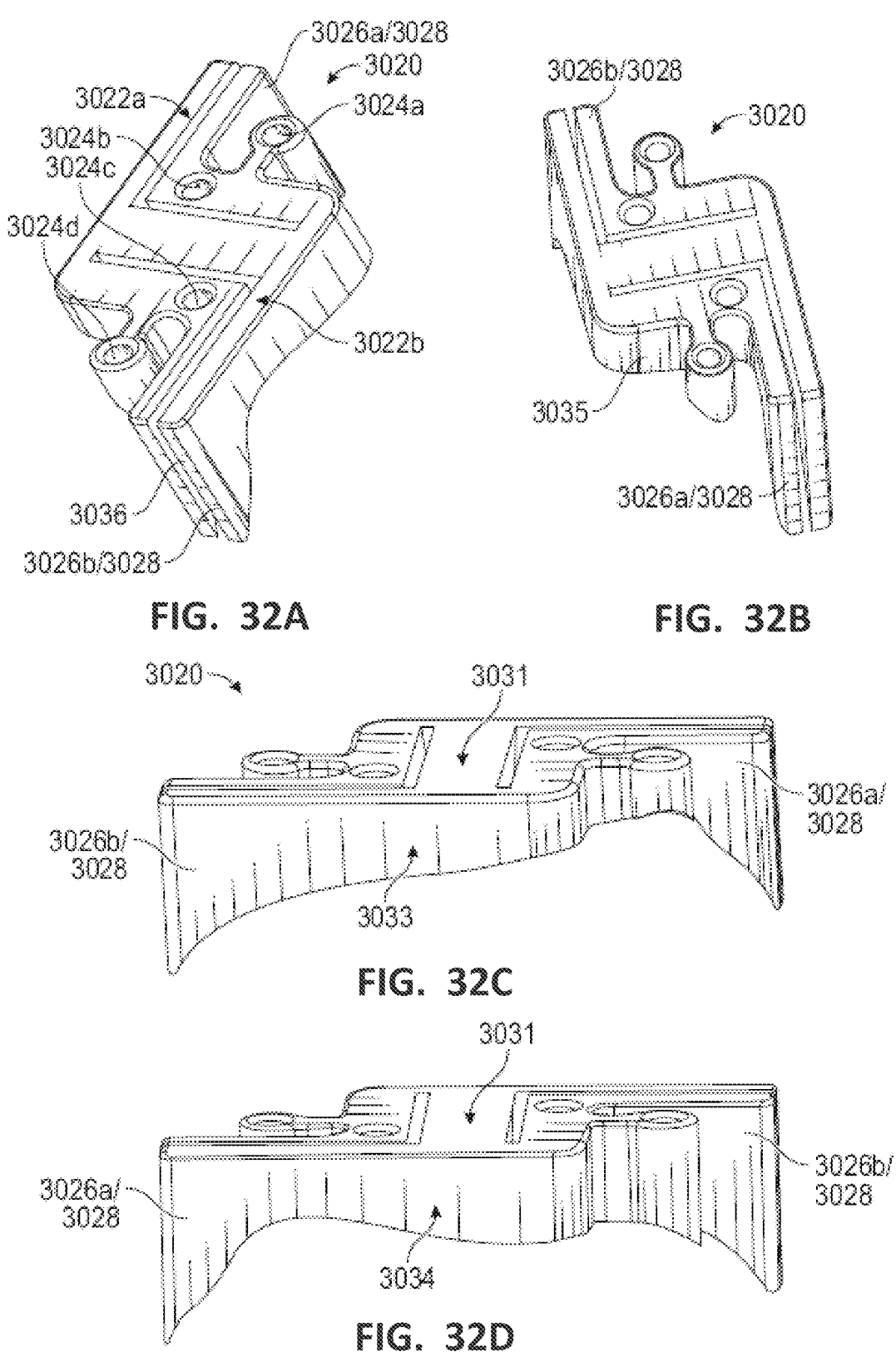
FIGS. 32A-32G illustrate views of a resection guide of an osteotomy system, according to one embodiment.
Figure 32E:
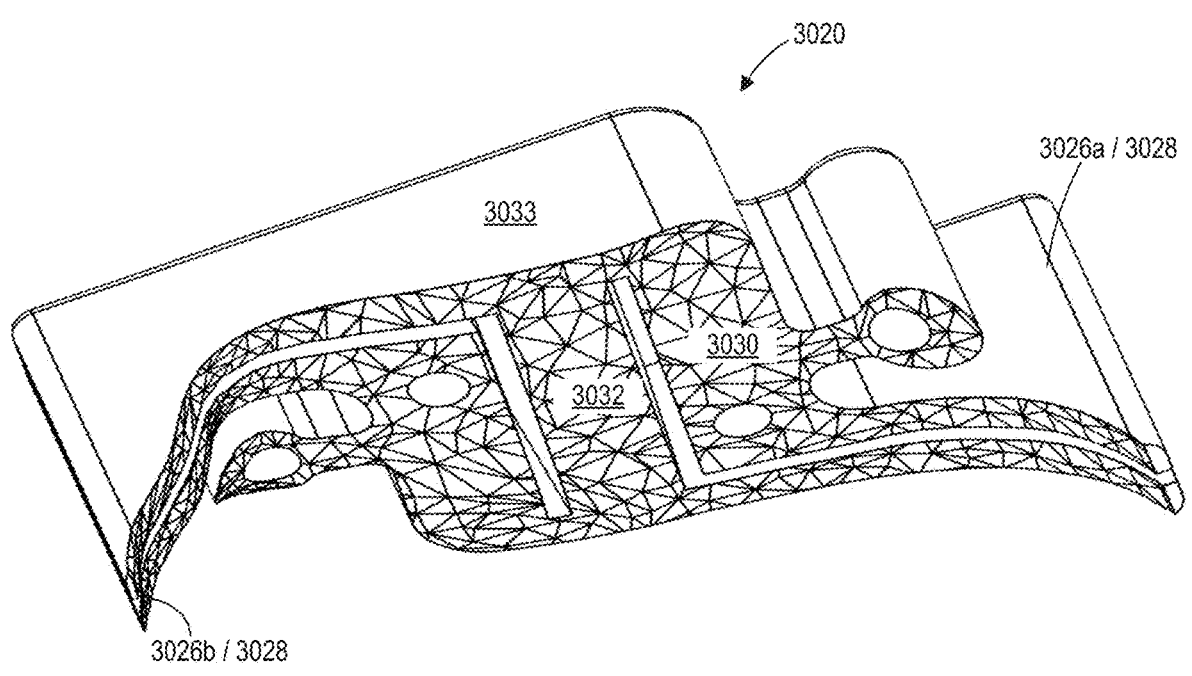
Figure 32F:
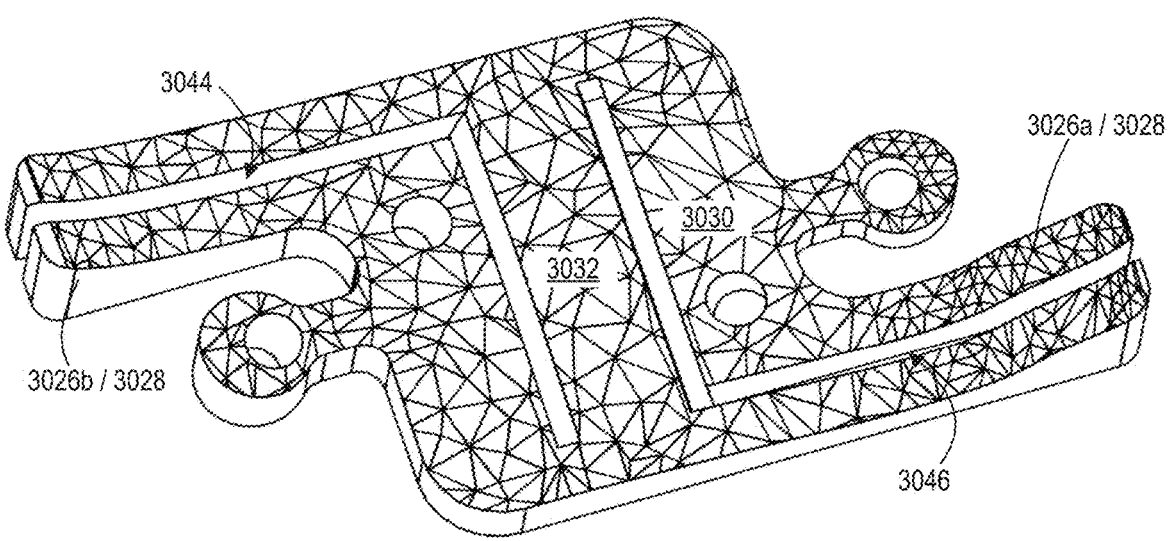

FIGS. 32E-32F illustrate views of the resection guide of FIGS. 27A-27D, according to another embodiment. These figures illustrate the medial side 3032 and the bone engagement surface 3030.

Figure 32G:
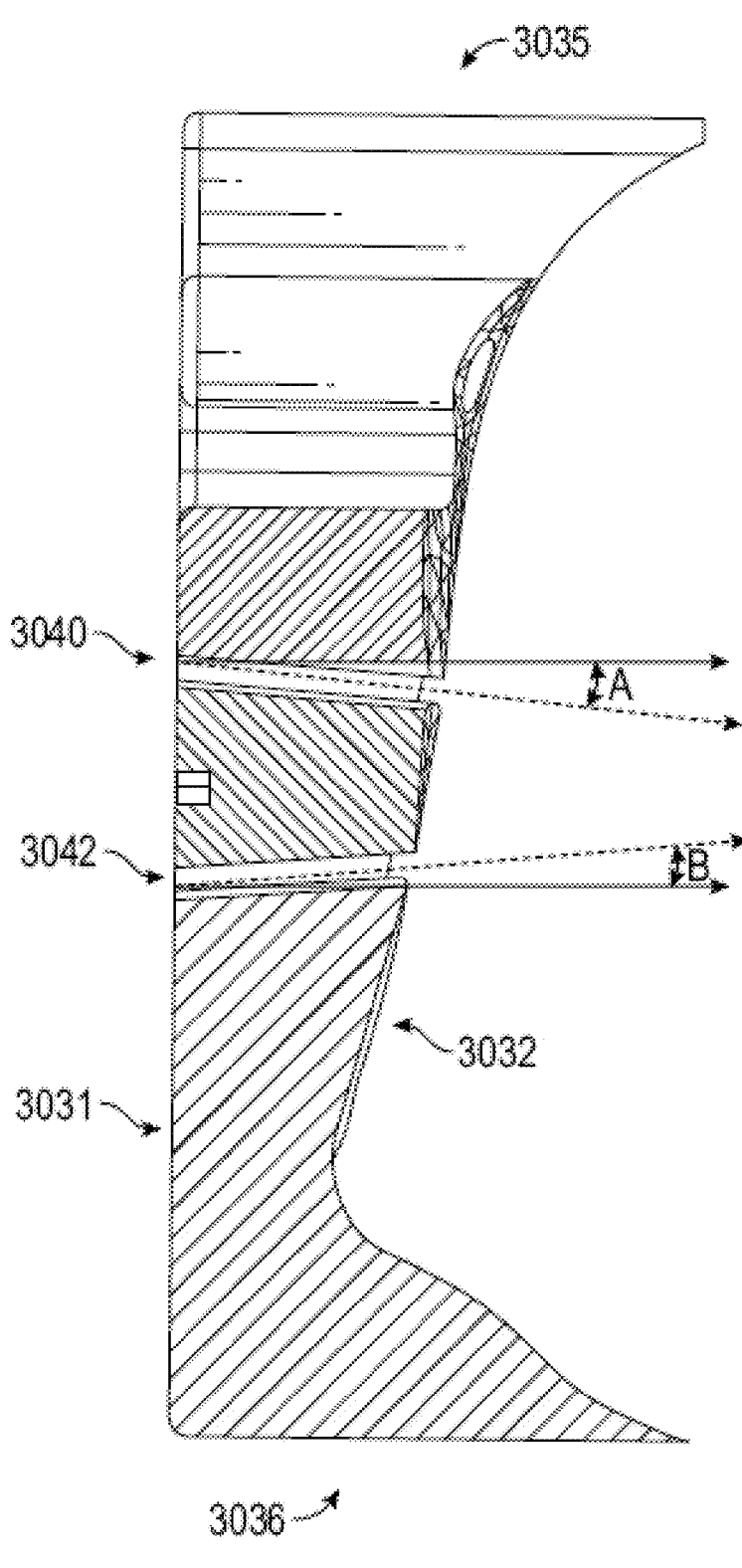

FIG. 32G illustrates a cross section view of the resection guide 3020 taken along a plane that extends from the inferior side 3036 to the superior side 3035. FIG. 32G illustrates two sections 3040, 3042 of the resection features 3022. On the lateral side 3031 the two sections 3040, 3042 may be parallel (horizontal). However, using the present disclosure the two sections 3040, 3042 can extend toward the medial side 3032 at the same or different angles. FIG. 32G illustrates one embodiment in which the dorsal section 3040 extends plantarly at an angle A and the plantar section 3042 extends dorsally at an angle B. Advantageously, using the apparatuses, methods, and systems of the present disclosure the angles for A and B can be determined preoperatively. Alternatively, or in addition, the angles can be predetermined to ensure that a resection through the dorsal section 3040 and/or plantar section 3042 will result in a wedge shape being resected. In addition, the wedge shape can be predefined to not extend to the medial cortex of the bone. In this manner, two parts of the bone can remain connected and that connection can be leveraged for subsequent steps in a surgical procedure.

Referring to FIG. 32F, those of skill in the art will appreciate that other sections 3044, 3046 (e.g., sections that run vertically when the resection guide 3020 is used) may also extend at one or more angles to guide resection of the bone along a desired path through the bone. The proximal section 3044 can be angled such that resection using the resection features 3022 resects in a single plane or in multiple planes. Similarly, The distal section 3046 can be angled such that resection using the resection features 3022 resects in a single plane or in multiple planes. Advantageously, the angles for the resection features 3022 can be patient-specific and/or can be predefined and included in multiple versions of the resection guide 3020 available in a kit for a surgeon to use.

Akin Osteotomy

Following Lapidus surgery, surgeons and/or patients may feel that the distal portion of the big toe is not straight and normal looking. Therefore, surgeons may recommend an Akin osteotomy in which a medial to lateral closing wedge osteotomy is performed to straighten the toe (e.g., the proximal and distal phalanx). It is advantageous when performing an Akin osteotomy to not cut completely through to the far cortex of the bone, but instead to leave a portion of bone at the far cortex to allow the closing distal portion of bone to pivot around the resected wedge of bone. Should the remaining bone portion at the far cortex be too thick, then during closure, the bone bridge (e.g., remaining bone portion) could fracture resulting on the proximal phalanx becoming two separate pieces. Should the remaining bone portion at the far cortex be too thin, the two bone portions could break also resulting in two separate pieces. Having two separate pieces makes for greater challenges during fixation as the bone parts are now floating (free to move) relative to each other.

The present disclosure relates to a resection guide 3320 for use in an Akin osteotomy in which a wedge angle for the closing wedge is defined by the amount of correction needed to bring the two into proper alignment and wherein the specific apex of the triangle for the two saw blade channels terminates at a position (e.g., vertex) relative to the far cortex of the proximal phalanx to optimize closure of the osteotomy while avoiding total fracture or resection (separation) of the two bone fragments. Advantageously, the angles for the closing wedge are patient-specific and are designed preoperatively and achieved using a resection guide 3320 built for a particular procedure and use on a particular patient.

Figure 33:
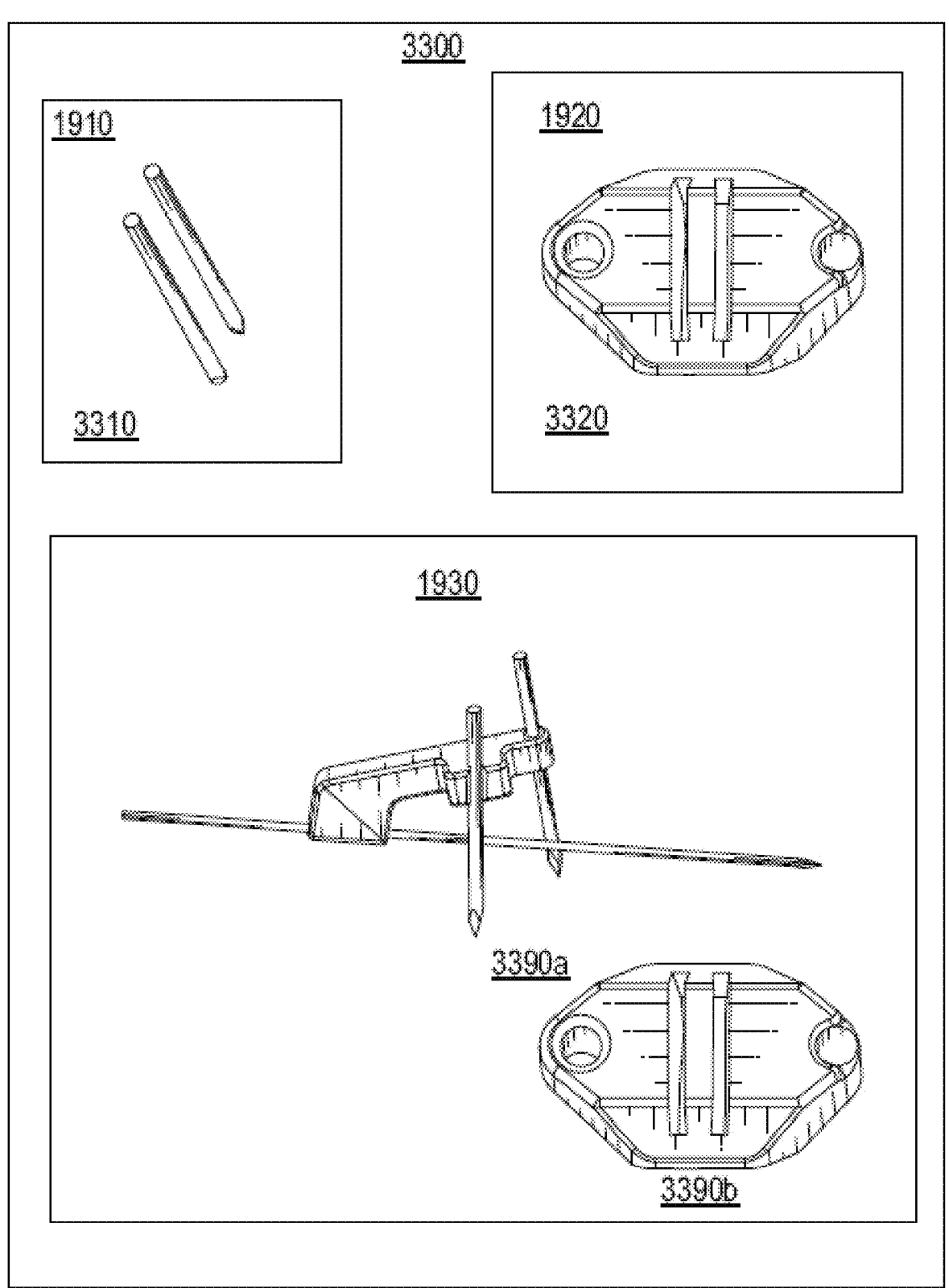
FIG. 33 illustrates an exemplary osteotomy system for an Akin osteotomy, according to one embodiment.
Figures 34A, 34B, 34C, 34D, 34E:
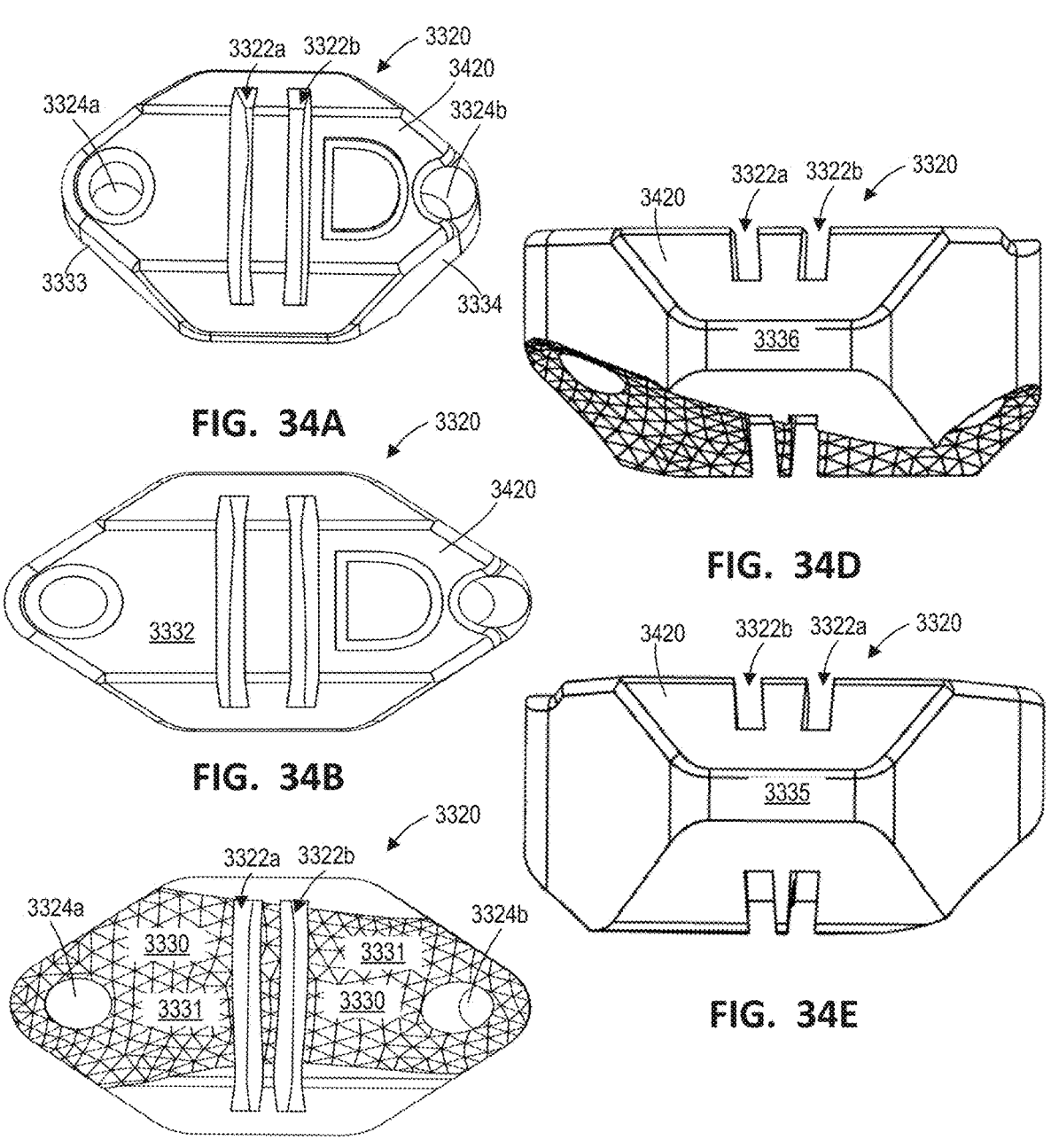
FIGS. 34A-34E illustrate views of a resection guide of an osteotomy system, according to one embodiment.

FIG. 33 illustrates an exemplary osteotomy system 3300 for an Akin osteotomy, according to one embodiment. The osteotomy system 3300 can include at least one fastener 3310 and a resection guide 3320. The fastener 3310 can be configured to engage a phalanx of a patient's foot. In another embodiment, the osteotomy system 3300 can include a resection guide 3320 and one or more complementary components 1930. Those of skill in the art will appreciate that complementary components 1930 similar in feature, purpose, design, implementation, configuration, and purpose as those described in relation to the wedge osteotomy system 2000 can be used for the osteotomy system 3300. Thus, the osteotomy system 3300 can include one or more alignment guides 1940, rotation guides 1950, correction guides 1960, compression guides 1970, positioning guides 1980, fixation guides 1990, one or more pin guides 1994, and/or implants 1996.

In the illustrated embodiment, the osteotomy system 3300 includes complementary components 1930 such as a fixation guide 3390. In certain embodiments, the osteotomy system 3300 includes two different kinds of fixation guides 3390. Fixation guide 3390a may serve to enable temporary fixation during the osteotomy procedure and the fixation guide 3390b may serve to enable permanent fixation. The fixation guide 3390a may facilitate fixation using a compression screw by guiding placement of a K-wire that is then used to deploy a cannulated compression screw. In one embodiment, the fixation guide 3390a may be referred to as a targeting jig. Of course, the fixation guide 3390a may be integrated with the resection guide 3320. The fixation guide 3390b may be an example of a fixation guide 3390 integrated with a resection guide 3320. The fixation guide 3390b may facilitate fixation using a bone staple, or other fastener, by providing pilot holes for staple legs that can be used to deploy a bone staple.

FIGS. 34A-34F illustrate views of a resection guide of an osteotomy system, according to one embodiment. The resection guide 3320 can include some, or all, of the same, or substantially the same, features, aspects, and/or components as the resection guide 2020. Accordingly, the resection guide 3320 can, or may, include one or more resection features 3322 (e.g., resection features 3322a-b), one or more bone attachment features 3324 (e.g., bone attachment features 3324a-b), one or more handles, one or more landmark registration features, one or more bone engagement surfaces 3330, or the like. Similarly, features of the resection guide 3320 (e.g., resection features 3322, bone attachment features 3324, and bone engagement surfaces 3330) may be the same, similar, or substantially similar to those of the resection guide 1920 or resection guide 2020 described herein. Of course, the features of the resection guide 3320 may be configured to facilitate the particular osteotomy procedure (e.g., Akin).

In addition, the resection guide 3320 includes a body 3420 having a lateral side 3331, a medial side 3332, a posterior side 3333, an anterior side 3334, a dorsal side 3335, and a plantar side 3336. Generally, the sides of the resection guide 3320 refer to the direction the sides face when the resection guide 3320 is in use. In certain embodiments, the resection guide 3320 may include an indicator 3338 that identifies for a user which side (proximal/posterior or distal/anterior) is the anterior side 3334. In the illustrated embodiment, the indicator 3338 may be a large letter "D" on the medial side 3332 to indicate a dorsal end of the resection guide 3320.

In one embodiment, the resection guide 3320 includes a posterior resection feature 3322a, an anterior resection feature 3322b, a first bone attachment feature 3324a, and a second bone attachment feature 3324b. The posterior resection feature 3322a is configured to guide a cutting tool to form a first osteotomy in a phalanx that follows a first trajectory. The first trajectory for first osteotomy can be determined, at least in part, based on a bone model or a portion of a bone model of the phalanx based, at least in part, on medical imaging of the patient's foot. The bone model may be configured to significantly resemble and/or match the anatomy of the patient's foot. The first trajectory and/or first osteotomy may be created, identified, and/or used in a similar manner to the first trajectory 2042 and/or the first osteotomy 2046. The anterior resection feature 3322b is configured to guide a cutting tool to form a second osteotomy in the phalanx that follows a second trajectory. The second trajectory for second osteotomy can be determined, at least in part, based on the bone model. The second trajectory and/or second osteotomy may be created, identified, and/or used in a similar manner to the second trajectory 2044 and/or the second osteotomy 2048.

In one embodiment, the resection guide 3320 can include a single bone attachment feature 3324. Alternatively, or in addition, the resection guide 3320 may include a first bone attachment feature 3324a and a second bone attachment feature 3324b. The one or more bone attachment features 3324 serve to secure the resection guide 3320 to a bone such as a phalanx of a patient. In certain embodiments, the one or more bone attachment features 3324 can be embodied as a hole in the body 3420 and a fastener (e.g., a K-wire).

Figure 35A:
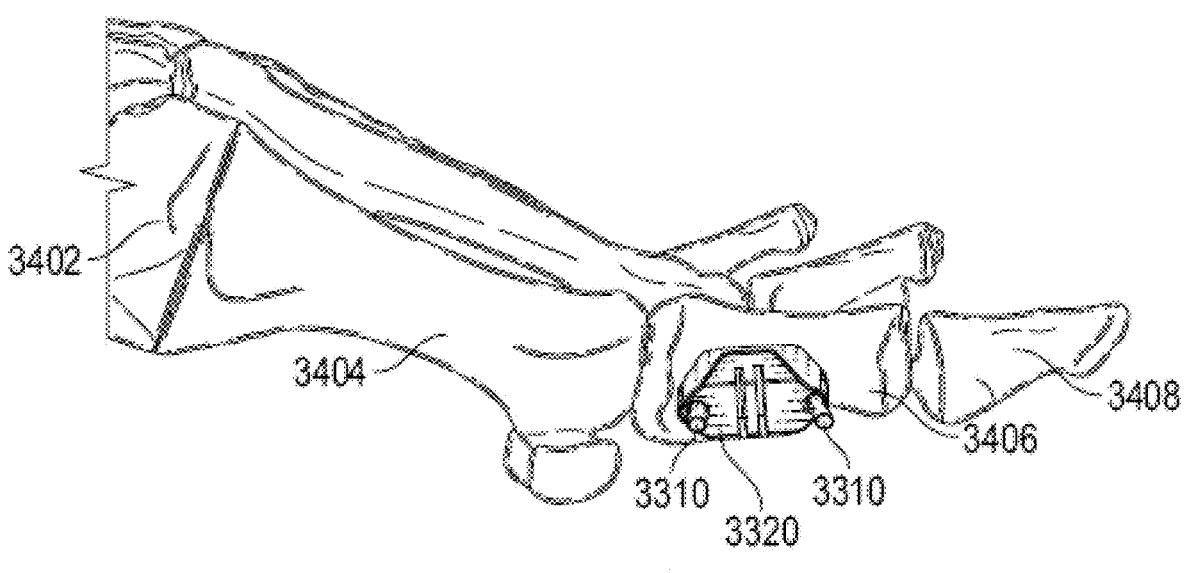
FIGS. 35A-35F illustrates different stages of performing a surgical osteotomy procedure using an osteotomy system, according to one embodiment.
Figure 35B:
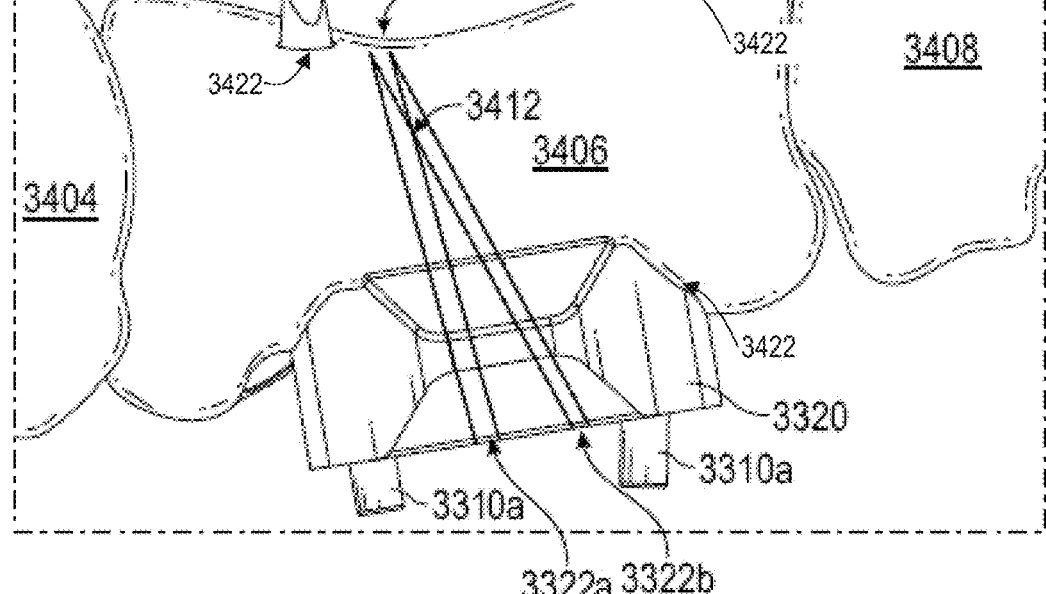
Figure 35C:
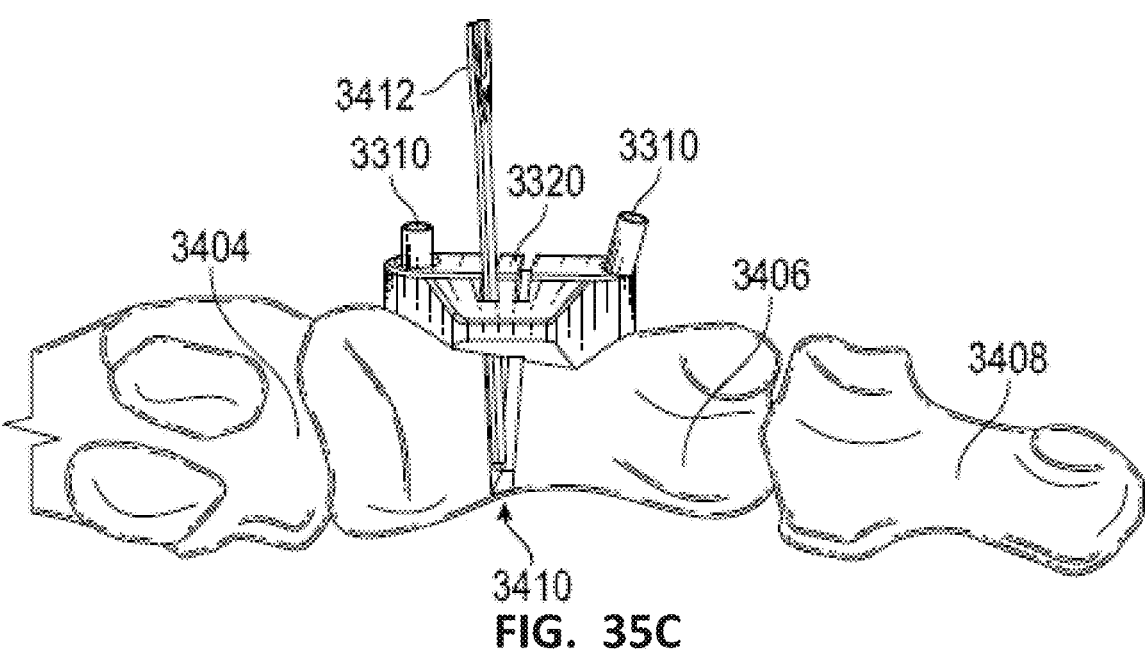

FIGS. 35A-35C illustrate different stages of performing a surgical osteotomy procedure (e.g., an Akin osteotomy) using an osteotomy system, according to one embodiment. FIGS. 35A-35B illustrate a medial cuneiform bone 3402, first metatarsal bone 3404, first proximal phalanx 3406, first distal phalanx 3408, and other bones of a foot. Typically, the preferred approach for an Akin osteotomy is on the medial side of the proximal phalanx (e.g., first proximal phalanx 3406). FIG. 35A illustrates the resection guide 3320 secured to the proximal phalanx by way of fasteners 3310.

FIG. 35B illustrates a dorsal view of the resection guide 3320 secured to the first proximal phalanx 3406. The resection guide 3320 includes resection features 3322a,b (e.g. cut channels). The cut channels are designed to create an angled cut in the bone to address a patient deformity (e.g., provide an anatomical correction) The channels may converge to form an apex 3412 of a resection wedge. The apex 3412 may be proximal to a far cortex of the bone, but not be at the far cortex of the bone.

In one embodiment, one or the other or both of the first bone attachment feature 3324a and/or the second bone attachment feature 3324b can be designed together with a bone model of the bone of the patient (e.g., a phalanx). The bone attachment features 3324 can be specifically configured to include a hole for a fastener that enters a bone of a patient to a depth, at an orientation, and/or having a diameter such that the hole formed by the fastener can be utilized for subsequent fixation of an osteotomy formed using the resection guide 3320. Advantageously, the fasteners 3310 can be positioned, oriented, and configured to be directed by way of the resection guide 3320 such that upon closure of an osteotomy, holes formed by removal of the fasteners 3310 create a guide hole 3422, or a pilot hole 3422. The guide hole and/or pilot hole can, upon closure, accept a fastener. The fastener may be a temporary fastener or a permanent fastener such as bone screw and/or a bone staple. In one embodiment, the fastener is suitable for spanning the osteotomy.

In certain embodiments, fasteners 3310 can be configured to facilitate resection using the resection features 3322. For example, the bone attachment features 3324 can be configured such that fastener 3310a enters at substantially the same angle as the posterior resection feature 3322a. In addition, fastener 3310b may be shorter such that the fastener 3310b does not interfere with resection using the anterior resection feature 3322b. Alternatively, or in addition, the bone attachment feature 3324 that receives the fastener 3310b can be angled to extend at substantially the same angle as the anterior resection feature 3322b.

FIG. 35C is a plantar view of the bones and resection guide 3320. FIG. 35C illustrates a closer view of the stage in the surgical osteotomy procedure (e.g., an Akin osteotomy) of FIG. 35A with the resection guide 3320 secured and positioned on the first proximal phalanx 3406. FIG. 35C illustrates a stage in the surgical osteotomy procedure (e.g., an Akin osteotomy) in which a wedge resection has been performed. Fasteners 3310 serve to engage the proximal and distal parts of the first proximal phalanx 3406 after the resection and/or for subsequent repositioning of the proximal and distal parts of the first proximal phalanx 3406. FIG. 35B illustrates a cutting tool such as an oscillating saw 3414 inserted into one of the resection features 3322.

Cutting a wedge shape for an Akin procedure while leaving a desired amount of bone (cortical bone) on the opposite side can be a challenge to do without the solutions of the present disclosure. Advantageously, the resection features 3322 of the resection guide 3320 are configured to make this resection straightforward once the resection guide 3320 is positioned on the bone in the desired location. The bone engagement surface 3330 facilitates proper placement of the resection guide 3320.

Note that FIG. 35C illustrates a wedge cut that does not extend to the opposite side of the bone, instead approximately a 1-3 mm section, portion 3410, of bone may be left on the other side (lateral side) of the bone. This section 3410 can facilitate handling of the parts of the first proximal phalanx 3406 during the surgical osteotomy procedure (e.g., an Akin osteotomy). In certain embodiments, the remaining portion 3410 can be used as a living hinge to keep the two parts of the bone together during a fixation step or during one or more steps of the surgical osteotomy procedure. Advantageously, using the methods of this disclosure one can define how thick to make the section 3410 as well as what angles to cut in the bone for the wedge.

Figure 35D:
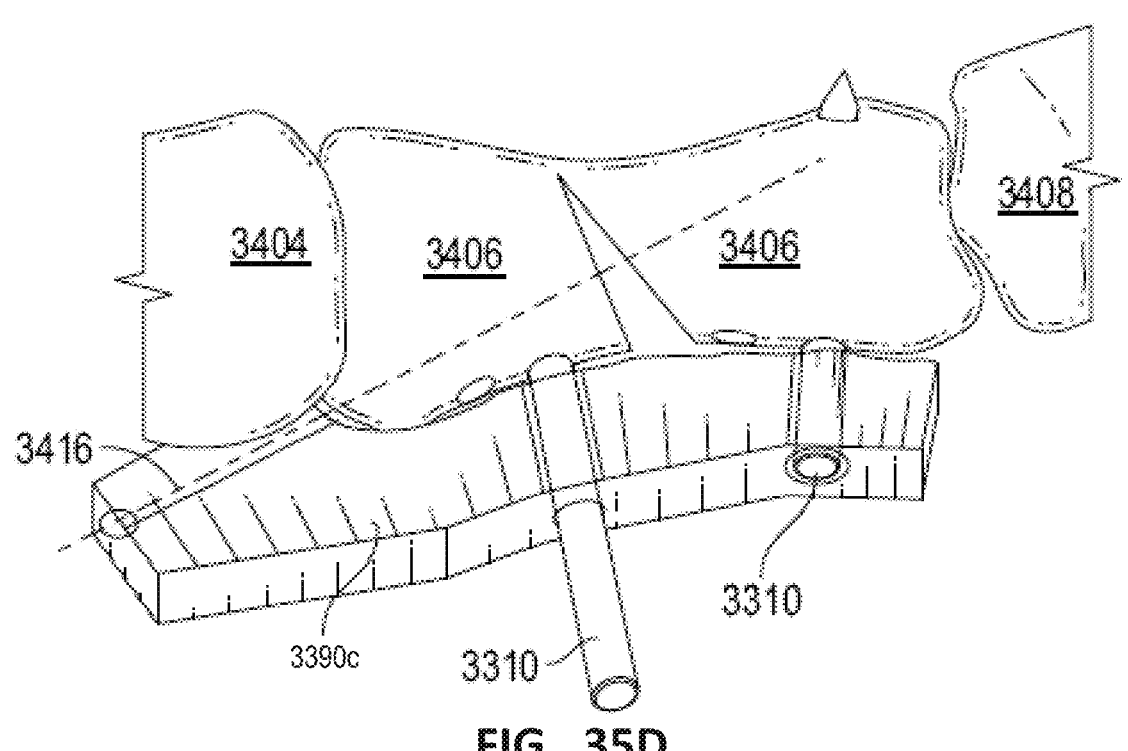

FIG. 35D illustrates a dorsal view of a first proximal phalanx 3406 after the resection cuts are made. FIG. 35D illustrates how one embodiment of a fixation guide 3390c can use the same fasteners 3310 used to form the osteotomy to position a fixation guide 3390 for deploying a K-wire that can be used to deploy a cannulated compression screw. The fixation guide 3390 is positioned for deployment of a K-wire along line 3416.

Figure 35E:
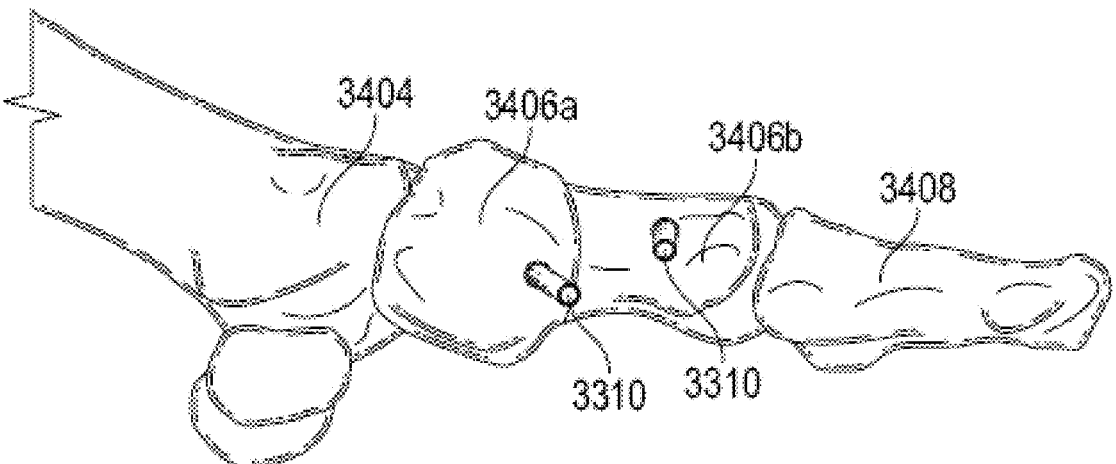

FIG. 35E illustrates the first proximal phalanx 3406 after one embodiment of a resection guide 3320 is removed and the osteotomy is closed. In the illustrated embodiment, the osteotomy may be an oblique osteotomy preplanned by a surgeon to assist in providing a correction. Note that the bone attachment features 3324 and/or resection features 3322 can be configured in the resection guide 3320 such that once the resection guide 3320 is removed the fasteners 3310 can be used to align, reorient, and/or correct positioning of the proximal part 3406*a* relative to the distal part 3406*b* of the first proximal phalanx 3406. Advantageously, each of the aspects and/or attributes of a resection guide 3320 and/or a one or more bone attachment features 3324 and/or resection features 3322 and/or position and/or orientation of fasteners 3310 can be patient-specific and/or can be predetermined before the surgical procedure.

Figure 35F:
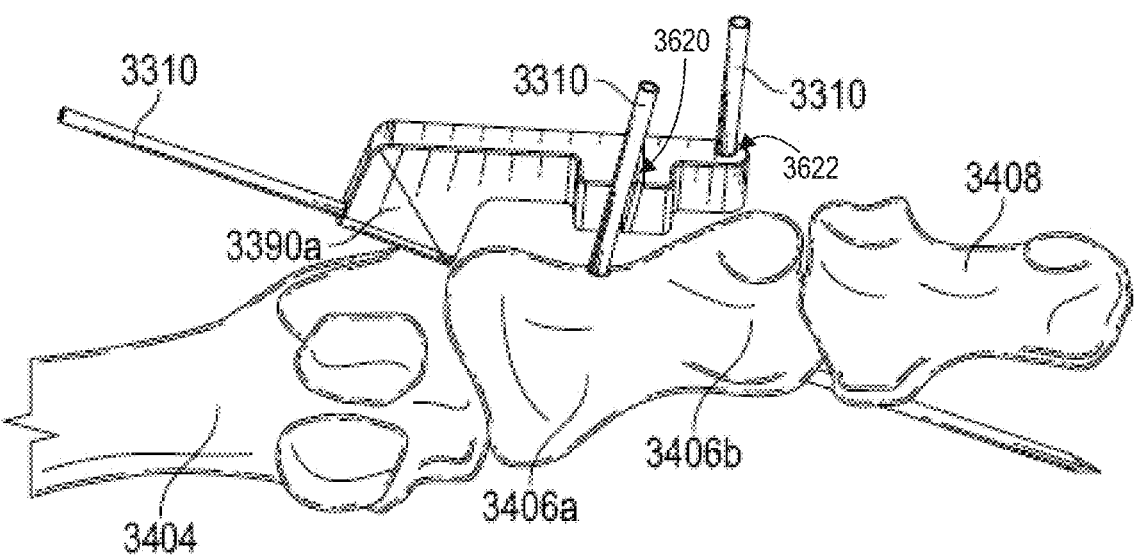
Figures 36A, 36B, 36C, 36D, 36E:
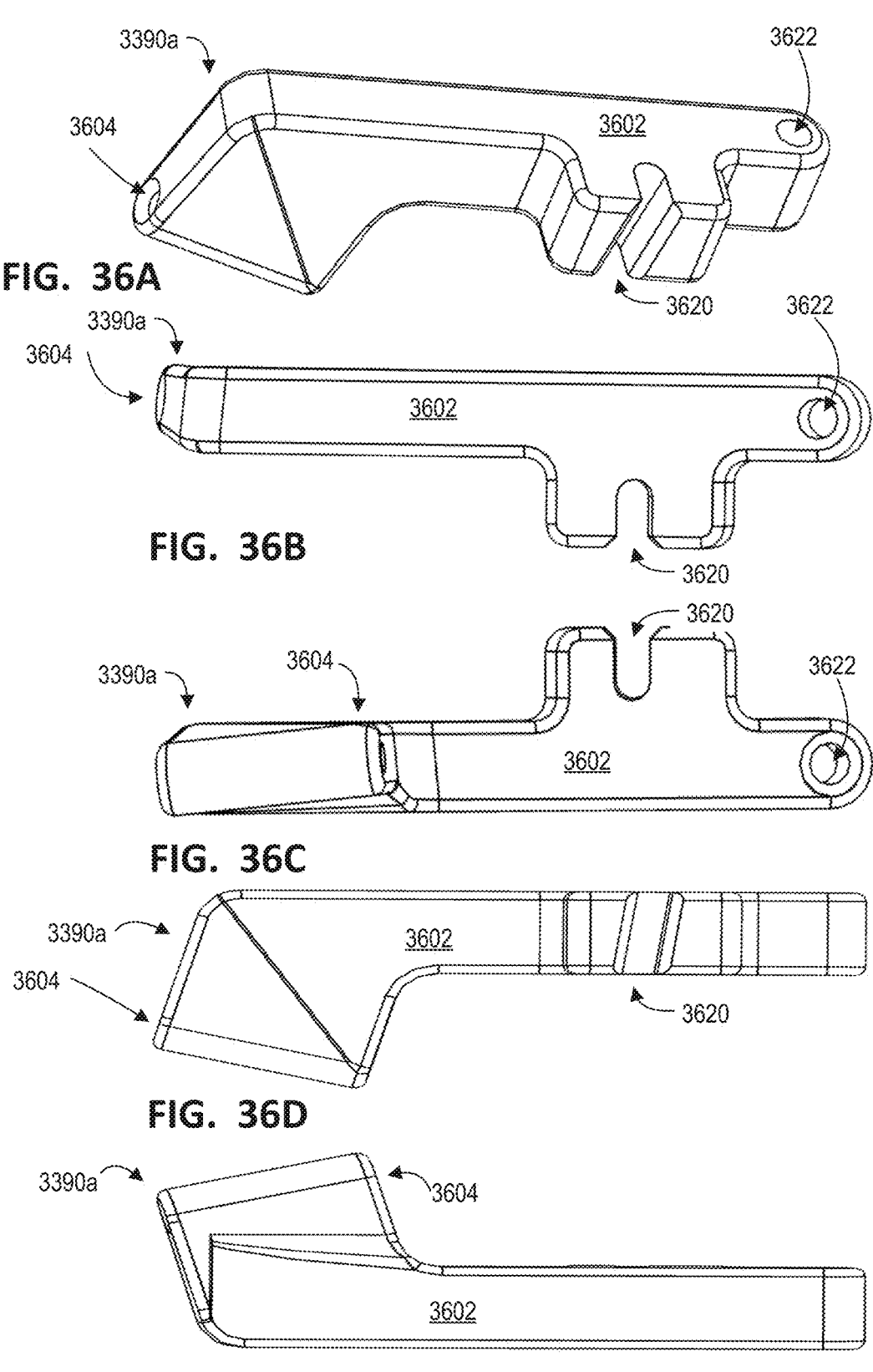
FIGS. 36A-36E illustrate views of a fixation guide of an osteotomy system, according to one embodiment.

FIG. 35F illustrates the first proximal phalanx 3406 after a resection guide 3320, such as the example of FIG. 35E, is removed, the osteotomy is closed, and a fixation guide 3390*a* is deployed. In the illustrated embodiment of FIG. 35F, the osteotomy may be an oblique osteotomy. The fixation guide 3390*a* can be used to direct or guide a temporary fastener 3310 that can hold a proximal part 3406*a* in contact with a distal part 3406*b* until permanent fixation is deployed. The fixation guide 3390 may include positioning features (such as holes or openings in a body of the fixation guide 3390). These positioning feature may engage fasteners 3310 originally deployed with the resection guide 3320. The positioning features can ensure that a fixation guide 3390*a* guides a fastener 3310 in a desired orientation.

In certain embodiments, the positioning feature 3620, 3622 may include additional aides to ensure a surgeon has properly positioned the fixation guide 3390*a*. For example, in one embodiment, the positioning feature 3620 may include tabs or nubs configured to pliably deform as a fastener 3310 is slid into the positioning feature 3620. Once the fastener 3310 slides past the tabs or nubs into the positioning feature 3620, an audible snap or click may be produced and/or a tactile feedback snap may signal to a surgeon that the fastener 3310 is properly positioned in the positioning feature 3620. Alternatively, or in addition, the positioning feature 3620 may be shaped such that at an open end the opening is smaller than an interior part of the opening. With such a shape, the smaller opening can provide interference as a fastener 3310 is pressed into the positioning feature 3620. With added pressure, the fastener 3310 may then "pop" into the wider part of the opening of the positioning feature 3620 to seat the fastener 3310 so that the fixation guide 3390*a* is "locked" into position relative to the two fasteners 3310.

Alternatively, or in addition, the resection guide 3320 may also function as a fixation guide 3390, fixation guide 3390*b*. For example, holes for the bone attachment features 3324 of the resection guide 3320 may be angled and positioned such at once the fasteners 3310 are removed, the holes in the bone can serve as openings for deployment of a permanent fastener such as a bone staple and/or bone screws of a bone plate. In such an embodiment, the fixation guide 3390*b* serves both as a resection guide 3320 and as a fixation guide 3390.

FIGS. 36A-36E illustrate views of fixation guide 3390*a* of an osteotomy system, according to one embodiment. The fixation guide 3390*a* may include a body 3602, an alignment guide 3604, and one or more of a positioning feature 3620 and/or a positioning feature 3622. The fixation guide 3390*a* also includes a lateral side, a medial side, a proximal side, a distal side, a superior side, and an inferior side.

In certain embodiments, the size, shape, and configuration of the fixation guide 3390*a* may be patient-specific and/or may be designed preoperatively to guide placement of a fastener 3310 during an Akin procedure. In such embodiments, the size, position, angle and/or orientation of the alignment guide 3604 may be such that a fastener 3310 guided by the alignment guide 3604 will engage both the proximal part 3406*a* and the distal part 3406*b* of the first proximal phalanx 3406. In certain embodiments, the alignment guide 3604 is a hole in the body 3602.

A surgeon may engage the positioning feature 3620 with a fastener 3310 (e.g., a proximal fastener) and the positioning feature 3622 with a fastener 3310 (e.g., a distal fastener) in such an engagement, the body 3602 is configured to position the alignment guide 3604 for a desired entry point for a fastener 3310. A surgeon may then deploy the fastener 3310 through the proximal part 3406*a* and the distal part 3406*b* of the first proximal phalanx 3406 and then remove the fixation guide 3390*a*. In one embodiment, the positioning feature 3620 is implemented as a hole in the body 3602. The positioning feature 3622 may also be a hole. In the illustrated embodiment, the positioning feature 3620 is implemented as an elongated opening in the body 3602.

Figures 37A, 37B:
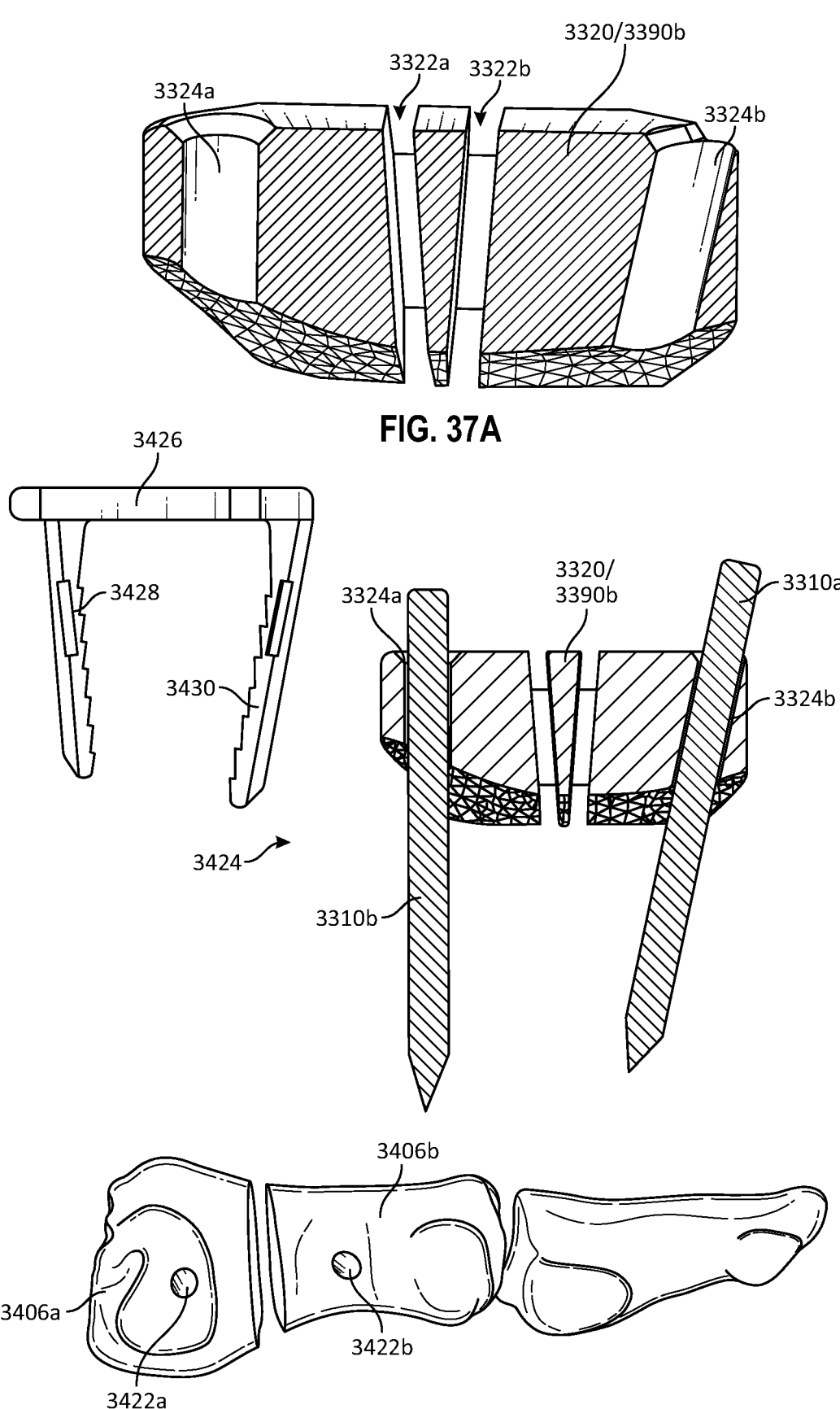
FIGS. 37A-37B illustrate views of a fixation guide of an osteotomy system, according to another embodiment.

FIGS. 37A-37B illustrate views of a fixation guide of an osteotomy system, according to another embodiment. FIG. 37A is a cross section view of the resection guide 3320 taken from a posterior side 3333 to an anterior side 3334 between the dorsal side 3335 and the plantar side 3336. Note that the bone attachment feature 3324*b* is angled. In certain embodiments, the bone attachment feature 3324*b* may be angled based on what kind of permanent fixation will be used to complete the procedure and based on where the bones will be once the bones are reoriented and/or repositioned after the osteotomy.

In the illustrated embodiment, the bone attachment feature 3324*b* may be angled such that the same hole in the bone that the fastener 3310 created while being used to secure the resection guide 3320 to the bone, may be reused together with a hole made by the bone attachment feature 3324*a*. These holes may be used for deployment of a bone stable that may permanently secure the proximal part 3406*a* to the distal part 3406*b* of the first proximal phalanx 3406 after the resection. In this manner, the resection guide 3320 can serve as both a resection guide and a fixation guide 3390*b*. FIG. 37B is a similar cross section view, with the fasteners 3310 in place to show the angles more clearly.

In one embodiment, the fasteners 3310 may be deployed parallel to cut faces that are formed when resection is done using the resection features 3322, by way of an angle of the holes in the resection guide 3320. After resection using each of the resection features 3322, the fasteners 3310 may be at an angle relative to each other (as illustrated in FIG. 37B). Next, a surgeon may remove the resection guide 3320. A surgeon may also remove a fastener 3310, such as distal fastener 3310*a*. The resection guide 3320 can then be removed. Next, the surgeon may redeploy distal fastener 3310*a* into its original hole in the bone. The distal fastener 3310*a* can then be used to position a fixation guide 3390 such as fixation guide 3390*a*. In certain embodiments, engaging the fasteners 3310 with a fixation guide 3390*a* may close a resected wedge and/or rotate the fasteners 3310 so that they are aligned with each other, which in turn moves the bones to a desired orientation. Alternatively, or in addition, closing a resected wedge may move the fasteners 3310 into alignment with each other such that using the fixation guide 3390*a* places an alignment guide 3604 in a desired position.

Following closure of an osteotomy (closing the resected wedge), the osteotomy is fixated to facilitate fusion of the bone. Two methods may be used, staples and crossing-the-cut fully threaded compression screws. For surgeons that prefer staples, the present disclosure includes two pin holes (e.g., attachment feature 3324a and attachment feature 3324b having a diameter of about 2 mm but could be any diameter). Advantageously in one embodiment, these pin holes can be positioned and/or oriented in the resection guide 3320 relative to the desired cut angle for one or more cuts in the bone (which is patient specific) such that following closure of the resected wedge, the holes in the bone left by the pins are parallel to each other and set approx. 10 mm apart (which is a common spanning distance for conventional closing wedge staples).

For example, in one embodiment, a first bone attachment feature 3324a (which may include fastener 3310b and an opening through a resection guide 3320) is configured to form a first guide hole 3422a in the phalanx. The second bone attachment feature 3324b is configured to form a second guide hole 3422b in the phalanx. Advantageously, in the illustrated embodiment, a surgeon decides to use a bone staple, such as bone staple 3424. The bone staple 3424 may include a bridge 3426 that connects a first leg 3428 and a second leg 3430.

In one embodiment, the first guide hole 3422a has a depth, diameter, and/or orientation configured to receive a first leg 3428 of the bone staple 3424. Similarly, the second guide hole 3422b has a depth, diameter, and/or orientation configured to receive a second leg 3430 of the bone staple 3424. In this manner, the holes formed for the resection guide 3320 can be reused for fixation. Minimizing the number of holes in a bone, especially, a small bone such as those in the foot of a patient can significantly improve the outcomes for the patient and/or the recovery.

Should surgeons prefer to use a crossing screw, the resection guide 3320 can include saw/cut channels configured to allow for a crossing cut compression screw. The compression screws may be cannulated. To deploy the compression screws, a K-wire may be placed across the resected section at a desired location (which may be predefined) to target a middle of the osteotomy where sufficient bone stock may exist so as to prevent bone fracture and provide the greatest bone stock for fixation. Advantageously, the present disclosure enables a surgeon to preoperatively identify a desired targeting angle for a crossing resection k-wires for installation of a compression screw. The targeting angle can be used to configure a fixation guide 3390 such as fixation guide 3390a.

FIG. 37A and FIG. 37B illustrate the idea of designing and/or fabricating a resection guide 3320 that includes one or more patient-specific aspects. In particular, the resection guide 3320 can include bone attachment features 3324 that accommodate fasteners used later in a surgical procedure. Those of skill in the art will appreciate that while this concept is explained and/or applied in relation to the example resection guide 3320, the same concept can be applied and falls within the scope of the present disclosure for other example instrumentation and/or implants including but not limited to an example resection guide 2020 such as resection guide 2020a or any other instrument described herein.

Figure 38:
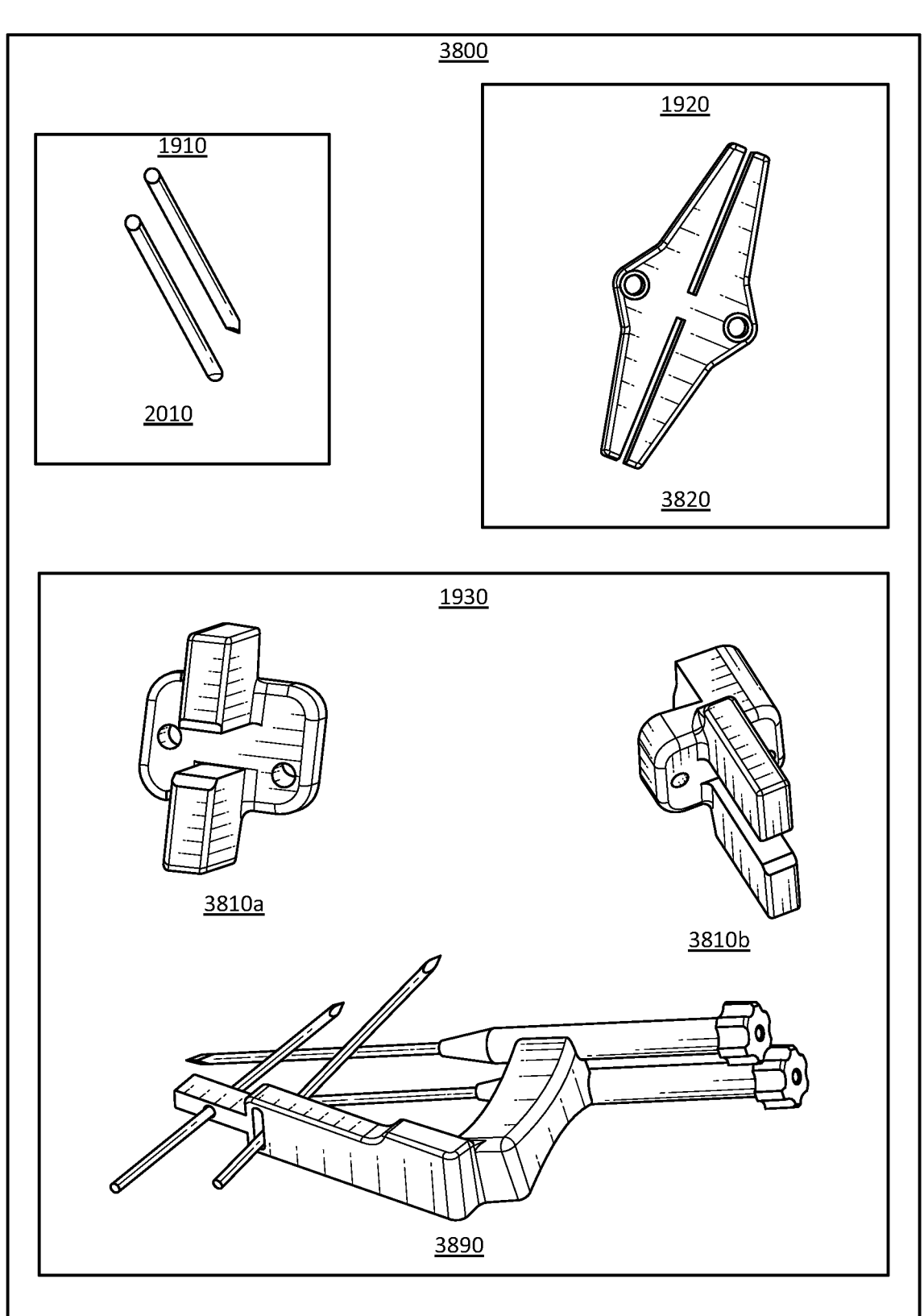
FIG. 38 illustrates an exemplary osteotomy system for an osteotomy, according to one embodiment.

FIG. 38 illustrates an exemplary osteotomy system for an osteotomy, according to one embodiment. In one embodiment, the osteotomy system 3800 is for a Koutsogiannis' osteotomy ("Kouts") surgical procedure. The osteotomy system 3800 may include fasteners 2010, a resection guide 3820, one or more positioning guides 3810, and/or a fixation guide 3890.

The osteotomy system 3800 can include some, or all, of the same, or substantially the same, features, aspects, and/or components as the other systems included in the present disclosure. Accordingly, the resection guide 3820 can, or may, include one or more resection features 3822 (e.g., resection features 3822a-b), one or more bone attachment features 3824 (e.g., bone attachment features 3824a-b), one or more handles, one or more landmark registration features, one or more bone engagement surfaces 3830, or the like. Similarly, any of the features and/or aspects of the resection guide 3820 (e.g., resection features 3822, bone attachment features 3824, and bone engagement surfaces 3830) may be patient-specific as described herein and may be based at least in part on bone models of one or more bones or portions of bones of a patient. Of course, the features of the resection guide 3820 may be configured to facilitate the particular osteotomy procedure (e.g., Kouts).

Similarly, the positioning guides 3810 (e.g., positioning guide 3810a and/or positioning guide 3810b) can, or may, include alignment features (e.g., anterior alignment feature 3804 and/or posterior alignment feature 3806), one or more offset features 3808, one or more handles 3812, one or more landmark registration features, one or more bone engagement surfaces 3814, or the like. Similarly, any of the features and/or aspects of the positioning guides 3810 (e.g., alignment features, offset features 3808, and/or bone engagement surfaces 3814) may be patient-specific as described herein and may be based, at least in part, on bone models of one or more bones or portions of bones of a patient.

Alternatively, or in addition, the fixation guide 3890 can, or may, include trajectory guide, a bone attachment feature, one or more sleeves, one or more fasteners, also referred to as guide pins, or the like. Similarly, any of the features and/or aspects of the fixation guide 3890 (e.g., trajectory guide, a bone attachment feature, one or more sleeves, etc.) may be patient-specific as described herein and may be based, at least in part, on bone models of one or more bones or portions of bones of a patient.

FIGS. 39A-39G illustrates different stages of performing a surgical osteotomy procedure (e.g., a Kouts osteotomy) using an osteotomy system of FIG. 38, according to one embodiment. Typically, a preferred approach for a Kouts osteotomy is on the lateral side of the calcaneus 1806. In the illustrated embodiment, the surgical procedure creates a single osteotomy through the calcaneus 1806. According to one embodiment, a surgeon may access a lateral surface of the calcaneus 1806. Next a surgeon may position a resection guide 3820 on the lateral surface in a position predetermined using a calcaneus model of the patient's calcaneus 1806. In certain embodiments, the step of positioning can include seating or registration of the resection guide 3820 to a surface of the calcaneus 1806 (a bone). The resection guide 3820 may be configured, for example, as one of the resection guides described herein.

Once positioned, a surgeon may deploy a first fastener 2010a into a first bone attachment feature 3824a and a second fastener 2010b into second bone attachment feature 3824b. In one embodiment, the bone attachment features 3824 are configured such that the first fastener and second fastener are parallel relative to each other. Next, a surgeon may direct a cutting tool into one or more resection features 3822. In the illustrated embodiment, the resection guide 3820 may include a first resection feature 3822a and a second resection feature 3822b.

In certain embodiments, the osteotomy system 3800 may include a guide for managing how deep a surgeon cuts into the calcaneus 1806 using the cutting tool. In one embodiment, the depth may be recommended in a preoperative plan and a surgeon may configure the cutting tool to indicate when that depth is reached. Alternatively, or in addition, the resection guide 3820 may include a stop that prevents cutting below the recommended depth. For example, the resection guide 3820 may have a height that is such that a lateral side of the resection guide 3820 may serve as a stop to prevent cutting beyond a particular depth. Alternatively, or in addition, a separate structure may be provided with the osteotomy system 3800 and/or the resection guide 3820 to serve as a stop to control cutting depth into a bone.

FIG. 39A illustrates the resection guide 3820 secured to the calcaneus 1806 by way of fasteners 2010a,b. A surgeon has created the osteotomy. The anterior bone fragment 1806a is separated from the posterior bone fragment 1806b. Advantageously, fastener 2010a engages with the anterior bone fragment 1806a and fastener 2010b engages with the posterior bone fragment 1806b. Thus, a surgeon can manipulate these bone fragments as needed. At this stage, a surgeon can remove the resection guide 3820 and the fasteners 2010 remain in the bone fragments.

Referring now to FIG. 39B, next, a surgeon may slide a positioning guide 3810 over fastener 2010a and fastener 2010b until the positioning guide 3810 contacts the anterior bone fragment 1806a and the posterior bone fragment 1806b. FIG. 39B illustrates a positioning guide 3810a seated on the calcaneus 1806.

The positioning guide 3810a may not include an offset feature 3808. Alternatively, or in addition, the positioning guide 3810a may include an offset feature 3808 in which the amount of offset is zero.

FIG. 39C illustrates a stage in the surgical osteotomy procedure. The resection guide 3820 has been removed. The fasteners 2010 remain engaged with the bone fragments of the calcaneus 1806. An alternative embodiment of a positioning guide 2300 has been deployed. In contrast to the positioning guide 3810a illustrated in FIG. 39B, FIG. 39C illustrates a surgeon's use of positioning guide 3810b. Positioning guide 3810b may include an offset feature 3808 having a non-zero amount of offset.

In the illustrated embodiment, the action of sliding positioning guides 3810 on the fasteners 2010 can cause the posterior bone fragment 1806b to translate relative to the anterior bone fragment 1806a. This movement of bone fragments can be caused by an offset feature 3808 and/or by a configuration of the anterior alignment feature 3804 and/or the posterior alignment feature 3806.

In certain embodiments, the positioning guide 3810b can include an offset feature (translation feature) that facilitates positioning the posterior bone fragment 1806b with a desired (preplanned and/or patient-specific) translation, rotation, and/or orientation relative to the anterior bone fragment 1806a. In addition, in certain embodiments, one or more of the fasteners 2010 may permit rotation of one part of the bone in relation to another part or another landmark.

In one embodiment, one or the other, or both, of the anterior alignment feature 3804 and the posterior alignment feature 3806 are configured to facilitate translation and/or rotation of one or more of the anterior bone fragment 1806a and the posterior bone fragment 1806b.

In one embodiment, The alignment features 3804 may be embodied as a hole or opening that extends from one side to the other. The angle of the hole through the alignment feature may cause a desired translation and/or rotation of a bone fragment connected to a fastener 2010. Advantageously, the angle of the hole can be a patient-specific aspect designed as part of the osteotomy system 3800 and can be based, at least in part, on a bone model of a bone of a patient.

FIG. 39C illustrates one embodiment of a positioning guide 3810b. In this embodiment, the posterior alignment feature 3806 is configured to rotate the posterior bone fragment 1806b dorsally by a predetermined and/or patient-specific angle, such as about 4 degrees. As the positioning guide 3810b slides over fastener 2010a and fastener 2010b, the posterior bone fragment 1806b slides medially and rotates dorsally.

FIG. 39D illustrates an alternative embodiment of the positioning guide 3810b in which the posterior alignment feature 3806 is configured to rotate the posterior bone fragment 1806b dorsally by a predetermined and/or patient-specific angle, such as about 8 degrees. As the positioning guide 3810b slides over fastener 2010a and fastener 2010b, the posterior bone fragment 1806b slides medially and rotates dorsally.

One challenge with osteotomies is how to maintain control over one or more bone fragments throughout the surgical procedure. Advantageously, the fastener 2010a and fastener 2010b connected or coupled to the anterior bone fragment 1806a and/or posterior bone fragment 1806b enable a surgeon to maintain control over these bone fragments. With the osteotomy completed, a surgeon can then focus on positioning and/or reorienting bone fragments to remediate a bone condition of the patient.

The positioning guides 3810 (e.g., positioning guide 3810a and/or positioning guide 3810b) are configured to engage with fastener 2010a and fastener 2010b such that the bone fragments connected to the fasteners remain connected, stable, and positioned in a desired position, until a surgeon takes steps to change the position. This stability can be very helpful to a surgeon to achieve a desired positioning and desired eventual patient outcome. In one embodiment, with the positioning guide 3810b seated and the bone fragments translated and/or rotated, a surgeon can confirm that the bone fragments are in a desired position. This may be done using medical imaging such as flouroscopy. Advantageously, the osteotomy system 3800 (e.g., positioning guide 3810b and fasteners 2010a,b) retains the bone fragments in the same position prior to, during, and after capturing imaging using flouroscopy. This can be a great help to a surgeon as their hands are free during the flouroscopy check and they are assured that the bone fragments have not moved during the flouroscopy check. The surgeon can have confidence that bone fragments are in a desired position and will maintain that position until either repositioned and/or fixation is deployed to secure the bone fragments in place. Such reliability and assurance can greatly assist a surgeon because once fixation is deployed, repositioning of the bone fragments may be very challenging and may lead to less than desirable outcomes. Therefore, a surgeon may strive to ensure that the bone fragments are in a desired position and maintain that position up until permanent fixation is deployed. The embodiments of the present disclosure provide this advantage to the surgeon.

Figures 39E, 39F, 39G:
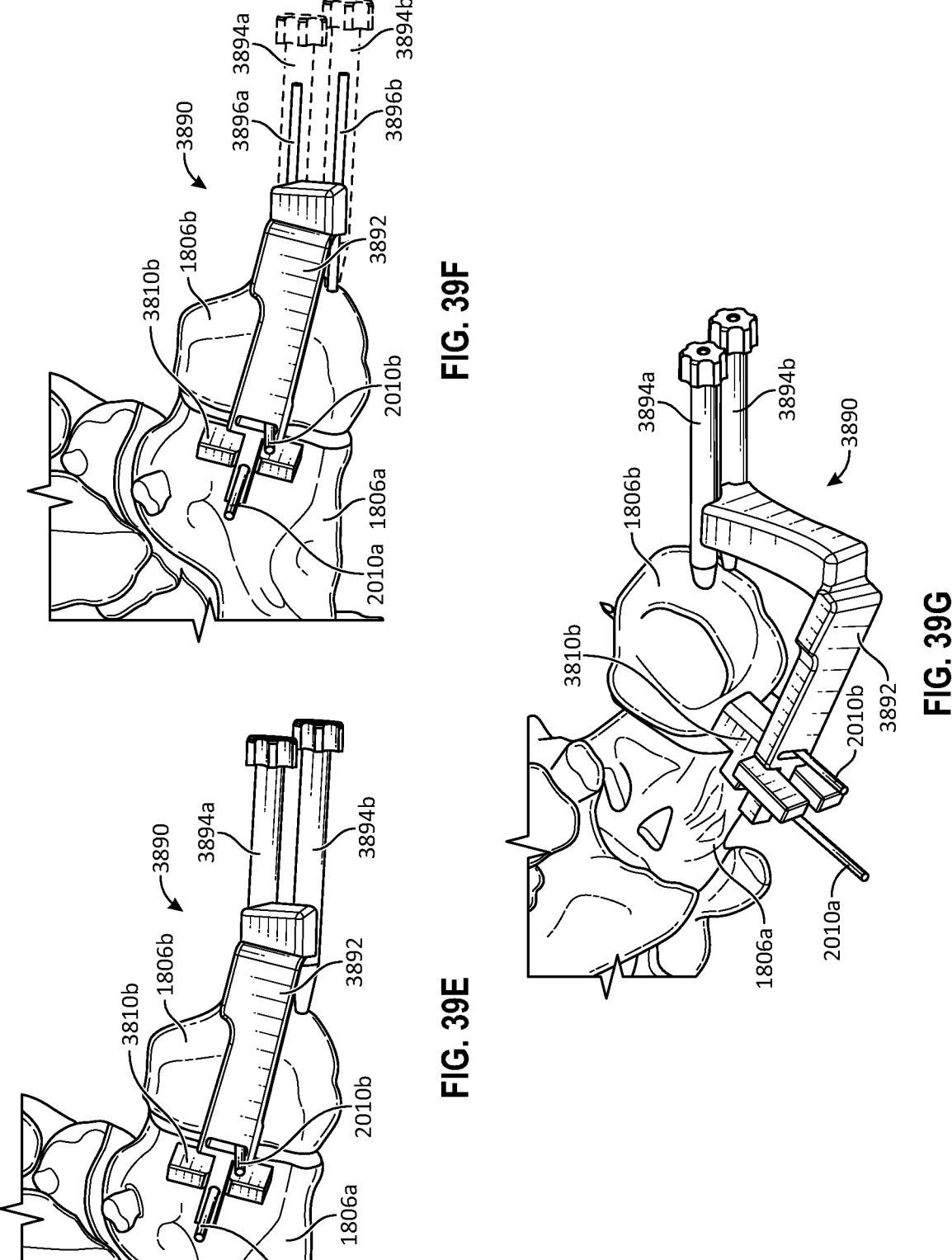

FIG. 39E illustrates a stage in the surgical osteotomy procedure. The positioning guide 3810b is seated and in place and a fixation guide 3890 can been coupled to fastener 2010a and fastener 2010b. In one embodiment, the fixation guide 3890 includes openings that are slid over the fastener 2010a and fastener 2010b. In one embodiment, a posterior opening that receives fastener 2010b may be oversized and/or in a slot shape to account for different angles of rotation that a positioning guide 3810*b* may use in the osteotomy system 3800.

Advantageously, the fixation guide 3890 references off of fastener 2010*a* and fastener 2010*b* to position guides for deployment of fixation. For example, the fixation guide 3890 may include an arm 3892 that extends posteriorly and couples to one or more sleeves 3894 that are configured to receive guide pins 3896. While certain embodiments may include certain aspects of the fixation guide 3890 set as defaults, those of skill in the art will appreciate each aspect of the design and/or configuration of the fixation guide 3890 may be patient-specific and can be customized to a patient by using a model of one or more bones of a patient.

In FIG. 39E, the fixation guide 3890 engages with fastener 2010*a* and passes between handles of the positioning guide 3810*b* and also engages with fastener 2010*b*. The fixation guide 3890 then extends posteriorly and positions two sleeves 3894 for deployment of guide pins 3896. The guide pins 3896 are deployed across the osteotomy and serve to guide permanent fixation such as cannulated bone screws or the like. In one embodiment, using embodiments of the present disclosure, a surgeon can determine where the guide pins 3896 will enter the bones preoperatively using a bone model of one or more bones of a patient and can adjust a trajectory for one or more of the guide pins 3896 and/or a location of entry for the guide pins 3896.

FIG. 39F illustrates the stage illustrated in FIG. 39E, however the sleeves 3894 are shown transparent so that the position of the guide pins 3896 are visible.

FIG. 39G illustrates the stage illustrated in FIG. 39E from a different perspective to show different aspects of the positioning guide 3810*b* and/or fixation guide 3890.

FIGS. 40A-40E illustrate views of a resection guide 3820 of an osteotomy system, according to one embodiment. In the illustrated embodiment, the resection guide 3820 includes one or more resection features 3822, one or more bone attachment features 3824, one or more bone engagement surfaces 3830, and a body 4002. The body 4002 includes a lateral side 4004, a medial side 4006, a dorsal side 4008, a plantar side 4010, an anterior side 4012, and a posterior side 4014.

In the illustrated embodiment, the resection features 3822 include an open end and a closed end. The bone attachment features 3824 may be embodied by a hole that is configured to accept a fastener 2010.

FIG. 40A is a perspective view of one example embodiment of a resection guide 3820 that can be used in the osteotomy system 3800.

FIG. 40B is a front/lateral view of one example embodiment of a resection guide 3820 that can be used in the osteotomy system 3800.

FIG. 40C is a rear/medial view of one example embodiment of a resection guide 3820 that can be used in the osteotomy system 3800. FIG. 40C illustrates a bone engagement surface 3830 that may be patient-specific and can be used to register the resection guide 3820 to a bone of a patient. Advantageously, the bone engagement surface 3830 can be generated based at least in part on a bone model of a bone of a patient.

FIG. 40D is an anterior/left side view of one example embodiment of a resection guide 3820 that can be used in the osteotomy system 3800. In the illustrated embodiment, the posterior side view (e.g., posterior side 4014) may be the same, substantially the same, and/or similar to the anterior/left side view of FIG. 40D.

FIG. 40E is a dorsal/superior side view of one example embodiment of a resection guide 3820 that can be used in the osteotomy system 3800. In the illustrated embodiment, the plantar side view (e.g., plantar side 4010) may be the same, substantially the same, and/or similar to the dorsal/superior side view of FIG. 40E.

FIGS. 41A-41E illustrate views of a positioning guide 3810*a* of an osteotomy system, according to one embodiment. In the illustrated embodiment, the positioning guide 3810*a* includes a body 4102, an anterior alignment feature 4104, a posterior alignment feature 4106, optionally an offset feature 4108, optionally a bone engagement surface 4110, one or more handles 4112.

The body 4102 includes a lateral side 4114, a medial side 4116, a dorsal side 4118, a plantar side 4120, an anterior side 4122, and a posterior side 4124.

In the illustrated embodiment, the alignment features of the positioning guide 3810*a* may extend from a lateral side 4114 to a medial side 4116 at an angle other than perpendicular each of the sides. Advantageously, the angle used for one or more of the alignment features may be predetermined and/or may be patient-specific. Those of skill in the art will appreciate that other aspects of the alignment features may be predetermined and/or patient-specific. For example, the position of the alignment features may be patient-specific.

In the illustrated embodiment, the positioning guide 3810*a* may include an offset feature 4108 in which the offset is zero. Alternatively, or in addition, the positioning guide 3810*a* may not include an offset feature 4108. Advantageously, whether or not the positioning guide 3810*a* includes an offset feature 4108 and/or a size for an offset feature 4108 may be a patient-specific aspect.

Figures 41A, 41B, 41C, 41D, 41E:
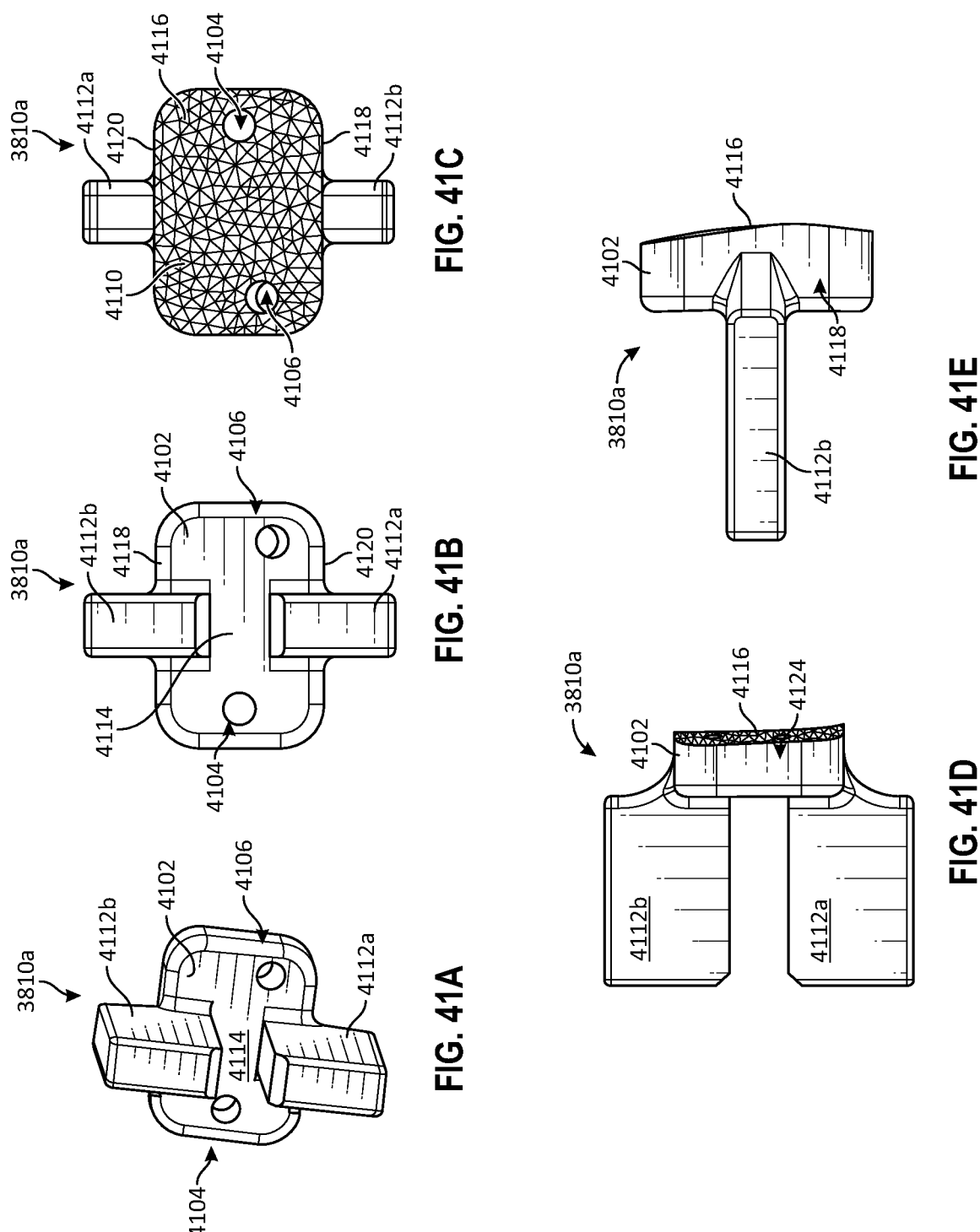
FIGS. 41A-41E illustrate views of a positioning guide of an osteotomy system, according to one embodiment.

FIG. 41A is a perspective view of one example embodiment of a positioning guide 3810*a* that can be used in the osteotomy system 3800.

FIG. 41B is a front/lateral view of one example embodiment of a positioning guide 3810*a* that can be used in the osteotomy system 3800.

FIG. 41C is a rear/medial view of one example embodiment of a positioning guide 3810*a* that can be used in the osteotomy system 3800. FIG. 41C illustrates a bone engagement surface 4110 that may be patient-specific and can be used to register the positioning guide 3810*a* to a bone of a patient. Advantageously, the bone engagement surface 4110 can be generated based at least in part on a bone model of a bone of a patient.

FIG. 41D is a posterior/right side view of one example embodiment of a positioning guide 3810*a* that can be used in the osteotomy system 3800. In the illustrated embodiment, the anterior side view (e.g., anterior side 4122) may be the same, substantially the same, and/or similar to the posterior/right side view of FIG. 41D.

FIG. 41E is a dorsal/superior side view of one example embodiment of a positioning guide 3810*a* that can be used in the osteotomy system 3800. In the illustrated embodiment, the plantar side view (e.g., plantar side 4120) may be the same, substantially the same, and/or similar to the dorsal/superior side view of FIG. 41E.

FIGS. 42A-42E illustrate views of a positioning guide 3810*b* of an osteotomy system, according to one embodiment. In the illustrated embodiment, the positioning guide 3810 includes a body 4202, an anterior alignment feature 4204, a posterior alignment feature 4206, an offset feature 4208, optionally a bone engagement surface 4210, one or more handles 4212.

The body 4202 includes a lateral side 4214, a medial side 4216, a dorsal side 4218, a plantar side 4220, an anterior side 4222, and a posterior side 4224.

In the illustrated embodiment, the alignment features of the positioning guide 3810*b* may extend from a lateral side 4214 to a medial side 4216 at an angle other than perpendicular each of the sides. Advantageously, the angle used for one or more of the alignment features may be predetermined and/or may be patient-specific. Those of skill in the art will appreciate that other aspects of the alignment features may be predetermined and/or patient-specific. For example, the position of the alignment features may be patient-specific.

In the illustrated embodiment, the positioning guide 3810*b* may include an offset feature 4208 in which the offset is nonzero. Alternatively, or in addition, the positioning guide 3810*a* may not include an offset feature 4108. Where a positioning guide 3810*b* has an offset feature 4208 that is nonzero, the bone engagement surface 4210 may include more than one section, such as a bone engagement surface 4210*a* and a bone engagement surface 4210*b*.

Advantageously, whether or not the positioning guide 3810*a* includes an offset feature 4208 and/or a size (offset distance 4226) for an offset feature 4208 may be a patient-specific aspect. The offset distance 4226 may determine how much translation is provided between two bone fragments. In one embodiment, the offset distance 4226 can range from about 0 millimeters (i.e., no translation) to about 10 millimeters. Advantageously, the magnitude of the offset distance 4226 can be set using a model of one or more bones of the patient and/or a model of the positioning guide 3810*b*. In this manner, the offset feature 4208 and/or the offset distance 4226 can be a patient-specific feature that can be defined based, at least in part, on a model of a bone of a patient. A surgeon, or other user, can define the offset distance 4226 based on a desired about of translation.

Figures 42A, 42B, 42C, 42D, 42E, 42F, 42G, 42H:
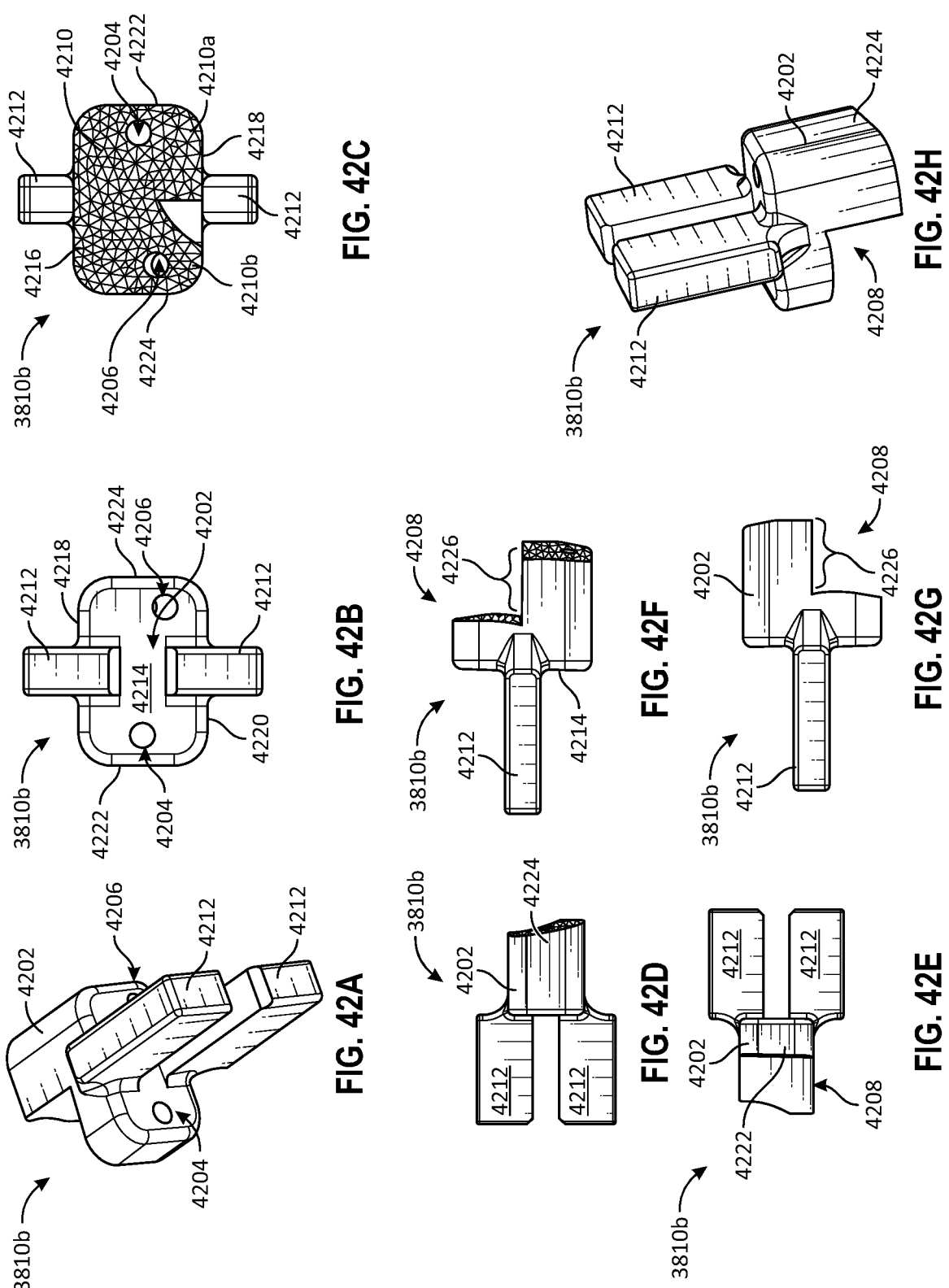
FIGS. 42A-42H illustrate views of a positioning guide of an osteotomy system, according to one embodiment.

FIG. 42A is a perspective view of one example embodiment of a positioning guide 3810*b* that can be used in the osteotomy system 3800.

FIG. 42B is a front/lateral view of one example embodiment of a positioning guide 3810*b* that can be used in the osteotomy system 3800.

FIG. 42C is a rear/medial view of one example embodiment of a positioning guide 3810*b* that can be used in the osteotomy system 3800. FIG. 42C illustrates a bone engagement surface 4210 that may be patient-specific and can be used to register the positioning guide 3810*b* to a bone of a patient. Advantageously, the bone engagement surface 4210 can be generated based at least in part on a bone model of a bone of a patient.

FIG. 42D is a posterior/right side view of one example embodiment of a positioning guide 3810*b* that can be used in the osteotomy system 3800. FIG. 42E is an anterior/left side view (e.g., anterior side 4122) of one example embodiment of a positioning guide 3810*b* that can be used in the osteotomy system 3800.

FIG. 42F is a dorsal/superior side view of one example embodiment of a positioning guide 3810*b* that can be used in the osteotomy system 3800. FIG. 42G is a plantar/inferior side view of one example embodiment of a positioning guide 3810*b* that can be used in the osteotomy system 3800.

FIG. 42H is a perspective view of one example embodiment of a positioning guide 3810.

Figures 43A, 43B:
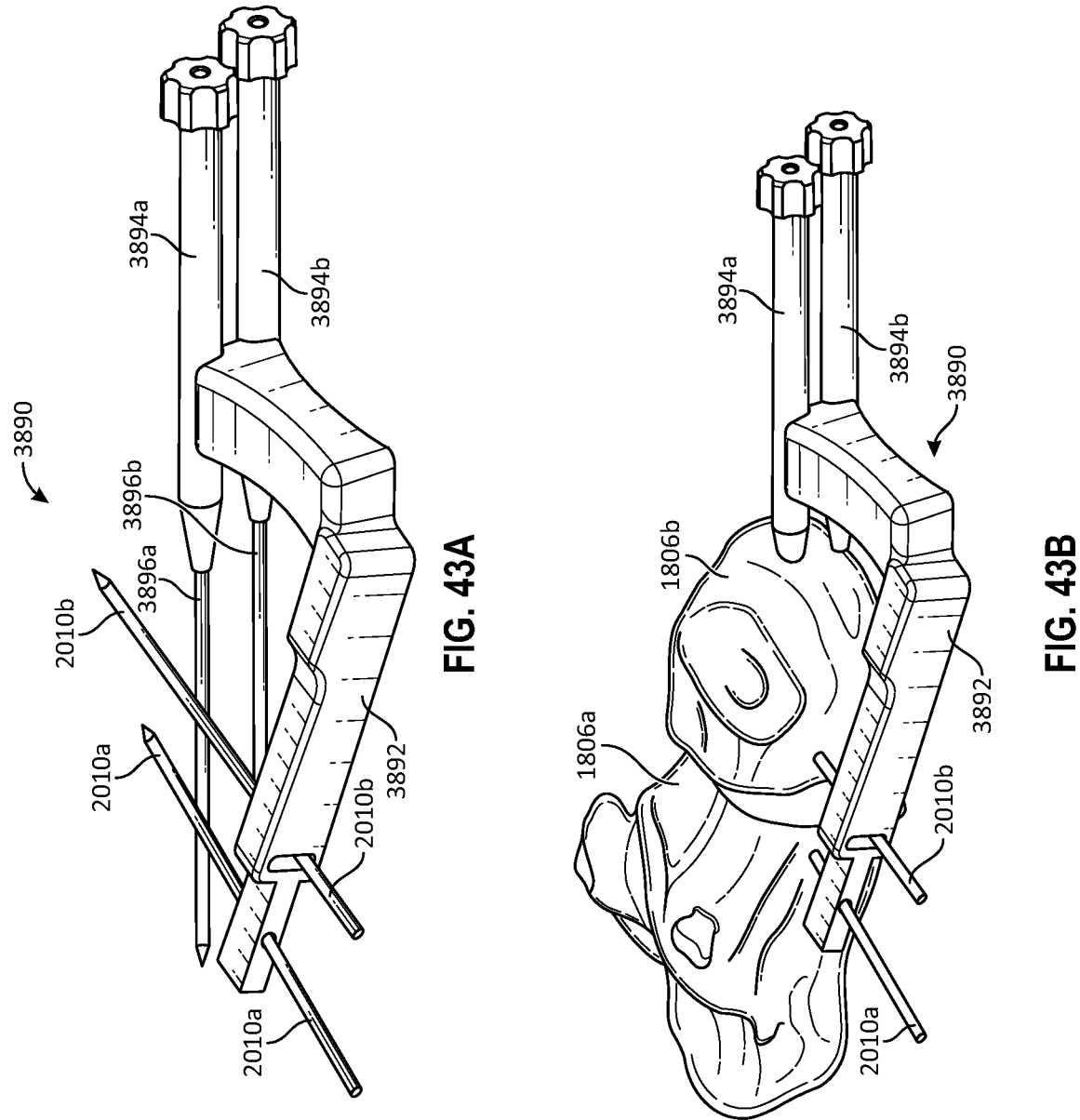
FIGS. 43A-43B illustrate views of a fixation guide of an osteotomy system, according to another embodiment.

FIGS. 43A-43B illustrate views of a fixation guide 3890 of an osteotomy system, according to another embodiment. A cooperating positioning guide 3810 is omitted. The fixation guide 3890 includes an arm 3892 and one or more sleeves 3894 that are configured to receive guide pins 3896.

FIG. 43A illustrates one embodiment of a fixation guide 3890. A first fastener 2010*a* and a second fastener 2010*b* are illustrated, with the patient bone omitted for clarity. The arm 3892 and one or more sleeves 3894 and receive guide pins 3896 are illustrated.

FIG. 43B illustrates one embodiment of a fixation guide 3890. A first fastener 2010*a* and a second fastener 2010*b* are illustrated. The patient bone (e.g., patient calcaneus 1806) is illustrated for perspective. The arm 3892 and one or more sleeves 3894 and receive guide pins 3896 are illustrated.

Those of skill in the art will appreciate that the trajectories, the lengths and/or configuration of the arm 3892, the size of the sleeves 3894, are among some of the aspects of the fixation guide 3890 that can be predetermined and/or defined and/or adjusted using a model of a patient's bone(s) and a model of the instruments to be used. Any of the methods, systems, apparatus, and/or techniques of the present disclosure can be used in any combination to provide a customized system, set of instruments, preoperative plan, and/or surgical technique for treatment of a patient.

Figure 44:
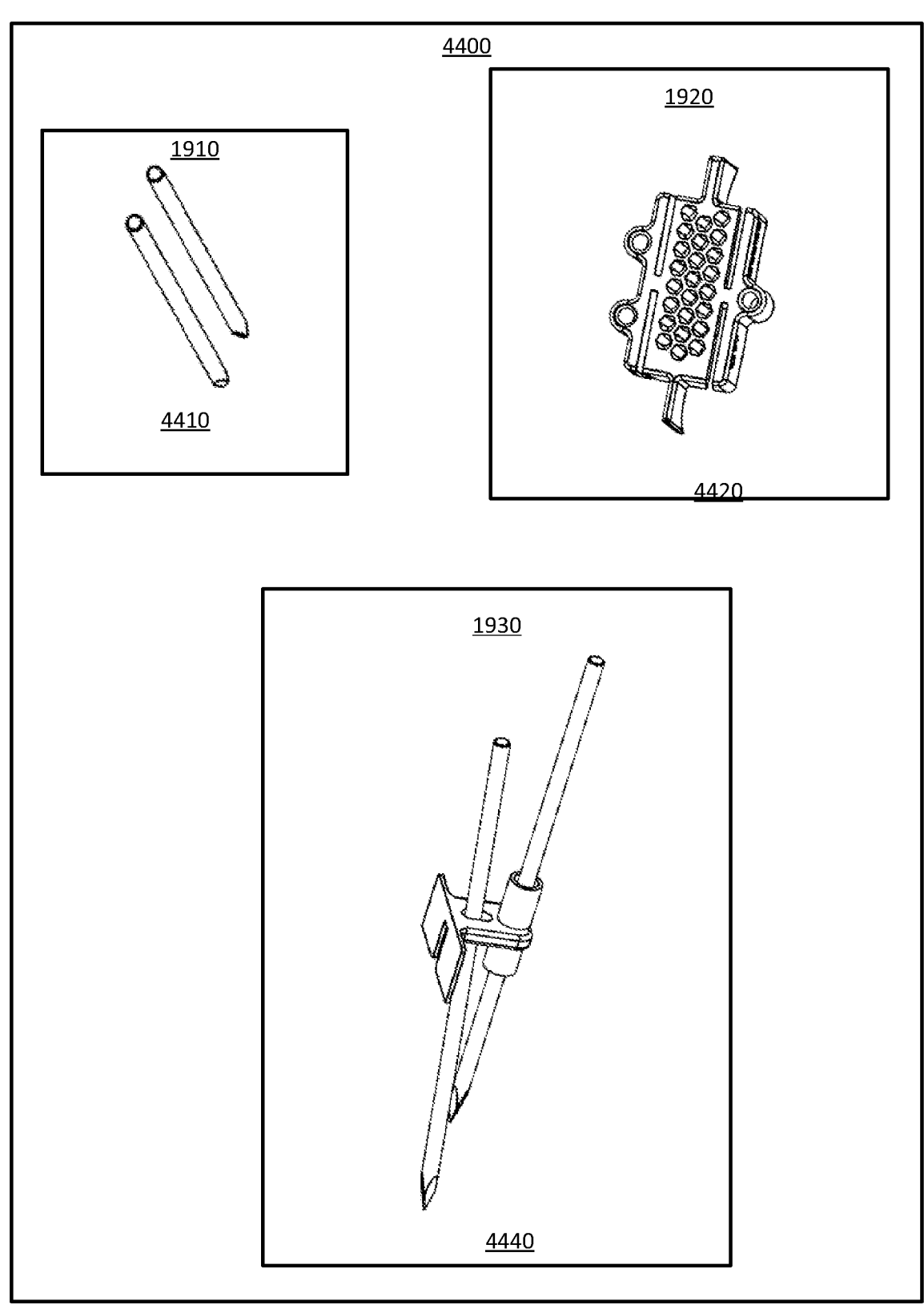
FIG. 44 illustrates an exemplary osteotomy system for an osteotomy, according to one embodiment.

FIG. 44 illustrates an exemplary osteotomy system 4400 for an osteotomy, according to one embodiment. The osteotomy system 4400 may include fasteners 4410, a resection guide 4420, one or more and/or pin guides 4440. Of course, the osteotomy system 4400 may include other complementary components 1930 as well.

The osteotomy system 4400 can include some, or all, of the same, or substantially the same, features, aspects, and/or components as the other systems included in the present disclosure. Accordingly, the resection guide 4420 can, or may, include one or more resection features 4422 (e.g., resection features 4422*a*-*b*), one or more bone attachment features 4424 (e.g., bone attachment features 4424*a*-*c*), one or more handles, one or more landmark registration features, one or more bone engagement surfaces 4430, or the like. Similarly, any of the features and/or aspects of the resection guide 4420 (e.g., resection features 4422, bone attachment features 4424, and bone engagement surfaces 4430) may be patient-specific as described herein and may be based at least in part on bone models of one or more bones or portions of bones of a patient. Of course, the features of the resection guide 4420 may be configured to facilitate the particular osteotomy procedure.

A pin guide 4440 may include an arm 4406 configured to engage at least one of a first resection feature 4422*a* and a second resection feature 4422*b*. The arm 4406 may be connected to a bone engagement feature 4408 configured to receive a fastener such as a pin or K-wire. Similarly, any of the features and/or aspects of the pin guide 4440 (e.g., arm 4406, bone engagement feature 4408, etc.) may be patient-specific as described herein and may be based, at least in part, on bone models of one or more bones or portions of bones of a patient.

FIGS. 45A-45D illustrates different stages of performing a surgical osteotomy procedure using an osteotomy system of FIG. 44, according to one embodiment. Typically, a preferred approach for the osteotomy is on the lateral side of the calcaneus 1806. In the illustrated embodiment, the surgical procedure creates a wedge osteotomy. According to one embodiment, a surgeon may access a lateral surface of the calcaneus 1806. Next a surgeon may position a resection guide 4420 on the lateral surface in a position predetermined using a calcaneus model of the patient's calcaneus 1806. In certain embodiments, the step of positioning can include seating or registration of the resection guide 4420 to a surface of the calcaneus 1806 (a bone). The resection guide 4420 may be configured, for example, as one of the resection guides described herein.

Once positioned, a surgeon may deploy a first fastener 4410a into a first bone attachment feature 4424a, a second fastener 4410b into a second bone attachment feature 4424b, and a third fastener 4410c into a third bone attachment feature 4424c. In one embodiment, the bone attachment features 4424 are configured such that the first fastener 4410a, second fastener 4410b, and third fastener 4410c are parallel relative to each other. Next, a surgeon may direct a cutting tool into one or more resection features 4422. In the illustrated embodiment, the resection guide 4420 may include a first resection feature 4422a and a second resection feature 4422b.

In certain embodiments, the osteotomy system 4400 may include a guide for managing how deep a surgeon cuts into the calcaneus 1806 using the cutting tool. In one embodiment, the depth may be recommended in a preoperative plan and a surgeon may configure the cutting tool to indicate when that depth is reached. Alternatively, or in addition, the resection guide 4420 may include a stop that prevents cutting below the recommended depth. For example, the resection guide 4420 may have a height that is such that a lateral side of the resection guide 4420 may serve as a stop to prevent cutting beyond a particular depth. Alternatively, or in addition, a separate structure may be provided with the osteotomy system 4400 and/or the resection guide 4420 to serve as a stop to control cutting depth into a bone.

Figures 45A, 45B, 45C, 45D:
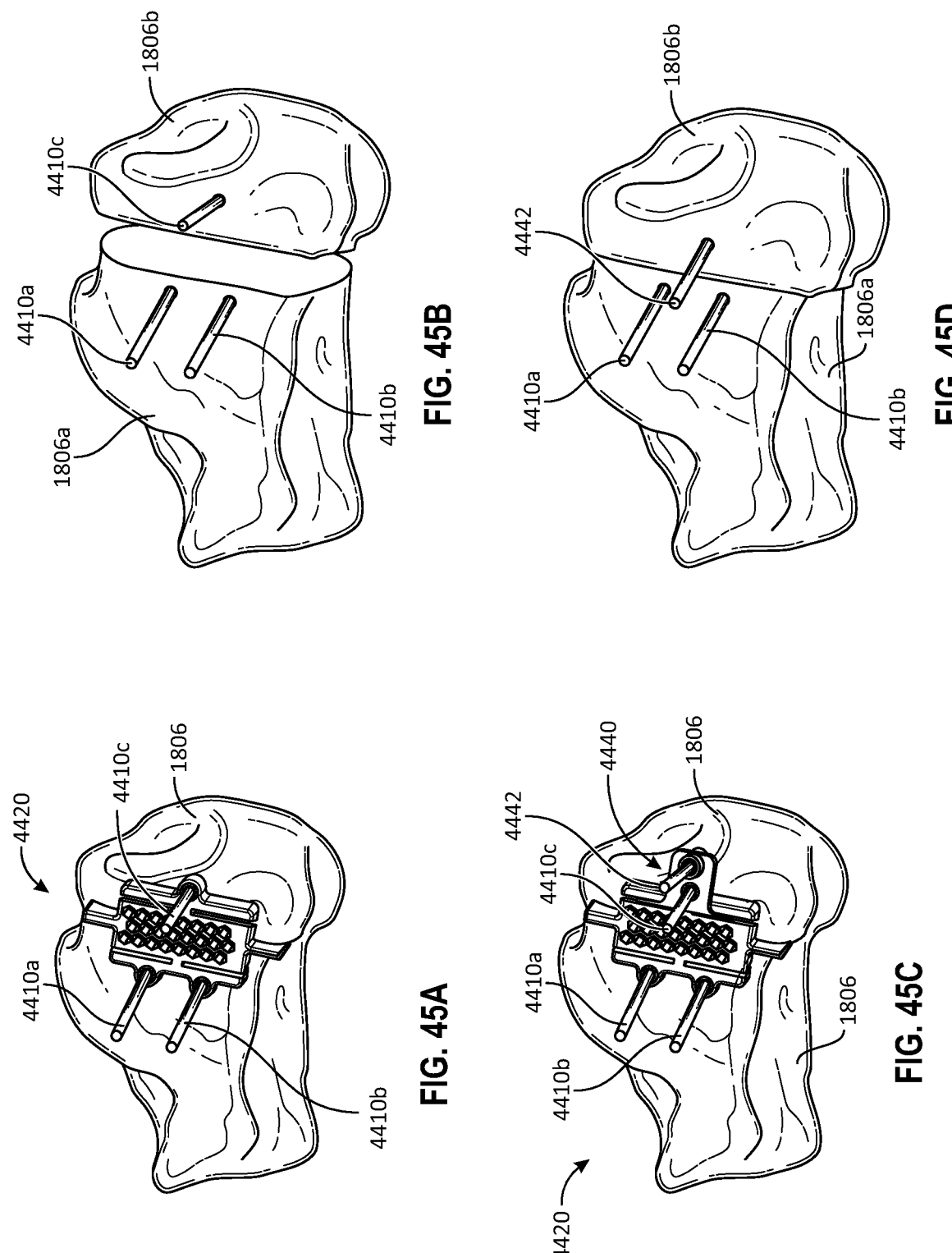
FIGS. 45A-45D illustrates different stages of performing a surgical osteotomy procedure using an osteotomy system of FIG. 44, according to one embodiment.

FIG. 45A illustrates the resection guide 4420 secured to the calcaneus 1806 by way of fasteners 4410a,b,c. In this embodiment, the resection guide 4420 includes a different set of bone attachment features 4424 than other embodiments described. The resection guide 4420 includes a first bone attachment feature 4424a and a second bone attachment feature 4424b on an anterior side of the resection guide 4420 and a third bone attachment feature 4424c on a posterior side of the resection guide 4420. In certain embodiments, the first bone attachment feature 4424a and second bone attachment feature 4424b may be configured such that a first fastener 4410a and second fastener 4410b deployed in the first bone attachment feature 4424a and the second bone attachment feature 4424b can be used in subsequent steps of the surgical procedure. In this embodiment, a wedge bone fragment formed by the osteotomy may not be connected to a fastener 4410. However, a surgeon may remove the wedge bone fragment using forceps.

FIG. 45B illustrates a stage in the procedure in which the surgeon has created the osteotomy. In one embodiment, the anterior bone fragment 1806a is separated from the posterior bone fragment 1806b. The resection guide 4420 is not shown in this view. In another embodiment, the anterior bone fragment 1806a may be connected to the posterior bone fragment 1806b by way of a living hinge (e.g., a portion of a medial cortex opposite the osteotomy). Advantageously, fastener 4410a and fastener 4410b engage with the anterior bone fragment 1806a and fastener 2010c engages with the posterior bone fragment 1806b. Thus, a surgeon can manipulate these bone fragments as needed.

Referring now to FIG. 45C, a surgeon may couple a pin guide 4440 to one of the resection features 4422 of the resection guide 4420. In this manner, a surgeon can position a reduction fastener 4442. In one embodiment, a reduction fastener 4442 can be used to assist in reducing the osteotomy. Advantageously, the angle and position of the reduction fastener 4442 can be predetermined and/or can be patient-specific for this patient and the needs of the patient and/or surgeon for the surgical procedure.

In certain embodiments, the pin guide 4440 can be used before forming one or more osteotomies. Alternatively, or in addition, a surgeon may form the osteotomies and then use the pin guide 4440 to deploy the reduction fastener 4442.

Next, a surgeon can remove the pin guide 4440, the resection guide 4420, and the third fastener 4410c. The first fastener 4410a, second fastener 4410b, and reduction fastener 4442 remain in the bone fragments.

FIG. 45D illustrates a stage in the surgical osteotomy procedure. The pin guide 4440, the resection guide 4420, and the third fastener 4410c have been removed. The fasteners 4410a,b and reduction fastener 4442 remain engaged with the bone fragments of the calcaneus 1806. The anterior bone fragment 1806a and posterior bone fragment 1806b are shown reduced. The surgeon may reduce the bone fragments manually or the surgeon may use a complementary component 1930 such as one embodiment of a positioning guide 2300. In the illustrated embodiment, the action of sliding a positioning guide 2300 on the first fastener 4410a, second fastener 4410b, and reduction fastener 4442 can cause the posterior bone fragment 1806b to translate relative to the anterior bone fragment 1806a.

FIGS. 46A-46G illustrate views of a resection guide of an osteotomy system, according to one embodiment. The resection guide 4420 can include some, or all, of the same, or substantially the same, features, aspects, and/or components as the other resection guides included in the present disclosure. Accordingly, the resection guide 4420 can, or may, include one or more resection features 4422 (e.g., resection features 4422a-b), one or more bone attachment features 4424 (e.g., bone attachment features 4424a-c), one or more handles, one or more landmark registration features, one or more bone engagement surfaces 4430, or the like.

In the illustrated embodiment, the resection guide 4420 includes a first resection feature 4422a and a second resection feature 4422b. The first resection feature 4422a may be configured to guide a cutting tool to form a first osteotomy. The second resection feature 4422b may be configured to guide a cutting tool (which may be the same cutting tool) to form a second osteotomy.

In certain embodiments, one or more of the handles 4426 can serve as both a handle used by a user to position the resection guide 4420 and/or as a landmark registration feature 4428. The landmark registration feature 4428 can provide the same features, advantages, and/or benefits as the landmark registration feature 2042 described above.

Figures 46A, 46B, 46C, 46D, 46E, 46F, 46G:
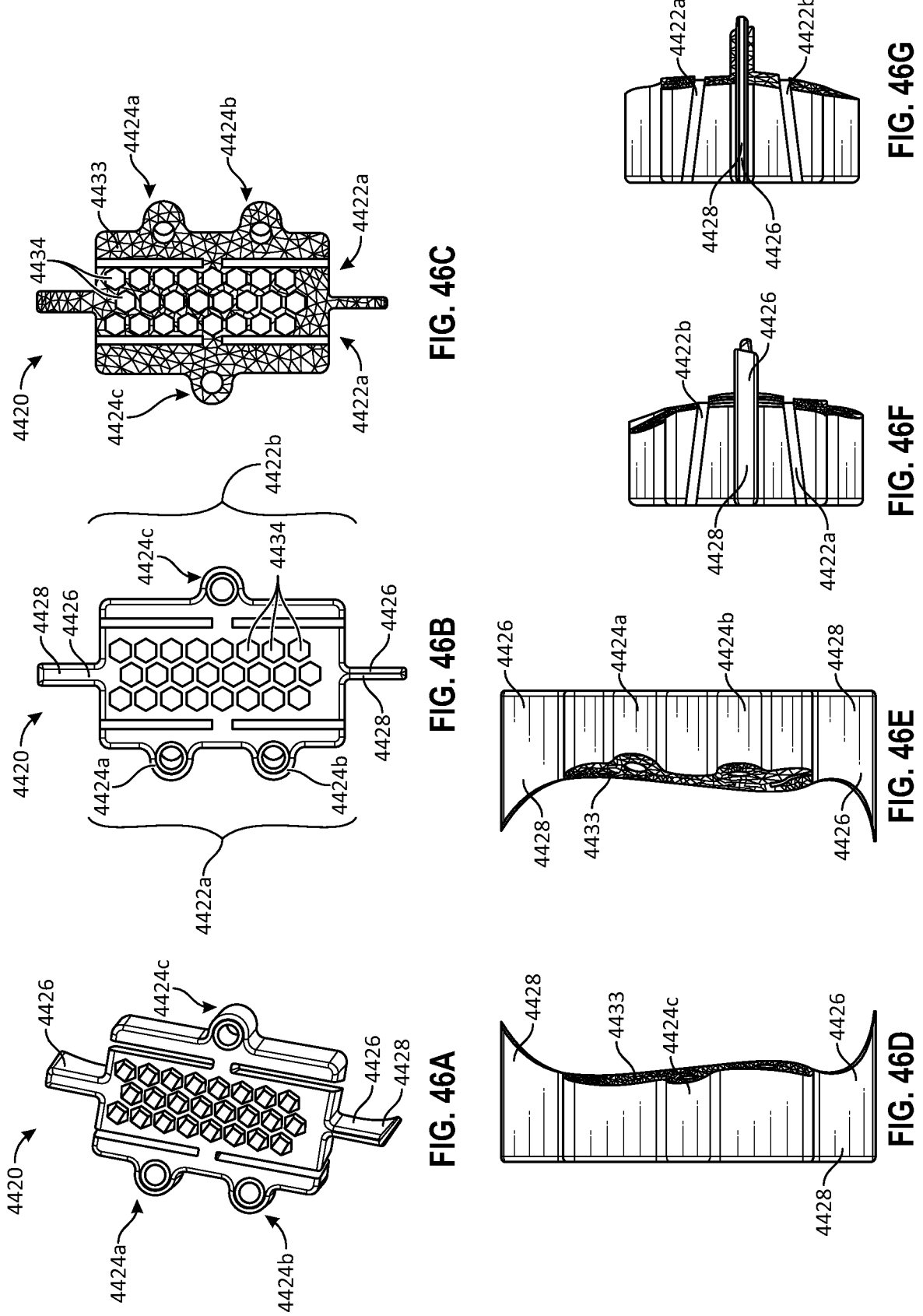
FIGS. 46A-46G illustrate views of a resection guide of an osteotomy system, according to one embodiment.

FIG. 46A illustrates a perspective view of the resection guide 4420. FIG. 46B illustrates a front/lateral view (showing the lateral side) of the resection guide 4420. FIG. 46C illustrates a rear/medial view (showing the medial side) of the resection guide 4420. The resection guide 4420 can include a bone engagement surface 4433. The bone engagement surface 4433 may include any or all or some of the features, advantages, structures, and/or benefits as the bone engagement surface 2033 described herein. In one embodiment, the resection guide 4420 may include a plurality of openings 4434 that extend from a lateral side to a medial side. The plurality of openings 4434 may assist a surgeon by giving more visibility to anatomy below the resection guide 4420.

FIG. 46D illustrates a right/posterior view (showing the posterior side) of the resection guide 4420. FIG. 46E illustrates a left/anterior view (showing the anterior side) of the resection guide 4420. FIG. 46F illustrates a dorsal view (showing the dorsal side) of the resection guide 4420. FIG. 46G illustrates a plantar view (showing the plantar side) of the resection guide 4420.

FIGS. 47A-47F illustrate views of a pin guide 4440 or alignment guide of an osteotomy system, according to one embodiment.

A pin guide 4440 may include an arm 4406 configured to engage at least one of a first resection feature 4422*a* and a second resection feature 4422*b*. The arm 4406 may be connected to a bone engagement feature 4408 configured to receive a fastener such as a reduction fastener 4442, a pin, and/or a K-wire. Similarly, any of the features and/or aspects of the pin guide 4440 (e.g., arm 4406, bone engagement feature 4408, etc.) may be patient-specific as described herein and may be based, at least in part, on bone models of one or more bones or portions of bones of a patient.

Figures 47A, 47B, 47C, 47D, 47E, 47F:
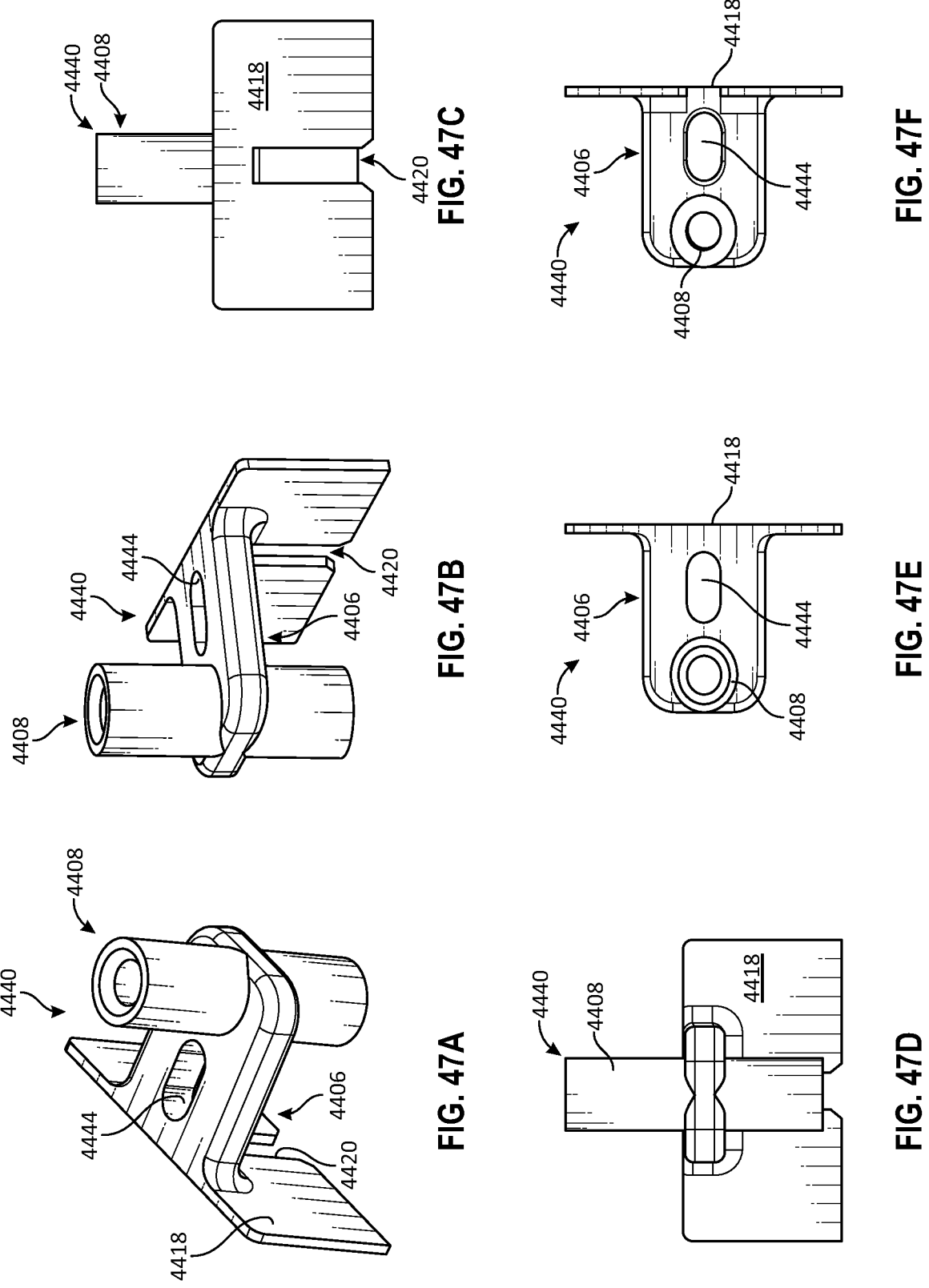
FIGS. 47A-47F illustrate views of a pin guide or alignment guide of an osteotomy system, according to one embodiment.

FIG. 47A illustrates a plantar perspective view of the pin guide 4440. The arm 4406 may include an opening 4420 sized and/or configured to receive a bridge (e.g., posterior bridge and/or anterior bridge) of a resection feature 4422. In certain embodiments, the arm 4406 may engage the resection feature 4422 by sliding the opening 4420 over the bridge. Alternatively, or in addition, another part of the arm 4406 may slide down into one or more openings of a resection feature 4422. In one embodiment, the resection guide 4420 may be similar to the resection guide 2220 described herein.

In one embodiment, the resection guide 4420 may be part of a coupler 4412. The coupler 4412 may be similar to coupler 2212 described herein. The coupler 4412 enables the pin guide 4440 to be connected and/or disconnected from a complementary component 1930. The complementary component 1930 may serve as a reference or guide for the placement, positioning, and/or orientation of fasteners (e.g., reduction fastener 4442) into bone and/or bone fragments during a surgical procedure. Those of skill in the art will appreciate that the coupler 4412 may be implemented using a variety of configurations.

In the illustrated embodiment, the coupler 4412 may be implemented as a fin 4418 that includes the opening 4420. The fin 4418 may slide down into one or more openings of a resection feature 4422 and secure the orientation and/or position of the pin guide 4400. The fin 4418 may be similar to fin 2218 and may be planar.

FIG. 47B illustrates a dorsal perspective view of the pin guide 4440. In one embodiment, the pin guide 4440 include a passage slot 4444. The resection features 4422 may be configured to accept and pass an end of a fastener such as first fastener 4410*a*, second fastener 4410*b*, and/or third fastener 4410*c*. Referring to FIG. 45C, the passage slot 4444 allows the pin guide 4440 to slide over the third fastener 4410*c* to take its desired position for deployment of the passage slot 4444

FIG. 47C illustrates a an anterior view in one embodiment (showing the anterior side) of the pin guide 4440. FIG. 47D illustrates a posterior view in one embodiment (showing the posterior side) of the pin guide 4440. FIG. 47E illustrates a top/superior view (showing the superior side) of the pin guide 4440. FIG. 47F illustrates a bottom/inferior view (showing the inferior side) of the pin guide 4440.

A patient may present with a variety of conditions. To correct or mitigate these conditions an osteotomy guide according to the present disclosure can be used to address dorsiflexion, plantar flexion, or angular correction of a bone segment or any bone. The osteotomy guide could fit on any aspect in the angles would be determined based on the desired degree of correction. In certain embodiments, this osteotomy guide can be used within a portion of bone as opposed to over a joint.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

The invention claimed is:

1. An osteotomy system for remediating a bone condition present in a patient's foot, the system comprising:
   a resection guide comprising:
      a body having an anterior side, a posterior side, a medial side, a lateral side, a dorsal side, and a plantar side;
      a posterior resection feature configured to guide a cutting tool to form a first osteotomy in the bone, the posterior resection feature extending through the resection guide from the lateral side to the medial side along a first trajectory at least partially determined based on a bone model of at least a portion of the patient's foot, the bone model based on medical imaging of the patient's foot and configured to resemble the anatomy of the patient's foot;
      an anterior resection feature configured to guide a cutting tool to form a second osteotomy in the bone, the anterior resection feature extending through the resection guide from the lateral side to the medial side along a second trajectory at least partially determined based on the bone model;

wherein the first trajectory converges with the second trajectory at a vertex having a position determined before fabrication of the resection guide;

a bone attachment feature configured to secure the resection guide to the bone; and at least one complementary component selected from the group consisting of:

an alignment guide;

a rotation guide;

a compression guide;

a correction guide;

a positioning guide;

a pin guide; and a fixation guide.

2. The system of claim 1, wherein the first trajectory converges with the second trajectory at a vertex having a wedge angle, such that posterior resection feature and the anterior resection feature form a wedge osteotomy comprising a wedge bone fragment after formation of the first osteotomy and the second osteotomy, the wedge angle determined based, at least in part, on the bone model.

3. The system of claim 2, wherein the bone attachment feature is configured to secure the resection guide to a portion of the bone that forms the wedge bone fragment after formation of the wedge osteotomy.

4. The system of claim 2, wherein the vertex is prepositioned to be between a medial cortex of the bone and the resection guide when the resection guide is designed for the patient's foot.

5. The system of claim 1, wherein the medial side of the resection guide comprises a bone engagement surface configured to register to a lateral surface of the bone, the bone engagement surface defined based a lateral surface of the bone model and a planned position of the resection guide on a lateral surface of the bone.

6. The system of claim 1, wherein the at least one complementary component comprises the positioning guide and wherein the positioning guide comprises:

a body having an anterior side, a posterior side, a medial side, a lateral side, a dorsal side, and a plantar side;

an anterior alignment feature;

a posterior alignment feature; and an offset feature on the medial side of the body, the offset feature configured to translate a posterior bone fragment relative to an anterior bone fragment, the posterior bone fragment and anterior bone fragment formed by way of one of the first osteotomy and the second osteotomy.

7. The system of claim 6, wherein the positioning guide comprises:

a bone engagement surface on the medial side, the bone engagement surface configured to register to a lateral surface of the posterior bone fragment and the anterior bone fragment; and wherein the bone engagement surface is defined based on a lateral surface of the bone model and a planned reduced position of the posterior bone fragment and the anterior bone fragment.

8. An osteotomy system for remediating a bone condition present in a patient's foot, the system comprising:

at least one fastener configured to engage a phalanx of a patient's foot;

a resection guide comprising:

a body having an anterior side, a posterior side, a medial side, a lateral side, a dorsal side, and a plantar side;

a posterior resection feature configured to guide a cutting tool to form a first osteotomy in the phalanx, a first trajectory for the first osteotomy determined based on a bone model of the phalanx based on medical imaging of the patient's foot, the bone model configured to significantly resemble the anatomy of the patient's foot;

an anterior resection feature configured to guide a cutting tool to form a second osteotomy in the phalanx, a second trajectory for the second osteotomy determined based on the bone model;

wherein the first trajectory converges with the second trajectory at a vertex within a bone of the patient;

a first bone attachment feature configured to secure the resection guide to the phalanx; and a second bone attachment feature configured to secure the resection guide to the phalanx.

9. The system of claim 8, wherein at least one of the first bone attachment feature and the second bone attachment feature are configured to form a guide hole for a fastener within the phalanx when the at least one of the first bone attachment feature and the second bone attachment feature are disengaged from the phalanx.

10. The system of claim 8, wherein the first bone attachment feature is configured to form a first guide hole and the second bone attachment feature is configured to form a second guide hole and wherein the first guide hole is configured for a first leg of a bone staple and the second guide hole is configured for a second leg of the bone staple.

* * * * *